US012735422B2

(12) United States Patent
von Deyn et al.

(10) Patent No.: US 12,735,422 B2
(45) Date of Patent: Sep. 15, 2026

(54) IMIDAZO-PYRIMIDONE COMPOUNDS AS PESTICIDES

(71) Applicant: BASF SE, Ludwigshafen (DE)

(72) Inventors: Wolfgang von Deyn, Ludwigshafen (DE); Ashokkumar Adisechan, Navi Mumbai (IN); Rizwan Shabbir Shaikh, Navi Mumbai (IN)

(73) Assignee: BASF SE, Ludwigshafen (DE)

( * ) Notice: Subject to any disclaimer, the term of this patent is extended or adjusted under 35 U.S.C. 154(b) by 855 days.

(21) Appl. No.: 17/916,818

(22) PCT Filed: Mar. 29, 2021

(86) PCT No.: PCT/EP2021/058135

§ 371 (c)(1),
(2) Date: Oct. 4, 2022

(87) PCT Pub. No.: WO2021/204577

PCT Pub. Date: Oct. 14, 2021

(65) Prior Publication Data

US 2023/0183245 A1 Jun. 15, 2023

(30) Foreign Application Priority Data

Apr. 6, 2020 (EP) .................................... 20168197
Sep. 14, 2020 (EP) .................................... 20195918
Mar. 26, 2021 (WO) ................ PCT/EP2021/057865

(51) Int. Cl.
*C07D 487/04* (2006.01)
*A01N 43/90* (2006.01)

(52) U.S. Cl.
CPC .......... *C07D 487/04* (2013.01); *A01N 43/90* (2013.01)

(58) Field of Classification Search
None
See application file for complete search history.

(56) References Cited

FOREIGN PATENT DOCUMENTS

WO WO-2017167832 A1 * 10/2017 ............ A01N 43/90
WO WO-2018/206479 A1 11/2018
WO WO-2019/053182 A1 3/2019
WO WO-2021/099240 A1 5/2021

OTHER PUBLICATIONS

European Search Report for EP Patent Application No. 20168197.0, Issued on Sep. 2, 2020, 3 pages.
Unpublished European Patent Application No. 21153132.2, filed on Jan. 25, 2021, titled "Sulfoximine derivative of ethyl sulfone", 110 pages.
International Application No. PCT/EP2021/058135, International Search Report and Written Opinion, mailed Jul. 5, 2021.

* cited by examiner

*Primary Examiner* — Bethany P Barham
*Assistant Examiner* — Paul Hoerner
(74) *Attorney, Agent, or Firm* — MARSHALL, GERSTEIN & BORUN LLP

(57) ABSTRACT

The invention relates to a compound of formula (I), wherein the variables are defined in the specification. It also relates to a pesticidal mixture comprising the compound of formula (I); the use of compounds of formula (I) as an agrochemical pesticide; a method for combating or controlling invertebrate pests, a method for protecting growing plants from attack or infestation by invertebrate pests, seed comprising a compound of the formula (I); and the use of a compound of the formula (I) for protecting growing plants from attack or infestation by invertebrate pests.

13 Claims, No Drawings

IMIDAZO-PYRIMIDONE COMPOUNDS AS PESTICIDES

CROSS-REFERENCE TO RELATED APPLICATIONS

This is the U.S. national phase of International Application No. PCT/EP2021/058135, filed Mar. 29, 2021, which claims the benefit of European Patent Application No. 20168197.0, filed Apr. 6, 2020, European Patent Application No. 20195918.6, filed Sep. 14, 2020, and PCT/EP2021/057865, filed Mar. 26, 2021.

The invention relates to compounds of formula (I) or an agrochemically or verterinarily acceptable salt, stereoisomer, tautomer, or N-oxide thereof (I)

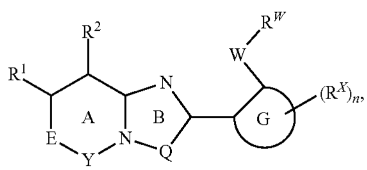

wherein the variables are as defined below. The invention also relates to the use of compounds of formula (I) as an agrochemical pesticide; to pesticidal mixtures comprising a compound of formula (I) and another pesticidal ingredient; to a method for combating or controlling invertebrate pests, which method comprises contacting said pest or its food supply, habitat or breeding grounds with a pesticidally effective amount of at least one compound of the formula (I) or the pesticidal mixture; to a method for protecting growing plants from attack or infestation by invertebrate pests, which method comprises contacting a plant, or soil or water in which the plant is growing, with a pesticidally effective amount of at least one compound of the formula (I) or the pesticidal mixture; and to seeds comprising a compound of the formula (I) or the pesticidal mixture in an amount of from 0.1 g to 10 kg per 100 kg of seeds; to a use of a compound of the formula (I) or of the pesticidal mixture for protecting growing plants from attack or infestation by invertebrate pests; and to a method for treating or protecting an animal from infestation or infection by invertebrate pests which comprises bringing the animal in contact with a pesticidally effective amount of a compound of the formula (I) or the pesticidal mixture.

Invertebrate pests and in particular insects, arachnids and nematodes destroy growing and harvested crops and attack wooden dwelling and commercial structures, thereby causing large economic loss to the food supply and to property. Accordingly, there is an ongoing need for new agents for combating invertebrate pests.

WO2017/167832A1 discloses bicyclic pyrimidone compounds and their pesticidal activity.

Due to the ability of target pests to develop resistance to pesticidally-active agents, there is an ongoing need to identify further compounds, which are suitable for combating invertebrate pests such as insects, arachnids and nematodes. Furthermore, there is a need for new compounds having a high pesticidal activity and showing a broad activity spectrum against a large number of different invertebrate pests, especially against difficult to control insects, arachnids and nematodes.

It is therefore an object of the present invention to identify and provide compounds, which exhibit a high pesticidal activity and have a broad activity spectrum against invertebrate pests.

It has been found that these objects can be achieved by substituted bicyclic compounds of formula (I), as depicted and defined below, including their stereoisomers, their salts, in particular their agriculturally or veterinarily acceptable salts, their tautomers and their N-oxides.

In a first aspect, the present invention relates to a compound of formula (I), (I)

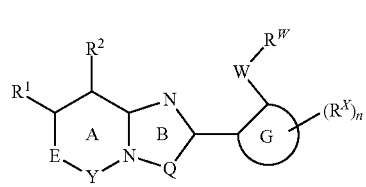

wherein the rings A and B are fully unsaturated;

Y is C═X, wherein X is O or S;

E is $N(R^3)$ or $C(R^4)$;

Q is N, $N(R^5)$ or $C(R^6)$;

$R^1$ is H, halogen, $C_1$-$C_6$-alkyl, $C_2$-$C_6$-alkenyl, $C_2$-$C_6$-alkynyl, $C_1$-$C_6$-alkoxy, $C_1$-$C_6$-alkoxy-$C_1$-$C_6$-alkyl, $C_3$-$C_6$-cycloalkyl, $C_3$-$C_6$-cycloalkoxy, $C_1$-$C_6$-sulfenyl, $C_1$-$C_6$-sulfinyl, or $C_1$-$C_6$-sulfonyl, which groups are unsubstituted or halogenated;

$R^3$, $R^5$ are independently $C_1$-$C_6$-alkyl, $C_1$-$C_6$-alkoxy, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkyl-$C_1$-$C_4$-alkyl, or $C_3$-$C_6$-cycloalkoxy-$C_1$-$C_4$-alkyl, which are unsubstituted or halogenated;
 $C(═O)OR^A$, $NR^BR^C$, $C_1$-$C_6$-alkylen-$NR^BR^C$, O—$C_1$-$C_6$-alkylen-$NR^BR^C$, $C_1$-$C_6$-alkylen-CN, NH—$C_1$-$C_6$-alkylen-$NR^BR^C$, $C(═O)NR^BR^C$, $C(═O)R^D$, $C(═S)R^D$, $SO_2NR^BR^C$, $S(═O)_mR^E$;

phenyl or benzyl, wherein the phenyl ring is unsubstituted or substituted with one or more, same or different substituents $R^F$;

$R^2$, $R^4$, $R^6$ are independently H, halogen, $N_3$, CN, $NO_2$, SCN, $SF_5$;

$C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxyx-$C_1$-$C_4$-alkyl, which groups are unsubstituted or substituted with halogen, $C(═O)OR^A$, $NR^BR^C$, $NOR^A$, $ONR^BR^C$, $C_1$-$C_6$-alkylen-$NR^BR^C$, O—$C_1$-$C_6$-alkylen-$NR^BR^C$, $C_1$-$C_6$-alkylen-CN, NH—$C_1$-$C_6$-alkylen-$NR^BR^C$, $C(═O)NR^BR^C$, $C(═O)R^D$, $C(═S)R^D$, $SO_2NR^BR^C$, $S(═O)_mR^E$;

phenyl or benzyl, wherein the phenyl ring is unsubstituted or substituted with one or more, same or different substituents $R^F$;

G is phenyl, or a 5- or 6-membered hetaryl;

W is S, S(O), or $S(O)_2$;

each $R^X$ independently is —$C(CN)R^7R^8$, —$C(R^O)$═N—$N(R^MR^N)$, —$C(R^O)$═N—$O(R^L)$;

$C_3$-$C_6$-cycloalkyl, which is substituted with CN and which either does not have any further substituents, or which is further substituted with one or more, same or different substituents $R^9$; or a group of formula (I.1)

(I.1)

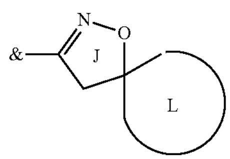

wherein the ring L is a 5- or 6-membered saturated, partially or fully unsaturated carbo- or heterocycle;

wherein the ring L is a saturated, partially or fully saturated carbo- or heterocycle, which carbo- or heterocycle is unsubstituted or substituted with one or more, same or different substituents $R^{10}$, and wherein said heterocycle contains one or more, same or different heteroatoms N, O, or S, and wherein said heteroatoms N and S are oxidized or non-oxidized;

wherein ring J is partially or fully unsaturated and unsubstituted or substituted with one or more, same or different substituents $R^{11}$; and wherein "&" means the connection to the remainder of the molecule at the position of $R^X$ in formula (I);

$R^7$, $R^8$ are independently H, halogen, CN, $C_1$-$C_6$-alkyl, $C_1$-$C_6$-haloalkyl, $C_3$-$C_6$-cycloalkyl, $C_1$-$C_4$-alkoxy, $C_1$-$C_4$-alkoxy-$C_1$-$C_4$-alkyl, $C_1$-$C_4$-alkylsulfanyl, $C_1$-$C_4$-alkylsulfanyl-$C_1$-$C_4$-alkyl, $C_1$-$C_4$-alkylsulfinyl-$C_1$-$C_4$-alkyl, $C_1$-$C_4$-alkylsulfonyl-$C_1$-$C_4$-alkyl or $C_1$-$C_4$-alkoxycarbonyl;

$R^9$ CN, $NH_2$, C(═O)H, OH, $C_3$-$C_6$-cycloalkyl, C(═O)OH, C(═O)$NH_2$, $C_1$-$C_4$-haloalkoxy, $C_1$-$C_4$-alkoxy, $C_1$-$C_4$-haloalkylsulfanyl, $C_1$-$C_4$-haloalkylsulfinyl, $C_1$-$C_4$-haloalkylsulfonyl, $C_1$-$C_4$-alkoxycarbonyl, $C_1$-$C_4$-haloalkoxycarbonyl, $C_1$-$C_4$-alkylcarbonyl, $C_1$-$C_4$-haloalkylcarbonyl, di-($C_1$-$C_4$)alkylaminocarbonyl, $C_1$-$C_4$-alkylaminocarbonyl, $C_1$-$C_4$-alkylcarbonylamino, di-($C_1$-$C_4$)alkylcarbonylamino, $C_1$-$C_4$-alkoxycarbonylamino, or a group —C($R^{91}$)═NO$R^{92}$;

phenyl, which is unsubstituted or substituted with one or more, same or different substituents selected from halogen, CN, $C_1$-$C_4$-alkyl, $C_1$-$C_4$-haloalkyl, $C_1$-$C_4$-haloalkoxy, $C_1$-$C_4$-alkoxy, $C_1$-$C_4$-haloalkylsulfanyl, $C_1$-$C_4$-haloalkylsulfinyl, $C_1$-$C_4$haloalkylsulfonyl and C(═O) $C_1$-$C_4$-haloalkyl;

$C_1$-$C_4$-alkyl which is unsubstituted or substituted with one or more, same or different substituents $R^{93}$;

$R^{91}$ and $R^{92}$ are independently H, $C_1$-$C_4$-alkyl, or $C_1$-$C_4$-haloalkyl;

$R^{93}$ is halogen, CN, $NH_2$, C(═O)H, OH, $C_3$-$C_6$-cycloalkyl, hydroxycarbonyl, aminocarbonyl, $C_1$-$C_4$-haloalkoxy, $C_1$-$C_4$-alkoxy, $C_1$-$C_4$-haloalkylsulfanyl, $C_1$-$C_4$-haloalkylsulfinyl, $C_1$-$C_4$-haloalkylsulfonyl, $C_1$-$C_4$-alkoxycarbonyl, $C_1$-$C_4$-haloalkoxycarbonyl, $C_1$-$C_4$-alkylcarbonyl, $C_1$-$C_4$-haloalkylcarbonyl, di-($C_1$-$C_4$)alkylaminocarbonyl, $C_1$-$C_4$alkylaminocarbonyl, $C_1$-$C_4$-alkylcarbonylamino, di-($C_1$-$C_4$)alkylcarbonylamino, $C_1$-$C_4$-alkoxycarbonylamino, a group-C($R^{91}$)═NO$R^{92}$;

each $R^{10}$, $R^{11}$ is independently H, halogen, CN, OH;

$C_1$-$C_6$-alkyl, $C_3$-$C_6$-cycloalkyl, $C_1$-$C_4$-alkoxy, or $C_1$-$C_4$-alkoxy-$C_1$-$C_4$-alkyl, which groups are unsubstituted or halogenated;

each $R^A$ is independently H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are unsubstituted or substituted with halogen;

phenyl or benzyl, wherein the phenyl ring is unsubstituted or substituted with one or more, same or different substitutents $R^F$;

each $R^B$ is independently H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, $C_1$-$C_6$-alkyl-carbonyl, $C_1$-$C_6$-alkoxy-carbonyl, which groups are unsubstituted or substituted with halogen;

phenyl or benzyl, which groups are unsubstituted or substituted with one or more, same or different substituents $R^F$;

each $R^C$ is independently H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, $C_1$-$C_6$-alkyl-carbonyl, $C_1$-$C_6$-alkoxy-carbonyl, which groups are unsubstituted or substituted with halogen;

phenyl or benzyl, wherein the phenyl ring is unsubstituted or substituted with one or more, same or different substitutents $R^F$;

each moiety $NR^BR^C$ may also form an N-bound, saturated 5- to 8-membered heterocycle, which in addition to the nitrogen atom may have 1 or 2 further heteroatoms or heteroatom moieties selected from O, S(═O)$_m$ and N—R', wherein R' is H or $C_1$-$C_6$-alkyl and wherein the N-bound heterocycle is unsubstituted or substituted with one or more, same or different substituents selected from halogen, $C_1$-$C_4$-alkyl, $C_1$-$C_4$-haloalkyl, $C_1$-$C_4$-alkoxy and $C_1$-$C_4$-haloalkoxy;

each $R^D$ is independently H, CN, OH, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are unsubstituted or substituted with halogen;

phenyl or benzyl, wherein the phenyl ring is unsubstituted or substituted with one or more, same or different substitutents $R^F$;

each $R^E$ is independently $C_1$-$C_6$-alkyl, $C_3$-$C_6$-cycloalkyl, $C_3$-$C_6$-cycloalkyl-$C_1$-$C_4$-alkyl, which are unsubstituted or substituted with halogen; or phenyl or benzyl, wherein the phenyl ring is unsubstituted or substituted with one or more, same or different substitutents $R^F$;

each $R^L$ is independently H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are unsubstituted or substituted with one or more, same or different substituents selected from halogen and CN;

phenyl or benzyl, wherein the phenyl ring is unsubstituted or substituted with one or more, same or different substitutents $R^F$;

each $R^M$ is independently H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, $C_1$-$C_6$-alkyl-carbonyl, $C_1$-$C_6$-alkoxy-carbonyl, which groups are unsubstituted or substituted with halogen;

phenyl or benzyl, which groups are unsubstituted or substituted with one or more, same or different substituents $R^F$;

each $R^N$ is independently H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, $C_1$-$C_6$-alkyl-carbonyl, $C_1$-$C_6$-alkoxy-carbonyl, which groups are unsubstituted or substituted with halogen;

phenyl or benzyl, wherein the phenyl ring is unsubstituted or substituted with one or more, same or different substituents $R^F$;

each moiety $NR^MR^N$ may also form an N-bound, saturated 5- to 8-membered heterocycle, which in addition to the nitrogen atom may have 1 or 2 further heteroatoms or heteroatom moieties selected from O, $S(=O)_m$ and N—R', wherein R' is H or $C_1$-$C_6$-alkyl and wherein the N-bound heterocycle is unsubstituted or substituted with one or more, same or different substituents selected from halogen, $C_1$-$C_4$-alkyl, $C_1$-$C_4$-haloalkyl, $C_1$-$C_4$-alkoxy and $C_1$-$C_4$-haloalkoxy;

each $R^O$ is independently H, CN, OH, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are unsubstituted or substituted with halogen;

phenyl or benzyl, wherein the phenyl ring is unsubstituted or substituted with one or more, same or different substituents $R^F$;

each $R^F$ is independently halogen, $N_3$, OH, CN, $NO_2$, SCN, $SF_5$, $C_1$-$C_6$ alkyl, $C_1$-$C_6$ alkoxy, $C_2$-$C_6$ alkenyl, $C_2$-$C_6$ alkynyl, $C_1$-$C_6$ alkoxy-$C_1$-$C_4$ alkyl, $C_1$-$C_6$ alkoxy-$C_1$-$C_4$ alkoxy, $C_3$-$C_6$ cycloalkyl, $C_3$-$C_6$ cycloalkoxy, $C_3$-$C_6$ cycloalkyl-$C_1$-$C_4$ alkyl, $C_3$-$C_6$ cycloalkoxy-$C_1$-$C_4$ alkyl, which groups are unsubstituted or substituted with halogen;

$R^W$ is $C_1$-$C_6$-alkyl, $C_3$-$C_6$-cycloalkyl, $C_3$-$C_6$-cycloalkyl-$C_1$-$C_4$-alkyl, which groups are halogenated or non-halogenated; $CH_2R^6$, or phenyl, which is unsubstituted or substituted with $R^{11}$;

the index n is 0, 1, 2, 3, or 4 if G is phenyl or a 6-membered hetaryl;

or 0, 1, 2, or 3 if G is a 5-membered hetaryl; and the index m is 0, 1 or 2;

and the N-oxides, stereoisomers, tautomers and agriculturally or veterinarily acceptable salts thereof.

The compounds of the formula (I), and their agriculturally acceptable salts are highly active against animal pest, i.e. harmful arthropodes and nematodes, especially against insects and acaridae which are difficult to control by other means.

Moreover, the present invention relates to and includes the following embodiments:

compositions comprising at least one compound of formula (I) as defined above and a liquid or solid carrier;

agricultural and veterinary compositions comprising an amount of at least one compound of formula (I) or an enantiomer, diasteromer or salt thereof as defined above;

methods for combating invertebrate pests, infestation, or infection by invertebrate pests, which method comprises contacting said pest or its food supply, habitat or breeding grounds with a pesticidally effective amount of at least one compound of formula (I) as defined above or a composition thereof;

methods for controlling invertebrate pests, infestation, or infection by invertebrate pests, which method comprises contacting said pest or its food supply, habitat or breeding grounds with a pesticidally effective amount of at least one compound of formula (I) as defined above or a composition comprising at least one compound of formula (I);

methods for preventing or protecting against invertebrate pests comprising contacting the invertebrate pests, or their food supply, habitat or breeding grounds with compounds of formula (I) as defined above or a composition comprising at least one compound of formula (I) as defined above;

methods for protecting crops, plants, plant propagation material and/or growing plants from attack or infestation by invertebrate pests comprising contacting or treating the crops, plants, plant propagation material and growing plants, or soil, material, surface, space, area or water in which the crops, plants, plant propagation material is stored or the plant is growing, with a pesticidally effective amount of at least one compound of formula (I) as defined above or a composition comprising at least one compound of formula (I);

non-therapeutic methods for treating animals infested or infected by parasites or preventing animals of getting infected or infested by parasites or protecting animals against infestation or infection by parasites which comprises orally, topically or parenterally administering or applying to the animals a parasiticidally effective amount of a compound of formula (I) as defined above or a composition comprising at least one compound of formula (I);

methods for treating, controlling, preventing or protecting animals against infestation or infection by parasites by administering or applying orally, topically or parenterally to the animals a compound of the general formula (I) as defined above or a composition comprising at least one compound of formula (I);

seed comprising a compound of formula (I) as defined above, in an amount of from 0.1 g to 10 kg per 100 kg of seed;

the use of the compounds of formula (I) as defined above for protecting growing plants or plant propagation material from attack or infestation by invertebrate pests;

the use of compounds of formula (I) or the enantiomers, diastereomers or veterinary acceptable salts thereof for combating parasites in and on animals;

a process for the preparation of a veterinary composition for treating, controlling, preventing or protecting animals against infestation or infection by parasites which comprises adding a parasiticidally effective amount of a compound of formula (I) or the enantiomers, diastereomers and/or veterinary acceptable salt thereof to a carrier composition suitable for veterinary use;

the use of a compound of formula (I) or the enantiomers, diastereomers and/or veterinary acceptable salt thereof for the preparation of a medicament for treating, controlling, preventing or protecting animals against infestation or infection by parasites.

All the compounds of formula (I) and, if applicable, their stereoisomers, their tautomers, their salts or their N-oxides as well as compositions thereof are particularly useful for controlling invertebrate pests, in particular for controlling arthropods and nematodes and especially insects. Therefore, the invention relates to the use of a compound of formula (I) as an agrochemical pesticide, preferably for combating or controlling invertebrate pests, in particular invertebrate pests of the group of insects, arachnids or nematodes.

The term "compound(s) according to the invention" or "compound(s) of formula (I)" as used in the present invention refers to and comprises the compound(s) as defined herein and/or stereoisomer(s), salt(s), tautomer(s) or N-oxide(s) thereof. The term "compound(s) of the present invention" is to be understood as equivalent to the term "compound(s) according to the invention", therefore also comprising stereoisomer(s), salt(s), tautomer(s) or N-oxide(s) of compounds of formula (I).

The term "composition(s) according to the invention" or "composition(s) of the present invention" encompasses composition(s) comprising at least one compound of formula (I) according to the invention as defined above, therefore also including a stereoisomer, an agriculturally or veterinary acceptable salt, tautomer or an N-oxide of the compounds of formula (I).

The compounds of the present invention may be amorphous or may exist in one or more different crystalline states (polymorphs) or modifications which may have a different macroscopic properties such as stability or show different biological properties such as activities. The present invention includes both amorphous and crystalline compounds of the formula (I), mixtures of different crystalline states or modifications of the respective compound I, as well as amorphous or crystalline salts thereof.

The compounds of the formula (I) may have one or, depending on the substitution pattern, more centers of chirality, in which case they are present as mixtures of enantiomers or diastereomers. The invention provides both the single pure enantiomers or pure diastereomers of the compounds of formula (I), and their mixtures and the use according to the invention of the pure enantiomers or pure diastereomers of the compound of formula (I) or its mixtures. Suitable compounds of the formula (I) also include all possible geometrical stereoisomers (cis/trans isomers) and mixtures thereof. Cis/trans isomers may be present with respect to an alkene, carbon-nitrogen double-bond or amide group. The term "stereoisomer(s)" encompasses both optical isomers, such as enantiomers or diastereomers, the latter existing due to more than one center of chirality in the molecule, as well as geometrical isomers (cis/trans isomers). The present invention relates to every possible stereoisomer of the compounds of formula (I), i.e. to single enantiomers or diastereomers, as well as to mixtures thereof.

Depending on the substitution pattern, the compounds of the formula (I) may be present in the form of their tautomers. Hence the invention also relates to the tautomers of the formula (I) and the stereoisomers, salts, tautomers and N-oxides of said tautomers.

Salts of the compounds of the formula (I) are preferably agriculturally and/or veterinary acceptable salts. They can be formed in a customary method, e.g. by reacting the compound with an acid of the anion in question if the compound of formula (I) has a basic functionality or by reacting an acidic compound of formula (I) with a suitable base.

Suitable agriculturally or veterinary useful salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy) ethyl-ammonium, bis(2-hydroxyethyl) ammonium, benzyltrimethylammonium and benzyltriethylammonium, furthermore phosphonium ions, sulfonium ions, preferably tri($C_1$-$C_4$-alkyl) sulfonium, and sulfoxonium ions, preferably tri($C_1$-$C_4$-alkyl) sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting the compounds of formula (I) with an acid of the corresponding anion, preferably of hydrochloric acid, hydrobromic acid, sulfuric acid, phosphoric acid or nitric acid.

The term "N-oxide" includes any compound of the present invention which has at least one tertiary nitrogen atom that is oxidized to an N-oxide moiety.

The organic moieties groups mentioned in the above definitions of the variables are—like the term halogen-collective terms for individual listings of the individual group members. The prefix $C_n$-$C_m$ indicates in each case the possible number of carbon atoms in the group. "Halogen" will be taken to mean F, Cl, Br, and I, preferably F.

The term "substituted with", e.g. as used in "partially, or fully substituted with" means that one or more, e.g. 1, 2, 3, 4 or 5 or all of the hydrogen atoms of a given radical have been replaced by one or more, same or different substituents, such as a halogen, in particular F. Accordingly, for substituted cyclic moieties, e.g. 1-cyanocyclopropyl, one or more of the hydrogen atoms of the cyclic moiety may be replaced by one or more, same or different substituents.

The term "$C_n$-$C_m$-alkyl" as used herein (and also in $C_n$-$C_m$-alkylamino, di-$C_n$-$C_m$-alkylamino, $C_n$-$C_m$-alkylaminocarbonyl, di-($C_n$-$C_m$-alkylamino) carbonyl, $C_n$-$C_m$-alkylthio, $C_n$-$C_m$-alkylsulfinyl and $C_n$-$C_m$-alkylsulfonyl) refers to a branched or unbranched saturated hydrocarbon group having n to m, e.g. 1 to 10 carbon atoms, preferably 1 to 6 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_n$-$C_m$-haloalkyl" as used herein (and also in $C_n$-$C_m$-haloalkylsulfinyl and $C_n$-$C_m$-haloalkylsulfonyl) refers to a straight-chain or branched alkyl group having n to m carbon atoms, e.g. 1 to 10 in particular 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like. The term $C_1$-$C_{10}$-haloalkyl in particular comprises $C_1$-$C_2$-fluoroalkyl, which is synonym with methyl or ethyl, wherein 1, 2, 3, 4 or 5 hydrogen atoms are substituted with fluorine atoms, such as fluoromethyl, difluoromethyl, trifluoromethyl, 1-fluoroethyl, 2-fluoroethyl, 2,2-difluoroethyl, 2,2,2-trifluoroethyl and pentafluoromethyl.

Similarly, "$C_n$-$C_m$-alkoxy" and "$C_n$-$C_m$-alkylthio" (or $C_n$-$C_m$-alkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen (or sulfur linkages, respectively) at any bond in the alkyl group. Examples include $C_1$-$C_4$-alkoxy such as methoxy, ethoxy, propoxy, isopropoxy, butoxy, sec-butoxy, isobutoxy and tert-butoxy, further $C_1$-$C_4$-alkylthio such as methylthio, ethylthio, propylthio, isopropylthio, and n-butylthio.

Accordingly, the terms "$C_n$-$C_m$-haloalkoxy" and "$C_n$-$C_m$-haloalkylthio" (or $C_n$-$C_m$-haloalkyl-sulfenyl, respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group, where some or all of the hydrogen atoms in these groups may be replaced by halogen atoms as mentioned above, for example $C_1$-$C_2$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, further $C_1$-$C_2$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio and the like. Similarly, the terms $C_1$-$C_2$-fluoroalkoxy and $C_1$-$C_2$-fluoroalkylthio refer to $C_1$-$C_2$-fluoroalkyl which is bound to the remainder of the molecule via an oxygen atom or a sulfur atom, respectively.

The term "$C_2$-$C_m$-alkenyl" as used herein intends a branched or unbranched unsaturated hydrocarbon group having 2 to m, e.g. 2 to 10 or 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_2$-$C_m$-alkynyl" as used herein refers to a branched or unbranched unsaturated hydrocarbon group having 2 to m, e.g. 2 to 10 or 2 to 6 carbon atoms and containing at least one triple bond, such as ethynyl, propynyl, 1-butynyl, 2-butynyl, and the like.

The term "$C_n$-$C_m$-alkoxy-$C_n$-$C_m$-alkyl" as used herein refers to alkyl having n to m carbon atoms, e.g. like specific examples mentioned above, wherein one hydrogen atom of the alkyl radical is replaced by an $C_n$-$C_m$-alkoxy group; wherein the value of n and m of the alkoxy group are independently chosen from that of the alkyl group.

The suffix "-carbonyl" in a group or "C(═O)" denotes in each case that the group is bound to the remainder of the molecule via a carbonyl C═O group. This is the case e.g. in alkylcarbonyl, haloalkylcarbonyl, aminocarbonyl, alkylaminocarbonyl, dialkylaminocarbonyl, alkoxycarbonyl, haloalkoxycarbonyl.

The term "aryl" as used herein refers to a mono-, bi- or tricyclic aromatic hydrocarbon radical such as phenyl or naphthyl, in particular phenyl (also referred as to $C_6H_5$ as substituent).

The term "$C_3$-$C_m$-cycloalkyl" as used herein refers to a monocyclic ring of 3- to m-membered saturated cycloaliphatic radicals, e.g. cyclopropyl, cyclobutyl, cyclopentyl, cyclohexyl, cycloheptyl, cyclooctyl and cyclodecyl.

The term "alkylcycloalkyl" denotes as well as the term "alkyl which may be substituted with cycloalkyl" an alkyl group which is substituted with a cycloalkyl ring, wherein alkyl and cycloakyl are as herein defined.

The term "cycloalkylalkyl" denotes as well as the term "cycloalkyl which may be substituted with alkyl" a cycloalkyl ring which is substituted with an alkyl group, wherein alkyl and cycloakyl are as herein defined.

The term "alkylcycloalkylalkyl" denotes as well as the term "alkylcycloalkyl which may be substituted with alkyl" an alkylcycloalkyl group which is substituted with an alkyl, wherein alkyl and alkylcycloakyl are as herein defined.

The term "$C_3$-$C_m$-cycloalkenyl" as used herein refers to a monocyclic ring of 3- to m-membered partially unsaturated cycloaliphatic radicals.

The term "cycloalkylcycloalkyl" denotes as well as the term "cycloalkyl which may be substituted with cycloalkyl" a cycloalkyl substitution on another cycloalkyl ring, wherein each cycloalkyl ring independently has from 3 to 7 carbon atom ring members and the cycloalkyls are linked through one single bond or have one common carbon atom. Examples of cycloalkylcycloalkyl include cyclopropylcyclopropyl (e.g. 1,1'-bicyclopropyl-2-yl), cyclohexylcyclohexyl wherein the two rings are linked through one single common carbon atom (e.g. 1,1'-bicyclohexyl-2-yl), cyclohexylcyclopentyl wherein the two rings are linked through one single bond (e.g. 4-cyclopentylcyclohexyl) and their different stereoisomers such as (1R,2S)-1,1'-bicyclopropyl-2-yl and (1R,2R)-1,1'-bicyclopropyl-2-yl. The term "carbocycle" or "carbocyclyl" includes, unless otherwise indicated, in general a 3- to 12-membered, preferably a 3- to 8-membered or a 5- to 8-membered, more preferably a 5- or 6-membered mono-cyclic, ring comprising 3 to 12, preferably 3 to 8 or 5 to 8, more preferably 5 or 6 carbon atoms.

The carbocyclic radicals may be saturated, partially unsaturated, or fully unsaturated. Preferably, the term "carbocycle" covers cycloalkyl and cycloalkenyl groups as defined above, for example cyclopropane, cyclobutane, cyclopentane and cyclohexane rings. When it is referred to "fully unsaturated" carbocycles, this term also includes "aromatic" carbocycles. In certain preferred embodiments, a fully unsaturated carbocycle is an aromatic carbocycle as defined below, preferably a 6-membered aromatic carbocycle.

The term "hetaryl" or "aromatic heterocycle" or "aromatic heterocyclic ring" includes monocyclic 5- or 6-membered heteroaromatic radicals comprising as ring members 1, 2, 3 or 4 heteroatoms selected from N, O and S. Examples of 5- or 6-membered heteroaromatic radicals include pyridyl, i.e. 2-, 3-, or 4-pyridyl, pyrimidinyl, i.e. 2-, 4- or 5-pyrimidinyl, pyrazinyl, pyridazinyl, i.e. 3- or 4-pyridazinyl, thienyl, i.e. 2- or 3-thienyl, furyl, i.e. 2- or 3-furyl, pyrrolyl, i.e. 2- or 3-pyrrolyl, oxazolyl, i.e. 2-, 3- or 5-oxazolyl, isoxazolyl, i.e. 3-, 4- or 5-isoxazolyl, thiazolyl, i.e. 2-, 3- or 5-thiazolyl, isothiazolyl, i.e. 3-, 4- or 5-isothiazolyl, pyrazolyl, i.e. 1-, 3-, 4- or 5-pyrazolyl, i.e. 1-, 2-, 4- or 5-imidazolyl, oxadiazolyl, e.g. 2- or 5-[1,3,4]oxadiazolyl, 4- or 5-(1,2,3-oxadiazol) yl, 3- or 5-(1,2,4-oxadiazol) yl, 2- or 5-(1,3,4-thiadiazol) yl, thiadiazolyl, e.g. 2- or 5-(1,3,4-thiadiazol) yl, 4- or 5-(1,2,3-thiadiazol) yl, 3- or 5-(1,2,4-thiadiazol) yl, triazolyl, e.g. 1H-, 2H- or 3H-1,2,3-triazol-4-yl, 2H-triazol-3-yl, 1H-, 2H-, or 4H-1,2,4-triazolyl and tetrazolyl, i.e. 1H- or 2H-tetrazolyl. The term "hetaryl" also includes bicyclic 8 to 10-membered heteroaromatic radicals comprising as ring members 1, 2 or 3 heteroatoms selected from N, O and S, wherein a 5- or 6-membered heteroaromatic ring is fused to a phenyl ring or to a 5- or 6-membered heteroaromatic radical. Examples of a 5- or 6-membered heteroaromatic ring fused to a phenyl ring or to a 5- or 6-membered heteroaromatic radical include benzofuranyl, benzothienyl, indolyl, indazolyl, benzimidazolyl, benzoxathiazolyl, benzoxadiazolyl, benzothiadiazolyl, benzoxazinyl, chinolinyl, isochinolinyl, purinyl, 1,8-naphthyridyl, pteridyl, pyrido[3,2-d]pyrimidyl or pyridoimidazolyl and the like. These fused hetaryl radicals may be bonded to the remainder of the molecule via any ring atom of 5- or 6-membered heteroaromatic ring or via a carbon atom of the fused phenyl moiety.

The terms "heterocycle", "heterocyclyl" or "heterocyclic ring" includes, unless otherwise indicated, in general 3- to 12-membered, preferably 3- to 8-membered, 3- to 7-membered, or 5- to 8-membered, more preferably 5- or 6-membered, in particular 6-membered monocyclic heterocyclic radicals. The heterocyclic radicals may be saturated, partially unsaturated, or fully unsaturated. As used in this context, the term "fully unsaturated" also includes "aromatic". In a preferred embodiment, a fully unsaturated heterocycle is thus an aromatic heterocycle, preferably a 5- or 6-membered aromatic heterocycle comprising one or more, e.g. 1, 2, 3, or 4, preferably 1, 2, or 3 heteroatoms selected from N, O and S as ring members. Examples of aromatic heterocycles are provided above in connection with the definition of "hetaryl". Unless otherwise indicated, "hetaryls" are thus covered by the term "heterocycles". The heterocyclic non-aromatic radicals usually comprise 1, 2, 3, 4 or 5, preferably 1, 2 or 3 heteroatoms selected from N, O and S as ring members, where S-atoms as ring members may be present as S, SO or $SO_2$. Examples of 5- or 6-membered heterocyclic radicals comprise saturated or unsaturated, non-aromatic heterocyclic rings, such as oxiranyl, oxetanyl, thietanyl, thietanyl-S-oxid (S-oxothietanyl), thietanyl-S-dioxid (S-dioxothiethanyl), pyrrolidinyl, pyrrolinyl, pyrazolinyl, tetrahydrofuranyl, dihydrofuranyl, 1,3-dioxolanyl, thiolanyl, S-oxothiolanyl, S-dioxothiolanyl, dihydrothienyl, S-oxodihydrothienyl, S-dioxodihydrothienyl, oxazolidinyl, oxazolinyl, thiazolinyl, oxathiolanyl, piperidinyl, piperazinyl, pyranyl, dihydropyranyl, tetrahydropyranyl, 1,3- and 1,4-dioxanyl, thiopyranyl, S.oxothiopyranyl, S-dioxothiopyranyl, dihydrothiopyranyl, S-oxodihydrothiopyranyl, S-dioxodihydrothiopyranyl, tetrahydrothiopyranyl, S-oxotetrahydrothiopyranyl, S-dioxotetrahydrothiopyranyl, morpholinyl, thiomorpholinyl, S-oxothiomorpholinyl, S-dioxothiomorpholinyl, thiazinyl and the like. Examples for heterocyclic ring also comprising 1 or 2 carbonyl groups as ring members comprise pyrrolidin-2-onyl, pyrrolidin-2,5-dionyl, imidazolidin-2-onyl, oxazolidin-2-onyl, thiazolidin-2-onyl and the like.

The terms "alkylene", "alkenylene", and "alkynylene" refer to alkyl, alkenyl, and alkynyl as defined above, respectively, which are bonded to the remainder of the molecule, via two atoms, preferably via two carbon atoms, of the respective group, so that they represent a linker between two moieties of the molecule. In particular, the term "alkylene" may refer to alkyl chains such as $CH_2CH_2$, $—CH(CH_3)—$, $CH_2CH_2CH_2$, $CH(CH_3)$ $CH_2$, $CH_2CH(CH_3)$, $CH_2CH_2CH_2CH_2$, $CH_2CH_2CH_2CH_2CH_2$, $CH_2CH_2CH_2CH_2CH_2CH_2$, and $CH_2CH_2CH_2CH_2CH_2CH_2CH_2$. Similarly, "alkenylene" and "alkynylene" may refer to alkenyl and alkynyl chains, respectively.

The term "5- to 6-membered carbocyclic ring" as used herein refers to cyclopentane and cyclohexane rings.

Examples of 5- or 6-membered saturated heterocyclic rings include: 2-tetrahydrofuranyl, 3-tetrahydrofuranyl, 2-tetrahydrothienyl, 3-tetrahydrothienyl, 2-pyrrolidinyl, 3-pyrrolidinyl, 3-pyrazolidinyl, 4-pyrazolidinyl, 5-pyrazolidinyl, 2-imidazolidinyl, 4-imidazolidinyl, 2-oxazolidinyl, 4-oxazolidinyl, 5-oxazolidinyl, 3-isoxazolidinyl, 4-isoxazolidinyl, 5-isoxazolidinyl, 2-thiazolidinyl, 4-thiazolidinyl, 5-thiazolidinyl, 3-isothiazolidinyl, 4-isothiazolidinyl, 5-isothiazolidinyl, 1,2,4-oxadiazolidin-3-yl, 1,2,4-oxadiazolidin 5 yl, 1,2,4-thiadiazolidin-3-yl, 1,2,4-thiadiazolidin-5-yl, 1,2,4-triazolidin-3-yl,-1,3,4-oxadiazolidin-2-yl, 1,3,4-thiadiazolidin-2-yl, 1,3,4-triazolidin-2-yl, 2-tetrahydropyranyl, 4-tetrahydropyranyl, 1,3-dioxan-5-yl, 1,4-dioxan-2-yl, 2-piperidinyl, 3-piperidinyl, 4-piperidinyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl, 2-morpholinyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl.

Examples of 5- or 6-membered partially unsaturated heterocyclyl or heterocyclic rings include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin 3 yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3 dihydropyrazol-1-yl, 2,3-dihydropyrazol-2-yl, 2,3-dihydropyrazol-3-yl, 2,3- dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl.

Examples of 5- or 6-membered fully unsaturated heterocyclic (hetaryl) or heteroaromatic rings are: 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

A "$C_2$-$C_m$-alkylene" is divalent branched or preferably unbranched saturated aliphatic chain having 2 to m, e.g. 2 to 7 carbon atoms, for example $CH_2CH_2$, —$CH(CH_3)$—, $CH_2CH_2CH_2$, $CH(CH_3)$ $CH_2$, $CH_2CH(CH_3)$, $CH_2CH_2CH_2CH_2$, $CH_2CH_2CH_2CH_2CH_2$, $CH_2CH_2CH_2CH_2CH_2CH_2$, and $CH_2CH_2CH_2CH_2CH_2CH_2CH_2$.

The term "alkylamino" as used herein refers to a straight-chain or branched saturated alkyl group having 1 to 10 carbon atoms, preferably 1 to 4 carbon atoms, more preferably 1 to 3 carbon atoms, which is bonded via a nitrogen atom, e.g. an —NH— group.

The term "dialkylamino" as used herein refers to a straight-chain or branched saturated alkyl group having 1 to 10 carbon atoms, preferably 1 to 4 carbon atoms, more preferably 1 to 3 carbon atoms, which is bonded via a nitrogen atom, which is substituted by another straight-chain or branched saturated alkyl group having 1 to 10 carbon atoms, preferably 1 to 4 carbon atoms, more preferably 1 to 3 carbon atoms, e.g. a methylamino or ethylamino group.

The term "alkylthio "(alkylsulfanyl: alkyl-S-)" as used herein refers to a straight-chain or branched saturated alkyl group having 1 to 10 carbon atoms, preferably 1 to 4 carbon atoms (=$C_1$-$C_4$-alkylthio), more preferably 1 to 3 carbon atoms, which is attached via a sulfur atom. Examples include methylthio, ethylthio, propylthio, isopropylthio, and n-butylthio.

The term "haloalkylthio" as used herein refers to an alkylthio group as mentioned above wherein the hydrogen atoms are partially or fully substituted by fluorine, chlorine, bromine and/or iodine. Examples include chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio and the like.

The term "alkylsulfinyl" (alkylsulfoxyl: $C_1$-$C_6$-alkyl-S(=O)—), as used herein refers to a straight-chain or branched saturated alkyl group (as mentioned above) having 1 to 10 carbon atoms, preferably 1 to 4 carbon atoms (=$C_1$-$C_4$-alkylsulfinyl), more preferably 1 to 3 carbon atoms bonded through the sulfur atom of the sulfinyl group at any position in the alkyl group.

The term "alkylsulfonyl" (alkyl-S(=O)$_2$—) as used herein refers to a straight-chain or branched saturated alkyl group having 1 to 10 carbon atoms, preferably 1 to 4 carbon atoms (=$C_1$-$C_4$-alkylsulfonyl), preferably 1 to 3 carbon atoms, which is bonded via the sulfur atom of the sulfonyl group at any position in the alkyl group.

The term "alkylcarbonyl" ($C_1$-$C_6$—C(=O)—) refers to a straight-chain or branched alkyl group as defined above, which is bonded via the carbon atom of a carbonyl group (C=O) to the remainder of the molecule.

The term "alkoxycarbonyl" refers to an alkoxygroup group as defined above, which is bonded via the carbon atom of a carbonyl group (C=O) to the remainder of the molecule.

The term "alkylaminocarbonyl" ($C_1$-$C_6$—NH—C(=O)—) refers to a straight-chain or branched alkylamino group as defined above, which is bonded via the carbon atom of a carbonyl group (C=O) to the remainder of the molecule. Similarly, the term "dialkylaminocarbonyl" refers to a straight-chain or branched saturated alkyl group as defined above, which is bonded to a nitrogen atom, which is substituted with another straight-chain or branched saturated alkyl group as defined above, which nitrogen atom in turn is bonded via a carbonyl group (C=O) to the remainder of the molecule.

Preparation Methods

The compounds of formula (I) can be prepared by standard methods of organic chemistry. If certain derivatives cannot be prepared by the processes outlined below, they can be obtained by derivatization of other compounds of formula (I) that are accessible by these methods.

Preparation methods that are generally useful for the preparation of compounds of formula (I) have been disclosed in WO2017/167832A1, especially p. 4-6 and in the experimental section, in the international patent application number PCT/EP2020/082186, and in European patent application number 2115353132.2, p. 21-34 and the experimental section. In the following depicted Processes and Schemes, variables of formulae have a meaning as defined for formula (I) if not described otherwise. The variable "LG" refers to a leaving group, such as Cl, Br, I, triflate, tosylate etc.

Compounds (3), falling under the definition of compounds (I) wherein Q is C($R^6$), may be prepared by reaction of compounds (1) with compounds (2) as displayed under Process 1.

Process 1:

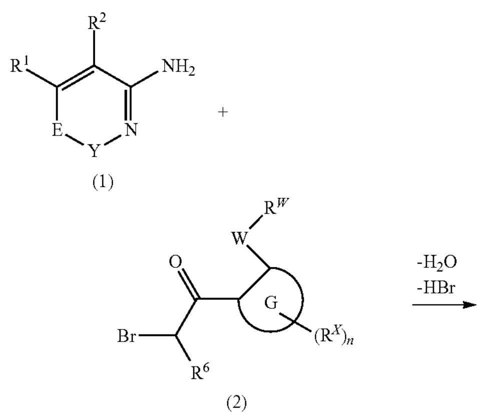

(1)

+

(2)

-continued

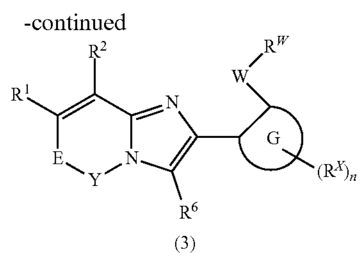

(3)

Reactions of this type have been described in EP3257853A1 and WO2018206479. The reaction is typically carried out under elevated temperatures of from 50-160° C. in an inert solvent. Suitable solvents are aliphatic hydrocarbons, such as pentane, hexane, cyclohexane, or petrol ether; aromatic hydrocarbons, such as benzene, toluene, o-, m-, and p-xylene; halogenated hydrocarbons, or halogenated aromatic $C_6$-$C_{10}$-hydrocarbons, such as $CH_2Cl_2$, $CHCl_3$, $CCl_4$, $CH_2ClCH_2Cl$, $CCl_3CH_3$, $CHCl_2CH_2Cl$, $CCl_2CCl_2$, or chlorobenzene; ethers, such as $CH_3CH_2OCH_2CH_3$, $(CH_3)_2CHOCH(CH_3)_2$, $CH_3OC(CH_3)_3$ (MTBE), $CH_3OCH_3$ (DME), $CH_3OCH_2CH_2OCH_3$, $CH_3OC(CH_3)_2CH_2CH_3$, dioxane, anisole, 2-methyltetrahydrofuran, tetrahydrofurane (THF), and diethylene glycol; nitriles, such as $CH_3CN$, and $CH_3CH_2CN$; alcohols, such as $CH_3OH$, $CH_3CH_2OH$, $CH_3CH_2CH_2OH$, $CH_3CH(OH)CH_3$, $CH_3(CH_2)_3OH$, and $C(CH_3)_3OH$, $CH_2(OH)CH_2(OH)$, $CH_3CH(OH)CH_2OH$; amides and urea derivatives, such as dimethyl formamide (DMF), N-methyl-2-pyrrolidone (NMP), dimethyl acetamide (DMA), 1,3-dimethyl-2-imidazolidinone (DMI), 1,3-dimethyl-3,4,5,6-tetrahydro-2 (1H)-pyrimidinone (DMPU), hexamethylphosphamide (HMPA); moreover dimethyl sulfoxide (DMSO), sulfolane, and water. Mixtures of the above solvents are also possible.

The reaction may be carried out in the presence of a catalyst, such as an acid or a base, preferably a base. Suitable bases are, in general, inorganic bases, such as LiOH, NaOH, KOH, and $Ca(OH)_2$; alkali metal and alkaline earth metal oxides, such as $Li_2O$, $Na_2O$, CaO, and MgO; alkali metal and alkaline earth metal hydrides, such as LiH, NaH, KH and $CaH_2$; alkali metal and alkaline earth metal carbonates, such as $Li_2CO_3$, $K_2CO_3$ and $CaCO_3$; alkali metal bicarbonates, such as $NaHCO_3$; organic bases, such as pyrrolidine; tertiary amines, such as diisopropylethylamine, trimethylamine, triethylamine, triisopropylamine and N-methylpiperidine, imidazol, pyridine; substituted pyridines, such as collidine, lutidine and 4-dimethylaminopyridine, and polycyclic amides and amidines, such as 1,8-diazabicycloundec-7-ene (DBU), 1,4-Diazabicyclo[2.2.2]octane (DABCO); alkali metal salts of secondary amines, such as alkali diisopropylamide, alkali bis(trimethylsilytetramethylpiperidinemethylpiperidene; alcoholates, such as alkali methanolate, alkali ethanolate, alkali isopropanolate, alkali tert-butanolate; alkali metal-alkyl, and alkali metal-aryl salts, such as n-butyl lithium, tert-butyl lithium, phenyl lithium. Mixtures of the aforementioned bases are also possible. The bases are generally employed in catalytic amounts; however, they can also be used in equimolar amounts, in excess or, if appropriate, as solvent.

Compounds (1) can be prepared as described in WO2017/167832A1, e.g. Example C-1. Compounds (1) and compounds (2) are typically reacted with one another in equimolar amounts. In terms of yield, it may be advantageous to employ an excess of compounds (2).

Compounds of formula (4), corresponding to compounds of formula (I) wherein Q is $N(R^5)$ can be prepared by reaction of compounds of formula (5) with compounds of formula (6), as shown under Process 2 below.

Process 2:

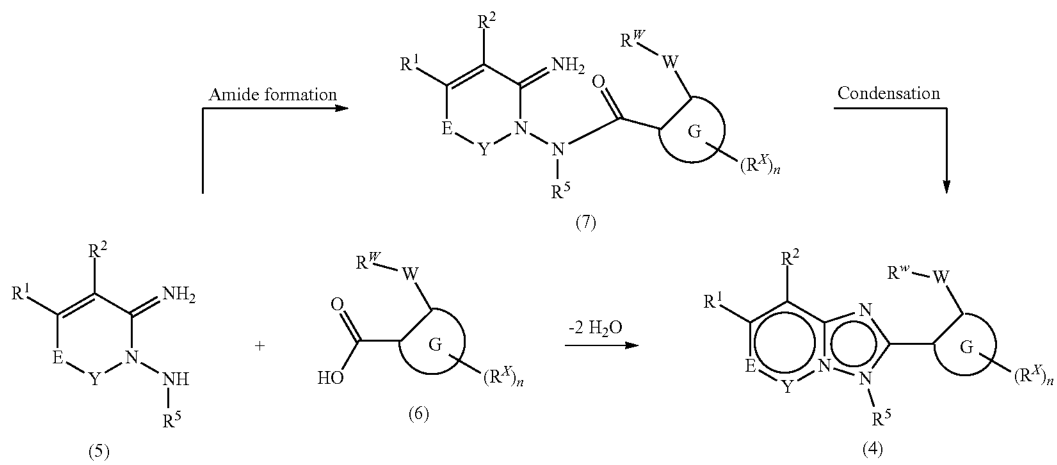

(7)

(5)

(6)

(4)

Reactions of this type have been described in EP3257853A1, WO2019/234160 and WO2016162318A1. The reaction is typically carried out at elevated temperatures, e.g. 60 to 160° C., in an inert solvent, optionally in the presence of an acid, or a coupling agent and a base. Suitable solvents are aliphatic hydrocarbons, such as pentane, hexane, cyclohexane, or petrol ether; aromatic hydrocarbons, such as benzene, toluene, o-, m-, and p-xylene; halogenated hydrocarbons, or halogenated aromatic $C_6$-$C_{10}$-hydrocarbons, such as $CH_2Cl_2$, $CHCl_3$, $CCl_4$, $CH_2ClCH_2Cl$, $CCl_3CH_3$, $CHCl_2CH_2Cl$, $CCl_2CCl_2$, or chlorobenzene; ethers, such as $CH_3CH_2OCH_2CH_3$, $(CH_3)_2CHOCH(CH_3)_2$, $CH_3OC(CH_3)_3$ (MTBE), $CH_3OCH_3$ (DME), $CH_3OCH_2CH_2OCH_3$, $CH_3OC(CH_3)_2CH_2CH_3$, dioxane, anisole, 2-methyltetrahydrofuran, tetrahydrofurane (THF), and diethylene glycol; nitriles, such as $CH_3CN$, and $CH_3CH_2CN$; alcohols, such as $CH_3OH$, $CH_3CH_2OH$, $CH_3CH_2CH_2OH$, $CH_3CH(OH)CH_3$, $CH_3(CH_2)_3OH$, and $C(CH_3)_3OH$, $CH_2(OH)CH_2(OH)$, and $CH_3CH(OH)CH_2OH$. Mixtures of the above solvents are also possible. Suitable acids are in general inorganic acids such as HF, HCl, hBr, $H_2SO_4$ and $HClO_4$; Lewis acids, such as $BF_3$, $AlCl_3$, $FeCl_3$, $SnCl_4$, $TiCl_4$ and $ZnCl_2$, moreover organic acids such as HCOOH, $CH_3COOH$, $CH_3CH_2COOH$, oxalic acid, toluene sulphonic acid, benzene sulphonic acid, camphor sulphonic acid, citric acid, and $CF_3COOH$.

Suitable coupling agents are selected from carbodiimides, such as DCC (dicyclohexyl-carbodiimide) and DIC (diisopropylcarbodiimide), benzotriazole derivatives, such as HATU (O-(7-azabenzotri'zo'-1-yl)-N,N,N',N'-tetramethyluronium hexafluorophosphate), HBTU ((Obenzotri'zo'-1-yl)-N,N,N',N'-tetramethyluronium hexafluorophosphate) and HCTU (1H-benzotriazolium-1-[bis(dimethylamino) methylene]-5-chloro tetrafluoroborate) and phosphonium-derived activators, such as BOP ((benzotriazol-1-yloxy)-tris (dimethylamino)phosphonium hexafluorophosphate), PyBOP ((benzotriazol-1-yloxy)-tripyrrolidinphosphonium hexafluorophosphate) and PyBrOP (bromotripyrrolidin-phosphonium hexafluorophosphate). In case a coupling agent is applied, suitable solvents are aliphatic hydrocarbons, such as pentane, hexane, cyclohexane, or petrol ether; aromatic hydrocarbons, such as benzene, toluene, o-, m-, and p-xylene; halogenated hydrocarbons, or halogenated aromatic $C_6$-$C_{10}$-hydrocarbons, such as $CH_2Cl_2$, $CHCl_3$, $CCl_4$, $CH_2ClCH_2Cl$, $CCl_3CH_3$, $CHCl_2CH_2Cl$, $CCl_2CCl_2$, or chlorobenzene; ethers, such as $CH_3CH_2OCH_2CH_3$, $(CH_3)_2CHOCH(CH_3)_2$, $CH_3OC(CH_3)_3$ (MTBE), $CH_3OCH_3$ (DME), $CH_3OCH_2CH_2OCH_3$, $CH_3OC(CH_3)_2CH_2CH_3$, dioxane, anisole, 2-methyltetrahydrofuran, tetrahydrofurane (THF), and diethylene glycol; nitriles, such as $CH_3CN$, and $CH_3CH_2CN$; alcohols, such as $CH_3OH$, $CH_3CH_2OH$, $CH_3CH_2CH_2OH$, $CH_3CH(OH)CH_3$, $CH_3(CH_2)_3OH$, and $C(CH_3)_3OH$, $CH_2(OH)CH_2(OH)$, and $CH_3CH(OH)CH_2OH$. Mixtures of the above solvents are also possible. Suitable bases are those listed for Process 1.

Alternatively, compounds (6) may be replaced by their corresponding carbonic acid halogenides, e.g. acid chlorides. In this case the reaction is typically carried out in the presence of a base. Suitable bases are those listed for Process 1 above.

In a first step, compounds (7) are thus obtained, which undergo in a second step a condensation reaction as described for Process 1 to yield compounds (4).

Compounds (5) and compounds (6) are typically reacted with one another in equimolar amounts. In terms of yield, it may be advantageous to employ an excess of compounds (6).

Compounds of formula (6) may be prepared in analogy to those as described in EP3257853A1, p. 51-53 by modification of the starting materials, or as described in WO2018/153778, p. 14 ff and Scheme 4. Compounds of formula (5) can be prepared as described in WO2017/167832A1, Bashandy et al. Journal of Enzyme Inhibition and Medicinal Chemistry, 29 (5), 619-627, 2014.

Alternatively, Compounds of formula (4) may be prepared by a two-step reaction, comprising of a reaction of compounds of formula (8) with compounds of formula (9) to yield compounds of formula (10) as displayed under Process 3

Process 3:

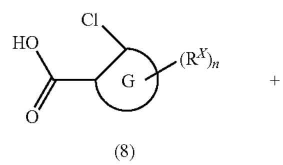

(8)

+

-continued

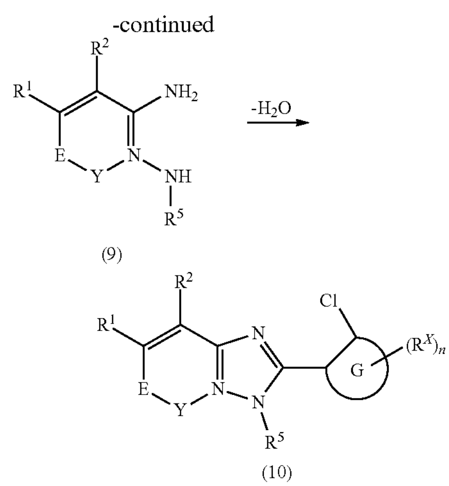

(9)

(10)

This reaction may be carried out under the same conditions as described for Process 2 above.

In a second step, compounds of formula (10) are then reacted with a compound of formula (11) to yield compounds of formula (4), falling under the definition of compounds of formula (I), as displayed under Process 4.

Process 4:

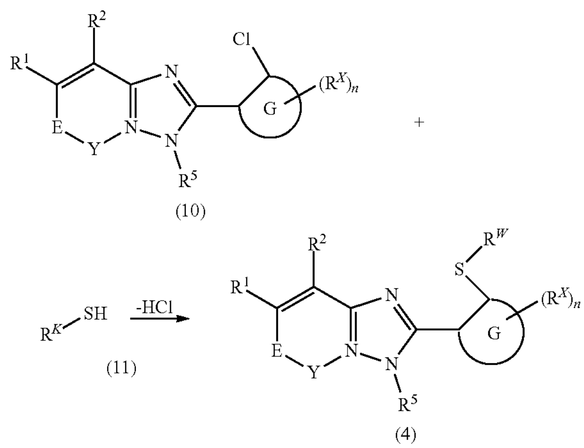

(10)

+

(11)

(4)

Reactions of this type have been described in WO2016162318A1, p. 89. The reaction is typically carried out at a temperature of from 15 to 60° C. in an inert solvent in the presence of a base. Suitable solvents are aliphatic hydrocarbons, such as pentane, hexane, cyclohexane, or petrol ether; or aromatic hydrocarbons, such as benzene, toluene, o-, m-, and p-xylene. Mixtures of the above solvents are also possible. Suitable bases are, in general, inorganic bases, preferably alkali metal and alkaline earth metal hydrides, such as LiH, NaH, KH and $CaH_2$; organic bases, preferably secondary amines, such as pyrrolidine; or tertiary amines, such as diisopropylethylamine, trimethylamine, triethylamine, triisopropylamine and N-methylpiperidine, imidazol, pyridine; substituted pyridines, such as collidine, lutidine and 4-dimethylaminopyridine, and polycyclic amides and amidines, such as 1,8-diazabicycloundec-7-ene (DBU), 1,4-Diazabicyclo[2.2.2]octane (DABCO); or alkali metal salts of secondary amines, such as alkali diisopropylamide, alkali bis(trimethylsilyl)amide, alkali tetramethylpiperidene; alcoholates, such as alkali methanolate, alkali ethanolate, alkali isopropanolate, alkali tert-butanolate; alkali metal-alkyl, and alkali metal-aryl salts, such as n-butyl lithium, tert-butyl lithium, phenyl lithium. The base is typically reacted with compounds of formula (11) before compounds of formula (10) are added to form the thiolate anion.

The bases are generally employed in catalytic amounts; however, they can also be used in equimolar amounts, in excess or, if appropriate, as solvent.

Compounds (4) may also be prepared from compounds (12) as displayed below under Process 5 in a rearrangement reaction.

Process 5:

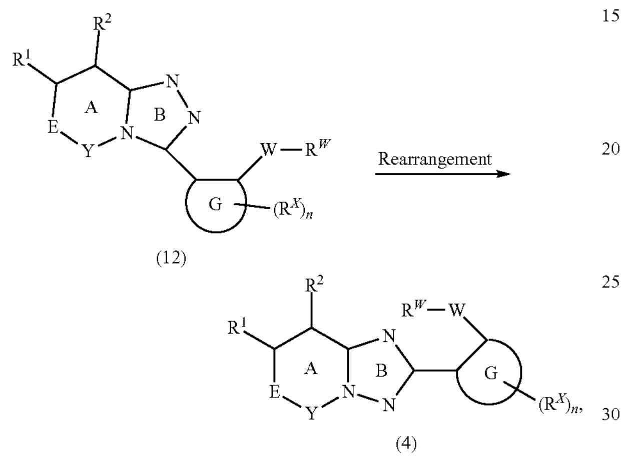

(12)

(4)

wherein the rings A and B are fully unsaturated.

Reactions of this type have been described in Potts K. T., Surapaneni C. R., 1970, Journal of Heterocyclic Chemistry, or Nagamatsu T., Fujita T., 2002, Heterocycles, 57 (4), 631-636. The reaction is typically carried out in the presence of a catalyst, usually an acid or a base, such as NaOH or formic acid, in an inert organic solvent or $H_2O$ at a temperature of from 0 to 80° C. If no catalyst is used, the reaction may be carried out at elevated temperatures, e.g. from 30 to 100° C.

Compounds of formula (12) may be prepared by reaction of hydrazine compounds of formula (13) with Lewis acids, as displayed under Process 6, Process 6:

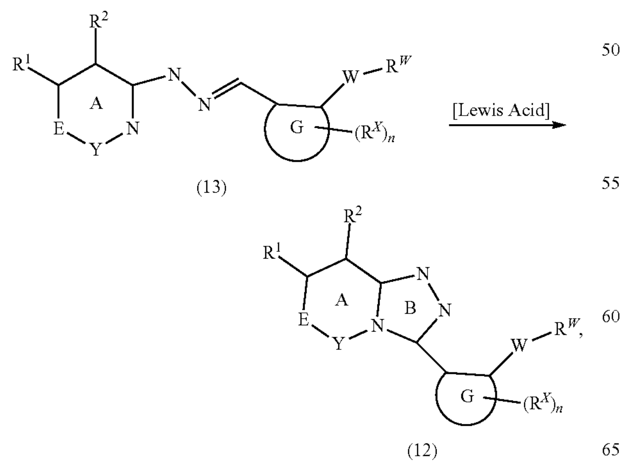

(13)

(12)

wherein the rings A and B are fully unsaturated. Reactions of this type have been described by Glushkov V. A. et al., 1998, Pharmaceutical Chemistry Journal, vol. 32 (5), p. 29-32, or WO2012148808, p. 143. The reaction is typically performed in the presence of a Lewis acid, such as $FeCl_3$ or $AlCl_3$, at elevated temperatures of from 50 to 150° C. in an inert organic solvent. The reaction may be carried out in the presence of an oxidizing agent, e.g. $H_2O_2$ or $CuCl_2$.

Compounds of formula (13) are accessible by reaction of hydrazine compounds of formula (14) with aldehyde compounds of formula (15), as displayed under Process 7.

Process 7:

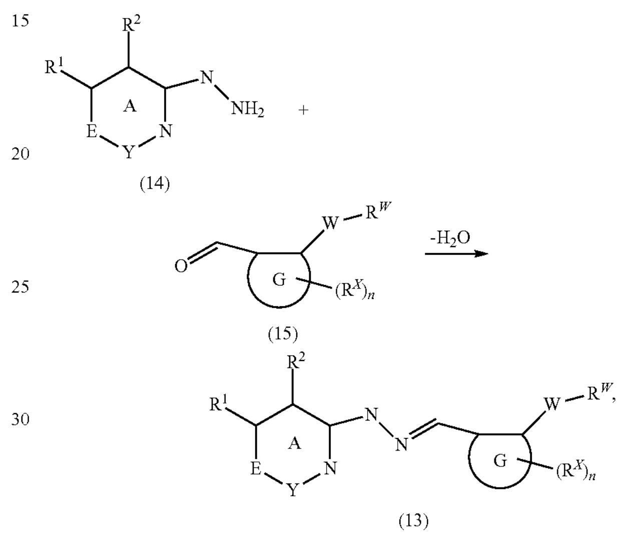

(14)

(15)

(13)

wherein ring A is fully unsaturated.

The reaction is typically carried out in the presence of an acid catalyst, such as toluene sulfonic acid, in an inert organic solvent. Suitable solvents are aliphatic hydrocarbons, such as pentane, hexane, cyclohexane, or petrol ether; or aromatic hydrocarbons, such as benzene, toluene, o-, m-, and p-xylene. Mixtures of the above solvents are also possible Hydrazine derivatives of formula (10) are commercially available or may be derived from commercially available compounds. Alternatively, compounds of formula (14) may also be prepared by reaction of hydrazine with compound of formula (16), as displayed under Process 8.

Process 8:

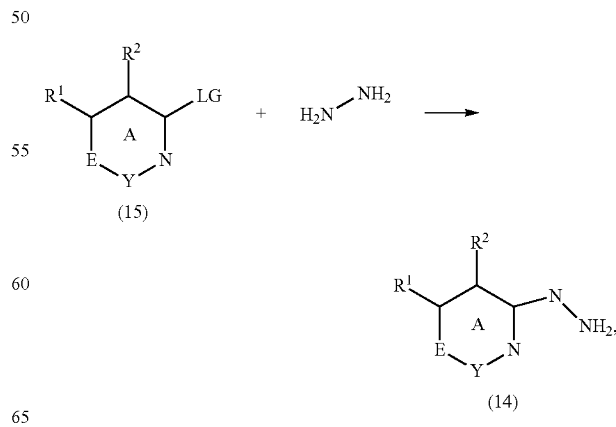

(15)

(14)

wherein ring A is fully unsaturated.

Typical leaving groups LG are triflate, iodide and chloride. Reactions of this type have been described in Mao, Y. et al, 2014, Journal of Heterocyclic Chemistry, 51 (3), p. 594-597. The reaction is typically carried out in a polar solvent, such as $CH_3CH_2OH$ under elevated temperatures, such as from 50 to 100° C. Compounds of formula (15) are commercially available or can be prepared by standard methods of organic chemistry.

The reaction mixtures are worked up in a customary manner, for example by mixing with water, separating the phases and, if appropriate, chromatographic purification of the crude products. Some of the intermediates and end products are obtained in the form of colorless or slightly brownish viscous oils which are purified or freed from volatile components under reduced pressure and at moderately elevated temperature. If the intermediates and end products are obtained as solids, purification can also be carried out by recrystallization or digestion.

The N-oxides may be prepared from the inventive compounds according to conventional oxidation methods, e.g. by treating compounds of formula (I) with an organic peracid such as metachloroperbenzoic acid (cf. WO 03/64572 or J. Med. Chem. 38 (11), 1892-903, 1995); or with inorganic oxidizing agents such as hydrogen peroxide (cf. J. Heterocyc. Chem. 18 (7), 1305-8, 1981) or oxone (cf. J. Am. Chem. Soc. 123 (25), 5962-5973, 2001). The oxidation may lead to pure mono-N-oxides or to a mixture of different N-oxides, which can be separated by conventional methods such as chromatography.

If the synthesis yields mixtures of isomers, a separation is generally not necessarily required since in some cases the individual isomers can be interconverted during work-up for use or during application (for example under the action of light, acids or bases). Such conversions may also take place after use, for example in the treatment of plants in the treated plant, or in the harmful fungus to be controlled.

A skilled person will readily understand that the preferences for the substituents, also in particular the ones given in the tables below for the respective substituents, given herein in connection with compounds of formula (I) apply for the intermediates accordingly. Thereby, the substituents in each case have independently of each other or more preferably in combination the meanings as defined herein.

In an alternative synthesis route, the Processes 1, 2, 5, 6, and 7 may be modified in such a way that educts are used that have (a) leaving group(s) LG instead of substituents $(R^X)_n$ at ring G. Processes 9-13 below illustrate the modified Processes 1, 2, 5, 6, and 7.

Process 9:

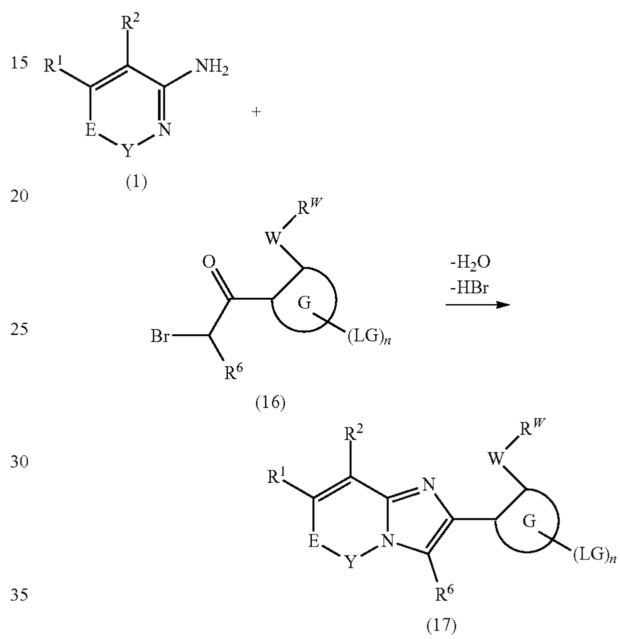

(1) (16) (17)

Process 10:

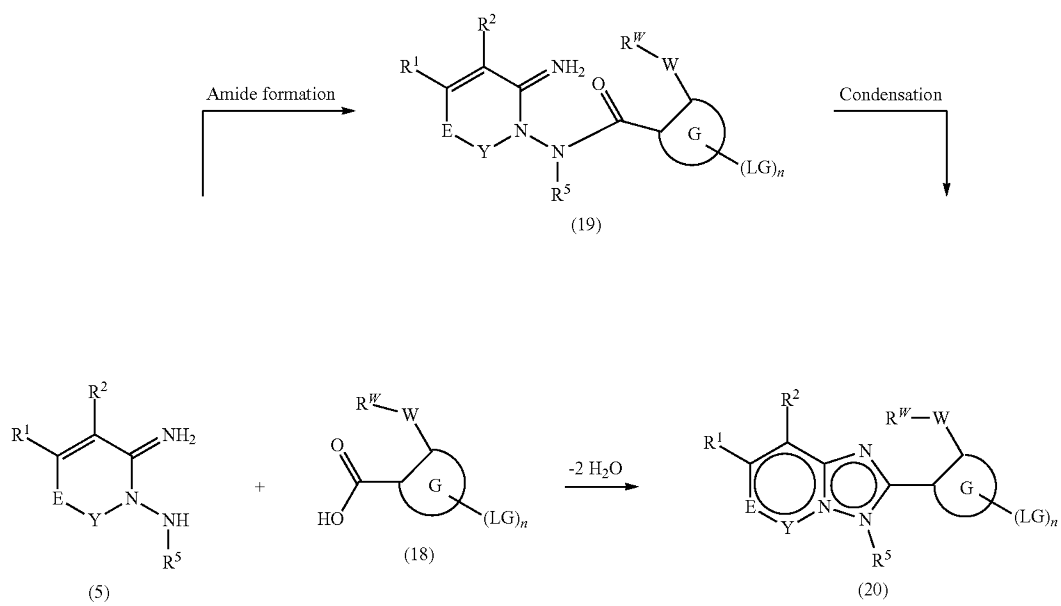

(19) (5) (18) (20)

Process 11:

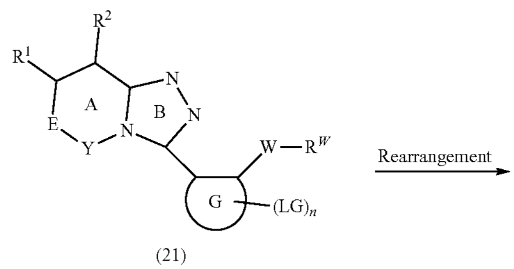

(21)

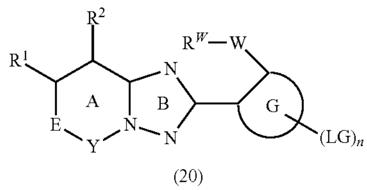

(20)

Process 12:

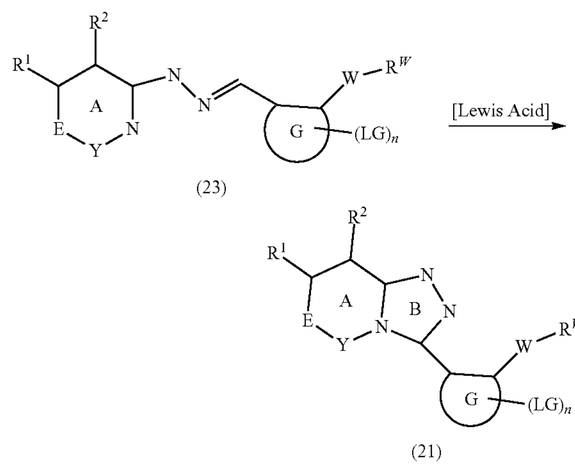

(23)

(21)

Process 13:

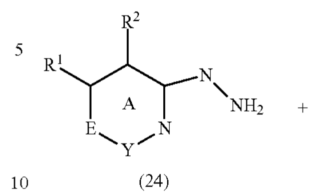

(24)

+

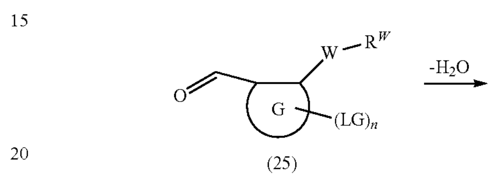

(25)

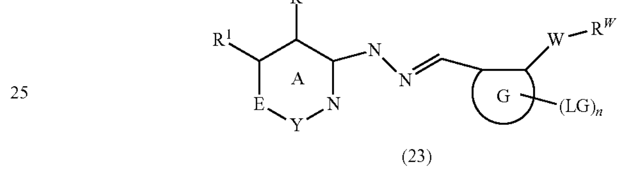

(23)

Such Processes 9-13 may be carried out under the same conditions as described for Processes 1, 2, 5, 6, and 7. Compounds of formulae (17) and (20) are valuable educts in cross-coupling reactions to yield compounds of formula (I) as described below. Compounds of formulae (16), (18), and (25) are commercially available, or can be prepared by standard methods of organic chemistry. For example, compounds of formula (18) may be prepared as described in WO2016/026848, p. 18-19 and Scheme 10b. Compounds of formula (18) may then be converted into compounds of formulae (16) or (25) by standard synthesis methods.

Accordingly, compounds of formula (26), corresponding to compounds of formula (I) wherein $R^X$ is —C(CN)$R^7R^8$, may be obtained by methods described below in General Scheme 1.

General Scheme 1

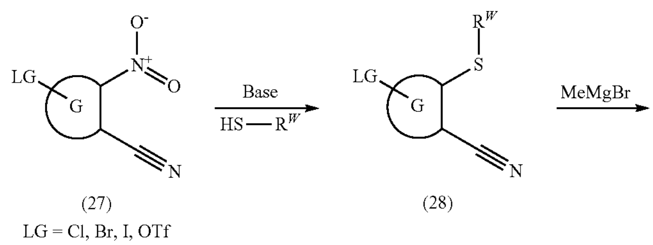

(27)

LG = Cl, Br, I, OTf (28)

-continued
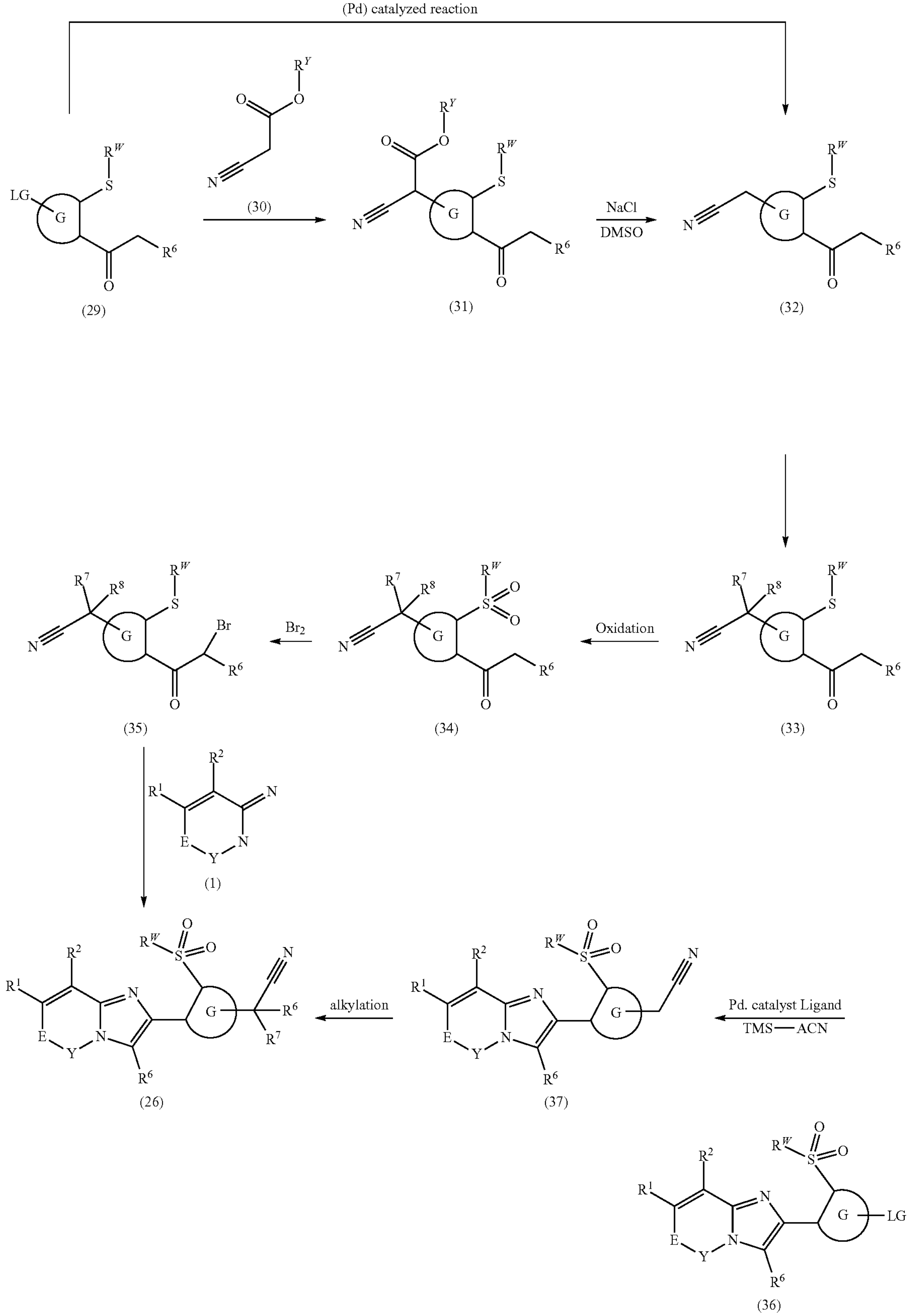
(29) (31) (32)
(35) (34) (33)
(1)
(26) (37)
(36)

Compounds of formula (28) can be obtained by the treatment of compounds of formula (27) wherein X can be Cl, Br, I, -OTf (triflate), by displacement reaction with HS-$R^W$ in the presence of a base e.g. potassium carbonate, sodium carbonate, cesium carbonate, sodium hydride etc in an organic solvent like DMF, THF and DMSO at cooling to 20 to 25° C. Such method has been described in literature like Tetrahedron Letters, 2014, vol. 55, #22, p. 3295-3298. Compounds of formula (29) may be prepared by reaction of compounds of formula (28) with Grignard reagent MeMgBr in an organic solvent like THF, MTBE or toluene at 0° C. as described in WO 2018095795, WO 2016012395 and Tetrahedron Letters 1981, vol. 22, 3815-3818.

Compounds of formula (31) can be prepared by reacting compounds of formula (29) with compounds of formula (30) wherein $R^Y$ stands preferably for ethyl, methyl or tert-butyl. This reaction can be done in in polar aprotic solvents such as dimethyl sulfoxide (DMSO), N,N-dimethylformamide (DMF), or N-methyl pyrrolidone (NMP), in the presence of a base, such as $K_2CO_3$ or $Cs_2CO_3$, in the presence of absence of a phase-transfer catalyst ("PTC") preferably at temperature between 80-140° C. Such method is described in literature in the Journal of Organic Chemistry, 2008, vol. 73, #4, 1643-1645 and Chemical & Pharmaceutical Bulletin 1988, vol. 36, #. 5, 1664-8.

Compounds of formula (31) can be further converted to compounds of formula (32) via a Krapcho-Decarboxylation using LiCl or NaCl using polar organic solvents like DMSO within a temperature range of 100-140° C.

Compounds of formula (31) can also be prepared via palladium-catalysed reaction of compounds of formula (29) with trimethylsilyl-acetonitrile as described in Angew. Chem Int. Ed. 2011, vol. 50, 4470-4474.

Compounds of formula (33) can be synthesized via reaction of compounds of formula (32) with compounds $R^7$-LG and $R^8$-LG. The reaction is typically carried out in the presence of bases like $Cs_2CO_3$, $K_2CO_3$, $Na_2CO_3$, potassium tert.-butoxide, NaH, LiHMDS at 0° C. to 25° C. using polar protic solvents like DMF, DMSO, THF or N-methylpyrrolidone (NMP). Such methods have been described in literature like WO2013067264 A1 or Tetrahedron Letters, 2018, vol. 59, #0.14, 1443-1445.

The sulfanyl-group $R^W$—S— in compounds of formula (33) can be further oxidised to SO (sulfoxide) and/or $SO_2$ (sulfone), in an oxidation reaction of compounds of formula (33) involving reagents such as, m-chloroperoxybenzoic acid, $H_2O_2$, oxone, $NaIO_4$, NaOCl or tert-butyl hypochlorite and in organic solvents including aliphatic halogenated hydrocarbons such as dichloromethane and chloroform; and alcohols such as methanol and ethanol; acetic acid; water. The amount of the oxidant to be used in the reaction is generally 1 to 3 moles, preferably 1 to 1.2 moles, relative to 1 mole of the sulfide compounds of formula (I) to produce the sulfoxide compounds of formula (34), and preferably 2 to 2.2 moles of oxidant, relative to 1 mole of the sulfide compounds of formula (33) as descried in WO 2015/091945 AI, WO 2016107742 and WO 2018095795.

Compounds of formula (35), falling under the definition of compounds of formula (2), can be prepared by dissolving compounds of formula (34) in polar organic solvents like ethyl acetate, chloroform or DCM and reaction with brominating agents like CuBr, $CuBr_2$, $Br_2$, HBr in acetic acid, trimethyl phenyl ammonium tribromide at 20 to 25° C. or on heating to 60° C. to obtain compounds of formula (35). Such procedure can be found in WO 2016107742.

Reaction condition for the synthesis of compounds of formula (26) form compounds of formula (25) and compounds of formula (2) have been described for Process 1 above.

Alternatively compounds of formula (26), falling under the definition of compounds of formula (I) can be prepared from compounds of formula (36) in a Pd-catalyzed reaction with trimethylsilylacetonitrile (TMS-ACN). Such reactions have for example been described in Angew. Chem Int. Ed. 2011, vol. 50, 4470-4474. Compounds of formula (36) may be prepared as described in Process 9 above or as described in in WO 2017/167832 A1 and WO 2018/206479 A1). Further alkylation of compounds of formula (26) with compounds of formula $R^6$-LG and $R^7$-LG under conditions as described above for the synthesis of compounds of formula (33) yield compounds of formula (26).

Compounds of formula (38)

(38)

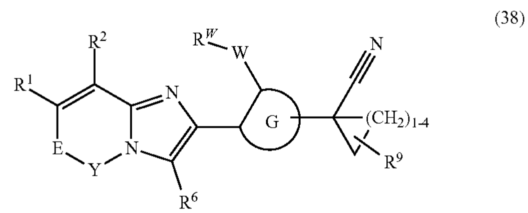

may be prepared in a sequence or reactions similar to those displayed under General Scheme 1 by replacing the reagents $R^6$-LG and $R^7$-LG with a reagent LG-$(CH_2)_{2-5}$-LG, wherein the group —$(CH_2)_{2-5}$— may be substituted with one or more, same or different substituents $R^9$ and wherein each group LG is independently a halogen or triflate. The reaction is typically carried out in a polar solvent like $CH_3CN$, DMSO, THF or the like in the presence of a base, preferably an inorganic base like $K_3CO_3$ at a temperature of from 10 to 40° C.

Compounds of formula (35) fall under the definition of compounds of formula (2). Accordingly, compounds of formula (6), wherein $R^X$ is —C(CN)$R^7R^8$ or wherein $R^X$ is substituted $C_3$-$C_6$-cycloalkyl as defined in the claims, may be prepared in analogy to the preparation steps displayed in General Scheme 1 above, by replacing the Grignard-reaction of compounds of formula (28) with the hydrolysis of the cyano-group as displayed for example in Process 14 below. The resulting carboxylic acid group may be protected in the form of an ester.

Process 14

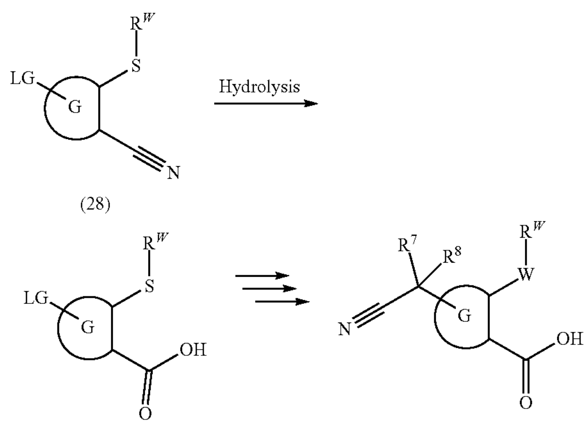

(28)

Compounds of formula (I), wherein $R^X$ is —C($R^O$)═N—N($R^MR^N$) or —C($R^O$)═N—O($R^L$) may be prepared by the methods described above by using compounds of formulae (2), (6), (8), or (15) having these substituents, or by replacing the leaving group LG in compounds of formulae (17), or (20) with the respective substituent $R^X$.

Compounds of formula (2) having as substituent $R^X$ a group —C($R^O$)═N—N($R^MR^N$) or —C($R^O$)═N—O($R^L$) may be prepared as described under General Scheme 2 below.

General scheme 2

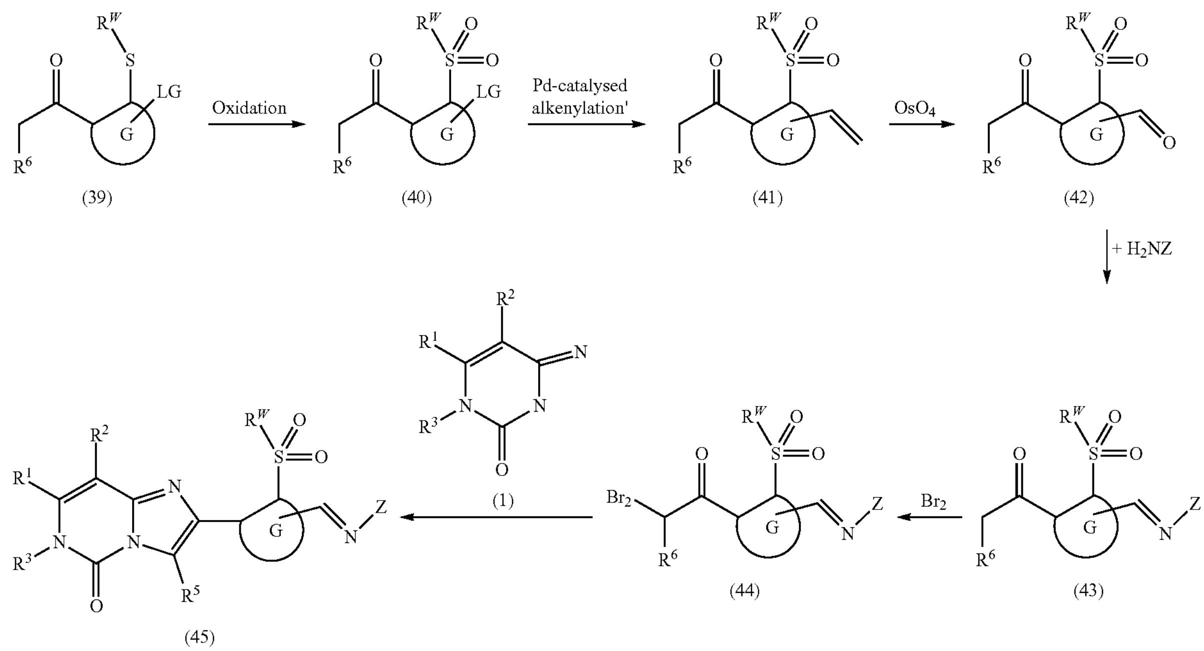

(39) (40) (41) (42) (1) (45) (44) (43)

wherein the substituent Z is —N($R^MR^N$) or —O($R^L$), respectively.

Compounds of formula (39) can be oxidized to the corresponding sulfoxide or sulfone by oxidation reaction involving reagents such as m-chloroperoxybenzoic acid, $H_2O_2$, oxone, $NalO_4$, NaOCl or tert-butyl hypochlorite in an inert solvent such as aliphatic halogenated hydrocarbons, e.g. $CHCl_3$ or $CH_2Cl_2$; alcohols such as $CH_3OH$ and $CH_3CH_2OH$; $CH_3COOH$; or $H_2O$. The amount of the oxidant to be used in the reaction is generally 1 to 3 moles, preferably 1 to 1.2 moles, relative to 1 mole of the sulfide compounds of formula (39) to produce the sulfoxide compounds of formula (40), and more preferably 2 to 2.2 moles of oxidant, relative to 1 mole of the sulfide compounds or formula (39) as descried in WO 2015/091945 AI, WO 2016107742 and WO 2018095795.

Compounds of formula (40) may then be reacted with a tin-based vinylation reagent like tributyl vinyl tin in a Pd-catalyzed Stille-type coupling reaction to afford compounds of formula (41). The reaction is carried out in the presence of a Pd-catalyst like palladium acetate, tetrakis (triphenylphosphine) palladium, di-μ-chlorobis[5-hydroxy-2-[1-(hydroxyimino-KN)ethyl]-phenylKC]dipalladium or a similar catalyst in an inert solvent like aromatic hydrocarbons like toluene or ethers like dioxane or dimethoxy ethane at a typical temperature of from 70° C. to 110° C. Compounds of formula (41) may then be reacted with an oxidant like sodium meta per-iodate, oxone N-methylmorpholine N-oxide in the presence of $OsO_4$ in an inert solvent like an ether, e.g. dioxane or MTBE, at a temperature range of from 0 to 25° C. over a period of approximately one hour, as reported in WO2015138220A1 and WO2016198908A1.

Compounds of formula (42) may then be converted to the respective imine of formula (43) by reaction with a primary amine $H_2NZ$, such as hydroxylamine, o-alkyl hydroxylamine, hydrazine, N-alkyl hydrazine, N-acyl hydrazine in the presence of a catalyst. Suitable catalysts are Lewis-acids like trifluorotoluene sulfonic acid and bases like potassium acetate, pyridine, triethylamine, sodium methoxide in an inert solvent like aromatic hydrocarbons like toluene or alcohols, e.g. $CH_3OH$, $CH_3CH_2OH$ at a temperature of from 20° C. to the refluxation temperature of the solvent. Literature reports of these reaction types can be found in Journal of Medicinal Chemistry (2006), 49 (24), 6987-7001 and Organic Letters (2001), 3 (26), 4209-4211, Journal of Organic Chemistry, 74 (11), 4166-4176; 2009.

Bromination of compounds of formula (43) to compounds of formula (44) may be achieved by methods described for General Scheme 1 above, while the conversion of compounds of formula (44) to compounds fo formula (45) has been described for Process 1 above.

Modification of the above General Scheme 2 by alteration of the starting compound of formula (39) yields compounds of formula (46)—falling under the definition of compounds of formula (6), respectively, wherein $R^X$ is a group —C($R^O$)=N—N($R^MR^N$) or —C($R^O$)=N—O($R^L$) as displayed under Process 15.

Process 15:

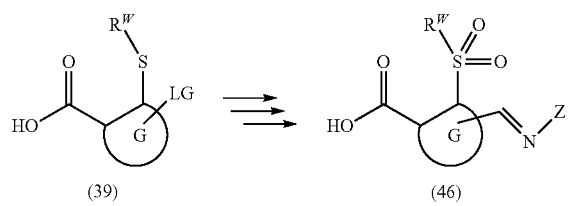

(39) (46)

The replacement of the leaving group LG may also take place after the bicyclic system of compounds of formula (I) has been build-up as described under General Scheme 3 below.

Genereal Scheme 3:

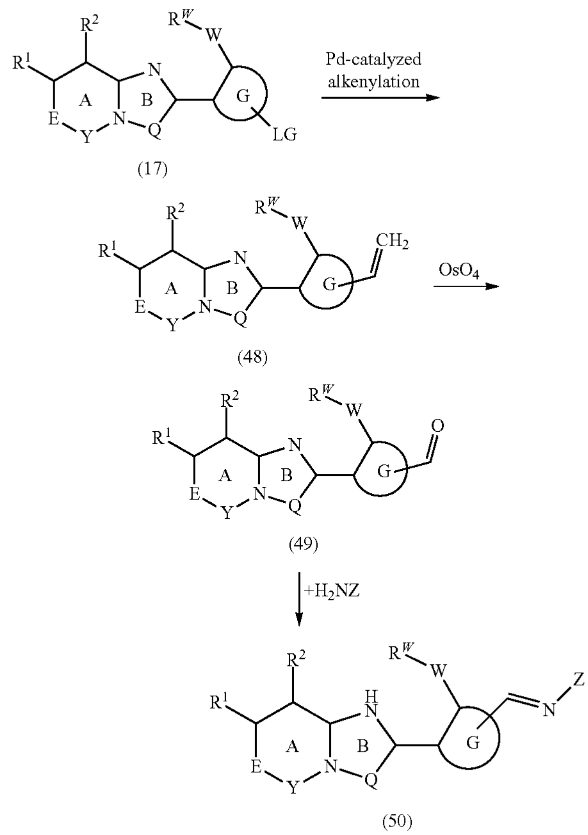

(17)

(48)

(49)

(50)

The reaction conditions of the above reactions have already beend described for the analogous conversions of compounds of formula (40) to compounds of formula (43) via compounds of formula (41) and compounds of formula (42) under General Scheme 2 above.

Compounds of formula (I), wherein $R^X$ is —C($R^O$)═N—N($R^M R^N$), —C($R^O$)═N—O($R^L$), and wherein $R^O$ is not H, may be prepared as described for example under General Scheme 5:

General Scheme 5

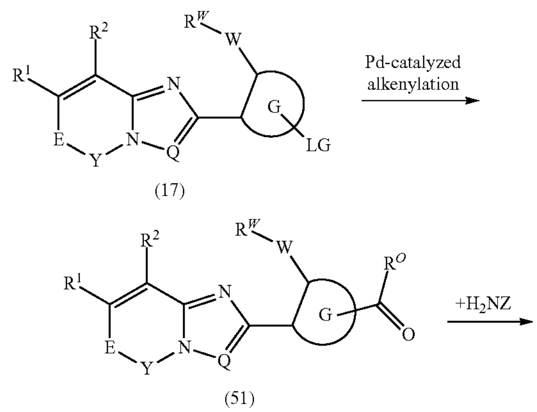

(17)

(51)

-continued

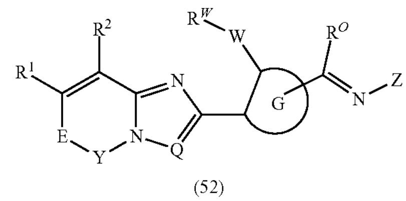

(52)

Compounds of formula (17) may be converted to compounds of formula (51) by a Pd-catalyzed Stille-type cross coupling reaction with tributyl(1-ethoxyvinyl) tin in an inert solvent like aromatic hydrocarbons, such as xylene or toluene at a temperature of from 80 to 150° C. Typical Pd-based catalysts have already been provided above for other Stille-type reactions, e.g. the conversion of compounds of formula (40) to compounds of formula (41).

Compounds of formula (51) may then be reacted with a primary amine $H_2NZ$ to yield compounds of formula (52). Such reactions may be carried out by using approaches as described in WO2018/084142 or WO2018/124129.

In case $R^O$ refers to CN, the compounds may be prepared by reacting a compound of formula (37) with isopentylnitrite in the presence of a base as displayed under Process 16 below.

Process 16

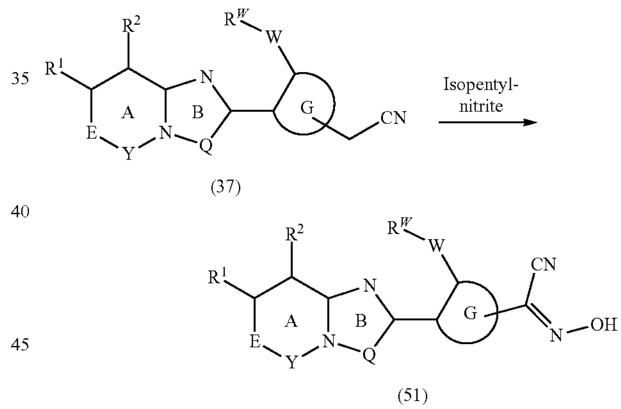

(37)

(51)

Such reactions have been described in WO2017/065183 and Journal of Medicinal Chemistry, 35 (12), 2274-83; 1992. Suitable solvents are for example alcohols, such as $CH_3OH$ or $CH_3CH_2OH$. Suitable bases are alcoholates such as sodium methanolate, sodium isobutanolate and the like.

Compounds of formula (I), wherein $R^X$ is a group (I.1) may be prepared under Process 17 as follows.

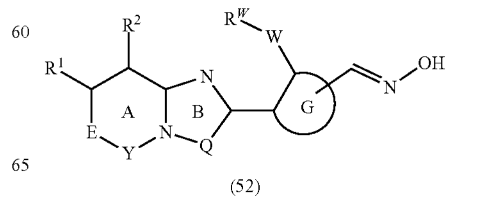

(52)

+

-continued

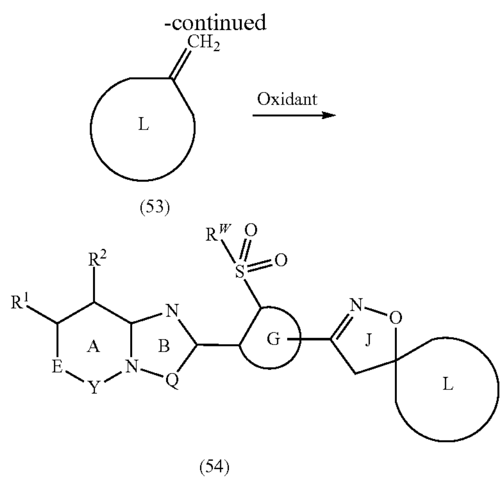

(53)

(54)

The reaction is typically carried out in the presence of an oxidant, such as NaOCl or $NaIO_4$, in an inert polar solvent such as $H_2O$, alcohols like $CH_3OH$, $CH_3CH_2OH$, or ethers like dioxane or THF and at a temperature of from 0 to 50° C.

The reaction mixtures are worked up in a customary manner, for example by mixing with water, separating the phases and, if appropriate, chromatographic purification of the crude products. Some of the intermediates and end products are obtained in the form of colorless or slightly brownish viscous oils which are purified or freed from volatile components under reduced pressure and at moderately elevated temperature. If the intermediates and end products are obtained as solids, purification can also be carried out by recrystallization or digestion.

The N-oxides may be prepared from the inventive compounds according to conventional oxidation methods, e.g. by treating compounds of formula (I) with an organic peracid such as metachloroperbenzoic acid (cf. WO 03/64572 or J. Med. Chem. 38 (11), 1892-903, 1995); or with inorganic oxidizing agents such as hydrogen peroxide (cf. J. Heterocyc. Chem. 18 (7), 1305-8, 1981) or potassium peroxymonosulfate (cf. J. Am. Chem. Soc. 123 (25), 5962-5973, 2001). The oxidation may lead to pure mono-N-oxides or to a mixture of different N-oxides, which can be separated by conventional methods such as chromatography.

If the synthesis yields mixtures of isomers, a separation is generally not necessarily required since in some cases the individual isomers can be interconverted during work-up for use or during application (for example under the action of light, acids or bases). Such conversions may also take place after use, for example in the treatment of plants in the treated plant, or in the harmful fungus to be controlled.

A skilled person will readily understand that the preferences for the substituents, also in particular the ones given in the tables below for the respective substituents, given herein in connection with compounds (I) apply for the intermediates accordingly. Thereby, the substituents in each case have independently of each other or more preferably in combination the meanings as defined herein.

Preferences

The variables have, each on their own and in combination, the following preferred meanings. Typically, the invention relates to a compound of formula (I)

(I)

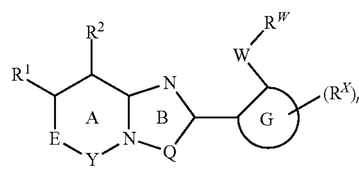

wherein the rings A and B are fully unsaturated;

Y is C═X, wherein X is O or S;

E is $N(R^3)$ or $C(R^4)$;

Q is N, $N(R^5)$ or $C(R^6)$;

$R^1$ is H, halogen, $C_1$-$C_6$-alkyl, $C_2$-$C_6$-alkenyl, $C_2$-$C_6$-alkynyl, $C_1$-$C_6$-alkoxy, $C_1$-$C_6$-alkoxy-$C_1$-$C_6$-alkyl, $C_3$-$C_6$-cycloalkyl, $C_3$-$C_6$-cycloalkoxy, $C_1$-$C_6$-sulfenyl, $C_1$-$C_6$-sulfinyl, or $C_1$-$C_6$-sulfonyl, which groups are unsubstituted or halogenated;

$R^3$, $R^5$ are independently $C_1$-$C_6$-alkyl, $C_1$-$C_6$-alkoxy, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which are unsubstituted or halogenated;

C(═O)$OR^A$, $NR^BR^C$, $C_1$-$C_6$-alkylen-$NR^BR^C$, O—$C_1$-$C_6$-alkylen-$NR^BR^C$, $C_1$-$C_6$-alkylen-CN, NH—$C_1$-$C_6$-alkylen-$NR^BR^C$, C(═O)$NR^BR^C$, C(═O)$R^D$, C(═S)$R^D$, $SO_2NR^BR^C$, $S(═O)_mR^E$;

phenyl or benzyl, wherein the phenyl ring is unsubstituted or substituted with one or more, same or different substituents $R^F$;

$R^2$, $R^4$, $R^6$ are independently H, halogen, $N_3$, CN, $NO_2$, SCN, $SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxyx-$C_1$-$C_4$-alkyl, which groups are unsubstituted or substituted with halogen, C(═O)$OR^A$, $NR^BR^C$, $NOR^A$, $ONR^BR^C$, $C_1$-$C_6$-alkylen-$NR^BR^C$, O—$C_1$-$C_6$-alkylen-$NR^BR^C$, $C_1$-$C_6$-alkylen-CN, NH—$C_1$-$C_6$-alkylen-$NR^BR^C$, C(═O)$NR^BR^C$, C(═O)$R^D$, C(═S)$R^D$, $SO_2NR^BR^C$, $S(═O)_mR^E$;

phenyl or benzyl, wherein the phenyl ring is unsubstituted or substituted with one or more, same or different substituents $R^F$;

G is phenyl, or a 5- or 6-membered hetaryl;

W is S, S(O), or $S(O)_2$;

$R^X$ is —C(CN)$R^7R^8$, —C($R^O$)═N—N($R^MR^N$), —C($R^O$)═N—O($R^L$); or $C_3$-$C_6$-cycloalkyl, which is substituted with CN and which either does not have any further substituents, or which is further substituted with one or more, same or different substituents $R^9$; or $R^7$, $R^8$ are independently H, halogen, CN, $C_1$-$C_6$-alkyl, $C_1$-$C_6$-haloalkyl, $C_3$-$C_6$-cycloalkyl, $C_1$-$C_4$-alkoxy, $C_1$-$C_4$-alkoxy-$C_1$-$C_4$-alkyl, $C_1$-$C_4$-alkylsulfanyl, $C_1$-$C_4$-alkylsulfanyl-$C_1$-$C_4$-alkyl, $C_1$-$C_4$-alkylsulfinyl-$C_1$-$C_4$-alkyl, $C_1$-$C_4$-alkylsulfonyl-$C_1$-$C_4$-alkyl or $C_1$-$C_4$-alkoxycarbonyl;

$R^9$ halogen, CN, $NH_2$, C(═O)H, OH, $C_3$-$C_6$-cycloalkyl, C(═O)OH, C(═O)$NH_2$, $C_1$-$C_4$-haloalkoxy, $C_1$-$C_4$-alkoxy, $C_1$-$C_4$-haloalkylsulfanyl, $C_1$-$C_4$-haloalkylsulfinyl, $C_1$-$C_4$-haloalkylsulfonyl, $C_1$-$C_4$-alkoxycarbonyl, $C_1$-$C_4$-haloalkoxycarbonyl, $C_1$-$C_4$-alkylcarbonyl, $C_1$-$C_4$-haloalkylcarbonyl, di-($C_1$-$C_4$)alkylaminocarbonyl, $C_1$-$C_4$-alkylaminocarbonyl, $C_1$-$C_4$-alkylcarbonylamino, di-($C_1$-$C_4$)alkylcarbonylamino, $C_1$-$C_4$-alkoxycarbonylamino, or a group-C($R^{91}$)=NOR$^{92}$;

phenyl, which is unsubstituted or substituted with one or more, same or different substituents selected from halogen, CN, $C_1$-$C_4$-alkyl, $C_1$-$C_4$-haloalkyl, $C_1$-$C_4$-haloalkoxy, $C_1$-$C_4$-alkoxy, $C_1$-$C_4$-haloalkylsulfanyl, $C_1$-$C_4$-haloalkylsulfinyl, $C_1$-$C_4$haloalkylsulfonyl and C(=O) $C_1$-$C_4$-haloalkyl;

$C_1$-$C_4$-alkyl which is unsubstituted or substituted with one or more, same or different substituents $R^{93}$;

$R^{91}$ and $R^{92}$ are independently H, $C_1$-$C_4$-alkyl, or $C_1$-$C_4$-haloalkyl;

$R^{93}$ is halogen, CN, $NH_2$, C(=O)H, OH, $C_3$-$C_6$-cycloalkyl, hydroxycarbonyl, aminocarbonyl, $C_1$-$C_4$-haloalkoxy, $C_1$-$C_4$-alkoxy, $C_1$-$C_4$-haloalkylsulfanyl, $C_1$-$C_4$-haloalkylsulfinyl, $C_1$-$C_4$-haloalkylsulfonyl, $C_1$-$C_4$-alkoxycarbonyl, $C_1$-$C_4$-haloalkoxycarbonyl, $C_1$-$C_4$-alkylcarbonyl, $C_1$-$C_4$-haloalkylcarbonyl, di-($C_1$-$C_4$) alkylaminocarbonyl, $C_1$-$C_4$alkylaminocarbonyl, $C_1$-$C_4$-alkylcarbonylamino, di-($C_1$-$C_4$)alkylcarbonylamino, $C_1$-$C_4$-alkoxycarbonylamino, a group —C($R^{91}$)=NOR$^{92}$;

each $R^A$ is independently H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are unsubstituted or substituted with halogen;

phenyl or benzyl, wherein the phenyl ring is unsubstituted or substituted with one or more, same or different substitutents $R^F$;

each $R^B$ is independently H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, $C_1$-$C_6$-alkyl-carbonyl, $C_1$-$C_6$-alkoxy-carbonyl, which groups are unsubstituted or substituted with halogen;

phenyl or benzyl, which groups are unsubstituted or substituted with one or more, same or different substituents $R^F$;

each $R^C$ is independently H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, $C_1$-$C_6$-alkyl-carbonyl, or $C_1$-$C_6$-alkoxy-carbonyl, which groups are unsubstituted or substituted with halogen;

phenyl or benzyl, wherein the phenyl ring is unsubstituted or substituted with one or more, same or different substituents $R^F$;

each moiety $NR^BR^C$ may also form an N-bound, saturated 5- to 8-membered heterocycle, which in addition to the nitrogen atom may have 1 or 2 further heteroatoms or heteroatom moieties selected from O, S(=O)$_m$ and N—R', wherein R' is H or $C_1$-$C_6$-alkyl and wherein the N-bound heterocycle is unsubstituted or substituted with one or more, same or different substituents selected from halogen, $C_1$-$C_4$-alkyl, $C_1$-$C_4$-haloalkyl, $C_1$-$C_4$-alkoxy and $C_1$-$C_4$-haloalkoxy;

each $R^D$ is independently H, CN, OH, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are unsubstituted or substituted with halogen;

phenyl or benzyl, wherein the phenyl ring is unsubstituted or substituted with one or more, same or different substituents $R^F$;

each $R^E$ is independently $C_1$-$C_6$-alkyl, $C_3$-$C_6$-cycloalkyl, $C_3$-$C_6$-cycloalkyl-$C_1$-$C_4$-alkyl, which are unsubstituted or substituted with halogen; or phenyl or benzyl, wherein the phenyl ring is unsubstituted or substituted with one or more, same or different substituents $R^F$;

each $R^L$ is independently H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are unsubstituted or substituted with halogen;

phenyl or benzyl, wherein the phenyl ring is unsubstituted or substituted with one or more, same or different substitutents $R^F$;

each $R^M$ is independently H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, $C_1$-$C_6$-alkyl-carbonyl, $C_1$-$C_6$-alkoxy-carbonyl, which groups are unsubstituted or substituted with halogen;

phenyl or benzyl, which groups are unsubstituted or substituted with one or more, same or different substituents $R^F$;

each $R^N$ is independently H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, $C_1$-$C_6$-alkyl-carbonyl, $C_1$-$C_6$-alkoxy-carbonyl, which groups are unsubstituted or substituted with halogen;

phenyl or benzyl, wherein the phenyl ring is unsubstituted or substituted with one or more, same or different substituents $R^F$;

each moiety $NR^MR^N$ may also form an N-bound, saturated 5- to 8-membered heterocycle, which in addition to the nitrogen atom may have 1 or 2 further heteroatoms or heteroatom moieties selected from O, S(=O)$_m$ and N—R', wherein R' is H or $C_1$-$C_6$-alkyl and wherein the N-bound heterocycle is unsubstituted or substituted with one or more, same or different substituents selected from halogen, $C_1$-$C_4$-alkyl, $C_1$-$C_4$-haloalkyl, $C_1$-$C_4$-alkoxy and $C_1$-$C_4$-haloalkoxy;

each $R^O$ is independently H, CN, OH, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are unsubstituted or substituted with halogen;

phenyl or benzyl, wherein the phenyl ring is unsubstituted or substituted with one or more, same or different substituents $R^F$;

each $R^F$ is independently halogen, $N_3$, OH, CN, $NO_2$, SCN, $SF_5$, $C_1$-$C_6$ alkyl, $C_1$-$C_6$-alkoxy, $C_2$-$C_6$-alkenyl, $C_2$-$C_6$-alkynyl, $C_1$-$C_6$-alkoxy-$C_1$-$C_4$ alkyl, $C_1$-$C_6$-alkoxy-$C_1$-$C_4$-alkoxy, $C_3$-$C_6$-cycloalkyl, $C_3$-$C_6$ cycloalkoxy, $C_3$-$C_6$-cycloalkyl-$C_1$-$C_4$ alkyl, $C_3$-$C_6$-cycloalkoxy-$C_1$-$C_4$ alkyl, which groups are unsubstituted or substituted with halogen;

$R^W$ is $C_1$-$C_6$-alkyl, $C_3$-$C_6$-cycloalkyl, $C_3$-$C_6$-cycloalkyl-$C_1$-$C_4$-alkyl, which groups are halogenated or non-halogenated;

benzyl, or phenyl, which is unsubstituted or substituted with $R^F$;

the index n is 0, 1, 2, 3, or 4 if G is phenyl or a 6-membered hetaryl;

or 0, 1, 2, or 3 if G is a 5-membered hetaryl; and the index m is 0, 1 or 2;

and the N-oxides, stereoisomers, tautomers and agriculturally or veterinarily acceptable salts thereof.

In one embodiment, X is O. In another embodiment of compounds of formula (I), X is S.

In one embodiment of compounds of formula (I), E is $NR^3$ and Q is $CR^6$. In another embodiment of compounds of formula (I), E is $CR^4$ and Q is $NR^5$. In another embodiment of compounds of formula (I), E is $NR^3$ and Q is N.

In one embodiment of the present invention the compound of formula (I) is compound of formula (I.A), a compound (I.B) or a compound of formula (I.C).

(I.A)

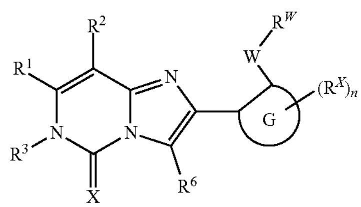

(I.B)

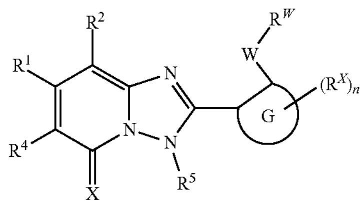

(I.C)

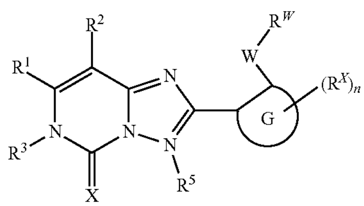

In one embodiment the compounds of formula (I) are compounds of formula (I.A). In another embodiment, the compounds of formula (I) are compounds of formula (I.B). In another embodiment, the compounds of formula (I) are compounds of formula (I.C). In one embodiment the compounds of formula (I) are compounds of formula (I.A) or (I.B).

$R^1$ is H, halogen, $C_1$-$C_6$-alkyl, $C_2$-$C_6$-alkenyl, $C_2$-$C_6$-alkynyl, $C_1$-$C_6$-alkoxy, $C_1$-$C_6$-alkoxy-$C_1$-$C_6$-alkyl, $C_3$-$C_6$-cycloalkyl, $C_3$-$C_6$-cycloalkoxy, $C_1$-$C_6$-sulfenyl, $C_1$-$C_6$-sulfinyl, or $C_1$-$C_6$-sulfonyl, which groups are unsubstituted or halogenated.

In one embodiment, $R^1$ is H, $C_1$-$C_3$-alkyl, $C_2$-$C_3$-alkenyl, $C_2$-$C_3$-alkynyl, $C_1$-$C_3$-alkoxy, $C_1$-$C_3$-alkoxy-$C_1$-$C_3$-alkyl, $C_3$-$C_8$-cycloalkyl, $C_3$-$C_5$-cycloalkoxy, which groups are unsubstituted or halogenate. In one embodiment, $R^1$ is H, $C_1$-$C_3$-alkyl, or $C_1$-$C_3$-alkoxy, which groups are unsubstituted or halogenated.

In another embodiment, $R^1$ is H, $C_1$-$C_3$-alkyl, $C_2$-$C_3$-alkenyl, $C_2$-$C_3$-alkynyl, $C_1$-$C_3$-alkoxy, which groups are unsubstituted or halogenated. In another embodiment, $R^1$ is $C_1$-$C_3$-alkyl, $C_1$-$C_3$-alkoxy, which groups are unsubstituted or halogenate. In another embodiment, $R^1$ is $C_1$-$C_3$-haloalkyl, preferably $CF_3$.

$R^2$, $R^4$, $R^6$ are independently H, halogen, $N_3$, CN, $NO_2$, SCN, $SF_5$; $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxyx-$C_1$-$C_4$-alkyl, which groups are unsubstituted or substituted with halogen; C(=O)$OR^A$, $NR^BR^C$, $NOR^A$, $ONR^BR^C$, $C_1$-$C_6$-alkylen-$NR^BR^C$, O—$C_1$-$C_6$-alkylen-$NR^BR^C$, $C_1$-$C_6$-alkylen-CN, NH—$C_1$-$C_6$-alkylen-$NR^BR^C$, C(=O)$NR^BR^C$, C(=O)$R^D$, C(=S)$R^D$, $SO_2NR^BR^C$, $S(=O)_n$ $R^E$; phenyl or benzyl, wherein the phenyl ring is unsubstituted or substituted with one or more, same or different substituents $R^F$.

In one embodiment, $R^2$ is H, halogen; $C_1$-$C_3$-alkyl, $C_1$-$C_3$-alkoxy, $C_2$-$C_3$-alkenyl, tri-$C_1$-$C_6$-alkylsilyl, $C_2$-$C_6$-alkynyl, $C_1$-$C_3$-alkoxy-$C_1$-$C_2$-alkyl, $C_1$-$C_3$-alkoxy-$C_1$-$C_2$-alkoxy, $C_3$-$C_5$-cycloalkyl, $C_3$-$C_8$-cycloalkoxy, $C_3$-$C_8$-cycloalkyl-$C_1$-$C_2$-alkyl, $C_3$-$C_5$-cycloalkoxyx-$C_1$-$C_2$-alkyl, which groups are unsubstituted or substituted with halogen. In another embodiment, $R^2$ is H, halogen; $C_1$-$C_3$-alkyl, $C_1$-$C_3$-alkoxy, $C_2$-$C_3$-alkenyl, $C_2$-$C_6$-alkynyl, which groups are unsubstituted or substituted with halogen. In another embodiment, $R^2$ is H, halogen; $C_1$-$C_3$-alkyl, $C_1$-$C_3$-alkoxy, which groups are unsubstituted or substituted with halogen. In another embodiment, $R^2$ is H, or $C_1$-$C_3$-alkyl. In another embodiment, $R^2$ is H.

$R^4$ is typically H, $C_1$-$C_3$-alkyl or $C_1$-$C_3$-haloalkyl, preferably H or $C_1$-$C_3$-alkyl, most preferably H.

$R^5$ is typically H, $C_1$-$C_3$-alkyl or $C_1$-$C_3$-haloalkyl, preferably $C_1$-$C_3$-alkyl or $C_1$-$C_3$-haloalkyl.

$R^6$ is typically H, $C_1$-$C_3$-alkyl or $C_1$-$C_3$-haloalkyl, preferably H or $C_1$-$C_3$-alkyl, most preferably H.

In case compounds of formula (I) are of formula (I.A), $R^3$ is typically $C_1$-$C_4$-alkyl, $C_2$-$C_4$ alkenyl, $C_2$-$C_4$ alkynyl, $C_1$-$C_3$-alkoxy-$C_1$-$C_3$-alkyl, $C_3$-$C_6$ cycloalkyl, $C_3$-$C_6$ cycloalkyl-$C_1$-$C_2$-alkyl, which groups are unsubstituted or halogenated;

phenyl or benzyl, in which groups the phenyl ring is unsubstituted or substituted with $R^F$;

and $R^6$ is H, or $C_1$-$C_3$-alkyl or $C_1$-$C_3$-haloalkyl.

In case compounds of formula (I) are of formula (I.B), $R^4$ is typically H, or $C_1$-$C_3$ alkyl, or $C_1$-$C_3$-haloalkyl; $R^5$ is $C_1$-$C_3$-alkyl, or $C_1$-$C_3$-haloalkyl.

Accordingly, in one embodiment, $R^1$ is H, $C_1$-$C_3$-alkyl, or $C_1$-$C_3$-alkoxy, which groups are unsubstituted or halogenated; and $R^2$ is H, halogen, $C_1$-$C_3$-alkyl, $C_1$-$C_3$-alkoxy, $C_2$-$C_3$-alkenyl, or $C_2$-$C_3$-alkynyl, which groups are unsubstituted or halogenated.

In another embodiment, $R^1$ is H, $C_1$-$C_3$-alkyl, or $C_1$-$C_3$-haloalkyl; and $R^2$ is H. In another embodiment, $R^1$ is $C_1$-$C_3$-haloalkyl; and $R^2$ is H.

In another embodiment, $R^1$ is H, $C_1$-$C_3$-alkyl, or $C_1$-$C_3$-alkoxy, which groups are unsubstituted or halogenated; and $R^2$ is H, halogen, $C_1$-$C_3$-alkyl, $C_1$-$C_3$-alkoxy, $C_2$-$C_3$-alkenyl, or $C_2$-$C_3$-alkynyl, which groups are unsubstituted or halogenated.

In one embodiment, $R^4$ is H, halogen; $C_1$-$C_3$-alkyl, $C_1$-$C_3$-alkoxy, $C_2$-$C_3$-alkenyl, tri-$C_1$-$C_6$-alkylsilyl, $C_2$-$C_6$-alkynyl, $C_1$-$C_3$-alkoxy-$C_1$-$C_2$-alkyl, $C_1$-$C_3$-alkoxy-$C_1$-$C_2$-alkoxy, $C_3$-$C_5$-cycloalkyl, $C_3$-$C_5$-cycloalkoxy, $C_3$-$C_8$-cycloalkyl-$C_1$-$C_2$-alkyl, $C_3$-$C_8$-cycloalkoxyx-$C_1$-$C_2$-alkyl, which groups are unsubstituted or substituted with halogen. In another embodiment, $R^4$ is H, halogen; $C_1$-$C_3$-alkyl, $C_1$-$C_3$-alkoxy, $C_2$-$C_3$-alkenyl, $C_2$-$C_6$-alkynyl, which groups are unsubstituted or substituted with halogen. In another embodiment, $R^4$ is H, halogen; $C_1$-$C_3$-alkyl, $C_1$-$C_3$-alkoxy, which groups are unsubstituted or substituted with halogen. In another embodiment, $R^4$ is H, $C_1$-$C_3$-alkyl, or $C_1$-$C_3$-haloalkyl. In another embodiment, $R^4$ is H, or $C_1$-$C_3$-alkyl. In another embodiment, $R^4$ is H.

In one embodiment, $R^6$ is H, halogen; $C_1$-$C_3$-alkyl, $C_1$-$C_3$-alkoxy, $C_2$-$C_3$-alkenyl, tri-$C_1$-$C_6$-alkylsilyl, $C_2$-$C_6$-alkynyl, $C_1$-$C_3$-alkoxy-$C_1$-$C_2$-alkyl, $C_1$-$C_3$-alkoxy-$C_1$-$C_2$-alkoxy, $C_3$-$C_5$-cycloalkyl, $C_3$-$C_5$-cycloalkoxy, $C_3$-$C_8$-cycloalkyl-$C_1$-$C_2$-alkyl, $C_3$-$C_5$-cycloalkoxyx-$C_1$-$C_2$-alkyl, which groups are unsubstituted or substituted with halogen. In another embodiment, $R^6$ is H, halogen; $C_1$-$C_3$-alkyl, $C_1$-$C_3$-alkoxy, $C_2$-$C_3$-alkenyl, $C_2$-$C_6$-alkynyl, which groups are unsubstituted or substituted with halogen. In another embodiment, $R^6$ is H, halogen; $C_1$-$C_3$-alkyl, $C_1$-$C_3$-alkoxy, which groups are unsubstituted or substituted with halogen. In another embodiment, $R^6$ is H, $C_1$-$C_3$-alkyl, $C_1$-$C_3$-haloalkyl. In another embodiment, $R^6$ is H, or $C_1$-$C_3$-alkyl. In another embodiment, $R^6$ is H.

$R^3$, $R^5$ are independently $C_1$-$C_6$-alkyl, $C_1$-$C_6$-alkoxy, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkyl-$C_1$-$C_4$-alkyl, or $C_3$-$C_6$-cycloalkoxy-$C_1$-$C_4$-alkyl, which are unsubstituted or halogenated; C(=O)OR$^A$, NR$^B$R$^C$, $C_1$-$C_6$-alkylen-NR$^B$R$^C$, O—$C_1$-$C_6$-alkylen-NR$^B$R$^C$, $C_1$-$C_6$-alkylen-CN, NH—$C_1$-$C_6$-alkylen-NR$^B$R$^C$, C(=O)NR$^B$R$^C$, C(=O)R$^D$, C(=S)R$^D$, SO$_2$NR$^B$R$^C$, S(=O)$_n$ R$^E$; phenyl or benzyl, wherein the phenyl ring is unsubstituted or substituted with one or more, same or different substituents R$^F$.

In one embodiment, $R^3$ is $C_1$-$C_6$-alkyl, $C_1$-$C_6$-alkoxy, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, or $C_1$-$C_3$-alkoxy-$C_1$-$C_3$-alkyl which are unsubstituted or halogenated; phenyl or benzyl, wherein the phenyl ring is unsubstituted or substituted with one or more, same or different substituents R$^F$. In another embodiment embodiment, $R^3$ is $C_1$-$C_4$-alkyl, $C_2$-$C_4$-alkenyl, $C_2$-$C_4$-alkynyl, $C_3$-$C_6$-cycloalkyl, $C_3$-$C_6$-cycloalkyl-$C_1$-$C_2$-alkyl, or $C_1$-$C_3$-alkoxy-$C_1$-$C_3$-alkyl, which are unsubstituted or halogenated; phenyl or benzyl, wherein the phenyl ring is unsubstituted or substituted with one or more, same or different substituents R$^F$. In another embodiment, $R^3$ is $C_1$-$C_4$-alkyl, $C_2$-$C_4$-alkenyl, $C_2$-$C_4$-alkynyl, $C_3$-$C_6$-cycloalkyl, $C_3$-$C_6$-cycloalkyl-$C_1$-$C_2$-alkyl, which are unsubstituted or halogenated; phenyl or benzyl, wherein the phenyl ring is unsubstituted or halogenated. In another embodiment, $R^3$ is $C_1$-$C_3$-alkyl, $C_3$-$C_6$-cycloalkyl, $C_3$-$C_6$-cycloalkyl-$C_1$-$C_2$-alkyl, which groups are unsubstituted or halogenated. In another embodiment, $R^3$ is $C_1$-$C_3$-alkyl, preferably methyl, which are unsubstituted or halogenated.

Accordingly, in one embodiment, $R^3$ is $C_1$-$C_3$-alkyl, $C_3$-$C_6$-cycloalkyl, $C_3$-$C_6$-cycloalkyl-$C_1$-$C_2$-alkyl, which groups are unsubstituted or halogenated; and $R^6$ is H, or $C_1$-$C_3$-alkyl or $C_1$-$C_3$-haloalkyl.

In one embodiment, $R^5$ is $C_1$-$C_6$-alkyl, $C_1$-$C_6$-alkoxy, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkyl-$C_1$-$C_4$-alkyl, or $C_3$-$C_6$-cycloalkoxy-$C_1$-$C_4$-alkyl, which are unsubstituted or halogenated.

In another embodiment embodiment, $R^5$ is $C_1$-$C_3$-alkyl, $C_1$-$C_3$-alkoxy, $C_2$-$C_3$-alkenyl, $C_2$-$C_3$-alkynyl, $C_3$-$C_6$-cycloalkyl, $C_3$-$C_6$-cycloalkyl-$C_1$-$C_2$-alkyl, which are unsubstituted or halogenated. In another embodiment, $R^5$ is $C_1$-$C_3$-alkyl, $C_2$-$C_3$-alkenyl, $C_2$-$C_3$-alkynyl, which are unsubstituted or halogenated. In another embodiment, $R^5$ is $C_1$-$C_3$-alkyl, or $C_1$-$C_3$-haloalkyl. In another embodiment, $R^5$ is $C_1$-$C_3$-alkyl, preferably methyl, which are unsubstituted or halogenated.

Each $R^7$ is independently H, halogen, CN, $C_1$-$C_6$-alkyl, $C_1$-$C_6$-haloalkyl, $C_3$-$C_6$-cycloalkyl, $C_1$-$C_4$-alkoxy, $C_1$-$C_4$-alkoxy-$C_1$-$C_4$-alkyl, $C_1$-$C_4$-alkylsulfanyl, $C_1$-$C_4$-alkylsulfanyl-$C_1$-$C_4$-alkyl, $C_1$-$C_4$-alkylsulfinyl-$C_1$-$C_4$-alkyl, $C_1$-$C_4$-alkylsulfonyl-$C_1$-$C_4$-alkyl or $C_1$-$C_4$-alkoxycarbonyl.

In one embodiment, each $R^7$ is independently H, halogen, CN, $C_1$-$C_6$-alkyl, $C_1$-$C_6$-haloalkyl, or $C_3$-$C_6$-cycloalkyl. In another embodiment, each $R^7$ is independently $C_1$-$C_4$-alkoxy, $C_1$-$C_4$-alkoxy-$C_1$-$C_4$-alkyl, $C_1$-$C_4$-alkylsulfanyl, $C_1$-$C_4$-alkylsulfanyl-$C_1$-$C_4$-alkyl, $C_1$-$C_4$-alkylsulfinyl-$C_1$-$C_4$-alkyl, $C_1$-$C_4$-alkylsulfonyl-$C_1$-$C_4$-alkyl or $C_1$-$C_4$-alkoxycarbonyl. In another embodiment, each $R^7$ is independently H or $C_1$-$C_6$-alkyl. In another embodiment, each $R^7$ is independently $C_1$-$C_6$-alkyl; preferably $CH_3$.

Each $R^8$ is independently H, halogen, CN, $C_1$-$C_6$-alkyl, $C_1$-$C_6$-haloalkyl, $C_3$-$C_6$-cycloalkyl, $C_1$-$C_4$-alkoxy, $C_1$-$C_4$-alkoxy-$C_1$-$C_4$-alkyl, $C_1$-$C_4$-alkylsulfanyl, $C_1$-$C_4$-alkylsulfanyl-$C_1$-$C_4$-alkyl, $C_1$-$C_4$-alkylsulfinyl-$C_1$-$C_4$-alkyl, $C_1$-$C_4$-alkylsulfonyl-$C_1$-$C_4$-alkyl or $C_1$-$C_4$-alkoxycarbonyl. In one embodiment, each $R^8$ is independently H, halogen, CN, $C_1$-$C_6$-alkyl, $C_1$-$C_6$-haloalkyl, or $C_3$-$C_6$-cycloalkyl. In another embodiment, each $R^8$ is independently $C_1$-$C_4$-alkoxy, $C_1$-$C_4$-alkoxy-$C_1$-$C_4$-alkyl, $C_1$-$C_4$-alkylsulfanyl, $C_1$-$C_4$-alkylsulfanyl-$C_1$-$C_4$-alkyl, $C_1$-$C_4$-alkylsulfinyl-$C_1$-$C_4$-alkyl, $C_1$-$C_4$-alkylsulfonyl-$C_1$-$C_4$-alkyl or $C_1$-$C_4$-alkoxycarbonyl. In another embodiment, each $R^8$ is independently H or $C_1$-$C_6$-alkyl. In another embodiment, each $R^8$ is independently $C_1$-$C_6$-alkyl; preferably $CH_3$.

Typically, $R^7$ and $R^8$ are both not H. Preferably, each $R^7$ and $R^8$ are independently selected from halogen, CN, $C_1$-$C_6$-alkyl, $C_1$-$C_6$-haloalkyl, $C_3$-$C_6$-cycloalkyl, $C_1$-$C_4$-alkoxy, $C_1$-$C_4$-alkoxy-$C_1$-$C_4$-alkyl, $C_1$-$C_4$-alkylsulfanyl, $C_1$-$C_4$-alkylsulfanyl-$C_1$-$C_4$-alkyl, $C_1$-$C_4$-alkylsulfinyl-$C_1$-$C_4$-alkyl, $C_1$-$C_4$-alkylsulfonyl-$C_1$-$C_4$-alkyl or $C_1$-$C_4$-alkoxycarbonyl, more preferably selected from $C_1$-$C_6$-alkyl, $C_1$-$C_6$-haloalkyl, $C_3$-$C_6$-cycloalkyl, $C_1$-$C_4$-alkoxy, and $C_1$-$C_4$-alkoxy-$C_1$-$C_4$-alkyl, most preferably from $C_1$-$C_6$-alkyl, $C_1$-$C_6$-haloalkyl, $C_3$-$C_6$-cycloalkyl, and $C_1$-$C_4$-alkoxy, especially preferably from $C_1$-$C_6$-alkyl and $C_1$-$C_6$-haloalkyl, in particular from $C_1$-$C_3$-alkyl and $C_1$-$C_3$-haloalkyl, such as from $C_1$-$C_3$-alkyl. In a particularly preferred embodiment, both $R^7$ and $R^8$ are $CH_3$.

Each $R^9$ is independently halogen, CN, $NH_2$, C(=O)H, OH, $C_3$-$C_6$-cycloalkyl, C(=O)OH, C(=O)$NH_2$, $C_1$-$C_4$-haloalkoxy, $C_1$-$C_4$-alkoxy, $C_1$-$C_4$-haloalkylsulfanyl, $C_1$-$C_4$-haloalkylsulfinyl, $C_1$-$C_4$-haloalkylsulfonyl, $C_1$-$C_4$-alkoxycarbonyl, $C_1$-$C_4$-haloalkoxycarbonyl, $C_1$-$C_4$-alkylcarbonyl, $C_1$-$C_4$-haloalkylcarbonyl, di-($C_1$-$C_4$)alkylaminocarbonyl, $C_1$-$C_4$-alkylaminocarbonyl, $C_1$-$C_4$-alkylcarbonylamino, di-($C_1$-$C_4$)alkylcarbonylamino, $C_1$-$C_4$-alkoxycarbonylamino, or a group-C($R^{91}$)=NOR$^{92}$; phenyl, which is unsubstituted or substituted with one or more, same or different substituents selected from halogen, CN, $C_1$-$C_4$-alkyl, $C_1$-$C_4$-haloalkyl, $C_1$-$C_4$-haloalkoxy, $C_1$-$C_4$-alkoxy, $C_1$-$C_4$-haloalkylsulfanyl, $C_1$-$C_4$-haloalkylsulfinyl, $C_1$-$C_4$haloalkylsulfonyl and C(=O) $C_1$-$C_4$-haloalkyl; $C_1$-$C_4$-alkyl which is unsubstituted or substituted with one or more, same or different substituents $R^{93}$.

In one embodiment, each $R^9$ is independently halogen, CN, $NH_2$, C(=O)H, OH, $C_3$-$C_6$-cycloalkyl, C(=O)OH, C(=O)$NH_2$, $C_1$-$C_4$-haloalkoxy, $C_1$-$C_4$-alkoxy, $C_1$-$C_4$-haloalkylsulfanyl, $C_1$-$C_4$-haloalkylsulfinyl, $C_1$-$C_4$-haloalkylsulfonyl, $C_1$-$C_4$-alkoxycarbonyl, $C_1$-$C_4$-haloalkoxycarbonyl, $C_1$-$C_4$-alkylcarbonyl, $C_1$-$C_4$-haloalkylcarbonyl, di-($C_1$-$C_4$)alkylaminocarbonyl, $C_1$-$C_4$-alkylaminocarbonyl, $C_1$-$C_4$-alkylcarbonylamino, di-($C_1$-$C_4$)alkylcarbonylamino, $C_1$-$C_4$-alkoxycarbonylamino, or a group —C($R^{91}$)=NOR$^{92}$.

In another embodiment, each $R^O$ is independently halogen, CN, $NH_2$, C(=O)H, OH, $C_3$-$C_6$-cycloalkyl, C(=O)OH, C(=O)$NH_2$, $C_1$-$C_4$-haloalkoxy, or $C_1$-$C_4$-alkoxy. In another embodiment, each $R^O$ is independently halogen, CN, $NH_2$, or OH.

Each $R^A$ is independently H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are unsubstituted or substituted with halogen; phenyl or benzyl, wherein the phenyl ring is unsubstituted or substituted with one or more, same or different substituents $R^F$.

In one embodiment, each $R^A$ is independently H, $C_1$-$C_3$-alkyl, $C_2$-$C_3$-alkenyl, $C_2$-$C_3$-alkynyl, $C_1$-$C_3$-alkoxy-$C_1$-$C_2$-alkyl, $C_3$-$C_6$-cycloalkyl, $C_3$-$C_6$-cycloalkyl-$C_1$-$C_2$-alkyl, $C_3$-$C_6$-cycloalkoxy-$C_1$-$C_2$-alkyl, which groups are unsubstituted or substituted with halogen; or phenyl or benzyl, wherein the phenyl ring is unsubstituted or substituted with one or more, same or different substitutents $R^F$.

In one embodiment, each $R^A$ is independently H, $C_1$-$C_3$-alkyl, $C_2$-$C_3$-alkenyl, $C_2$-$C_3$-alkynyl, $C_3$-$C_6$-cycloalkyl, which groups are unsubstituted or substituted with halogen; or phenyl or benzyl, wherein the phenyl ring is unsubstituted or substituted with one or more, same or different substitutents selected from halogen, $C_1$-$C_3$-alkyl, $C_1$-$C_3$-alkoxy, $C_1$-$C_3$-haloalkoxy, and $C_1$-$C_3$-haloalkyl.

Each $R^B$ is independently H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are unsubstituted or substituted with halogen; $C_1$-$C_6$-alkylen-CN; phenyl and benzyl, which groups are unsubstituted or substituted with one or more, same or different substituents $R^F$.

In one embodiment, each $R^B$ is independently H, $C_1$-$C_3$-alkyl, $C_2$-$C_3$-alkenyl, $C_2$-$C_3$-alkynyl, $C_3$-$C_6$-cycloalkyl, $C_3$-$C_6$-cycloalkyl-$C_1$-$C_4$-alkyl, which groups are unsubstituted or substituted with halogen; phenyl or benzyl, which groups are unsubstituted or substituted with one or more, same or different substituents $R^F$.

In another embodiment, each $R^B$ is independently H, $C_1$-$C_3$-alkyl, $C_2$-$C_3$-alkenyl, $C_2$-$C_3$-alkynyl, $C_3$-$C_6$-cycloalkyl, which groups are unsubstituted or substituted with halogen; phenyl or benzyl, which groups are unsubstituted or substituted with one or more, same or different substituents selected from halogen, $C_1$-$C_3$-alkyl, $C_1$-$C_3$-alkoxy, $C_1$-$C_3$-haloalkoxy, and $C_1$-$C_3$-haloalkyl.

Each $R^C$ is independently H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are unsubstituted or substituted with halogen; phenyl or benzyl, wherein the phenyl ring is unsubstituted or substituted with one or more, same or different substituents $R^F$.

In one embodiment, each $R^C$ is independently H, $C_1$-$C_3$-alkyl, $C_2$-$C_3$-alkenyl, $C_2$-$C_3$-alkynyl, $C_3$-$C_6$-cycloalkyl, $C_3$-$C_6$-cycloalkyl-$C_1$-$C_4$-alkyl, which groups are unsubstituted or substituted with halogen; phenyl or benzyl, which groups are unsubstituted or substituted with one or more, same or different substituents $R^F$.

In another embodiment, each $R^C$ is independently H, $C_1$-$C_3$-alkyl, $C_2$-$C_3$-alkenyl, $C_2$-$C_3$-alkynyl, $C_3$-$C_6$-cycloalkyl, which groups are unsubstituted or substituted with halogen; phenyl or benzyl, which groups are unsubstituted or substituted with one or more, same or different substituents selected from halogen, $C_1$-$C_3$-alkyl, $C_1$-$C_3$-alkoxy, $C_1$-$C_3$-haloalkoxy, and $C_1$-$C_3$-haloalkyl.

Alternatively, each moiety $NR^BR^C$ may also form an N-bound, saturated 5- to 8-membered heterocycle, which in addition to the nitrogen atom may have 1 or 2 further heteroatoms or heteroatom moieties selected from O, $S(=O)_m$ and N—R', wherein R' is H or $C_1$-$C_6$-alkyl and wherein the N-bound heterocycle is unsubstituted or substituted with one or more, same or different substituents selected from halogen, $C_1$-$C_4$-alkyl, $C_1$-$C_4$-haloalkyl, $C_1$-$C_4$-alkoxy and $C_1$-$C_4$-haloalkoxy. In one embodiment, each moiety $NR^BR^C$ may also form an N-bound, saturated 5- to 6-membered heterocycle, wherein the N-bound heterocycle is unsubstituted or substituted with one or more, same or different substituents selected from halogen, $C_1$-$C_3$-alkyl, $C_1$-$C_3$-haloalkyl, $C_1$-$C_3$-alkoxy and $C_1$-$C_3$-haloalkoxy.

Each $R^D$ is independently H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are unsubstituted or substituted with halogen; phenyl or benzyl, wherein the phenyl ring is unsubstituted or substituted with one or more, same or different substituents $R^F$.

In one embodiment, each $R^D$ is independently $C_1$-$C_3$-alkyl, $C_2$-$C_3$-alkenyl, $C_2$-$C_3$-alkynyl, $C_3$-$C_6$-cycloalkyl, $C_3$-$C_6$-cycloalkyl-$C_1$-$C_4$-alkyl, which groups are unsubstituted or substituted with halogen; phenyl or benzyl, which groups are unsubstituted or substituted with one or more, same or different substituents $R^F$. In another embodiment, each $R^D$ is independently $C_1$-$C_3$-alkyl, $C_2$-$C_3$-alkenyl, $C_2$-$C_3$-alkynyl, $C_3$-$C_6$-cycloalkyl, which groups are unsubstituted or substituted with halogen; phenyl or benzyl, which groups are unsubstituted or substituted with one or more, same or different substituents selected from halogen, $C_1$-$C_3$-alkyl, $C_1$-$C_3$-alkoxy, $C_1$-$C_3$-haloalkoxy, and $C_1$-$C_3$-haloalkyl.

Each $R^E$ is independently $C_1$-$C_6$-alkyl, $C_3$-$C_6$-cycloalkyl, $C_3$-$C_6$-cycloalkyl-$C_1$-$C_4$-alkyl, which are unsubstituted or substituted with halogen; or phenyl or benzyl, wherein the phenyl ring is unsubstituted or substituted with $R^F$.

In one embodiment, each $R^E$ is independently $C_1$-$C_3$-alkyl, $C_3$-$C_6$-cycloalkyl, $C_3$-$C_6$-cycloalkyl-$C_1$-$C_2$-alkyl, which are unsubstituted or substituted with halogen; or phenyl or benzyl, wherein the phenyl ring is unsubstituted or substituted with one or more, same or different substituents selected from halogen, $C_1$-$C_3$-alkyl, $C_1$-$C_3$-alkoxy, $C_1$-$C_3$-haloalkoxy, and $C_1$-$C_3$-haloalkyl. In one embodiment, each $R^E$ is independently $C_1$-$C_3$-alkyl, or $C_1$-$C_3$-haloalkyl.

Each $R^F$ is independently halogen, $N_3$, OH, CN, $NO_2$, SCN, $SF_5$; $C_1$-$C_6$ alkyl, $C_1$-$C_6$ alkoxy, $C_2$-$C_6$ alkenyl, $C_2$-$C_6$ alkynyl, $C_1$-$C_6$ alkoxy-$C_1$-$C_4$ alkyl, $C_1$-$C_6$ alkoxy-$C_1$-$C_4$ alkoxy, $C_3$-$C_6$ cycloalkyl, $C_3$-$C_6$ cycloalkoxy, $C_3$-$C_6$ cycloalkyl-$C_1$-$C_4$ alkyl, $C_3$-$C_6$ cycloalkoxy-$C_1$-$C_4$ alkyl, which groups are unsubstituted or substituted with halogen. In one embodiment, each $R^F$ is independently halogen, OH, CN, $NO_2$; $C_1$-$C_3$-alkyl, $C_1$-$C_3$-alkoxy, $C_2$-$C_3$ alkenyl, $C_2$-$C_3$-alkynyl, $C_3$-$C_6$-cycloalkyl, which groups are unsubstituted or substituted with halogen. In another embodiment, each $R^F$ is independently halogen; $C_1$-$C_3$-alkyl, $C_1$-$C_3$-alkoxy, $C_2$-$C_3$ alkenyl, $C_2$-$C_3$-alkynyl, which groups are unsubstituted or substituted with halogen. In another embodiment, each $R^F$ is independently halogen, $C_1$-$C_3$-alkyl, or $C_1$-$C_3$-haloalkyl.

Each $R^L$ is independently H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are unsubstituted or substituted with halogen; phenyl or benzyl, which groups are unsubstituted or substituted with one or more, same or different substituents $R^F$.

In one embodiment, $R^L$ is H, $C_1$-$C_3$-alkyl, $C_2$-$C_3$-alkenyl, $C_2$-$C_3$-alkynyl, $C_3$-$C_6$-cycloalkyl, $C_3$-$C_6$-cycloalkyl-$C_1$-$C_4$-alkyl, which groups are unsubstituted or substituted with halogen; phenyl or benzyl, which groups are unsubstituted or substituted with one or more, same or different substituents $R^F$.

In another embodiment, each $R^L$ is independently H, $C_1$-$C_3$-alkyl, $C_2$-$C_3$-alkenyl, $C_2$-$C_3$-alkynyl, $C_3$-$C_6$-cycloalkyl, which groups are unsubstituted or substituted with halogen; phenyl or benzyl, which groups are unsubstituted or substituted with one or more, same or different substituents selected from halogen, $C_1$-$C_3$-alkyl, $C_1$-$C_3$-alkoxy, $C_1$-$C_3$-haloalkoxy, and $C_1$-$C_3$-haloalkyl.

In another embodiment, each $R^L$ is independently H or $C_1$-$C_3$-alkyl, wherein the alkyl group is unsubstituted or substituted with halogen. In another embodiment, each $R^L$ is independently H or $C_1$-$C_3$-alkyl, wherein the alkyl group is unsubstituted. In another embodiment, each $R^L$ is independently H or $C_1$-$C_3$-alkyl, wherein the alkyl group is substituted with halogen. In another embodiment, each $R^L$ is independently $C_1$-$C_3$-alkyl, wherein the alkyl group is unsubstituted or substituted with halogen. In another embodiment, each $R^L$ is independently H; $C_1$-$C_3$-alkyl, $C_3$-$C_6$-cycloalkyl, or $C_3$-$C_6$-cycloalkyl-$C_1$-$C_2$-alkyl, which groups are unsubstituted or substituted with halogen or CN. In another embodiment, each $R^L$ is independently H; $C_1$-$C_3$-alkyl, or $C_3$-$C_5$-cycloalkyl-$C_1$-$C_2$-alkyl, which groups are unsubstituted or substituted with halogen or CN.

Each $R^M$ is is independently H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, $C_1$-$C_6$-alkyl-carbonyl, $C_1$-$C_6$-alkoxy-carbonyl, which groups are unsubstituted or substituted with halogen; phenyl or benzyl, which groups are unsubstituted or substituted with one or more, same or different substituents $R^F$.

In one embodiment, each $R^M$ is independently H, $C_1$-$C_6$-alkyl, $C_1$-$C_6$-alkyl-carbonyl, $C_1$-$C_6$-alkoxy-carbonyl, which groups are unsubstituted or substituted with halogen; phenyl or benzyl, which groups are unsubstituted or substituted with one or more, same or different substituents $R^F$.

In another embodiment, each $R^M$ is independently H, $C_1$-$C_6$-alkyl, $C_1$-$C_6$-alkyl-carbonyl, $C_1$-$C_6$-alkoxy-carbonyl, which groups are unsubstituted or substituted with halogen;

In another embodiment, each $R^M$ is independently H or $C_1$-$C_6$-alkyl-carbonyl, $C_1$-$C_6$-alkoxy-carbonyl, which groups are unsubstituted or substituted with halogen. In another embodiment, each $R^M$ is independently H, $C_1$-$C_3$-alkyl, or $C_1$-$C_3$-haloalkyl.

In another embodiment, each $R^M$ is phenyl or benzyl, which groups are unsubstituted or substituted with one or more, same or different substituents selected from halogen, $C_1$-$C_3$-alkyl, $C_1$-$C_3$-alkoxy, $C_1$-$C_3$-haloalkoxy, and $C_1$-$C_3$-haloalkyl.

Each $R^N$ is is independently H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, $C_1$-$C_6$-alkyl-carbonyl, $C_1$-$C_6$-alkoxy-carbonyl, which groups are unsubstituted or substituted with halogen; phenyl or benzyl, which groups are unsubstituted or substituted with one or more, same or different substituents $R^F$.

In one embodiment, each $R^N$ is independently H, $C_1$-$C_6$-alkyl, $C_1$-$C_6$-alkyl-carbonyl, $C_1$-$C_6$-alkoxy-carbonyl, which groups are unsubstituted or substituted with halogen; phenyl or benzyl, which groups are unsubstituted or substituted with one or more, same or different substituents $R^F$.

In another embodiment, each $R^N$ is independently H, $C_1$-$C_6$-alkyl, $C_1$-$C_6$-alkyl-carbonyl, $C_1$-$C_6$-alkoxy-carbonyl, which groups are unsubstituted or substituted with halogen. In another embodiment, each $R^N$ is independently H, $C_1$-$C_3$-alkyl, or $C_1$-$C_3$-haloalkyl.

In another embodiment, each $R^N$ is independently H or $C_1$-$C_6$-alkyl-carbonyl, $C_1$-$C_6$-alkoxy-carbonyl, which groups are unsubstituted or substituted with halogen.

In another embodiment, each $R^N$ is phenyl or benzyl, which groups are unsubstituted or substituted with one or more, same or different substituents selected from halogen, $C_1$-$C_3$-alkyl, $C_1$-$C_3$-alkoxy, $C_1$-$C_3$-haloalkoxy, and $C_1$-$C_3$-haloalkyl.

Alternatively, each moiety $N(R^MR^N)$, may also form an N-bound, saturated 5- to 8-membered heterocycle, which in addition to the nitrogen atom may have 1 or 2 further heteroatoms or heteroatom moieties selected from O, $S(=O)_m$ and N—R', wherein R' is H or $C_1$-$C_6$-alkyl and wherein the N-bound heterocycle is unsubstituted or substituted with one or more, same or different substituents selected from halogen, $C_1$-$C_4$-alkyl, $C_1$-$C_4$-haloalkyl, $C_1$-$C_4$-alkoxy and $C_1$-$C_4$-haloalkoxy.

In one embodiment, each moiety $NR^MR^N$ may also form an N-bound, saturated 5- to 6-membered heterocycle, wherein the N-bound heterocycle is unsubstituted or substituted with one or more, same or different substituents selected from halogen, $C_1$-$C_3$-alkyl, $C_1$-$C_3$-haloalkyl, $C_1$-$C_3$-alkoxy and $C_1$-$C_3$-haloalkoxy.

Each $R^O$ is independently H, CN, OH, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are unsubstituted or substituted with halogen; phenyl or benzyl, wherein the phenyl ring is unsubstituted or substituted with one or more, same or different substituents $R^F$.

In one embodiment, each $R^O$ is independently H, CN, or $C_1$-$C_6$-alkyl.

In another embodiment, each $R^O$ is independently H or CN.

In another embodiment, each $R^O$ is independently H.

In another embodiment, each $R^O$ is independently $C_1$-$C_6$-alkyl.

In another embodiment, each $R^O$ is independently CN. In one embodiment, $R^O$ is H, CN, or $C_1$-$C_3$-alkyl (e.g. $CH_3$).

$R^W$ is independently is $C_1$-$C_6$-alkyl, $C_3$-$C_6$-cycloalkyl, $C_3$-$C_6$-cycloalkyl-$C_1$-$C_4$-alkyl, which groups are halogenated or non-halogenated;

benzyl, or phenyl, which is unsubstituted or substituted with $R^F$;

In one embodiment, each $R^W$ is independently $C_1$-$C_3$-alkyl or $C_3$-$C_6$-cycloalkyl, which are unsubstituted or substituted with halogen; or phenyl or benzyl, wherein the phenyl ring is unsubstituted or substituted with one or more, same or different substituents selected from halogen, $C_1$-$C_3$-alkyl, $C_1$-$C_3$-alkoxy, $C_1$-$C_3$-haloalkoxy, and $C_1$-$C_3$-haloalkyl.

In another embodiment, each $R^W$ is independently $C_1$-$C_3$-alkyl, or $C_1$-$C_3$-haloalkyl.

In another embodiment, each $R^W$ is $C_1$-$C_3$-alkyl, which is unsubstituted or substituted with halogen. In another embodiment, $R^W$ is $C_1$-$C_3$-alkyl, which is unsubstituted or substituted with halogen.

In another embodiment, each $R^W$ is $C_1$-$C_3$-alkyl, preferably ethyl which is unsubstituted;

In another embodiment, each $R^W$ is $C_1$-$C_3$-alkyl, which is substituted with halogen;

In another embodiment, each $R^W$ is benzyl or phenyl, which is unsubstituted or substituted with $R^F$.

Each $R^X$ is —C(CN)$R^7R^8$, —C($R^O$)═N—N($R^MR^N$), —C($R^O$)═N—O($R^L$), $C_3$-$C_6$-cycloalkyl, which is substituted with CN and which either does not have any further substituents, or which is further substituted with one or more, same or different substituents $R^9$; or a group of formula (I.1)

(I.1)

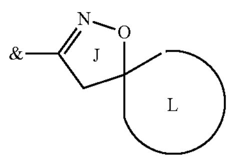

wherein the ring L is a 5- or 6-membered saturated, partially or fully unsaturated carbo- or heterocycle;

wherein the ring L is a saturated, partially or fully saturated carbo- or heterocycle, which carobo- or heterocycle is unsubstituted or substituted with one or more, same or different substituents $R^{10}$, and wherein said heterocycle contains one or more, same or different heteroatoms N, O, or S, and wherein said heteroatoms S and N are oxidized or non-oxidized; wherein ring J is partially or fully unsaturated and unsubstituted or substituted with one or more, same or different substituents $R^{11}$; and wherein "&" means the connection to the remainder of the molecule at the position of $R^X$ in formula (I).

Typically, the ring L is a 5-membered saturated carbocycle, which is substituted with one or more, same or different substituents $R^{10}$. In one embodiment, the ring L is a saturated 5-membered carbocycle having no substituents $R^{10}$. In another embodiment, the ring L is a saturated 5-membered carbocycle having one substituent $R^{10}$.

The ring J is typically partially unsaturated and has none or one substituent $R^{11}$, preferably none substituent $R^{11}$.

Each $R^{10}$, $R^{11}$ is independently H, halogen, CN, OH; $C_1$-$C_6$-alkyl, $C_3$-$C_6$-cycloalkyl, $C_1$-$C_4$-alkoxy, or $C_1$-$C_4$-alkoxy-$C_1$-$C_4$-alkyl, which groups are unsubstituted or halogenated. Typically, each $R^{10}$, $R^{11}$ is independently H, halogen, CN, $C_1$-$C_3$-alkyl, or $C_1$-$C_3$-haloalkyl.

In one embodiment, $R^X$ is —C(CN)$R^7R^8$. In another embodiment, $R^X$ is —C($R^O$)═N—N($R^MR^N$).

In another embodiment, $R^X$ is —C($R^O$)═N—O($R^L$). In another embodiment, $R^X$ is $C_3$-$C_6$-cycloalkyl, which is substituted with CN and which either does not have any further substituents, or which is further substituted with one or more, same or different substituents $R^9$. In another embodiment, $R^X$ is a group (1.1) as defined above. In another embodiment, $R^X$ is —C(CN)$R^7R^8$ or $C_3$-$C_6$-cycloalkyl, which is substituted with CN and which either does not have any further substituents, or which is further substituted with one or more, same or different substituents $R^9$.

In another embodiment, $R^X$ is $C_3$-$C_6$-cycloalkyl, which is substituted with CN.

In another embodiment, each $R^X$ is independently —C(CN)$R^7R^8$ or $C_3$-$C_6$-cycloalkyl, which is substituted with CN and which either does not have any further substituents, or which is further substituted with one or more, same or different substituents $R^9$;

$R^7$, $R^8$ are independently $C_1$-$C_3$-alkyl or $C_1$-$C_3$-haloalkyl;

$R^9$ is halogen, $C_1$-$C_3$-alkyl, or $C_1$-$C_3$-haloalkyl.

In another embodiment, each $R^X$ is independently —C(CN) ($CH_3$) 2 or cyclopropyl, which is substituted with CN and which either does not have any further substituents, or which is further substituted with one or more, same or different substituents $R^9$;

$R^9$ is halogen, $C_1$-$C_3$-alkyl, or $C_1$-$C_3$-haloalkyl.

In another embodiment, each $R^X$ is independently —C($R^O$)═N—O($R^L$) or —C($R^O$)═N—N($R^MR^N$); each $R^O$ is independently H, CN, $C_1$-$C_3$-alkyl, or $C_1$-$C_3$-haloalkyl;

each $R^L$ is independently H; or $C_1$-$C_3$-alkyl, $C_3$-$C_5$-cycloalkyl, $C_3$-$C_5$-cycloalkyl-$C_1$-$C_3$-alkyl, which groups are unsubstituted or substituted with halogen or CN;

each $R^M$, $R^N$ is independently H, $C_1$-$C_3$-alkyl, or $C_1$-$C_3$-haloalkyl;

or a group of formula (I.1), wherein the ring J is a 5-membered heterocycle; wherein the ring L is 5- or 6-membered saturated carbocycle, which is unsubstituted or substituted with one or more, same or different substituents selected from halogen, $C_1$-$C_3$-alkyl, and $C_1$-$C_3$-haloalkyl; and wherein ring J is unsubstituted or substituted with one or more, same or different substituents selected from halogen, $C_1$-$C_3$-alkyl, and $C_1$-$C_3$-haloalkyl.

In another embodiment, each $R^X$ is independently —C($R^O$)═N—O($R^L$) or —C($R^O$)═N—N($R^MR^N$);

each $R^O$ is independently H, CN, or $C_1$-$C_3$-alkyl;

each $R^L$ is independently H; or $C_1$-$C_3$-alkyl, $C_3$-$C_5$-cycloalkyl, $C_3$-$C_5$-cycloalkyl-$C_1$-$C_3$-alkyl, which groups are unsubstituted or substituted with halogen or CN;

each $R^M$, $R^N$ is independently H, or $C_1$-$C_3$-alkyl;

or a group of formula (I.1), wherein the ring J is a 5-membered heterocycle; wherein the ring L is 5-membered saturated carbocycle.

In one embodiment, W is S, S(O), or $S(O)_2$. In another embodiment, Wis S, S(O), or $S(O)_2$.

In another embodiment, Wis S or $S(O)_2$. In another embodiment, Wis S. In another embodiment, Wis $S(O)_2$. In another embodiment, Wis S(O).

In one embodiment, G is phenyl, or a 5- or 6-membered hetaryl. In another embodiment, G is phenyl. In another embodiment, G is phenyl, or 6-membered hetaryl. In another embodiment, G is a 5- or 6-membered hetaryl. In another embodiment, G is a 6-membered hetaryl. In another embodiment, G is a 5-membered hetaryl. In another embodiment, G is a 6-membered hetaryl, preferably pyridyl or pyrimidinyl. In another embodiment, G is pyridyl, pyrazinyl, or pyrimidinyl. In another embodiment, G is pyridyl or pyrazinyl. In another embodiment, G is phenyl, pyridyl, or pyrazinyl. In another embodiment, G is phenyl or pyridyl. In another embodiment, G is pyridyl, typically 2-pyridyl.

The index m is 0, 1, or 2. In one embodiment, the index m is 2. In another embodiment, the index m is 0.

In one embodiment, the index n is 0, 1, 2, 3, or 4 if G is phenyl or a 6-membered hetaryl; or 0, 1, 2, or 3 if G is a 5-membered hetaryl. In another embodiment, the index n is 1, or 2. In another embodiment, the index n is 1.

Preferred are the compound of formula (I), wherein $R^1$ is H, $C_1$-$C_3$-alkyl, $C_1$-$C_3$-alkoxy, which groups are unsubstituted or halogenated;

$R^2$ is H, halogen; $C_1$-$C_3$-alkyl, $C_1$-$C_3$-alkoxy, $C_2$-$C_3$-alkenyl, $C_2$-$C_3$-alkynyl, which groups are unsubstituted or halogenated, preferably H.

Preferred are the compound of formula (I.A), wherein $R^3$ is $C_1$-$C_4$-alkyl, $C_2$-$C_4$ alkenyl, $C_2$-$C_4$ alkynyl, $C_1$-$C_3$-alkoxy-$C_1$-$C_3$-alkyl, $C_3$-$C_6$ cycloalkyl, $C_3$-$C_6$ cycloalkyl-$C_1$-$C_2$-alkyl, which groups are unsubstituted or halogenated; phenyl or benzyl, in which groups the phenyl ring is unsubstituted or substituted with $R^F$;

$R^6$ is H, or $C_1$-$C_3$-alkyl or $C_1$-$C_3$-haloalkyl.

Preferred are the compound of formula (I.B), wherein $R^4$ is H, or $C_1$-$C_3$ alkyl, or $C_1$-$C_3$-haloalkyl;

$R^5$ is $C_1$-$C_3$-alkyl, or $C_1$-$C_3$-haloalkyl.

Preferred are the compound of formula (I), wherein $R^W$ is $C_1$-$C_3$-alkyl or $C_1$-$C_3$-haloalkyl, and m is 0 or 2.

Preferred are the compounds of formula (I), wherein $R^O$ is H, $CH_3$, or CN, such as H or CN.

In one preferred embodiment, the compound of formula (I) is the compound of formula I.A, I.B, or I.C, wherein $R^1$ is H, $C_1$-$C_3$-alkyl, $C_1$-$C_3$-alkoxy, which groups are unsubstituted or halogenated;

$R^2$ is H, halogen; $C_1$-$C_3$-alkyl, $C_1$-$C_3$-alkoxy, $C_2$-$C_3$-alkenyl, $C_2$-$C_3$-alkynyl, which groups are unsubstituted or halogenated, $R^3$ is $C_1$-$C_4$-alkyl, $C_2$-$C_4$ alkenyl, $C_2$-$C_4$ alkynyl, $C_1$-$C_3$-alkoxy-$C_1$-$C_3$-alkyl, $C_3$-$C_6$ cycloalkyl, $C_3$-$C_6$ cycloalkyl-$C_1$-$C_2$-alkyl, which groups are unsubstituted or halogenated;

phenyl or benzyl, in which groups the phenyl ring is unsubstituted or substituted with $R^F$;

$R^4$ is H, $C_1$-$C_3$ alkyl, or $C_1$-$C_3$-haloalkyl;

$R^5$ is $C_1$-$C_3$-alkyl, or $C_1$-$C_3$-haloalkyl;

$R^W$ is $C_1$-$C_3$-alkyl or $C_1$-$C_3$-haloalkyl, and m is 0 or 2;

$R^M$ is H or $C_1$-$C_6$-alkyl-carbonyl;

$R^N$ is H or $C_1$-$C_6$-alkyl-carbonyl;

$R^O$ is H or CN.

In another preferred embodiment, the compound of formula (I) is the compound of formula I.A, wherein $R^1$ is H, $C_1$-$C_3$-alkyl, $C_1$-$C_3$-alkoxy, which groups are unsubstituted or halogenated;

$R^2$ is H, halogen; $C_1$-$C_3$-alkyl, $C_1$-$C_3$-alkoxy, $C_2$-$C_3$-alkenyl, $C_2$-$C_3$-alkynyl, which groups are unsubstituted or halogenated, $R^3$ $C_1$-$C_4$-alkyl, $C_2$-$C_4$ alkenyl, $C_2$-$C_4$ alkynyl, $C_1$-$C_3$-alkoxy-$C_1$-$C_3$-alkyl, $C_3$-$C_6$ cycloalkyl, $C_3$-$C_6$ cycloalkyl-$C_1$-$C_2$-alkyl, which groups are unsubstituted or halogenated;

phenyl or benzyl, in which groups the phenyl ring is unsubstituted or substituted with $R^F$;

$R^4$ is H, $C_1$-$C_3$ alkyl, or $C_1$-$C_3$-haloalkyl;

$R^5$ is $C_1$-$C_3$-alkyl, or $C_1$-$C_3$-haloalkyl.

$R^W$ is $C_1$-$C_3$-alkyl or $C_1$-$C_3$-haloalkyl, and m is 0 or 2;

$R^M$ is H or $C_1$-$C_6$-alkyl-carbonyl;

$R^N$ is H or $C_1$-$C_6$-alkyl-carbonyl;

$R^O$ is H or CN.

In one preferred embodiment, the compound of formula (I) is the compound of formula I.A, I.B, or I.C, wherein $R^1$ is H, $C_1$-$C_3$-alkyl, $C_1$-$C_3$-alkoxy, which groups are unsubstituted or halogenated;

$R^2$ is H, halogen; $C_1$-$C_3$-alkyl, $C_1$-$C_3$-alkoxy, $C_2$-$C_3$-alkenyl, $C_2$-$C_3$-alkynyl, which groups are unsubstituted or halogenated, $R^3$ $C_1$-$C_4$-alkyl, $C_2$-$C_4$ alkenyl, $C_2$-$C_4$ alkynyl, $C_1$-$C_3$-alkoxy-$C_1$-$C_3$-alkyl, $C_3$-$C_6$ cycloalkyl, $C_3$-$C_6$ cycloalkyl-$C_1$-$C_2$-alkyl, which groups are unsubstituted or halogenated;

phenyl or benzyl, in which groups the phenyl ring is unsubstituted or substituted with $R^F$;

$R^4$ is H, $C_1$-$C_3$ alkyl, or $C_1$-$C_3$-haloalkyl;

$R^5$ is $C_1$-$C_3$-alkyl, or $C_1$-$C_3$-haloalkyl.

$R^X$ is —C(CN)$R^7R^8$, —C($R^O$)═N—O($R^L$), or $C_3$-$C_6$-cycloalkyl, which is substituted with CN and which either does not have any further substituents, or which is further substituted with one or more, same or different substituents $R^9$;

$R^W$ is $C_1$-$C_3$-alkyl or $C_1$-$C_3$-haloalkyl, and m is 0 or 2;

$R^M$ is H or $C_1$-$C_6$-alkyl-carbonyl;

$R^N$ is H or $C_1$-$C_6$-alkyl-carbonyl;

$R^O$ is H or CN.

In another preferred embodiment, the compound of formula (I) is the compound of formula I.A, wherein $R^1$ is H, $C_1$-$C_3$-alkyl, $C_1$-$C_3$-alkoxy, which groups are unsubstituted or halogenated;

$R^2$ is H, halogen; $C_1$-$C_3$-alkyl, $C_1$-$C_3$-alkoxy, $C_2$-$C_3$-alkenyl, $C_2$-$C_3$-alkynyl, which groups are unsubstituted or halogenated, $R^3$ $C_1$-$C_4$-alkyl, $C_2$-$C_4$ alkenyl, $C_2$-$C_4$ alkynyl, $C_1$-$C_3$-alkoxy-$C_1$-$C_3$-alkyl, $C_3$-$C_6$ cycloalkyl, $C_3$-$C_6$ cycloalkyl-$C_1$-$C_2$-alkyl, which groups are unsubstituted or halogenated;

phenyl or benzyl, in which groups the phenyl ring is unsubstituted or substituted with $R^F$;

$R^4$ is H, $C_1$-$C_3$ alkyl, or $C_1$-$C_3$-haloalkyl;

$R^5$ is $C_1$-$C_3$-alkyl, or $C_1$-$C_3$-haloalkyl.

$R^X$ is —C(CN)$R^7R^8$, —C($R^O$)═N—O($R^L$), or $C_3$-$C_6$-cycloalkyl, which is substituted with CN and which either does not have any further substituents, or which is further substituted with one or more, same or different substituents $R^9$;

$R^W$ is $C_1$-$C_3$-alkyl or $C_1$-$C_3$-haloalkyl, and m is 0 or 2;

$R^M$ is H or $C_1$-$C_6$-alkyl-carbonyl;

$R^N$ is H or $C_1$-$C_6$-alkyl-carbonyl;

$R^O$ is H or CN.

In another preferred embodiment, the compound of formula (I) is the compound of formula I.A, wherein G is phenyl or pyridyl, preferably 2-pyridyl;

$R^1$ is H, $C_1$-$C_3$-alkyl or $C_1$-$C_3$-haloalkyl, which groups are unsubstituted or halogenated, preferably $CF_3$;

$R^2$ is H, halogen; $C_1$-$C_3$-alkyl, $C_1$-$C_3$-alkoxy, $C_2$-$C_3$-alkenyl, $C_2$-$C_3$-alkynyl, which groups are unsubstituted or halogenated, preferably H;

$R^3$ is $C_1$-$C_3$-alkyl, cyclopropyl, cyclopropyl-$C_1$-$C_2$-alkyl, which groups are unsubstituted or halogenated, preferably unsubstituted;

$R^6$ is H, $CH_3$, or $CF_3$, preferably H;

each $R^X$ is independently —C(CN) ($CH_3$) 2;

1-cyano-cyclopropyl, which is unsubstituted or which is further substituted with one or more, same or different substituents selected from halogen, $C_1$-$C_3$-alkyl, or $C_1$-$C_3$-haloalkyl, preferably unsubstituted;

—C($R^O$)═N—O($R^L$), or —C($R^O$)═N—N($R^MR^N$), wherein $R^O$ is H, CN, $C_1$-$C_3$-alkyl, or $C_1$-$C_3$-haloalkyl; preferably H, CN, or $CH_3$;

$R^L$ is H;

$C_1$-$C_3$-alkyl, which is unsubstituted or substituted with one or more, same or different substituents selected from halogen, and CN; or $C_3$-$C_6$-cycloalkyl, $C_3$-$C_6$-cycloalkyl-$C_1$-$C_2$-alkyl;

Each $R^M$, $R^N$ is independently H, $C_1$-$C_3$-alkyl, or $C_1$-$C_3$-haloalkyl;

$R^N$ or a group of formula (I.2) falling under the definition of formula (I.1)

(I.2)

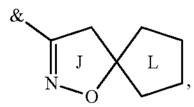

wherein "&" means the connection to the remainder of the molecule at the position of $R^x$ in formula (I);

wherein rings J, L are both independently unsubstituted or substituted with one or more, same or different substituents selected from halogen, CN, $C_1$-$C_3$-alkyl, and $C_1$-$C_3$-haloalkyl, preferably unsubstituted;

$R^W$ is $C_1$-$C_3$-alkyl or $C_1$-$C_3$-haloalkyl, and the index m is 0 or 2; and the index n is 1.

In another preferred embodiment, the compound of formula (I) is the compound of formula I.A, wherein G is phenyl or pyridyl, preferably 2-pyridyl;

$R^1$ is H, $C_1$-$C_3$-alkyl or $C_1$-$C_3$-haloalkyl, which groups are unsubstituted or halogenated, preferably $CF_3$;

$R^2$ is H, halogen; $C_1$-$C_3$-alkyl, $C_1$-$C_3$-alkoxy, $C_2$-$C_3$-alkenyl, $C_2$-$C_3$-alkynyl, which groups are unsubstituted or halogenated, preferably H;

$R^3$ is $C_1$-$C_3$-alkyl, cyclopropyl, cyclopropyl-$C_1$-$C_2$-alkyl, which groups are unsubstituted or halogenated, preferably unsubstituted;

$R^6$ is H, $CH_3$, or $CF_3$, preferably H;

each $R^X$ is independently —$C(CN)(CH_3)_2$;

1-cyano-cyclopropyl, which is unsubstituted or which is further substituted with one or more, same or different substituents selected from halogen, $C_1$-$C_3$-alkyl, or $C_1$-$C_3$-haloalkyl, preferably unsubstituted;

—$C(R^O)$═N—$O(R^L)$, wherein $R^O$ is H, or CN;

$R^L$ is H;

$C_1$-$C_3$-alkyl, which is unsubstituted or substituted with one or more, same or different substituents selected from halogen, and CN; or $C_3$-$C_6$-cycloalkyl, $C_3$-$C_6$-cycloalkyl-$C_1$-$C_2$-alkyl, which groups are unsubstituted or halogenated, preferably unsubstituted;

or a group of formula (I.2) falling under the definition of formula (I.1)

(I.2)

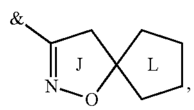

wherein "&" means the connection to the remainder of the molecule at the position of $R^x$ in formula (I);

wherein rings J, L are both independently unsubstituted or substituted with one or more, same or different substituents selected from halogen, CN, $C_1$-$C_3$-alkyl, and $C_1$-$C_3$-haloalkyl, preferably unsubstituted;

$R^W$ is $C_1$-$C_3$-alkyl or $C_1$-$C_3$-haloalkyl, and the index m is 0 or 2; and the index n is 1.

Compounds of formula (I) have a moiety of formula (H)

(H)

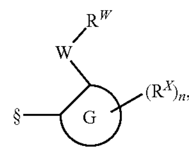

wherein all variables are defined as for formula (I) and wherein "S" means the connection to the bicyclic part of formula (I), i.e. the remainder of the molecule.

Preferably, groups H are selected from the following groups of formulae H-1 to H-144;

H-1

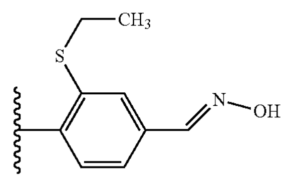

H-2

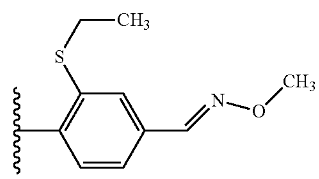

H-3

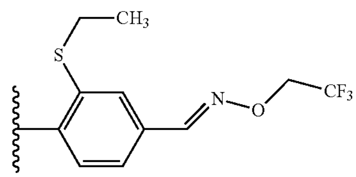

H-4

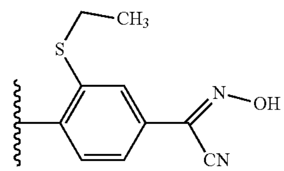

H-5

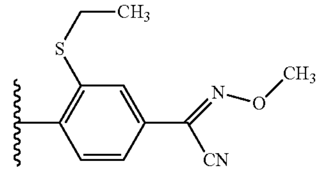

H-6

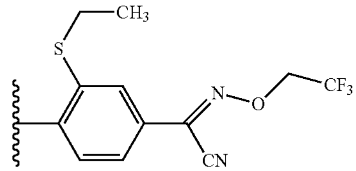

-continued
H-7
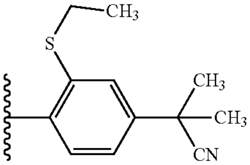
H-8
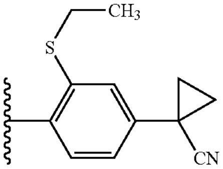
H-9
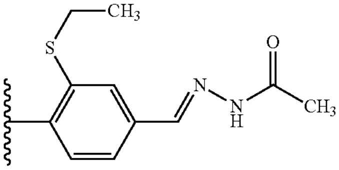
H-10
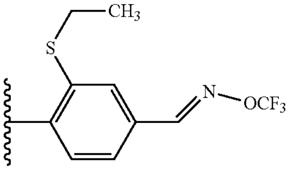
H-11
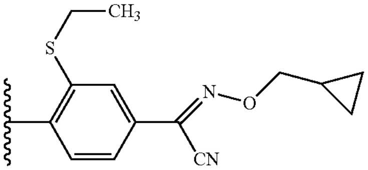
H-12
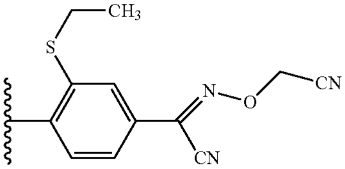
H-13
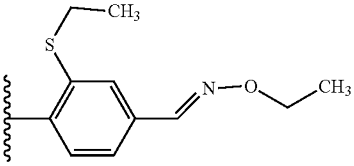
H-14
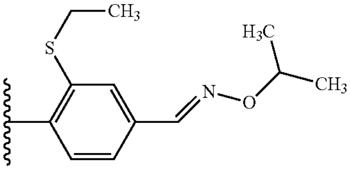
H-15
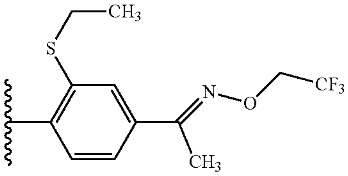
-continued
H-16
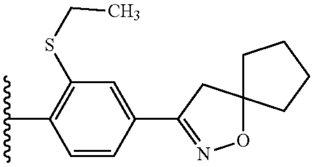
H-17
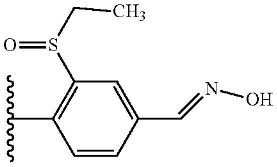
H-18
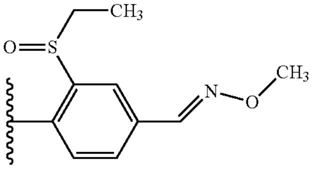
H-19
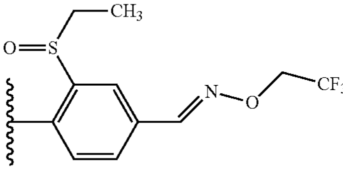
H-20
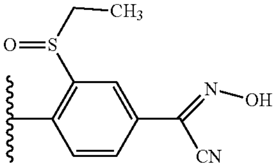
H-21
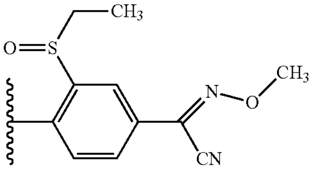
H-22
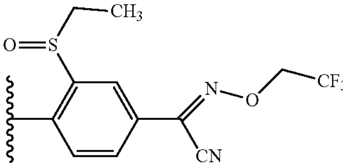
H-23
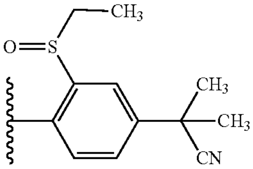
H-24
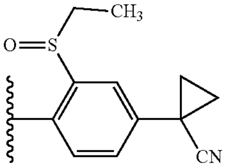

-continued
H-25
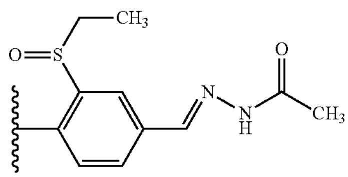
H-26
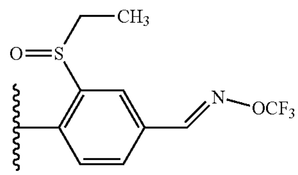
H-27
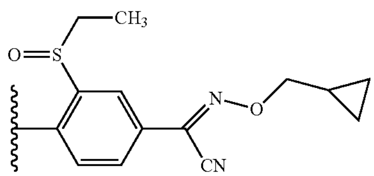
H-28
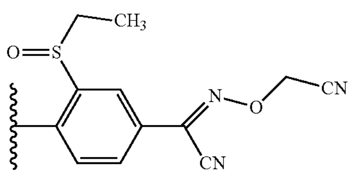
H-29
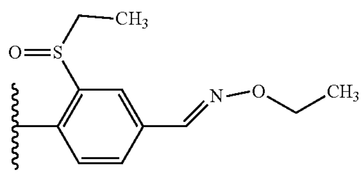
H-30
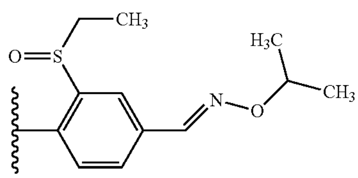
H-31
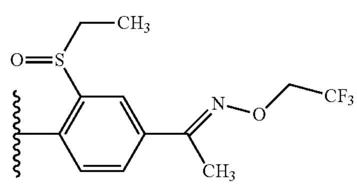
H-32
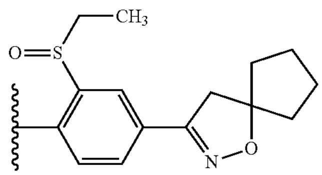
H-33
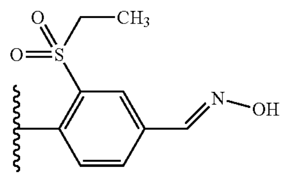
-continued
H-34
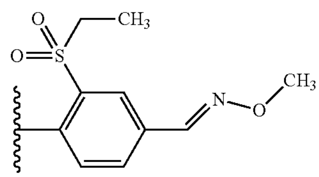
H-35
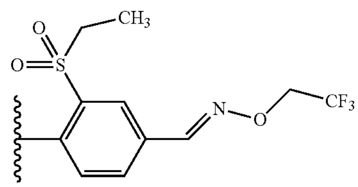
H-36
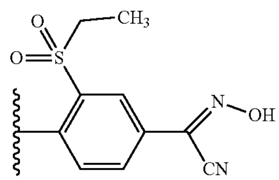
H-37
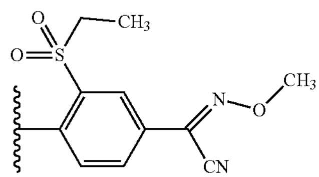
H-38
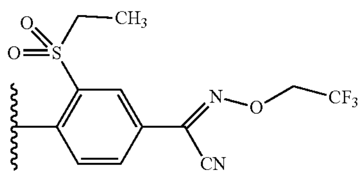
H-39
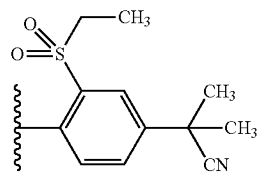
H-40
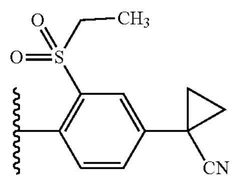
H-41
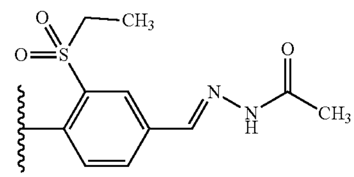

-continued
H-42
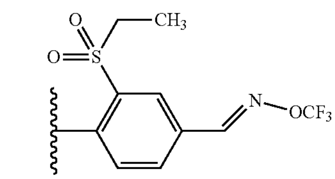
H-43
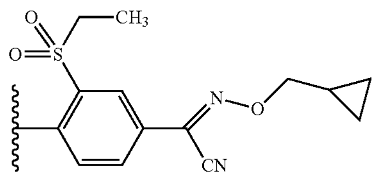
H-44
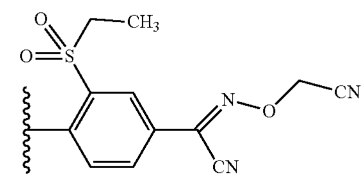
H-45
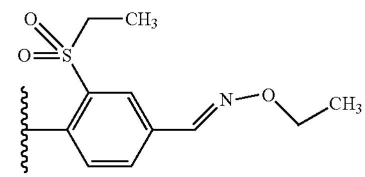
H-46
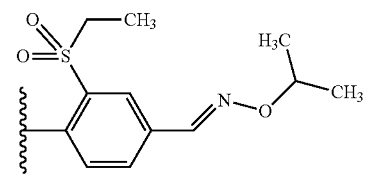
H-47
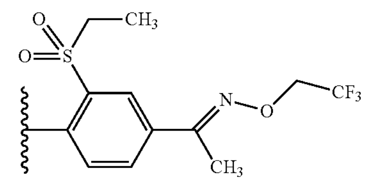
H-48
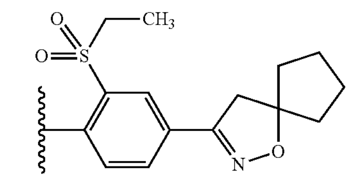
H-49
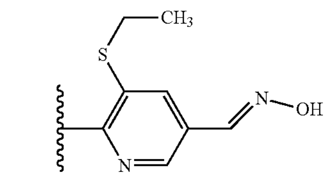
H-50
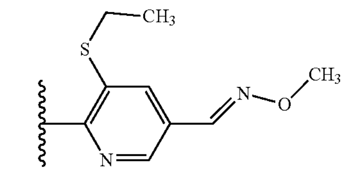
-continued
H-51
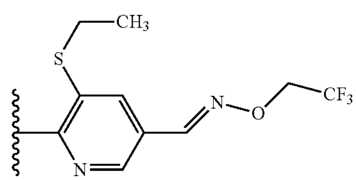
H-52
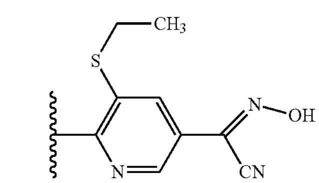
H-53
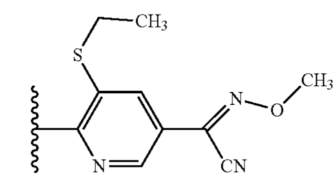
H-54
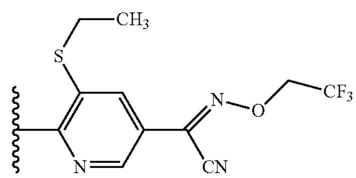
H-55
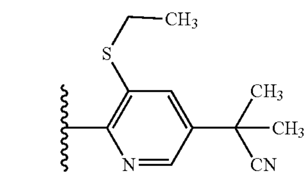
H-56
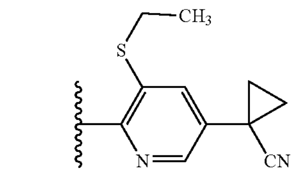
H-57
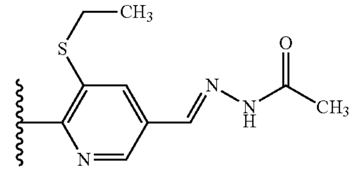
H-58
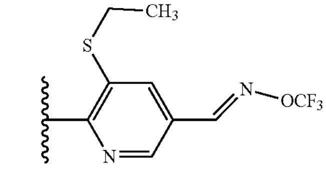
H-59
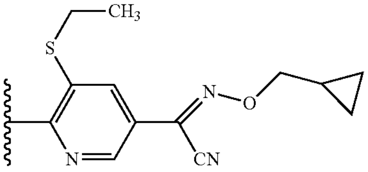

H-60
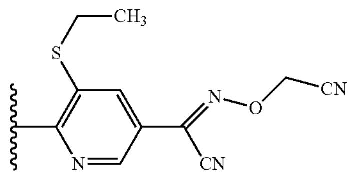
H-61
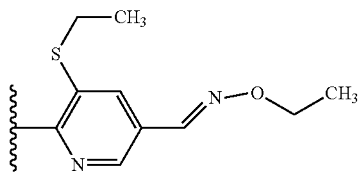
H-62
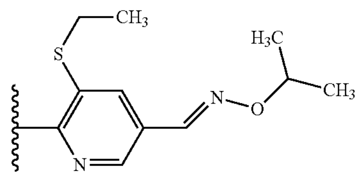
H-63
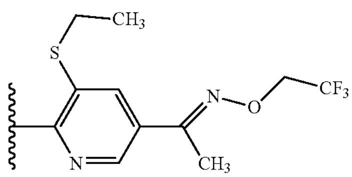
H-64
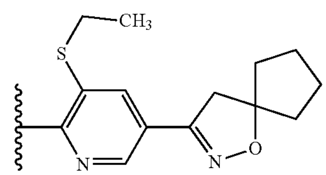
H-65
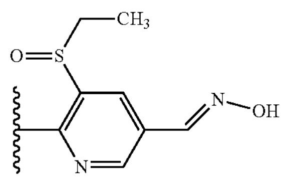
H-66
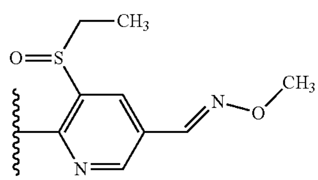
H-67
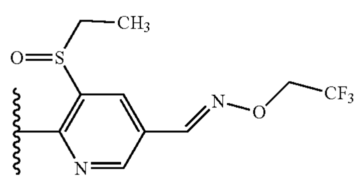
H-68
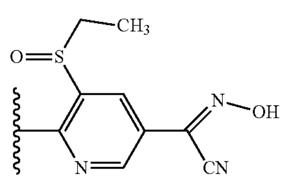
H-69
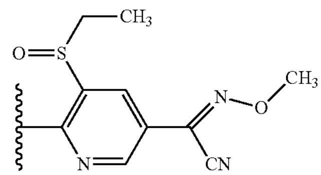
H-70
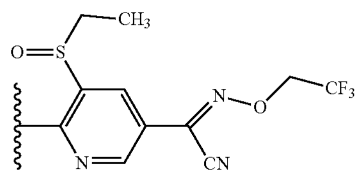
H-71
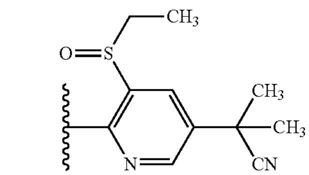
H-72
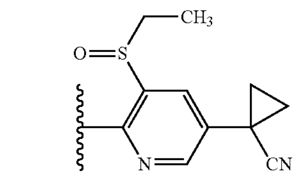
H-73
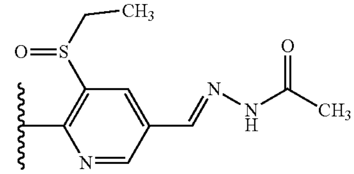
H-74
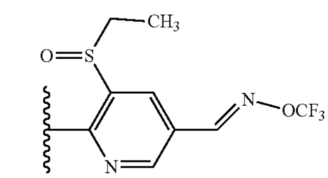
H-75
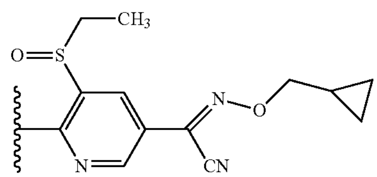
H-76
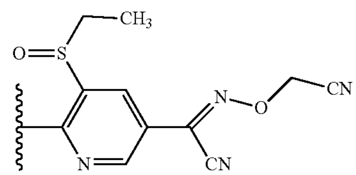
H-77
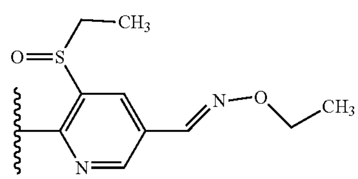

-continued
H-78
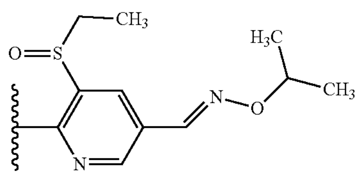
H-79
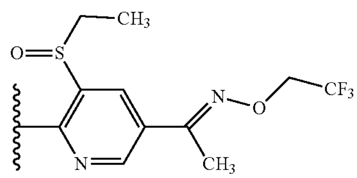
H-80
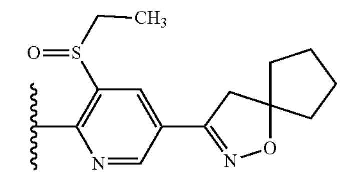
H-81
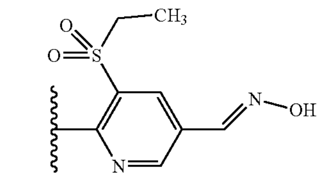
H-82
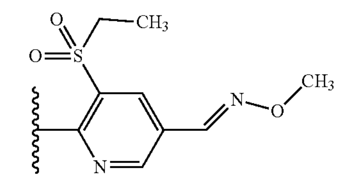
H-83
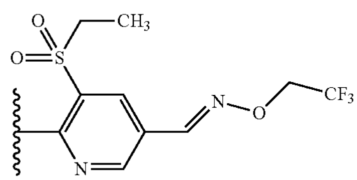
H-84
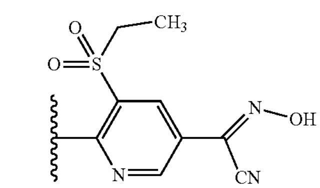
H-85
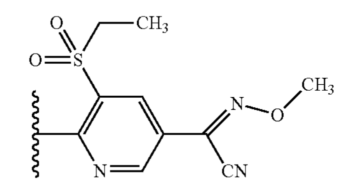
H-86
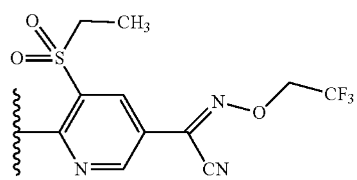
-continued
H-87
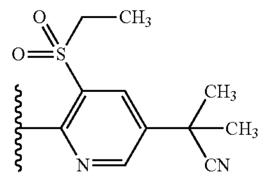
H-88
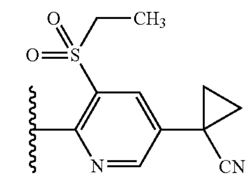
H-89
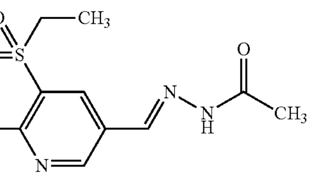
H-90
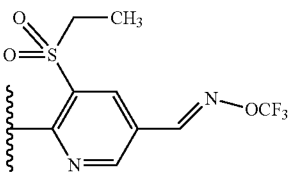
H-91
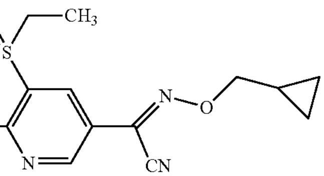
H-92
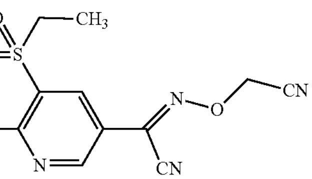
H-93
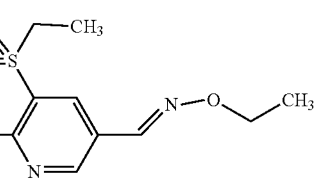
H-94
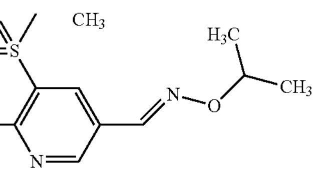
H-95
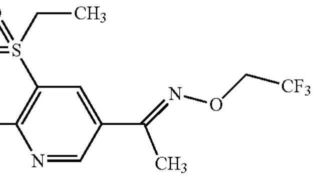

-continued
H-96
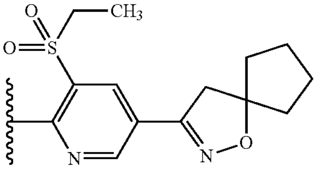
H-97
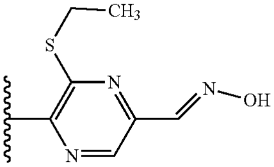
H-98
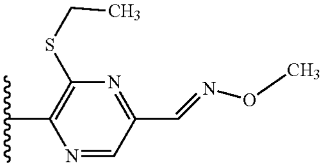
H-99
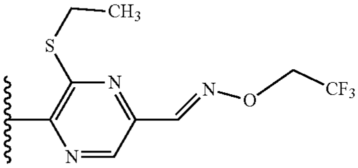
H-100
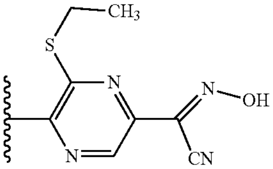
H-101
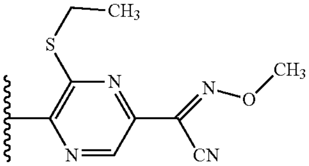
H-102
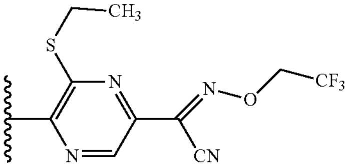
H-103
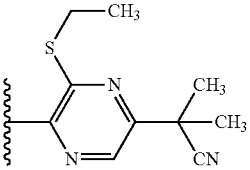
H-104
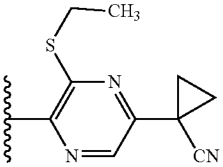
-continued
H-105
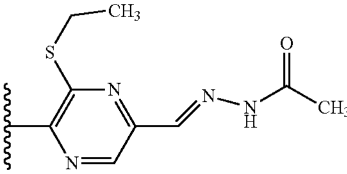
H-106
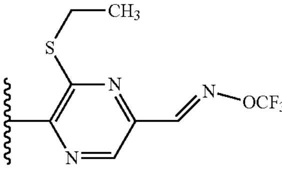
H-107
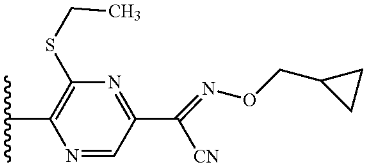
H-108
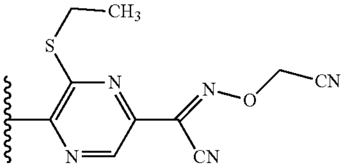
H-109
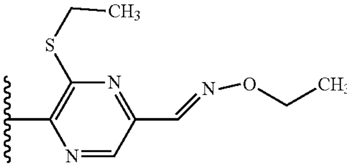
H-110
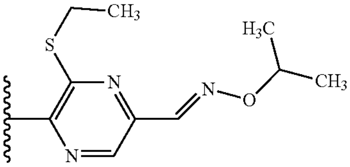
H-111
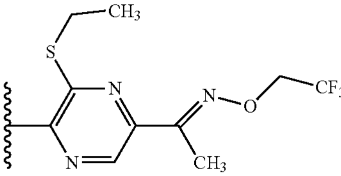
H-112
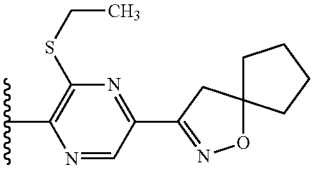
H-113
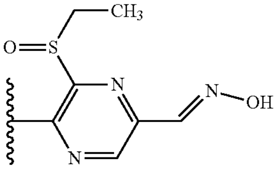

-continued
H-114
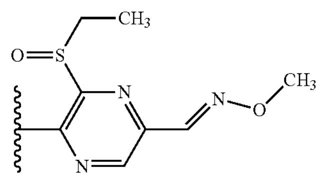
H-115
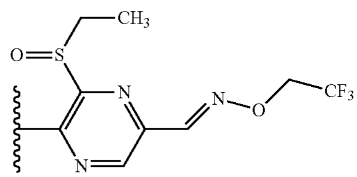
H-116
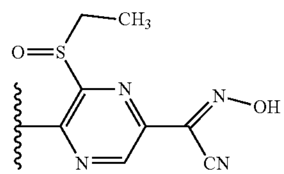
H-117
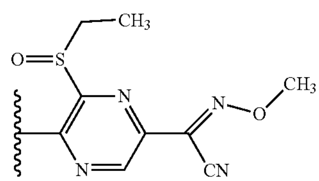
H-118
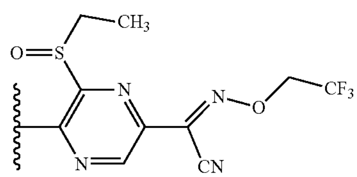
H-119
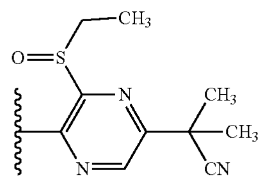
H-120
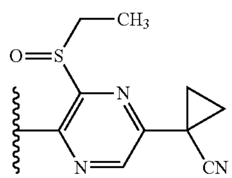
H-121
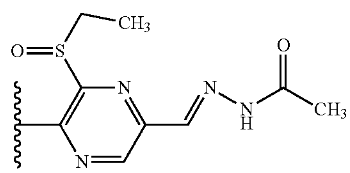
H-122
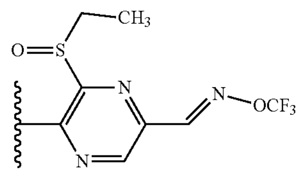
-continued
H-123
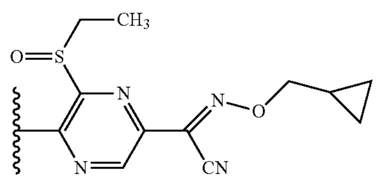
H-124
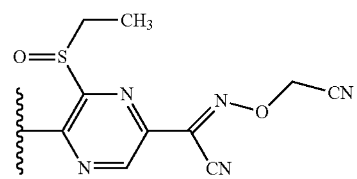
H-125
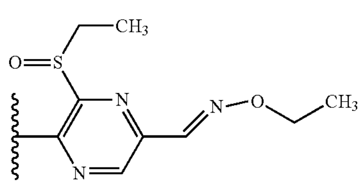
H-126
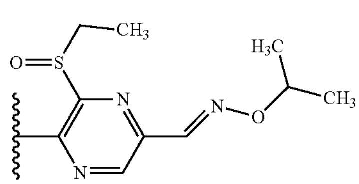
H-127
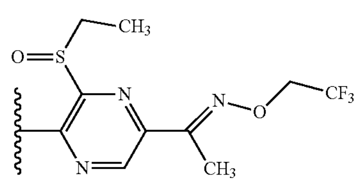
H-128
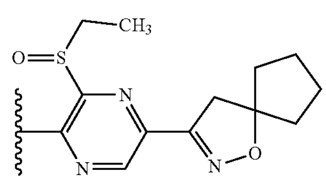
H-129
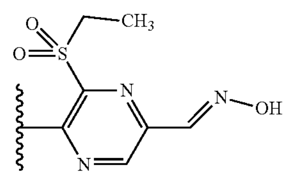
H-130
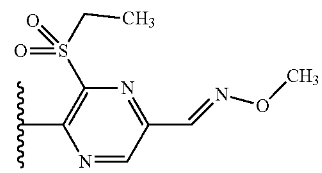
H-131
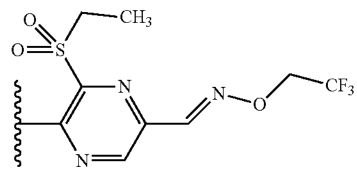

-continued
H-132
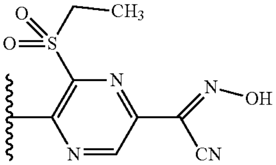
H-133
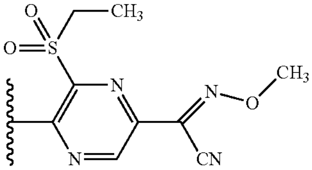
H-134
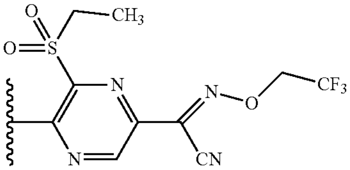
H-135
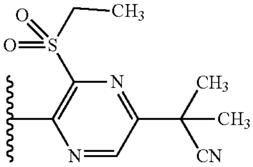
H-136
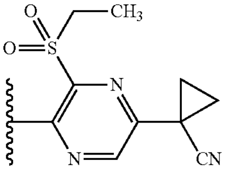
H-137
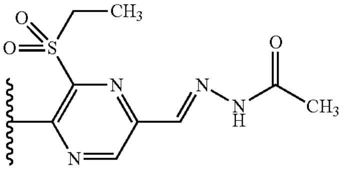
H-138
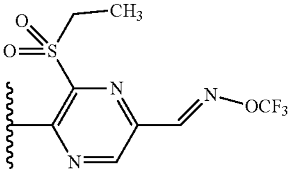
H-139
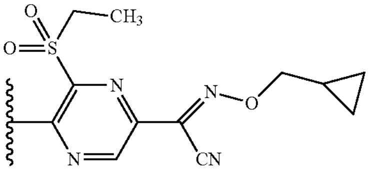
-continued
H-140
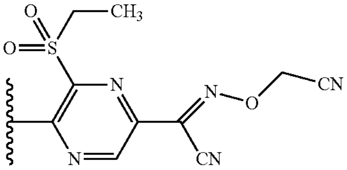
H-141
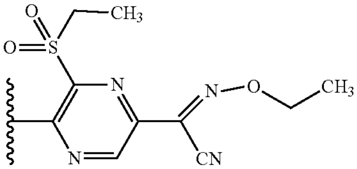
H-142
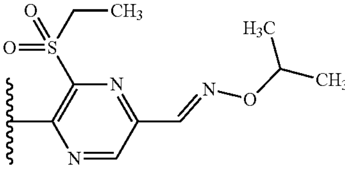
H-143
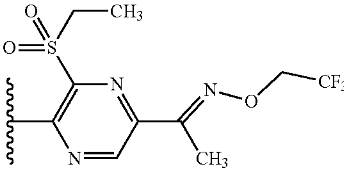
H-144
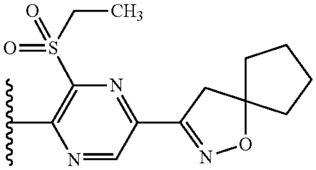
H-145
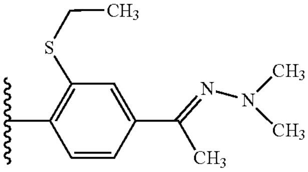
H-146
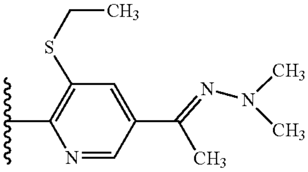
H-147
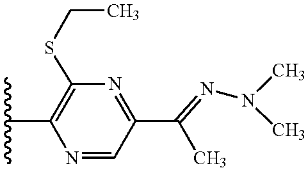

-continued

H-148

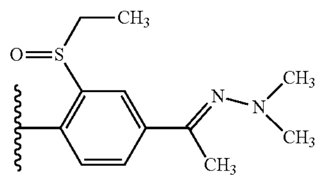

H-149

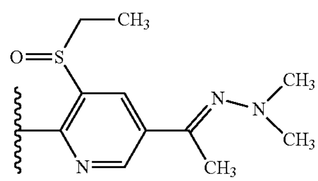

H-150

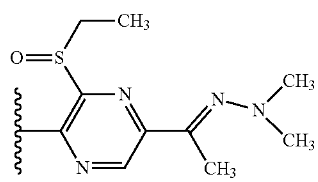

H-151

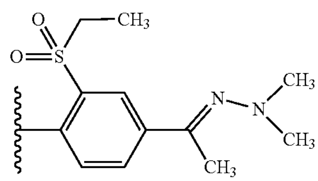

H-152

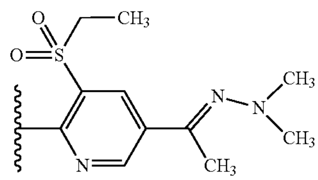

H-153

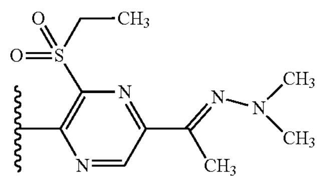

H-154

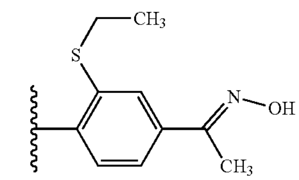

H-155

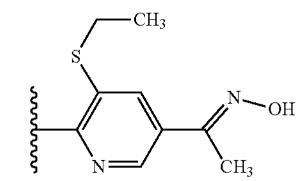

-continued

H-156

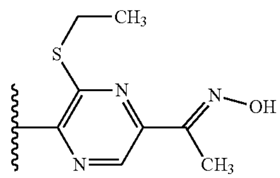

H-157

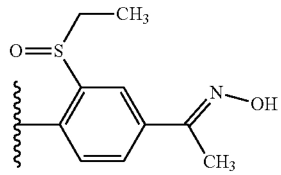

H-158

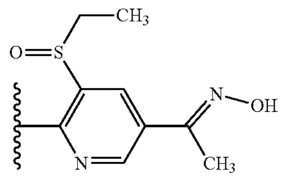

H-159

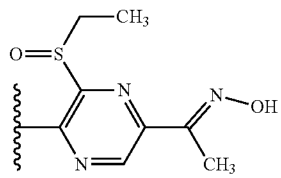

H-160

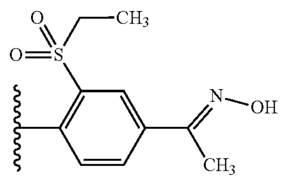

H-161

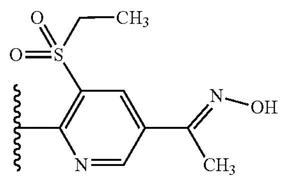

H-162

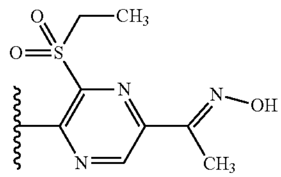

Typically, the moiety of formula (H) is of formula H-33 to H-41, H-81 to H-89, and H-129 to H-137, preferably of formula H-81 to H-89. In another embodiment, the moiety of formula (H) is of formula H-33 to H-48, H-81 to H-96, and H-129 to H-144. In another embodiment, the moiety of formula (H) is of formula H-33 to H-48, H-81 to H-96, H-129 to H-144, H-151 to H-153, and H-160 to H-162, preferably from H-33 to H-48, H-81 to H-88, H-91 to to H-96, H-151, H-152, H-160, and H-161, most preferably from H-33 to H-40, H-43 to H-48, H-81 to H-96, H-151, H-152, H-160, and H-161.

According to particularly preferred embodiment of the compound of formula (I), compounds of the invention are the compounds that are compiled in Tables 1 to Table 90.

Table 1. Compounds of formula I.A in which X is O, $R^3$ is $CH_3$, $R^6$ is H and the meaning for the combination of $R^1$, $R^2$ and the moiety of formula (H) for each individual compound corresponds in each case to one line of Table A.

Table 2. Compounds of formula I.A in which X is O, $R^3$ is $C_2H_5$, $R^6$ is H and the meaning for the combination of $R^1$, $R^2$ and the moiety of formula (H) for each individual compound corresponds in each case to one line of Table A.

Table 3. Compounds of formula I.A in which X is O, $R^3$ is c-$C_3H_5$, $R^6$ is H and the meaning for the combination of $R^1$, $R^2$ and moiety of formula (H) for each individual compound corresponds in each case to one line of Table A.

Table 4. Compounds of formula I.A in which X is O, $R^3$ is c-$C_3H_5$—$CH_2$—, $R^6$ is H and the meaning for the combination of $R^1$, $R^2$ and moiety of formula (H) for each individual compound corresponds in each case to one line of Table A.

Table 5. Compounds of formula I.A in which X is O, $R^3$ is $CH_2CF_3$, $R^6$ is H and the meaning for the combination of $R^1$, $R^2$ and the moiety of formula (H) for each individual compound corresponds in each case to one line of Table A.

Table 6. Compounds of formula I.A in which X is O, $R^3$ is $CH_3$, $R^6$ is $CH_3$ and the meaning for the combination of $R^1$, $R^2$ and the moiety of formula (H) for each individual compound corresponds in each case to one line of Table A.

Table 7. Compounds of formula I.A in which X is O, $R^3$ is $C_2H_5$, $R^6$ is $CH_3$ and the meaning for the combination of $R^1$, $R^2$ and the moiety of formula (H) for each individual compound corresponds in each case to one line of Table A.

Table 8. Compounds of formula I.A in which X is O, $R^3$ is c-$C_3H_5$, $R^6$ is $CH_3$ and the meaning for the combination of $R^1$, $R^2$ and the moiety of formula (H) for each individual compound corresponds in each case to one line of Table A.

Table 9. Compounds of formula I.A in which X is O, $R^3$ is c-$C_3H_5$—$CH_2$, $R^6$ is $CH_3$ and the meaning for the combination of $R^1$, $R^2$ and the moiety of formula (H) for each individual compound corresponds in each case to one line of Table A.

Table 10. Compounds of formula I.A in which X is O, $R^3$ is $CH_2CF_3$, $R^6$ is $CH_3$ and the meaning for the combination of $R^1$, $R^2$ and the moiety of formula (H) for each individual compound corresponds in each case to one line of Table A.

Table 11. Compounds of formula I.A in which X is S, $R^3$ is $CH_3$, $R^6$ is H and the meaning for the combination of $R^1$, $R^2$ and the moiety of formula (H) for each individual compound corresponds in each case to one line of Table A.

Table 12. Compounds of formula I.A in which X is S, $R^3$ is $C_2H_5$, $R^6$ is H and the meaning for the combination of $R^1$, $R^2$ and the moiety of formula (H) for each individual compound corresponds in each case to one line of Table A.

Table 13. Compounds of formula I.A in which X is S, $R^3$ is c-$C_3H_5$, $R^6$ is H and the meaning for the combination of $R^1$, $R^2$ and the moiety of formula (H) for each individual compound corresponds in each case to one line of Table A.

Table 14. Compounds of formula I.A in which X is S, $R^3$ is c-$C_3H_5$—$CH_2$—, $R^6$ is H and the meaning for the combination of $R^1$, $R^2$ and the moiety of formula (H) for each individual compound corresponds in each case to one line of Table A.

Table 15. Compounds of formula I.A in which X is S, $R^3$ is $CH_2CF_3$, $R^6$ is H and the meaning for the combination of $R^1$, $R^2$ and the moiety of formula (H) for each individual compound corresponds in each case to one line of Table A.

Table 16. Compounds of formula I.A in which X is S, $R^3$ is $CH_3$, $R^6$ is $CH_3$ and the meaning for the combination of $R^1$, $R^2$ and the moiety of formula (H) for each individual compound corresponds in each case to one line of Table A.

Table 17. Compounds of formula I.A in which X is S, $R^3$ is $C_2H_5$, $R^6$ is $CH_3$ and the meaning for the combination of $R^1$, $R^2$ and the moiety of formula (H) for each individual compound corresponds in each case to one line of Table A.

Table 18. Compounds of formula I.A in which X is S, $R^3$ is c-$C_3H_5$, $R^6$ is $CH_3$ and the meaning for the combination of $R^1$, $R^2$ and the moiety of formula (H) for each individual compound corresponds in each case to one line of Table A.

Table 19. Compounds of formula I.A in which X is S, $R^3$ is c-$C_3H_5$—$CH_2$—, $R^6$ is $CH_3$ and the meaning for the combination of $R^1$, $R^2$ and the moiety of formula (H) for each individual compound corresponds in each case to one line of Table A.

Table 20. Compounds of formula I.A in which X is S, $R^3$ is $CH_2CF_3$, $R^6$ is $CH_3$ and the meaning for the combination of $R^1$, $R^2$ and the moiety of formula (H) for each individual compound corresponds in each case to one line of Table A.

Table 21. Compounds of formula I.B in which X is O, $R^4$ is $CH_3$, $R^5$ is H and the meaning for the combination of $R^1$, $R^2$ and the moiety of formula (H) for each individual compound corresponds in each case to one line of Table A.

Table 22. Compounds of formula I.B in which X is O, $R^4$ is H, $R^5$ is H and the meaning for the combination of $R^1$, $R^2$ and the moiety of formula (H) for each individual compound corresponds in each case to one line of Table A.

Table 23. Compounds of formula I.B in which X is O, $R^4$ is c-$C_3H_5$, $R^5$ is H and the meaning for the combination of $R^1$, $R^2$ and moiety of formula (H) for each individual compound corresponds in each case to one line of Table A.

Table 24. Compounds of formula I.B in which X is O, $R^4$ is c-$C_3H_5$—$CH_2$—, $R^5$ is H and the meaning for the combination of $R^1$, $R^2$ and moiety of formula (H) for each individual compound corresponds in each case to one line of Table A.

Table 25. Compounds of formula I.B in which X is O, $R^4$ is $CH_2CF_3$, $R^5$ is H and the meaning for the combination of $R^1$, $R^2$ and the moiety of formula (H) for each individual compound corresponds in each case to one line of Table A.

Table 26. Compounds of formula I.B in which X is O, $R^4$ is $CH_3$, $R^5$ is $CH_3$ and the meaning for the combination of $R^1$, $R^2$ and the moiety of formula (H) for each individual compound corresponds in each case to one line of Table A.

Table 27. Compounds of formula I.B in which X is O, $R^4$ is H, $R^5$ is $CH_3$ and the meaning for the combination of $R^1$, $R^2$ and the moiety of formula (H) for each individual compound corresponds in each case to one line of Table A.

Table 28. Compounds of formula I.B in which X is O, $R^4$ is c-$C_3H_5$, $R^5$ is $CH_3$ and the meaning for the combination of $R^1$, $R^2$ and the moiety of formula (H) for each individual compound corresponds in each case to one line of Table A.

Table 29. Compounds of formula I.B in which X is O, $R^4$ is c-$C_3H_5$—$CH_2$, $R^5$ is $CH_3$ and the meaning for the combination of $R^1$, $R^2$ and the moiety of formula (H) for each individual compound corresponds in each case to one line of Table A.

Table 30. Compounds of formula I.B in which X is O, $R^4$ is $CH_2CF_3$, $R^5$ is $CH_3$ and the meaning for the combination of $R^1$, $R^2$ and the moiety of formula (H) for each individual compound corresponds in each case to one line of Table A.

Table 31. Compounds of formula I.B in which X is S, $R^4$ is $CH_3$, $R^5$ is H and the meaning for the combination of $R^1$, $R^2$ and the moiety of formula (H) for each individual compound corresponds in each case to one line of Table A.

Table 32. Compounds of formula I.B in which X is S, $R^4$ is H, $R^5$ is H and the meaning for the combination of $R^1$, $R^2$ and the moiety of formula (H) for each individual compound corresponds in each case to one line of Table A.

Table 33. Compounds of formula I.B in which X is S, $R^4$ is c-$C_3H_5$, $R^5$ is H and the meaning for the combination of $R^1$, $R^2$ and the moiety of formula (H) for each individual compound corresponds in each case to one line of Table A.

Table 34. Compounds of formula I.B in which X is S, $R^4$ is c-$C_3H_5$—$CH_2$—, $R^5$ is H and the meaning for the combination of $R^1$, $R^2$ and the moiety of formula (H) for each individual compound corresponds in each case to one line of Table A.

Table 35. Compounds of formula I.B in which X is S, $R^4$ is $CH_2CF_3$, $R^5$ is H and the meaning for the combination of $R^1$, $R^2$ and the moiety of formula (H) for each individual compound corresponds in each case to one line of Table A.

Table 36. Compounds of formula I.B in which X is S, $R^4$ is $CH_3$, $R^5$ is $CH_3$ and the meaning for the combination of $R^1$, $R^2$ and the moiety of formula (H) for each individual compound corresponds in each case to one line of Table A.

Table 37. Compounds of formula I.B in which X is S, $R^4$ is H, $R^5$ is $CH_3$ and the meaning for the combination of $R^1$, $R^2$ and the moiety of formula (H) for each individual compound corresponds in each case to one line of Table A.

Table 38. Compounds of formula I.B in which X is S, $R^4$ is c-$C_3H_5$, $R^5$ is $CH_3$ and the meaning for the combination of $R^1$, $R^2$ and the moiety of formula (H) for each individual compound corresponds in each case to one line of Table A.

Table 39. Compounds of formula I.B in which X is S, $R^4$ is c-$C_3H_5$—$CH_2$—, $R^5$ is $CH_3$ and the meaning for the combination of $R^1$, $R^2$ and the moiety of formula (H) for each individual compound corresponds in each case to one line of Table A.

Table 40. Compounds of formula I.B in which X is S, $R^4$ is $CH_2CF_3$, $R^5$ is $CH_3$ and the meaning for the combination of $R^1$, $R^2$ and the moiety of formula (H) for each individual compound corresponds in each case to one line of Table A.

Table 41. Compounds of formula I.C in which X is O, $R^3$ is $CH_3$, and the meaning for the combination of $R^1$, $R^2$ and the moiety of formula (H) for each individual compound corresponds in each case to one line of Table A.

Table 42. Compounds of formula I.C in which X is O, $R^3$ is $C_2H_5$, and the meaning for the combination of $R^1$, $R^2$ and the moiety of formula (H) for each individual compound corresponds in each case to one line of Table A.

Table 43. Compounds of formula I.C in which X is O, $R^3$ is c-$C_3H_5$, and the meaning for the combination of $R^1$, $R^2$ and moiety of formula (H) for each individual compound corresponds in each case to one line of Table A.

Table 44. Compounds of formula I.C in which X is O, $R^3$ is c-$C_3H_5$—$CH_2$—, and the meaning for the combination of $R^1$, $R^2$ and moiety of formula (H) for each individual compound corresponds in each case to one line of Table A.

Table 45. Compounds of formula I.C in which X is O, $R^3$ is $CH_2CF_3$, and the meaning for the combination of $R^1$, $R^2$ and the moiety of formula (H) for each individual compound corresponds in each case to one line of Table A.

Table 46. Compounds of formula I.C in which X is O, $R^3$ is $CH_3$, and the meaning for the combination of $R^1$, $R^2$ and the moiety of formula (H) for each individual compound corresponds in each case to one line of Table A.

Table 47. Compounds of formula I.C in which X is O, $R^3$ is $C_2H_5$, and the meaning for the combination of $R^1$, $R^2$ and the moiety of formula (H) for each individual compound corresponds in each case to one line of Table A.

Table 48. Compounds of formula I.C in which X is O, $R^3$ is c-$C_3H_5$, and the meaning for the combination of $R^1$, $R^2$ and the moiety of formula (H) for each individual compound corresponds in each case to one line of Table A.

Table 49. Compounds of formula I.C in which X is O, $R^3$ is c-$C_3H_5$—$CH_2$, and the meaning for the combination of $R^1$, $R^2$ and the moiety of formula (H) for each individual compound corresponds in each case to one line of Table A.

Table 50. Compounds of formula I.C in which X is O, $R^3$ is $CH_2CF_3$, and the meaning for the combination of $R^1$, $R^2$ and the moiety of formula (H) for each individual compound corresponds in each case to one line of Table A.

Table 51. Compounds of formula I.C in which X is O, $R^3$ is $CH_3$, and the meaning for the combination of $R^1$, $R^2$ and the moiety of formula (H) for each individual compound corresponds in each case to one line of Table A.

Table 52. Compounds of formula I.C in which X is O, $R^3$ is $C_2H_5$, and the meaning for the combination of $R^1$, $R^2$ and the moiety of formula (H) for each individual compound corresponds in each case to one line of Table A.

Table 53. Compounds of formula I.C in which X is O, $R^3$ is c-$C_3H_5$, and the meaning for the combination of $R^1$, $R^2$ and the moiety of formula (H) for each individual compound corresponds in each case to one line of Table A.

Table 54. Compounds of formula I.C in which X is O, $R^3$ is c-$C_3H_5$—$CH_2$, and the meaning for the combination of $R^1$, $R^2$ and the moiety of formula (H) for each individual compound corresponds in each case to one line of Table A.

Table 55. Compounds of formula I.C in which X is O, $R^3$ is $CH_2CF_3$, and the meaning for the combination of $R^1$, $R^2$ and the moiety of formula (H) for each individual compound corresponds in each case to one line of Table A.

Table 56. Compounds of formula I.C in which X is S, $R^3$ is $CH_3$, and the meaning for the combination of $R^1$, $R^2$ and the moiety of formula (H) for each individual compound corresponds in each case to one line of Table A.

Table 57. Compounds of formula I.C in which X is S, $R^3$ is $C_2H_5$, and the meaning for the combination of $R^1$, $R^2$ and the moiety of formula (H) for each individual compound corresponds in each case to one line of Table A.

Table 58. Compounds of formula I.C in which X is S, $R^3$ is c-$C_3H_5$, and the meaning for the combination of $R^1$, $R^2$ and the moiety of formula (H) for each individual compound corresponds in each case to one line of Table A.

Table 59. Compounds of formula I.C in which X is S, $R^3$ is c-$C_3H_5$—$CH_2$—, and the meaning for the combination of $R^1$, $R^2$ and the moiety of formula (H) for each individual compound corresponds in each case to one line of Table A.

Table 60. Compounds of formula I.C in which X is S, $R^3$ is $CH_2CF_3$, and the meaning for the combination of $R^1$, $R^2$ and the moiety of formula (H) for each individual compound corresponds in each case to one line of Table A.

Table 61. Compounds of formula I.C in which X is S, $R^3$ is $CH_3$, and the meaning for the combination of $R^1$, $R^2$ and the moiety of formula (H) for each individual compound corresponds in each case to one line of Table A.

Table 62. Compounds of formula I.C in which X is S, $R^3$ is $C_2H_5$, and the meaning for the combination of $R^1$, $R^2$ and the moiety of formula (H) for each individual compound corresponds in each case to one line of Table A.

Table 63. Compounds of formula I.C in which X is S, $R^3$ is c-$C_3H_5$, and the meaning for the combination of $R^1$, $R^2$ and the moiety of formula (H) for each individual compound corresponds in each case to one line of Table A.

Table 64. Compounds of formula I.C in which X is S, $R^3$ is c-$C_3H_5$—$CH_2$—, and the meaning for the combination of $R^1$, $R^2$ and the moiety of formula (H) for each individual compound corresponds in each case to one line of Table A.

Table 65. Compounds of formula I.C in which X is S, $R^3$ is $CH_2CF_3$, and the meaning for the combination of $R^1$, $R^2$ and the moiety of formula (H) for each individual compound corresponds in each case to one line of Table A.

Table 66. Compounds of formula I.C in which X is S, $R^3$ is $CH_3$, and the meaning for the combination of $R^1$, $R^2$ and the moiety of formula (H) for each individual compound corresponds in each case to one line of Table A.

Table 67. Compounds of formula I.C in which X is S, $R^3$ is $C_2H_5$, and the meaning for the combination of $R^1$, $R^2$ and the moiety of formula (H) for each individual compound corresponds in each case to one line of Table A.

Table 68. Compounds of formula I.C in which X is S, $R^3$ is c-$C_3H_5$, and the meaning for the combination of $R^1$, $R^2$ and the moiety of formula (H) for each individual compound corresponds in each case to one line of Table A.

Table 69. Compounds of formula I.C in which X is S, $R^3$ is c-$C_3H_5$—$CH_2$—, and the meaning for the combination of $R^1$, $R^2$ and the moiety of formula (H) for each individual compound corresponds in each case to one line of Table A.

Table 70. Compounds of formula I.C in which X is S, $R^3$ is $CH_2CF_3$, and the meaning for the combination of $R^1$, $R^2$ and the moiety of formula (H) for each individual compound corresponds in each case to one line of Table A.

TABLE A

| Combination of meanings for $R^1$, $R^2$, and moiety of formula (H) | | | |
|---|---|---|---|
| Line | $R^1$ | $R^2$ | H |
| A-1 | $CF_3$ | H | H-1 |
| A-2 | $CF_3$ | H | H-2 |
| A-3 | $CF_3$ | H | H-3 |
| A-4 | $CF_3$ | H | H-4 |
| A-5 | $CF_3$ | H | H-5 |
| A-6 | $CF_3$ | H | H-6 |
| A-7 | $CF_3$ | H | H-7 |
| A-8 | $CF_3$ | H | H-8 |
| A-9 | $CF_3$ | H | H-9 |
| A-10 | $CF_3$ | H | H-10 |
| A-11 | $CF_3$ | H | H-11 |
| A-12 | $CF_3$ | H | H-12 |
| A-13 | $CF_3$ | H | H-13 |
| A-14 | $CF_3$ | H | H-14 |
| A-15 | $CF_3$ | H | H-15 |
| A-16 | $CF_3$ | H | H-16 |
| A-17 | $CF_3$ | H | H-17 |
| A-18 | $CF_3$ | H | H-18 |
| A-19 | $CF_3$ | H | H-19 |
| A-20 | $CF_3$ | H | H-20 |
| A-21 | $CF_3$ | H | H-21 |
| A-22 | $CF_3$ | H | H-22 |
| A-23 | $CF_3$ | H | H-23 |
| A-24 | $CF_3$ | H | H-24 |
| A-25 | $CF_3$ | H | H-25 |
| A-26 | $CF_3$ | H | H-26 |
| A-27 | $CF_3$ | H | H-27 |
| A-28 | $CF_3$ | H | H-28 |
| A-29 | $CF_3$ | H | H-29 |
| A-30 | $CF_3$ | H | H-30 |
| A-31 | $CF_3$ | H | H-31 |
| A-32 | $CF_3$ | H | H-32 |
| A-33 | $CF_3$ | H | H-33 |
| A-34 | $CF_3$ | H | H-34 |
| A-35 | $CF_3$ | H | H-35 |
| A-36 | $CF_3$ | H | H-36 |
| A-37 | $CF_3$ | H | H-37 |
| A-38 | $CF_3$ | H | H-38 |
| A-39 | $CF_3$ | H | H-39 |
| A-40 | $CF_3$ | H | H-40 |
| A-41 | $CF_3$ | H | H-41 |
| A-42 | $CF_3$ | H | H-42 |
| A-43 | $CF_3$ | H | H-43 |
| A-44 | $CF_3$ | H | H-44 |
| A-45 | $CF_3$ | H | H-45 |
| A-46 | $CF_3$ | H | H-46 |

TABLE A-continued

| Combination of meanings for $R^1$, $R^2$, and moiety of formula (H) | | | |
|---|---|---|---|
| Line | $R^1$ | $R^2$ | H |
| A-47 | $CF_3$ | H | H-47 |
| A-48 | $CF_3$ | H | H-48 |
| A-49 | $CF_3$ | H | H-49 |
| A-50 | $CF_3$ | H | H-50 |
| A-51 | $CF_3$ | H | H-51 |
| A-52 | $CF_3$ | H | H-52 |
| A-53 | $CF_3$ | H | H-53 |
| A-54 | $CF_3$ | H | H-54 |
| A-55 | $CF_3$ | H | H-55 |
| A-56 | $CF_3$ | H | H-56 |
| A-57 | $CF_3$ | H | H-57 |
| A-58 | $CF_3$ | H | H-58 |
| A-59 | $CF_3$ | H | H-59 |
| A-60 | $CF_3$ | H | H-60 |
| A-61 | $CF_3$ | H | H-61 |
| A-62 | $CF_3$ | H | H-62 |
| A-63 | $CF_3$ | H | H-63 |
| A-64 | $CF_3$ | H | H-64 |
| A-65 | $CF_3$ | H | H-65 |
| A-66 | $CF_3$ | H | H-66 |
| A-67 | $CF_3$ | H | H-67 |
| A-68 | $CF_3$ | H | H-68 |
| A-69 | $CF_3$ | H | H-69 |
| A-70 | $CF_3$ | H | H-70 |
| A-71 | $CF_3$ | H | H-71 |
| A-72 | $CF_3$ | H | H-72 |
| A-73 | $CF_3$ | H | H-73 |
| A-74 | $CF_3$ | H | H-74 |
| A-75 | $CF_3$ | H | H-75 |
| A-76 | $CF_3$ | H | H-76 |
| A-77 | $CF_3$ | H | H-77 |
| A-78 | $CF_3$ | H | H-78 |
| A-79 | $CF_3$ | H | H-79 |
| A-80 | $CF_3$ | H | H-80 |
| A-81 | $CF_3$ | H | H-81 |
| A-82 | $CF_3$ | H | H-82 |
| A-83 | $CF_3$ | H | H-83 |
| A-84 | $CF_3$ | H | H-84 |
| A-85 | $CF_3$ | H | H-85 |
| A-86 | $CF_3$ | H | H-86 |
| A-87 | $CF_3$ | H | H-87 |
| A-88 | $CF_3$ | H | H-88 |
| A-89 | $CF_3$ | H | H-89 |
| A-90 | $CF_3$ | H | H-90 |
| A-91 | $CF_3$ | H | H-91 |
| A-92 | $CF_3$ | H | H-92 |
| A-93 | $CF_3$ | H | H-93 |
| A-94 | $CF_3$ | H | H-94 |
| A-95 | $CF_3$ | H | H-95 |
| A-96 | $CF_3$ | H | H-96 |
| A-97 | $CF_3$ | H | H-97 |
| A-98 | $CF_3$ | H | H-98 |
| A-99 | $CF_3$ | H | H-99 |
| A-100 | $CF_3$ | H | H-100 |
| A-101 | $CF_3$ | H | H-101 |
| A-102 | $CF_3$ | H | H-102 |
| A-103 | $CF_3$ | H | H-103 |
| A-104 | $CF_3$ | H | H-104 |
| A-105 | $CF_3$ | H | H-105 |
| A-106 | $CF_3$ | H | H-106 |
| A-107 | $CF_3$ | H | H-107 |
| A-108 | $CF_3$ | H | H-108 |
| A-109 | $CF_3$ | H | H-109 |
| A-110 | $CF_3$ | H | H-110 |
| A-111 | $CF_3$ | H | H-111 |
| A-112 | $CF_3$ | H | H-112 |
| A-113 | $CF_3$ | H | H-113 |
| A-114 | $CF_3$ | H | H-114 |
| A-115 | $CF_3$ | H | H-115 |
| A-116 | $CF_3$ | H | H-116 |
| A-117 | $CF_3$ | H | H-117 |
| A-118 | $CF_3$ | H | H-118 |
| A-119 | $CF_3$ | H | H-119 |
| A-120 | $CF_3$ | H | H-120 |
| A-121 | $CF_3$ | H | H-121 |

TABLE A-continued

| Combination of meanings for $R^1$, $R^2$, and moiety of formula (H) | | | |
|---|---|---|---|
| Line | $R^1$ | $R^2$ | H |
| A-122 | $CF_3$ | H | H-122 |
| A-123 | $CF_3$ | H | H-123 |
| A-124 | $CF_3$ | H | H-124 |
| A-125 | $CF_3$ | H | H-125 |
| A-126 | $CF_3$ | H | H-126 |
| A-127 | $CF_3$ | H | H-127 |
| A-128 | $CF_3$ | H | H-128 |
| A-129 | $CF_3$ | H | H-129 |
| A-130 | $CF_3$ | H | H-130 |
| A-131 | $CF_3$ | H | H-131 |
| A-132 | $CF_3$ | H | H-132 |
| A-133 | $CF_3$ | H | H-133 |
| A-134 | $CF_3$ | H | H-134 |
| A-135 | $CF_3$ | H | H-135 |
| A-136 | $CF_3$ | H | H-136 |
| A-137 | $CF_3$ | H | H-137 |
| A-138 | $CF_3$ | H | H-138 |
| A-139 | $CF_3$ | H | H-139 |
| A-140 | $CF_3$ | H | H-140 |
| A-141 | $CF_3$ | H | H-141 |
| A-142 | $CF_3$ | H | H-142 |
| A-143 | $CF_3$ | H | H-143 |
| A-144 | $CF_3$ | H | H-144 |
| A-145 | $CF_3$ | H | H-145 |
| A-146 | $CF_3$ | H | H-146 |
| A-147 | $CF_3$ | H | H-147 |
| A-148 | $CF_3$ | H | H-148 |
| A-149 | $CF_3$ | H | H-149 |
| A-150 | $CF_3$ | H | H-150 |
| A-151 | $CF_3$ | H | H-151 |
| A-152 | $CF_3$ | H | H-152 |
| A-153 | $CF_3$ | H | H-153 |
| A-154 | $CF_3$ | H | H-154 |
| A-155 | $CF_3$ | H | H-155 |
| A-156 | $CF_3$ | H | H-156 |
| A-157 | $CF_3$ | H | H-157 |
| A-158 | $CF_3$ | H | H-158 |
| A-159 | $CF_3$ | H | H-159 |
| A-160 | $CF_3$ | H | H-160 |
| A-161 | $CF_3$ | H | H-161 |
| A-162 | $CF_3$ | H | H-162 |
| A-163 | $C_2F_5$ | H | H-1 |
| A-164 | $C_2F_5$ | H | H-2 |
| A-165 | $C_2F_5$ | H | H-3 |
| A-166 | $C_2F_5$ | H | H-4 |
| A-167 | $C_2F_5$ | H | H-5 |
| A-168 | $C_2F_5$ | H | H-6 |
| A-169 | $C_2F_5$ | H | H-7 |
| A-170 | $C_2F_5$ | H | H-8 |
| A-171 | $C_2F_5$ | H | H-9 |
| A-172 | $C_2F_5$ | H | H-10 |
| A-173 | $C_2F_5$ | H | H-11 |
| A-174 | $C_2F_5$ | H | H-12 |
| A-175 | $C_2F_5$ | H | H-13 |
| A-176 | $C_2F_5$ | H | H-14 |
| A-177 | $C_2F_5$ | H | H-15 |
| A-178 | $C_2F_5$ | H | H-16 |
| A-179 | $C_2F_5$ | H | H-17 |
| A-180 | $C_2F_5$ | H | H-18 |
| A-181 | $C_2F_5$ | H | H-19 |
| A-182 | $C_2F_5$ | H | H-20 |
| A-183 | $C_2F_5$ | H | H-21 |
| A-184 | $C_2F_5$ | H | H-22 |
| A-185 | $C_2F_5$ | H | H-23 |
| A-186 | $C_2F_5$ | H | H-24 |
| A-187 | $C_2F_5$ | H | H-25 |
| A-188 | $C_2F_5$ | H | H-26 |
| A-189 | $C_2F_5$ | H | H-27 |
| A-190 | $C_2F_5$ | H | H-28 |
| A-191 | $C_2F_5$ | H | H-29 |
| A-192 | $C_2F_5$ | H | H-30 |
| A-193 | $C_2F_5$ | H | H-31 |
| A-194 | $C_2F_5$ | H | H-32 |
| A-195 | $C_2F_5$ | H | H-33 |
| A-196 | $C_2F_5$ | H | H-34 |

TABLE A-continued

| Combination of meanings for $R^1$, $R^2$, and moiety of formula (H) | | | |
|---|---|---|---|
| Line | $R^1$ | $R^2$ | H |
| A-197 | $C_2F_5$ | H | H-35 |
| A-198 | $C_2F_5$ | H | H-36 |
| A-199 | $C_2F_5$ | H | H-37 |
| A-200 | $C_2F_5$ | H | H-38 |
| A-201 | $C_2F_5$ | H | H-39 |
| A-202 | $C_2F_5$ | H | H-40 |
| A-203 | $C_2F_5$ | H | H-41 |
| A-204 | $C_2F_5$ | H | H-42 |
| A-205 | $C_2F_5$ | H | H-43 |
| A-206 | $C_2F_5$ | H | H-44 |
| A-207 | $C_2F_5$ | H | H-45 |
| A-208 | $C_2F_5$ | H | H-46 |
| A-209 | $C_2F_5$ | H | H-47 |
| A-210 | $C_2F_5$ | H | H-48 |
| A-211 | $C_2F_5$ | H | H-49 |
| A-212 | $C_2F_5$ | H | H-50 |
| A-213 | $C_2F_5$ | H | H-51 |
| A-214 | $C_2F_5$ | H | H-52 |
| A-215 | $C_2F_5$ | H | H-53 |
| A-216 | $C_2F_5$ | H | H-54 |
| A-217 | $C_2F_5$ | H | H-55 |
| A-218 | $C_2F_5$ | H | H-56 |
| A-219 | $C_2F_5$ | H | H-57 |
| A-220 | $C_2F_5$ | H | H-58 |
| A-221 | $C_2F_5$ | H | H-59 |
| A-222 | $C_2F_5$ | H | H-60 |
| A-223 | $C_2F_5$ | H | H-61 |
| A-224 | $C_2F_5$ | H | H-62 |
| A-225 | $C_2F_5$ | H | H-63 |
| A-226 | $C_2F_5$ | H | H-64 |
| A-227 | $C_2F_5$ | H | H-65 |
| A-228 | $C_2F_5$ | H | H-66 |
| A-229 | $C_2F_5$ | H | H-67 |
| A-230 | $C_2F_5$ | H | H-68 |
| A-231 | $C_2F_5$ | H | H-69 |
| A-232 | $C_2F_5$ | H | H-70 |
| A-233 | $C_2F_5$ | H | H-71 |
| A-234 | $C_2F_5$ | H | H-72 |
| A-235 | $C_2F_5$ | H | H-73 |
| A-236 | $C_2F_5$ | H | H-74 |
| A-237 | $C_2F_5$ | H | H-75 |
| A-238 | $C_2F_5$ | H | H-76 |
| A-239 | $C_2F_5$ | H | H-77 |
| A-240 | $C_2F_5$ | H | H-78 |
| A-241 | $C_2F_5$ | H | H-79 |
| A-242 | $C_2F_5$ | H | H-80 |
| A-243 | $C_2F_5$ | H | H-81 |
| A-244 | $C_2F_5$ | H | H-82 |
| A-245 | $C_2F_5$ | H | H-83 |
| A-246 | $C_2F_5$ | H | H-84 |
| A-247 | $C_2F_5$ | H | H-85 |
| A-248 | $C_2F_5$ | H | H-86 |
| A-249 | $C_2F_5$ | H | H-87 |
| A-250 | $C_2F_5$ | H | H-88 |
| A-251 | $C_2F_5$ | H | H-89 |
| A-252 | $C_2F_5$ | H | H-90 |
| A-253 | $C_2F_5$ | H | H-91 |
| A-254 | $C_2F_5$ | H | H-92 |
| A-255 | $C_2F_5$ | H | H-93 |
| A-256 | $C_2F_5$ | H | H-94 |
| A-257 | $C_2F_5$ | H | H-95 |
| A-258 | $C_2F_5$ | H | H-96 |
| A-259 | $C_2F_5$ | H | H-97 |
| A-260 | $C_2F_5$ | H | H-98 |
| A-261 | $C_2F_5$ | H | H-99 |
| A-262 | $C_2F_5$ | H | H-100 |
| A-263 | $C_2F_5$ | H | H-101 |
| A-264 | $C_2F_5$ | H | H-102 |
| A-265 | $C_2F_5$ | H | H-103 |
| A-266 | $C_2F_5$ | H | H-104 |
| A-267 | $C_2F_5$ | H | H-105 |
| A-268 | $C_2F_5$ | H | H-106 |
| A-269 | $C_2F_5$ | H | H-107 |
| A-270 | $C_2F_5$ | H | H-108 |
| A-271 | $C_2F_5$ | H | H-109 |

TABLE A-continued

| Line | $R^1$ | $R^2$ | H |
|---|---|---|---|
| Combination of meanings for $R^1$, $R^2$, and moiety of formula (H) | | | |
| A-272 | $C_2F_5$ | H | H-110 |
| A-273 | $C_2F_5$ | H | H-111 |
| A-274 | $C_2F_5$ | H | H-112 |
| A-275 | $C_2F_5$ | H | H-113 |
| A-276 | $C_2F_5$ | H | H-114 |
| A-277 | $C_2F_5$ | H | H-115 |
| A-278 | $C_2F_5$ | H | H-116 |
| A-279 | $C_2F_5$ | H | H-117 |
| A-280 | $C_2F_5$ | H | H-118 |
| A-281 | $C_2F_5$ | H | H-119 |
| A-282 | $C_2F_5$ | H | H-120 |
| A-283 | $C_2F_5$ | H | H-121 |
| A-284 | $C_2F_5$ | H | H-122 |
| A-285 | $C_2F_5$ | H | H-123 |
| A-286 | $C_2F_5$ | H | H-124 |
| A-287 | $C_2F_5$ | H | H-125 |
| A-288 | $C_2F_5$ | H | H-126 |
| A-289 | $C_2F_5$ | H | H-127 |
| A-290 | $C_2F_5$ | H | H-128 |
| A-291 | $C_2F_5$ | H | H-129 |
| A-292 | $C_2F_5$ | H | H-130 |
| A-293 | $C_2F_5$ | H | H-131 |
| A-294 | $C_2F_5$ | H | H-132 |
| A-295 | $C_2F_5$ | H | H-133 |
| A-296 | $C_2F_5$ | H | H-134 |
| A-297 | $C_2F_5$ | \|? | H-135 |
| A-298 | $C_2F_5$ | H | H-136 |
| A-299 | $C_2F_5$ | H | H-137 |
| A-300 | $C_2F_5$ | H | H-138 |
| A-301 | $C_2F_5$ | H | H-139 |
| A-302 | $C_2F_5$ | H | H-140 |
| A-303 | $C_2F_5$ | H | H-141 |
| A-304 | $C_2F_5$ | H | H-142 |
| A-305 | $C_2F_5$ | H | H-143 |
| A-306 | $C_2F_5$ | H | H-144 |
| A-307 | $C_2F_5$ | H | H-145 |
| A-308 | $C_2F_5$ | H | H-146 |
| A-309 | $C_2F_5$ | H | H-147 |
| A-310 | $C_2F_5$ | H | H-148 |
| A-311 | $C_2F_5$ | H | H-149 |
| A-312 | $C_2F_5$ | H | H-150 |
| A-313 | $C_2F_5$ | H | H-151 |
| A-314 | $C_2F_5$ | H | H-152 |
| A-315 | $C_2F_5$ | H | H-153 |
| A-316 | $C_2F_5$ | H | H-154 |
| A-317 | $C_2F_5$ | H | H-155 |
| A-318 | $C_2F_5$ | H | H-156 |
| A-319 | $C_2F_5$ | H | H-157 |
| A-320 | $C_2F_5$ | H | H-158 |
| A-321 | $C_2F_5$ | H | H-159 |
| A-322 | $C_2F_5$ | H | H-160 |
| A-323 | $C_2F_5$ | H | H-161 |
| A-324 | $C_2F_5$ | H | H-162 |
| A-325 | $CF(CF_3)_2$ | H | H-1 |
| A-326 | $CF(CF_3)_2$ | H | H-2 |
| A-327 | $CF(CF_3)_2$ | H | H-3 |
| A-328 | $CF(CF_3)_2$ | H | H-4 |
| A-329 | $CF(CF_3)_2$ | H | H-5 |
| A-330 | $CF(CF_3)_2$ | H | H-6 |
| A-331 | $CF(CF_3)_2$ | H | H-7 |
| A-332 | $CF(CF_3)_2$ | H | H-8 |
| A-333 | $CF(CF_3)_2$ | H | H-9 |
| A-334 | $CF(CF_3)_2$ | H | H-10 |
| A-335 | $CF(CF_3)_2$ | H | H-11 |
| A-336 | $CF(CF_3)_2$ | H | H-12 |
| A-337 | $CF(CF_3)_2$ | H | H-13 |
| A-338 | $CF(CF_3)_2$ | H | H-14 |
| A-339 | $CF(CF_3)_2$ | H | H-15 |
| A-340 | $CF(CF_3)_2$ | H | H-16 |
| A-341 | $CF(CF_3)_2$ | H | H-17 |
| A-342 | $CF(CF_3)_2$ | H | H-18 |
| A-343 | $CF(CF_3)_2$ | H | H-19 |
| A-344 | $CF(CF_3)_2$ | H | H-20 |
| A-345 | $CF(CF_3)_2$ | H | H-21 |
| A-346 | $CF(CF_3)_2$ | H | H-22 |

TABLE A-continued

| Line | $R^1$ | $R^2$ | H |
|---|---|---|---|
| Combination of meanings for $R^1$, $R^2$, and moiety of formula (H) | | | |
| A-347 | $CF(CF_3)_2$ | H | H-23 |
| A-348 | $CF(CF_3)_2$ | H | H-24 |
| A-349 | $CF(CF_3)_2$ | H | H-25 |
| A-350 | $CF(CF_3)_2$ | H | H-26 |
| A-351 | $CF(CF_3)_2$ | H | H-27 |
| A-352 | $CF(CF_3)_2$ | H | H-28 |
| A-353 | $CF(CF_3)_2$ | H | H-29 |
| A-354 | $CF(CF_3)_2$ | H | H-30 |
| A-355 | $CF(CF_3)_2$ | H | H-31 |
| A-356 | $CF(CF_3)_2$ | H | H-32 |
| A-357 | $CF(CF_3)_2$ | H | H-33 |
| A-358 | $CF(CF_3)_2$ | H | H-34 |
| A-359 | $CF(CF_3)_2$ | H | H-35 |
| A-360 | $CF(CF_3)_2$ | H | H-36 |
| A-361 | $CF(CF_3)_2$ | H | H-37 |
| A-362 | $CF(CF_3)_2$ | H | H-38 |
| A-363 | $CF(CF_3)_2$ | H | H-39 |
| A-364 | $CF(CF_3)_2$ | H | H-40 |
| A-365 | $CF(CF_3)_2$ | H | H-41 |
| A-366 | $CF(CF_3)_2$ | H | H-42 |
| A-367 | $CF(CF_3)_2$ | H | H-43 |
| A-368 | $CF(CF_3)_2$ | H | H-44 |
| A-369 | $CF(CF_3)_2$ | H | H-45 |
| A-370 | $CF(CF_3)_2$ | H | H-46 |
| A-371 | $CF(CF_3)_2$ | H | H-47 |
| A-372 | $CF(CF_3)_2$ | H | H-48 |
| A-373 | $CF(CF_3)_2$ | H | H-49 |
| A-374 | $CF(CF_3)_2$ | H | H-50 |
| A-375 | $CF(CF_3)_2$ | H | H-51 |
| A-376 | $CF(CF_3)_2$ | H | H-52 |
| A-377 | $CF(CF_3)_2$ | H | H-53 |
| A-378 | $CF(CF_3)_2$ | H | H-54 |
| A-379 | $CF(CF_3)_2$ | H | H-55 |
| A-380 | $CF(CF_3)_2$ | H | H-56 |
| A-381 | $CF(CF_3)_2$ | H | H-57 |
| A-382 | $CF(CF_3)_2$ | H | H-58 |
| A-383 | $CF(CF_3)_2$ | H | H-59 |
| A-384 | $CF(CF_3)_2$ | H | H-60 |
| A-385 | $CF(CF_3)_2$ | H | H-61 |
| A-386 | $CF(CF_3)_2$ | H | H-62 |
| A-387 | $CF(CF_3)_2$ | H | H-63 |
| A-388 | $CF(CF_3)_2$ | H | H-64 |
| A-389 | $CF(CF_3)_2$ | H | H-65 |
| A-390 | $CF(CF_3)_2$ | H | H-66 |
| A-391 | $CF(CF_3)_2$ | H | H-67 |
| A-392 | $CF(CF_3)_2$ | H | H-68 |
| A-393 | $CF(CF_3)_2$ | H | H-69 |
| A-394 | $CF(CF_3)_2$ | H | H-70 |
| A-395 | $CF(CF_3)_2$ | H | H-71 |
| A-396 | $CF(CF_3)_2$ | H | H-72 |
| A-397 | $CF(CF_3)_2$ | H | H-73 |
| A-398 | $CF(CF_3)_2$ | H | H-74 |
| A-399 | $CF(CF_3)_2$ | H | H-75 |
| A-400 | $CF(CF_3)_2$ | H | H-76 |
| A-401 | $CF(CF_3)_2$ | H | H-77 |
| A-402 | $CF(CF_3)_2$ | H | H-78 |
| A-403 | $CF(CF_3)_2$ | H | H-79 |
| A-404 | $CF(CF_3)_2$ | H | H-80 |
| A-405 | $CF(CF_3)_2$ | H | H-81 |
| A-406 | $CF(CF_3)_2$ | H | H-82 |
| A-407 | $CF(CF_3)_2$ | H | H-83 |
| A-408 | $CF(CF_3)_2$ | H | H-84 |
| A-409 | $CF(CF_3)_2$ | H | H-85 |
| A-410 | $CF(CF_3)_2$ | H | H-86 |
| A-411 | $CF(CF_3)_2$ | H | H-87 |
| A-412 | $CF(CF_3)_2$ | H | H-88 |
| A-413 | $CF(CF_3)_2$ | H | H-89 |
| A-414 | $CF(CF_3)_2$ | H | H-90 |
| A-415 | $CF(CF_3)_2$ | H | H-91 |
| A-416 | $CF(CF_3)_2$ | H | H-92 |
| A-417 | $CF(CF_3)_2$ | H | H-93 |
| A-418 | $CF(CF_3)_2$ | H | H-94 |
| A-419 | $CF(CF_3)_2$ | H | H-95 |
| A-420 | $CF(CF_3)_2$ | H | H-96 |
| A-421 | $CF(CF_3)_2$ | H | H-97 |

TABLE A-continued

| Line | $R^1$ | $R^2$ | H |
|---|---|---|---|
| A-422 | $CF(CF_3)_2$ | H | H-98 |
| A-423 | $CF(CF_3)_2$ | H | H-99 |
| A-424 | $CF(CF_3)_2$ | H | H-100 |
| A-425 | $CF(CF_3)_2$ | H | H-101 |
| A-426 | $CF(CF_3)_2$ | H | H-102 |
| A-427 | $CF(CF_3)_2$ | H | H-103 |
| A-428 | $CF(CF_3)_2$ | H | H-104 |
| A-429 | $CF(CF_3)_2$ | H | H-105 |
| A-430 | $CF(CF_3)_2$ | H | H-106 |
| A-431 | $CF(CF_3)_2$ | H | H-107 |
| A-432 | $CF(CF_3)_2$ | H | H-108 |
| A-433 | $CF(CF_3)_2$ | H | H-109 |
| A-434 | $CF(CF_3)_2$ | H | H-110 |
| A-435 | $CF(CF_3)_2$ | H | H-111 |
| A-436 | $CF(CF_3)_2$ | H | H-112 |
| A-437 | $CF(CF_3)_2$ | H | H-113 |
| A-438 | $CF(CF_3)_2$ | H | H-114 |
| A-439 | $CF(CF_3)_2$ | H | H-115 |
| A-440 | $CF(CF_3)_2$ | H | H-116 |
| A-441 | $CF(CF_3)_2$ | H | H-117 |
| A-442 | $CF(CF_3)_2$ | H | H-118 |
| A-443 | $CF(CF_3)_2$ | H | H-119 |
| A-444 | $CF(CF_3)_2$ | H | H-120 |
| A-445 | $CF(CF_3)_2$ | H | H-121 |
| A-446 | $CF(CF_3)_2$ | H | H-122 |
| A-447 | $CF(CF_3)_2$ | H | H-123 |
| A-448 | $CF(CF_3)_2$ | H | H-124 |
| A-449 | $CF(CF_3)_2$ | H | H-125 |
| A-450 | $CF(CF_3)_2$ | H | H-126 |
| A-451 | $CF(CF_3)_2$ | H | H-127 |
| A-452 | $CF(CF_3)_2$ | H | H-128 |
| A-453 | $CF(CF_3)_2$ | H | H-129 |
| A-454 | $CF(CF_3)_2$ | H | H-130 |
| A-455 | $CF(CF_3)_2$ | H | H-131 |
| A-456 | $CF(CF_3)_2$ | H | H-132 |
| A-457 | $CF(CF_3)_2$ | H | H-133 |
| A-458 | $CF(CF_3)_2$ | H | H-134 |
| A-459 | $CF(CF_3)_2$ | H | H-135 |
| A-460 | $CF(CF_3)_2$ | H | H-136 |
| A-461 | $CF(CF_3)_2$ | H | H-137 |
| A-462 | $CF(CF_3)_2$ | H | H-138 |
| A-463 | $CF(CF_3)_2$ | H | H-139 |
| A-464 | $CF(CF_3)_2$ | H | H-140 |
| A-465 | $CF(CF_3)_2$ | H | H-141 |
| A-466 | $CF(CF_3)_2$ | H | H-142 |
| A-467 | $CF(CF_3)_2$ | H | H-143 |
| A-468 | $CF(CF_3)_2$ | H | H-144 |
| A-469 | $CF(CF_3)_2$ | H | H-145 |
| A-470 | $CF(CF_3)_2$ | H | H-146 |
| A-471 | $CF(CF_3)_2$ | H | H-147 |
| A-472 | $CF(CF_3)_2$ | H | H-148 |
| A-473 | $CF(CF_3)_2$ | H | H-149 |
| A-474 | $CF(CF_3)_2$ | H | H-150 |
| A-475 | $CF(CF_3)_2$ | H | H-151 |
| A-476 | $CF(CF_3)_2$ | H | H-152 |
| A-477 | $CF(CF_3)_2$ | H | H-153 |
| A-478 | $CF(CF_3)_2$ | H | H-154 |
| A-479 | $CF(CF_3)_2$ | H | H-155 |
| A-480 | $CF(CF_3)_2$ | H | H-156 |
| A-481 | $CF(CF_3)_2$ | H | H-157 |
| A-482 | $CF(CF_3)_2$ | H | H-158 |
| A-483 | $CF(CF_3)_2$ | H | H-159 |
| A-484 | $CF(CF_3)_2$ | H | H-160 |
| A-485 | $CF(CF_3)_2$ | H | H-161 |
| A-486 | $CF(CF_3)_2$ | H | H-162 |
| A-487 | $SCF_3$ | H | H-1 |
| A-488 | $SCF_3$ | H | H-2 |
| A-489 | $SCF_3$ | H | H-3 |
| A-490 | $SCF_3$ | H | H-4 |
| A-491 | $SCF_3$ | H | H-5 |
| A-492 | $SCF_3$ | H | H-6 |
| A-493 | $SCF_3$ | H | H-7 |
| A-494 | $SCF_3$ | H | H-8 |
| A-495 | $SCF_3$ | H | H-9 |
| A-496 | $SCF_3$ | H | H-10 |

TABLE A-continued

| Line | $R^1$ | $R^2$ | H |
|---|---|---|---|
| A-497 | $SCF_3$ | H | H-11 |
| A-498 | $SCF_3$ | H | H-12 |
| A-499 | $SCF_3$ | H | H-13 |
| A-500 | $SCF_3$ | H | H-14 |
| A-501 | $SCF_3$ | H | H-15 |
| A-502 | $SCF_3$ | H | H-16 |
| A-503 | $SCF_3$ | H | H-17 |
| A-504 | $SCF_3$ | H | H-18 |
| A-505 | $SCF_3$ | H | H-19 |
| A-506 | $SCF_3$ | H | H-20 |
| A-507 | $SCF_3$ | H | H-21 |
| A-508 | $SCF_3$ | H | H-22 |
| A-509 | $SCF_3$ | H | H-23 |
| A-510 | $SCF_3$ | H | H-24 |
| A-511 | $SCF_3$ | H | H-25 |
| A-512 | $SCF_3$ | H | H-26 |
| A-513 | $SCF_3$ | H | H-27 |
| A-514 | $SCF_3$ | H | H-28 |
| A-515 | $SCF_3$ | H | H-29 |
| A-516 | $SCF_3$ | H | H-30 |
| A-517 | $SCF_3$ | H | H-31 |
| A-518 | $SCF_3$ | H | H-32 |
| A-519 | $SCF_3$ | H | H-33 |
| A-520 | $SCF_3$ | H | H-34 |
| A-521 | $SCF_3$ | H | H-35 |
| A-522 | $SCF_3$ | H | H-36 |
| A-523 | $SCF_3$ | H | H-37 |
| A-524 | $SCF_3$ | H | H-38 |
| A-525 | $SCF_3$ | H | H-39 |
| A-526 | $SCF_3$ | H | H-40 |
| A-527 | $SCF_3$ | H | H-41 |
| A-528 | $SCF_3$ | H | H-42 |
| A-529 | $SCF_3$ | H | H-43 |
| A-530 | $SCF_3$ | H | H-44 |
| A-531 | $SCF_3$ | H | H-45 |
| A-532 | $SCF_3$ | H | H-46 |
| A-533 | $SCF_3$ | H | H-47 |
| A-534 | $SCF_3$ | H | H-48 |
| A-535 | $SCF_3$ | H | H-49 |
| A-536 | $SCF_3$ | H | H-50 |
| A-537 | $SCF_3$ | H | H-51 |
| A-538 | $SCF_3$ | H | H-52 |
| A-539 | $SCF_3$ | H | H-53 |
| A-540 | $SCF_3$ | H | H-54 |
| A-541 | $SCF_3$ | H | H-55 |
| A-542 | $SCF_3$ | H | H-56 |
| A-543 | $SCF_3$ | H | H-57 |
| A-544 | $SCF_3$ | H | H-58 |
| A-545 | $SCF_3$ | H | H-59 |
| A-546 | $SCF_3$ | H | H-60 |
| A-547 | $SCF_3$ | H | H-61 |
| A-548 | $SCF_3$ | H | H-62 |
| A-549 | $SCF_3$ | H | H-63 |
| A-550 | $SCF_3$ | H | H-64 |
| A-551 | $SCF_3$ | H | H-65 |
| A-552 | $SCF_3$ | H | H-66 |
| A-553 | $SCF_3$ | H | H-67 |
| A-554 | $SCF_3$ | H | H-68 |
| A-555 | $SCF_3$ | H | H-69 |
| A-556 | $SCF_3$ | H | H-70 |
| A-557 | $SCF_3$ | H | H-71 |
| A-558 | $SCF_3$ | H | H-72 |
| A-559 | $SCF_3$ | H | H-73 |
| A-560 | $SCF_3$ | H | H-74 |
| A-561 | $SCF_3$ | H | H-75 |
| A-562 | $SCF_3$ | H | H-76 |
| A-563 | $SCF_3$ | H | H-77 |
| A-564 | $SCF_3$ | H | H-78 |
| A-565 | $SCF_3$ | H | H-79 |
| A-566 | $SCF_3$ | H | H-80 |
| A-567 | $SCF_3$ | H | H-81 |
| A-568 | $SCF_3$ | H | H-82 |
| A-569 | $SCF_3$ | H | H-83 |
| A-570 | $SCF_3$ | H | H-84 |
| A-571 | $SCF_3$ | H | H-85 |

TABLE A-continued

| Combination of meanings for $R^1$, $R^2$, and moiety of formula (H) | | | |
|---|---|---|---|
| Line | $R^1$ | $R^2$ | H |
| A-572 | $SCF_3$ | H | H-86 |
| A-573 | $SCF_3$ | H | H-87 |
| A-574 | $SCF_3$ | H | H-88 |
| A-575 | $SCF_3$ | H | H-89 |
| A-576 | $SCF_3$ | H | H-90 |
| A-577 | $SCF_3$ | H | H-91 |
| A-578 | $SCF_3$ | H | H-92 |
| A-579 | $SCF_3$ | H | H-93 |
| A-580 | $SCF_3$ | H | H-94 |
| A-581 | $SCF_3$ | H | H-95 |
| A-582 | $SCF_3$ | H | H-96 |
| A-583 | $SCF_3$ | H | H-97 |
| A-584 | $SCF_3$ | H | H-98 |
| A-585 | $SCF_3$ | H | H-99 |
| A-586 | $SCF_3$ | H | H-100 |
| A-587 | $SCF_3$ | H | H-101 |
| A-588 | $SCF_3$ | H | H-102 |
| A-589 | $SCF_3$ | H | H-103 |
| A-590 | $SCF_3$ | H | H-104 |
| A-591 | $SCF_3$ | H | H-105 |
| A-592 | $SCF_3$ | H | H-106 |
| A-593 | $SCF_3$ | H | H-107 |
| A-594 | $SCF_3$ | H | H-108 |
| A-595 | $SCF_3$ | H | H-109 |
| A-596 | $SCF_3$ | H | H-110 |
| A-597 | $SCF_3$ | H | H-111 |
| A-598 | $SCF_3$ | H | H-112 |
| A-599 | $SCF_3$ | H | H-113 |
| A-600 | $SCF_3$ | H | H-114 |
| A-601 | $SCF_3$ | H | H-115 |
| A-602 | $SCF_3$ | H | H-116 |
| A-603 | $SCF_3$ | H | H-117 |
| A-604 | $SCF_3$ | H | H-118 |
| A-605 | $SCF_3$ | H | H-119 |
| A-606 | $SCF_3$ | H | H-120 |
| A-607 | $SCF_3$ | H | H-121 |
| A-608 | $SCF_3$ | H | H-122 |
| A-609 | $SCF_3$ | H | H-123 |
| A-610 | $SCF_3$ | H | H-124 |
| A-611 | $SCF_3$ | H | H-125 |
| A-612 | $SCF_3$ | H | H-126 |
| A-613 | $SCF_3$ | H | H-127 |
| A-614 | $SCF_3$ | H | H-128 |
| A-615 | $SCF_3$ | H | H-129 |
| A-616 | $SCF_3$ | H | H-130 |
| A-617 | $SCF_3$ | H | H-131 |
| A-618 | $SCF_3$ | H | H-132 |
| A-619 | $SCF_3$ | H | H-133 |
| A-620 | $SCF_3$ | H | H-134 |
| A-621 | $SCF_3$ | H | H-135 |
| A-622 | $SCF_3$ | H | H-136 |
| A-623 | $SCF_3$ | H | H-137 |
| A-624 | $SCF_3$ | H | H-138 |
| A-625 | $SCF_3$ | H | H-139 |
| A-626 | $SCF_3$ | H | H-140 |
| A-627 | $SCF_3$ | H | H-141 |
| A-628 | $SCF_3$ | H | H-142 |
| A-629 | $SCF_3$ | H | H-143 |
| A-630 | $SCF_3$ | H | H-144 |
| A-631 | $SCF_3$ | H | H-145 |
| A-632 | $SCF_3$ | H | H-146 |
| A-633 | $SCF_3$ | H | H-147 |
| A-634 | $SCF_3$ | H | H-148 |
| A-635 | $SCF_3$ | H | H-149 |
| A-636 | $SCF_3$ | H | H-150 |
| A-637 | $SCF_3$ | H | H-151 |
| A-638 | $SCF_3$ | H | H-152 |
| A-639 | $SCF_3$ | H | H-153 |
| A-640 | $SCF_3$ | H | H-154 |
| A-641 | $SCF_3$ | H | H-155 |
| A-642 | $SCF_3$ | H | H-156 |
| A-643 | $SCF_3$ | H | H-157 |
| A-644 | $SCF_3$ | H | H-158 |
| A-645 | $SCF_3$ | H | H-159 |
| A-646 | $SCF_3$ | H | H-160 |

TABLE A-continued

| Combination of meanings for $R^1$, $R^2$, and moiety of formula (H) | | | |
|---|---|---|---|
| Line | $R^1$ | $R^2$ | H |
| A-647 | $SCF_3$ | H | H-161 |
| A-648 | $SCF_3$ | H | H-162 |
| A-649 | $OCF_3$ | H | H-1 |
| A-650 | $OCF_3$ | H | H-2 |
| A-651 | $OCF_3$ | H | H-3 |
| A-652 | $OCF_3$ | H | H-4 |
| A-653 | $OCF_3$ | H | H-5 |
| A-654 | $OCF_3$ | H | H-6 |
| A-655 | $OCF_3$ | H | H-7 |
| A-656 | $OCF_3$ | H | H-8 |
| A-657 | $OCF_3$ | H | H-9 |
| A-658 | $OCF_3$ | H | H-10 |
| A-659 | $OCF_3$ | H | H-11 |
| A-660 | $OCF_3$ | H | H-12 |
| A-661 | $OCF_3$ | H | H-13 |
| A-662 | $OCF_3$ | H | H-14 |
| A-663 | $OCF_3$ | H | H-15 |
| A-664 | $OCF_3$ | H | H-16 |
| A-665 | $OCF_3$ | H | H-17 |
| A-666 | $OCF_3$ | H | H-18 |
| A-667 | $OCF_3$ | H | H-19 |
| A-668 | $OCF_3$ | H | H-20 |
| A-669 | $OCF_3$ | H | H-21 |
| A-670 | $OCF_3$ | H | H-22 |
| A-671 | $OCF_3$ | H | H-23 |
| A-672 | $OCF_3$ | H | H-24 |
| A-673 | $OCF_3$ | H | H-25 |
| A-674 | $OCF_3$ | H | H-26 |
| A-675 | $OCF_3$ | H | H-27 |
| A-676 | $OCF_3$ | H | H-28 |
| A-677 | $OCF_3$ | H | H-29 |
| A-678 | $OCF_3$ | H | H-30 |
| A-679 | $OCF_3$ | H | H-31 |
| A-680 | $OCF_3$ | H | H-32 |
| A-681 | $OCF_3$ | H | H-33 |
| A-682 | $OCF_3$ | H | H-34 |
| A-683 | $OCF_3$ | H | H-35 |
| A-684 | $OCF_3$ | H | H-36 |
| A-685 | $OCF_3$ | H | H-37 |
| A-686 | $OCF_3$ | H | H-38 |
| A-687 | $OCF_3$ | H | H-39 |
| A-688 | $OCF_3$ | H | H-40 |
| A-689 | $OCF_3$ | H | H-41 |
| A-690 | $OCF_3$ | H | H-42 |
| A-691 | $OCF_3$ | H | H-43 |
| A-692 | $OCF_3$ | H | H-44 |
| A-693 | $OCF_3$ | H | H-45 |
| A-694 | $OCF_3$ | H | H-46 |
| A-695 | $OCF_3$ | H | H-47 |
| A-696 | $OCF_3$ | H | H-48 |
| A-697 | $OCF_3$ | H | H-49 |
| A-698 | $OCF_3$ | H | H-50 |
| A-699 | $OCF_3$ | H | H-51 |
| A-700 | $OCF_3$ | H | H-52 |
| A-701 | $OCF_3$ | H | H-53 |
| A-702 | $OCF_3$ | H | H-54 |
| A-703 | $OCF_3$ | H | H-55 |
| A-704 | $OCF_3$ | H | H-56 |
| A-705 | $OCF_3$ | H | H-57 |
| A-706 | $OCF_3$ | H | H-58 |
| A-707 | $OCF_3$ | H | H-59 |
| A-708 | $OCF_3$ | H | H-60 |
| A-709 | $OCF_3$ | H | H-61 |
| A-710 | $OCF_3$ | H | H-62 |
| A-711 | $OCF_3$ | H | H-63 |
| A-712 | $OCF_3$ | H | H-64 |
| A-713 | $OCF_3$ | H | H-65 |
| A-714 | $OCF_3$ | H | H-66 |
| A-715 | $OCF_3$ | H | H-67 |
| A-716 | $OCF_3$ | H | H-68 |
| A-717 | $OCF_3$ | H | H-69 |
| A-718 | $OCF_3$ | H | H-70 |
| A-719 | $OCF_3$ | H | H-71 |
| A-720 | $OCF_3$ | H | H-72 |
| A-721 | $OCF_3$ | H | H-73 |

TABLE A-continued

| Combination of meanings for $R^1$, $R^2$, and moiety of formula (H) | | | |
|---|---|---|---|
| Line | $R^1$ | $R^2$ | H |
| A-722 | $OCF_3$ | H | H-74 |
| A-723 | $OCF_3$ | H | H-75 |
| A-724 | $OCF_3$ | H | H-76 |
| A-725 | $OCF_3$ | H | H-77 |
| A-726 | $OCF_3$ | H | H-78 |
| A-727 | $OCF_3$ | H | H-79 |
| A-728 | $OCF_3$ | H | H-80 |
| A-729 | $OCF_3$ | H | H-81 |
| A-730 | $OCF_3$ | H | H-82 |
| A-731 | $OCF_3$ | H | H-83 |
| A-732 | $OCF_3$ | H | H-84 |
| A-733 | $OCF_3$ | H | H-85 |
| A-734 | $OCF_3$ | H | H-86 |
| A-735 | $OCF_3$ | H | H-87 |
| A-736 | $OCF_3$ | H | H-88 |
| A-737 | $OCF_3$ | H | H-89 |
| A-738 | $OCF_3$ | H | H-90 |
| A-739 | $OCF_3$ | H | H-91 |
| A-740 | $OCF_3$ | H | H-92 |
| A-741 | $OCF_3$ | H | H-93 |
| A-742 | $OCF_3$ | H | H-94 |
| A-743 | $OCF_3$ | H | H-95 |
| A-744 | $OCF_3$ | H | H-96 |
| A-745 | $OCF_3$ | H | H-97 |
| A-746 | $OCF_3$ | H | H-98 |
| A-747 | $OCF_3$ | H | H-99 |
| A-748 | $OCF_3$ | H | H-100 |
| A-749 | $OCF_3$ | H | H-101 |
| A-750 | $OCF_3$ | H | H-102 |
| A-751 | $OCF_3$ | H | H-103 |
| A-752 | $OCF_3$ | H | H-104 |
| A-753 | $OCF_3$ | H | H-105 |
| A-754 | $OCF_3$ | H | H-106 |
| A-755 | $OCF_3$ | H | H-107 |
| A-756 | $OCF_3$ | H | H-108 |
| A-757 | $OCF_3$ | H | H-109 |
| A-758 | $OCF_3$ | H | H-110 |
| A-759 | $OCF_3$ | H | H-111 |
| A-760 | $OCF_3$ | H | H-112 |
| A-761 | $OCF_3$ | H | H-113 |
| A-762 | $OCF_3$ | H | H-114 |
| A-763 | $OCF_3$ | H | H-115 |
| A-764 | $OCF_3$ | H | H-116 |
| A-765 | $OCF_3$ | H | H-117 |
| A-766 | $OCF_3$ | H | H-118 |
| A-767 | $OCF_3$ | H | H-119 |
| A-768 | $OCF_3$ | H | H-120 |
| A-769 | $OCF_3$ | H | H-121 |
| A-770 | $OCF_3$ | H | H-122 |
| A-771 | $OCF_3$ | H | H-123 |
| A-772 | $OCF_3$ | H | H-124 |
| A-773 | $OCF_3$ | H | H-125 |
| A-774 | $OCF_3$ | H | H-126 |
| A-775 | $OCF_3$ | H | H-127 |
| A-776 | $OCF_3$ | H | H-128 |
| A-777 | $OCF_3$ | H | H-129 |
| A-778 | $OCF_3$ | H | H-130 |
| A-779 | $OCF_3$ | H | H-131 |
| A-780 | $OCF_3$ | H | H-132 |
| A-781 | $OCF_3$ | H | H-133 |
| A-782 | $OCF_3$ | H | H-134 |
| A-783 | $OCF_3$ | H | H-135 |
| A-784 | $OCF_3$ | H | H-136 |
| A-785 | $OCF_3$ | H | H-137 |
| A-786 | $OCF_3$ | H | H-138 |
| A-787 | $OCF_3$ | H | H-139 |
| A-788 | $OCF_3$ | H | H-140 |
| A-789 | $OCF_3$ | H | H-141 |
| A-790 | $OCF_3$ | H | H-142 |
| A-791 | $OCF_3$ | H | H-143 |
| A-792 | $OCF_3$ | H | H-144 |
| A-793 | $OCF_3$ | H | H-145 |
| A-794 | $OCF_3$ | H | H-146 |
| A-795 | $OCF_3$ | H | H-147 |
| A-796 | $OCF_3$ | H | H-148 |

TABLE A-continued

| Combination of meanings for $R^1$, $R^2$, and moiety of formula (H) | | | |
|---|---|---|---|
| Line | $R^1$ | $R^2$ | H |
| A-797 | $OCF_3$ | H | H-149 |
| A-798 | $OCF_3$ | H | H-150 |
| A-799 | $OCF_3$ | H | H-151 |
| A-800 | $OCF_3$ | H | H-152 |
| A-801 | $OCF_3$ | H | H-153 |
| A-802 | $OCF_3$ | H | H-154 |
| A-803 | $OCF_3$ | H | H-155 |
| A-804 | $OCF_3$ | H | H-156 |
| A-805 | $OCF_3$ | H | H-157 |
| A-806 | $OCF_3$ | H | H-158 |
| A-807 | $OCF_3$ | H | H-159 |
| A-808 | $OCF_3$ | H | H-160 |
| A-809 | $OCF_3$ | H | H-161 |
| A-810 | $OCF_3$ | H | H-162 |
| A-811 | $OCHF_2$ | H | H-1 |
| A-812 | $OCHF_2$ | H | H-2 |
| A-813 | $OCHF_2$ | H | H-3 |
| A-814 | $OCHF_2$ | H | H-4 |
| A-815 | $OCHF_2$ | H | H-5 |
| A-816 | $OCHF_2$ | H | H-6 |
| A-817 | $OCHF_2$ | H | H-7 |
| A-818 | $OCHF_2$ | H | H-8 |
| A-819 | $OCHF_2$ | H | H-9 |
| A-820 | $OCHF_2$ | H | H-10 |
| A-821 | $OCHF_2$ | H | H-11 |
| A-822 | $OCHF_2$ | H | H-12 |
| A-823 | $OCHF_2$ | H | H-13 |
| A-824 | $OCHF_2$ | H | H-14 |
| A-825 | $OCHF_2$ | H | H-15 |
| A-826 | $OCHF_2$ | H | H-16 |
| A-827 | $OCHF_2$ | H | H-17 |
| A-828 | $OCHF_2$ | H | H-18 |
| A-829 | $OCHF_2$ | H | H-19 |
| A-830 | $OCHF_2$ | H | H-20 |
| A-831 | $OCHF_2$ | H | H-21 |
| A-832 | $OCHF_2$ | H | H-22 |
| A-833 | $OCHF_2$ | H | H-23 |
| A-834 | $OCHF_2$ | H | H-24 |
| A-835 | $OCHF_2$ | H | H-25 |
| A-836 | $OCHF_2$ | H | H-26 |
| A-837 | $OCHF_2$ | H | H-27 |
| A-838 | $OCHF_2$ | H | H-28 |
| A-839 | $OCHF_2$ | H | H-29 |
| A-840 | $OCHF_2$ | H | H-30 |
| A-841 | $OCHF_2$ | H | H-31 |
| A-842 | $OCHF_2$ | H | H-32 |
| A-843 | $OCHF_2$ | H | H-33 |
| A-844 | $OCHF_2$ | H | H-34 |
| A-845 | $OCHF_2$ | H | H-35 |
| A-846 | $OCHF_2$ | H | H-36 |
| A-847 | $OCHF_2$ | H | H-37 |
| A-848 | $OCHF_2$ | H | H-38 |
| A-849 | $OCHF_2$ | H | H-39 |
| A-850 | $OCHF_2$ | H | H-40 |
| A-851 | $OCHF_2$ | H | H-41 |
| A-852 | $OCHF_2$ | H | H-42 |
| A-853 | $OCHF_2$ | H | H-43 |
| A-854 | $OCHF_2$ | H | H-44 |
| A-855 | $OCHF_2$ | H | H-45 |
| A-856 | $OCHF_2$ | H | H-46 |
| A-857 | $OCHF_2$ | H | H-47 |
| A-858 | $OCHF_2$ | H | H-48 |
| A-859 | $OCHF_2$ | H | H-49 |
| A-860 | $OCHF_2$ | H | H-50 |
| A-861 | $OCHF_2$ | H | H-51 |
| A-862 | $OCHF_2$ | H | H-52 |
| A-863 | $OCHF_2$ | H | H-53 |
| A-864 | $OCHF_2$ | H | H-54 |
| A-865 | $OCHF_2$ | H | H-55 |
| A-866 | $OCHF_2$ | H | H-56 |
| A-867 | $OCHF_2$ | H | H-57 |
| A-868 | $OCHF_2$ | H | H-58 |
| A-869 | $OCHF_2$ | H | H-59 |
| A-870 | $OCHF_2$ | H | H-60 |
| A-871 | $OCHF_2$ | H | H-61 |

TABLE A-continued

| Line | $R^1$ | $R^2$ | H |
|---|---|---|---|
| A-872 | $OCHF_2$ | H | H-62 |
| A-873 | $OCHF_2$ | H | H-63 |
| A-874 | $OCHF_2$ | H | H-64 |
| A-875 | $OCHF_2$ | H | H-65 |
| A-876 | $OCHF_2$ | H | H-66 |
| A-877 | $OCHF_2$ | H | H-67 |
| A-878 | $OCHF_2$ | H | H-68 |
| A-879 | $OCHF_2$ | H | H-69 |
| A-880 | $OCHF_2$ | H | H-70 |
| A-881 | $OCHF_2$ | H | H-71 |
| A-882 | $OCHF_2$ | H | H-72 |
| A-883 | $OCHF_2$ | H | H-73 |
| A-884 | $OCHF_2$ | H | H-74 |
| A-885 | $OCHF_2$ | H | H-75 |
| A-886 | $OCHF_2$ | H | H-76 |
| A-887 | $OCHF_2$ | H | H-77 |
| A-888 | $OCHF_2$ | H | H-78 |
| A-889 | $OCHF_2$ | H | H-79 |
| A-890 | $OCHF_2$ | H | H-80 |
| A-891 | $OCHF_2$ | H | H-81 |
| A-892 | $OCHF_2$ | H | H-82 |
| A-893 | $OCHF_2$ | H | H-83 |
| A-894 | $OCHF_2$ | H | H-84 |
| A-895 | $OCHF_2$ | H | H-85 |
| A-896 | $OCHF_2$ | H | H-86 |
| A-897 | $OCHF_2$ | H | H-87 |
| A-898 | $OCHF_2$ | H | H-88 |
| A-899 | $OCHF_2$ | H | H-89 |
| A-900 | $OCHF_2$ | H | H-90 |
| A-901 | $OCHF_2$ | H | H-91 |
| A-902 | $OCHF_2$ | H | H-92 |
| A-903 | $OCHF_2$ | H | H-93 |
| A-904 | $OCHF_2$ | H | H-94 |
| A-905 | $OCHF_2$ | H | H-95 |
| A-906 | $OCHF_2$ | H | H-96 |
| A-907 | $OCHF_2$ | H | H-97 |
| A-908 | $OCHF_2$ | H | H-98 |
| A-909 | $OCHF_2$ | H | H-99 |
| A-910 | $OCHF_2$ | H | H-100 |
| A-911 | $OCHF_2$ | H | H-101 |
| A-912 | $OCHF_2$ | H | H-102 |
| A-913 | $OCHF_2$ | H | H-103 |
| A-914 | $OCHF_2$ | H | H-104 |
| A-915 | $OCHF_2$ | H | H-105 |
| A-916 | $OCHF_2$ | H | H-106 |
| A-917 | $OCHF_2$ | H | H-107 |
| A-918 | $OCHF_2$ | H | H-108 |
| A-919 | $OCHF_2$ | H | H-109 |
| A-920 | $OCHF_2$ | H | H-110 |
| A-921 | $OCHF_2$ | H | H-111 |
| A-922 | $OCHF_2$ | H | H-112 |
| A-923 | $OCHF_2$ | H | H-113 |
| A-924 | $OCHF_2$ | H | H-114 |
| A-925 | $OCHF_2$ | H | H-115 |
| A-926 | $OCHF_2$ | H | H-116 |
| A-927 | $OCHF_2$ | H | H-117 |
| A-928 | $OCHF_2$ | H | H-118 |
| A-929 | $OCHF_2$ | H | H-119 |
| A-930 | $OCHF_2$ | H | H-120 |
| A-931 | $OCHF_2$ | H | H-121 |
| A-932 | $OCHF_2$ | H | H-122 |
| A-933 | $OCHF_2$ | H | H-123 |
| A-934 | $OCHF_2$ | H | H-124 |
| A-935 | $OCHF_2$ | H | H-125 |
| A-936 | $OCHF_2$ | H | H-126 |
| A-937 | $OCHF_2$ | H | H-127 |
| A-938 | $OCHF_2$ | H | H-128 |
| A-939 | $OCHF_2$ | H | H-129 |
| A-940 | $OCHF_2$ | H | H-130 |
| A-941 | $OCHF_2$ | H | H-131 |
| A-942 | $OCHF_2$ | H | H-132 |
| A-943 | $OCHF_2$ | H | H-133 |
| A-944 | $OCHF_2$ | H | H-134 |
| A-945 | $OCHF_2$ | H | H-135 |
| A-946 | $OCHF_2$ | H | H-136 |

TABLE A-continued

| Line | $R^1$ | $R^2$ | H |
|---|---|---|---|
| A-947 | $OCHF_2$ | H | H-137 |
| A-948 | $OCHF_2$ | H | H-138 |
| A-949 | $OCHF_2$ | H | H-139 |
| A-950 | $OCHF_2$ | H | H-140 |
| A-951 | $OCHF_2$ | H | H-141 |
| A-952 | $OCHF_2$ | H | H-142 |
| A-953 | $OCHF_2$ | H | H-143 |
| A-954 | $OCHF_2$ | H | H-144 |
| A-955 | $OCHF_2$ | H | H-145 |
| A-956 | $OCHF_2$ | H | H-146 |
| A-957 | $OCHF_2$ | H | H-147 |
| A-958 | $OCHF_2$ | H | H-148 |
| A-959 | $OCHF_2$ | H | H-149 |
| A-960 | $OCHF_2$ | H | H-150 |
| A-961 | $OCHF_2$ | H | H-151 |
| A-962 | $OCHF_2$ | H | H-152 |
| A-963 | $OCHF_2$ | H | H-153 |
| A-964 | $OCHF_2$ | H | H-154 |
| A-965 | $OCHF_2$ | H | H-155 |
| A-966 | $OCHF_2$ | H | H-156 |
| A-967 | $OCHF_2$ | H | H-157 |
| A-968 | $OCHF_2$ | H | H-158 |
| A-969 | $OCHF_2$ | H | H-159 |
| A-970 | $OCHF_2$ | H | H-160 |
| A-971 | $OCHF_2$ | H | H-161 |
| A-972 | $OCHF_2$ | H | H-162 |
| A-973 | $S(=O)CF_3$ | H | H-1 |
| A-974 | $S(=O)CF_3$ | H | H-2 |
| A-975 | $S(=O)CF_3$ | H | H-3 |
| A-976 | $S(=O)CF_3$ | H | H-4 |
| A-977 | $S(=O)CF_3$ | H | H-5 |
| A-978 | $S(=O)CF_3$ | H | H-6 |
| A-979 | $S(=O)CF_3$ | H | H-7 |
| A-980 | $S(=O)CF_3$ | H | H-8 |
| A-981 | $S(=O)CF_3$ | H | H-9 |
| A-982 | $S(=O)CF_3$ | H | H-10 |
| A-983 | $S(=O)CF_3$ | H | H-11 |
| A-984 | $S(=O)CF_3$ | H | H-12 |
| A-985 | $S(=O)CF_3$ | H | H-13 |
| A-986 | $S(=O)CF_3$ | H | H-14 |
| A-987 | $S(=O)CF_3$ | H | H-15 |
| A-988 | $S(=O)CF_3$ | H | H-16 |
| A-989 | $S(=O)CF_3$ | H | H-17 |
| A-990 | $S(=O)CF_3$ | H | H-18 |
| A-991 | $S(=O)CF_3$ | H | H-19 |
| A-992 | $S(=O)CF_3$ | H | H-20 |
| A-993 | $S(=O)CF_3$ | H | H-21 |
| A-994 | $S(=O)CF_3$ | H | H-22 |
| A-995 | $S(=O)CF_3$ | H | H-23 |
| A-996 | $S(=O)CF_3$ | H | H-24 |
| A-997 | $S(=O)CF_3$ | H | H-25 |
| A-998 | $S(=O)CF_3$ | H | H-26 |
| A-999 | $S(=O)CF_3$ | H | H-27 |
| A-1000 | $S(=O)CF_3$ | H | H-28 |
| A-1001 | $S(=O)CF_3$ | H | H-29 |
| A-1002 | $S(=O)CF_3$ | H | H-30 |
| A-1003 | $S(=O)CF_3$ | H | H-31 |
| A-1004 | $S(=O)CF_3$ | H | H-32 |
| A-1005 | $S(=O)CF_3$ | H | H-33 |
| A-1006 | $S(=O)CF_3$ | H | H-34 |
| A-1007 | $S(=O)CF_3$ | H | H-35 |
| A-1008 | $S(=O)CF_3$ | H | H-36 |
| A-1009 | $S(=O)CF_3$ | H | H-37 |
| A-1010 | $S(=O)CF_3$ | H | H-38 |
| A-1011 | $S(=O)CF_3$ | H | H-39 |
| A-1012 | $S(=O)CF_3$ | H | H-40 |
| A-1013 | $S(=O)CF_3$ | H | H-41 |
| A-1014 | $S(=O)CF_3$ | H | H-42 |
| A-1015 | $S(=O)CF_3$ | H | H-43 |
| A-1016 | $S(=O)CF_3$ | H | H-44 |
| A-1017 | $S(=O)CF_3$ | H | H-45 |
| A-1018 | $S(=O)CF_3$ | H | H-46 |
| A-1019 | $S(=O)CF_3$ | H | H-47 |
| A-1020 | $S(=O)CF_3$ | H | H-48 |
| A-1021 | $S(=O)CF_3$ | H | H-49 |

TABLE A-continued

| Combination of meanings for $R^1$, $R^2$, and moiety of formula (H) | | | |
|---|---|---|---|
| Line | $R^1$ | $R^2$ | H |
| A-1022 | $S(=O)CF_3$ | H | H-50 |
| A-1023 | $S(=O)CF_3$ | H | H-51 |
| A-1024 | $S(=O)CF_3$ | H | H-52 |
| A-1025 | $S(=O)CF_3$ | H | H-53 |
| A-1026 | $S(=O)CF_3$ | H | H-54 |
| A-1027 | $S(=O)CF_3$ | H | H-55 |
| A-1028 | $S(=O)CF_3$ | H | H-56 |
| A-1029 | $S(=O)CF_3$ | H | H-57 |
| A-1030 | $S(=O)CF_3$ | H | H-58 |
| A-1031 | $S(=O)CF_3$ | H | H-59 |
| A-1032 | $S(=O)CF_3$ | H | H-60 |
| A-1033 | $S(=O)CF_3$ | H | H-61 |
| A-1034 | $S(=O)CF_3$ | H | H-62 |
| A-1035 | $S(=O)CF_3$ | H | H-63 |
| A-1036 | $S(=O)CF_3$ | H | H-64 |
| A-1037 | $S(=O)CF_3$ | H | H-65 |
| A-1038 | $S(=O)CF_3$ | H | H-66 |
| A-1039 | $S(=O)CF_3$ | H | H-67 |
| A-1040 | $S(=O)CF_3$ | H | H-68 |
| A-1041 | $S(=O)CF_3$ | H | H-69 |
| A-1042 | $S(=O)CF_3$ | H | H-70 |
| A-1043 | $S(=O)CF_3$ | H | H-71 |
| A-1044 | $S(=O)CF_3$ | H | H-72 |
| A-1045 | $S(=O)CF_3$ | H | H-73 |
| A-1046 | $S(=O)CF_3$ | H | H-74 |
| A-1047 | $S(=O)CF_3$ | H | H-75 |
| A-1048 | $S(=O)CF_3$ | H | H-76 |
| A-1049 | $S(=O)CF_3$ | H | H-77 |
| A-1050 | $S(=O)CF_3$ | H | H-78 |
| A-1051 | $S(=O)CF_3$ | H | H-79 |
| A-1052 | $S(=O)CF_3$ | H | H-80 |
| A-1053 | $S(=O)CF_3$ | H | H-81 |
| A-1054 | $S(=O)CF_3$ | H | H-82 |
| A-1055 | $S(=O)CF_3$ | H | H-83 |
| A-1056 | $S(=O)CF_3$ | H | H-84 |
| A-1057 | $S(=O)CF_3$ | H | H-85 |
| A-1058 | $S(=O)CF_3$ | H | H-86 |
| A-1059 | $S(=O)CF_3$ | H | H-87 |
| A-1060 | $S(=O)CF_3$ | H | H-88 |
| A-1061 | $S(=O)CF_3$ | H | H-89 |
| A-1062 | $S(=O)CF_3$ | H | H-90 |
| A-1063 | $S(=O)CF_3$ | H | H-91 |
| A-1064 | $S(=O)CF_3$ | H | H-92 |
| A-1065 | $S(=O)CF_3$ | H | H-93 |
| A-1066 | $S(=O)CF_3$ | H | H-94 |
| A-1067 | $S(=O)CF_3$ | H | H-95 |
| A-1068 | $S(=O)CF_3$ | H | H-96 |
| A-1069 | $S(=O)CF_3$ | H | H-97 |
| A-1070 | $S(=O)CF_3$ | H | H-98 |
| A-1071 | $S(=O)CF_3$ | H | H-99 |
| A-1072 | $S(=O)CF_3$ | H | H-100 |
| A-1073 | $S(=O)CF_3$ | H | H-101 |
| A-1074 | $S(=O)CF_3$ | H | H-102 |
| A-1075 | $S(=O)CF_3$ | H | H-103 |
| A-1076 | $S(=O)CF_3$ | H | H-104 |
| A-1077 | $S(=O)CF_3$ | H | H-105 |
| A-1078 | $S(=O)CF_3$ | H | H-106 |
| A-1079 | $S(=O)CF_3$ | H | H-107 |
| A-1080 | $S(=O)CF_3$ | H | H-108 |
| A-1081 | $S(=O)CF_3$ | H | H-109 |
| A-1082 | $S(=O)CF_3$ | H | H-110 |
| A-1083 | $S(=O)CF_3$ | H | H-111 |
| A-1084 | $S(=O)CF_3$ | H | H-112 |
| A-1085 | $S(=O)CF_3$ | H | H-113 |
| A-1086 | $S(=O)CF_3$ | H | H-114 |
| A-1087 | $S(=O)CF_3$ | H | H-115 |
| A-1088 | $S(=O)CF_3$ | H | H-116 |
| A-1089 | $S(=O)CF_3$ | H | H-117 |
| A-1090 | $S(=O)CF_3$ | H | H-118 |
| A-1091 | $S(=O)CF_3$ | H | H-119 |
| A-1092 | $S(=O)CF_3$ | H | H-120 |
| A-1093 | $S(=O)CF_3$ | H | H-121 |
| A-1094 | $S(=O)CF_3$ | H | H-122 |
| A-1095 | $S(=O)CF_3$ | H | H-123 |
| A-1096 | $S(=O)CF_3$ | H | H-124 |
| A-1097 | $S(=O)CF_3$ | H | H-125 |
| A-1098 | $S(=O)CF_3$ | H | H-126 |
| A-1099 | $S(=O)CF_3$ | H | H-127 |
| A-1100 | $S(=O)CF_3$ | H | H-128 |
| A-1101 | $S(=O)CF_3$ | H | H-129 |
| A-1102 | $S(=O)CF_3$ | H | H-130 |
| A-1103 | $S(=O)CF_3$ | H | H-131 |
| A-1104 | $S(=O)CF_3$ | H | H-132 |
| A-1105 | $S(=O)CF_3$ | H | H-133 |
| A-1106 | $S(=O)CF_3$ | H | H-134 |
| A-1107 | $S(=O)CF_3$ | H | H-135 |
| A-1108 | $S(=O)CF_3$ | H | H-136 |
| A-1109 | $S(=O)CF_3$ | H | H-137 |
| A-1110 | $S(=O)CF_3$ | H | H-138 |
| A-1111 | $S(=O)CF_3$ | H | H-139 |
| A-1112 | $S(=O)CF_3$ | H | H-140 |
| A-1113 | $S(=O)CF_3$ | H | H-141 |
| A-1114 | $S(=O)CF_3$ | H | H-142 |
| A-1115 | $S(=O)CF_3$ | H | H-143 |
| A-1116 | $S(=O)CF_3$ | H | H-144 |
| A-1117 | $S(=O)CF_3$ | H | H-145 |
| A-1118 | $S(=O)CF_3$ | H | H-146 |
| A-1119 | $S(=O)CF_3$ | H | H-147 |
| A-1120 | $S(=O)CF_3$ | H | H-148 |
| A-1121 | $S(=O)CF_3$ | H | H-149 |
| A-1122 | $S(=O)CF_3$ | H | H-150 |
| A-1123 | $S(=O)CF_3$ | H | H-151 |
| A-1124 | $S(=O)CF_3$ | H | H-152 |
| A-1125 | $S(=O)CF_3$ | H | H-153 |
| A-1126 | $S(=O)CF_3$ | H | H-154 |
| A-1127 | $S(=O)CF_3$ | H | H-155 |
| A-1128 | $S(=O)CF_3$ | H | H-156 |
| A-1129 | $S(=O)CF_3$ | H | H-157 |
| A-1130 | $S(=O)CF_3$ | H | H-158 |
| A-1131 | $S(=O)CF_3$ | H | H-159 |
| A-1132 | $S(=O)CF_3$ | H | H-160 |
| A-1133 | $S(=O)CF_3$ | H | H-161 |
| A-1134 | $S(=O)CF_3$ | H | H-162 |
| A-1135 | $S(=O)_2CF_3$ | H | H-1 |
| A-1136 | $S(=O)_2CF_3$ | H | H-2 |
| A-1137 | $S(=O)_2CF_3$ | H | H-3 |
| A-1138 | $S(=O)_2CF_3$ | H | H-4 |
| A-1139 | $S(=O)_2CF_3$ | H | H-5 |
| A-1140 | $S(=O)_2CF_3$ | H | H-6 |
| A-1141 | $S(=O)_2CF_3$ | H | H-7 |
| A-1142 | $S(=O)_2CF_3$ | H | H-8 |
| A-1143 | $S(=O)_2CF_3$ | H | H-9 |
| A-1144 | $S(=O)_2CF_3$ | H | H-10 |
| A-1145 | $S(=O)_2CF_3$ | H | H-11 |
| A-1146 | $S(=O)_2CF_3$ | H | H-12 |
| A-1147 | $S(=O)_2CF_3$ | H | H-13 |
| A-1148 | $S(=O)_2CF_3$ | H | H-14 |
| A-1149 | $S(=O)_2CF_3$ | H | H-15 |
| A-1150 | $S(=O)_2CF_3$ | H | H-16 |
| A-1151 | $S(=O)_2CF_3$ | H | H-17 |
| A-1152 | $S(=O)_2CF_3$ | H | H-18 |
| A-1153 | $S(=O)_2CF_3$ | H | H-19 |
| A-1154 | $S(=O)_2CF_3$ | H | H-20 |
| A-1155 | $S(=O)_2CF_3$ | H | H-21 |
| A-1156 | $S(=O)_2CF_3$ | H | H-22 |
| A-1157 | $S(=O)_2CF_3$ | H | H-23 |
| A-1158 | $S(=O)_2CF_3$ | H | H-24 |
| A-1159 | $S(=O)_2CF_3$ | H | H-25 |
| A-1160 | $S(=O)_2CF_3$ | H | H-26 |
| A-1161 | $S(=O)_2CF_3$ | H | H-27 |
| A-1162 | $S(=O)_2CF_3$ | H | H-28 |
| A-1163 | $S(=O)_2CF_3$ | H | H-29 |
| A-1164 | $S(=O)_2CF_3$ | H | H-30 |
| A-1165 | $S(=O)_2CF_3$ | H | H-31 |
| A-1166 | $S(=O)_2CF_3$ | H | H-32 |
| A-1167 | $S(=O)_2CF_3$ | H | H-33 |
| A-1168 | $S(=O)_2CF_3$ | H | H-34 |
| A-1169 | $S(=O)_2CF_3$ | H | H-35 |
| A-1170 | $S(=O)_2CF_3$ | H | H-36 |
| A-1171 | $S(=O)_2CF_3$ | H | H-37 |

TABLE A-continued

| Combination of meanings for $R^1$, $R^2$, and moiety of formula (H) | | | |
|---|---|---|---|
| Line | $R^1$ | $R^2$ | H |
| A-1172 | $S(=O)_2CF_3$ | H | H-38 |
| A-1173 | $S(=O)_2CF_3$ | H | H-39 |
| A-1174 | $S(=O)_2CF_3$ | H | H-40 |
| A-1175 | $S(=O)_2CF_3$ | H | H-41 |
| A-1176 | $S(=O)_2CF_3$ | H | H-42 |
| A-1177 | $S(=O)_2CF_3$ | H | H-43 |
| A-1178 | $S(=O)_2CF_3$ | H | H-44 |
| A-1179 | $S(=O)_2CF_3$ | H | H-45 |
| A-1180 | $S(=O)_2CF_3$ | H | H-46 |
| A-1181 | $S(=O)_2CF_3$ | H | H-47 |
| A-1182 | $S(=O)_2CF_3$ | H | H-48 |
| A-1183 | $S(=O)_2CF_3$ | H | H-49 |
| A-1184 | $S(=O)_2CF_3$ | H | H-50 |
| A-1185 | $S(=O)_2CF_3$ | H | H-51 |
| A-1186 | $S(=O)_2CF_3$ | H | H-52 |
| A-1187 | $S(=O)_2CF_3$ | H | H-53 |
| A-1188 | $S(=O)_2CF_3$ | H | H-54 |
| A-1189 | $S(=O)_2CF_3$ | H | H-55 |
| A-1190 | $S(=O)_2CF_3$ | H | H-56 |
| A-1191 | $S(=O)_2CF_3$ | H | H-57 |
| A-1192 | $S(=O)_2CF_3$ | H | H-58 |
| A-1193 | $S(=O)_2CF_3$ | H | H-59 |
| A-1194 | $S(=O)_2CF_3$ | H | H-60 |
| A-1195 | $S(=O)_2CF_3$ | H | H-61 |
| A-1196 | $S(=O)_2CF_3$ | H | H-62 |
| A-1197 | $S(=O)_2CF_3$ | H | H-63 |
| A-1198 | $S(=O)_2CF_3$ | H | H-64 |
| A-1199 | $S(=O)_2CF_3$ | H | H-65 |
| A-1200 | $S(=O)_2CF_3$ | H | H-66 |
| A-1201 | $S(=O)_2CF_3$ | H | H-67 |
| A-1202 | $S(=O)_2CF_3$ | H | H-68 |
| A-1203 | $S(=O)_2CF_3$ | H | H-69 |
| A-1204 | $S(=O)_2CF_3$ | H | H-70 |
| A-1205 | $S(=O)_2CF_3$ | H | H-71 |
| A-1206 | $S(=O)_2CF_3$ | H | H-72 |
| A-1207 | $S(=O)_2CF_3$ | H | H-73 |
| A-1208 | $S(=O)_2CF_3$ | H | H-74 |
| A-1209 | $S(=O)_2CF_3$ | H | H-75 |
| A-1210 | $S(=O)_2CF_3$ | H | H-76 |
| A-1211 | $S(=O)_2CF_3$ | H | H-77 |
| A-1212 | $S(=O)_2CF_3$ | H | H-78 |
| A-1213 | $S(=O)_2CF_3$ | H | H-79 |
| A-1214 | $S(=O)_2CF_3$ | H | H-80 |
| A-1215 | $S(=O)_2CF_3$ | H | H-81 |
| A-1216 | $S(=O)_2CF_3$ | H | H-82 |
| A-1217 | $S(=O)_2CF_3$ | H | H-83 |
| A-1218 | $S(=O)_2CF_3$ | H | H-84 |
| A-1219 | $S(=O)_2CF_3$ | H | H-85 |
| A-1220 | $S(=O)_2CF_3$ | H | H-86 |
| A-1221 | $S(=O)_2CF_3$ | H | H-87 |
| A-1222 | $S(=O)_2CF_3$ | H | H-88 |
| A-1223 | $S(=O)_2CF_3$ | H | H-89 |
| A-1224 | $S(=O)_2CF_3$ | H | H-90 |
| A-1225 | $S(=O)_2CF_3$ | H | H-91 |
| A-1226 | $S(=O)_2CF_3$ | H | H-92 |
| A-1227 | $S(=O)_2CF_3$ | H | H-93 |
| A-1228 | $S(=O)_2CF_3$ | H | H-94 |
| A-1229 | $S(=O)_2CF_3$ | H | H-95 |
| A-1230 | $S(=O)_2CF_3$ | H | H-96 |
| A-1231 | $S(=O)_2CF_3$ | H | H-97 |
| A-1232 | $S(=O)_2CF_3$ | H | H-98 |
| A-1233 | $S(=O)_2CF_3$ | H | H-99 |
| A-1234 | $S(=O)_2CF_3$ | H | H-100 |
| A-1235 | $S(=O)_2CF_3$ | H | H-101 |
| A-1236 | $S(=O)_2CF_3$ | H | H-102 |
| A-1237 | $S(=O)_2CF_3$ | H | H-103 |
| A-1238 | $S(=O)_2CF_3$ | H | H-104 |
| A-1239 | $S(=O)_2CF_3$ | H | H-105 |
| A-1240 | $S(=O)_2CF_3$ | H | H-106 |
| A-1241 | $S(=O)_2CF_3$ | H | H-107 |
| A-1242 | $S(=O)_2CF_3$ | H | H-108 |
| A-1243 | $S(=O)_2CF_3$ | H | H-109 |
| A-1244 | $S(=O)_2CF_3$ | H | H-110 |
| A-1245 | $S(=O)_2CF_3$ | H | H-111 |
| A-1246 | $S(=O)_2CF_3$ | H | H-112 |

TABLE A-continued

| Combination of meanings for $R^1$, $R^2$, and moiety of formula (H) | | | |
|---|---|---|---|
| Line | $R^1$ | $R^2$ | H |
| A-1247 | $S(=O)_2CF_3$ | H | H-113 |
| A-1248 | $S(=O)_2CF_3$ | H | H-114 |
| A-1249 | $S(=O)_2CF_3$ | H | H-115 |
| A-1250 | $S(=O)_2CF_3$ | H | H-116 |
| A-1251 | $S(=O)_2CF_3$ | H | H-117 |
| A-1252 | $S(=O)_2CF_3$ | H | H-118 |
| A-1253 | $S(=O)_2CF_3$ | H | H-119 |
| A-1254 | $S(=O)_2CF_3$ | H | H-120 |
| A-1255 | $S(=O)_2CF_3$ | H | H-121 |
| A-1256 | $S(=O)_2CF_3$ | H | H-122 |
| A-1257 | $S(=O)_2CF_3$ | H | H-123 |
| A-1258 | $S(=O)_2CF_3$ | H | H-124 |
| A-1259 | $S(=O)_2CF_3$ | H | H-125 |
| A-1260 | $S(=O)_2CF_3$ | H | H-126 |
| A-1261 | $S(=O)_2CF_3$ | H | H-127 |
| A-1262 | $S(=O)_2CF_3$ | H | H-128 |
| A-1263 | $S(=O)_2CF_3$ | H | H-129 |
| A-1264 | $S(=O)_2CF_3$ | H | H-130 |
| A-1265 | $S(=O)_2CF_3$ | H | H-131 |
| A-1266 | $S(=O)_2CF_3$ | H | H-132 |
| A-1267 | $S(=O)_2CF_3$ | H | H-133 |
| A-1268 | $S(=O)_2CF_3$ | H | H-134 |
| A-1269 | $S(=O)_2CF_3$ | H | H-135 |
| A-1270 | $S(=O)_2CF_3$ | H | H-136 |
| A-1271 | $S(=O)_2CF_3$ | H | H-137 |
| A-1272 | $S(=O)_2CF_3$ | H | H-138 |
| A-1273 | $S(=O)_2CF_3$ | H | H-139 |
| A-1274 | $S(=O)_2CF_3$ | H | H-140 |
| A-1275 | $S(=O)_2CF_3$ | H | H-141 |
| A-1276 | $S(=O)_2CF_3$ | H | H-142 |
| A-1277 | $S(=O)_2CF_3$ | H | H-143 |
| A-1278 | $S(=O)_2CF_3$ | H | H-144 |
| A-1279 | $S(=O)_2CF_3$ | H | H-145 |
| A-1280 | $S(=O)_2CF_3$ | H | H-146 |
| A-1281 | $S(=O)_2CF_3$ | H | H-147 |
| A-1282 | $S(=O)_2CF_3$ | H | H-148 |
| A-1283 | $S(=O)_2CF_3$ | H | H-149 |
| A-1284 | $S(=O)_2CF_3$ | H | H-150 |
| A-1285 | $S(=O)_2CF_3$ | H | H-151 |
| A-1286 | $S(=O)_2CF_3$ | H | H-152 |
| A-1287 | $S(=O)_2CF_3$ | H | H-153 |
| A-1288 | $S(=O)_2CF_3$ | H | H-154 |
| A-1289 | $S(=O)_2CF_3$ | H | H-155 |
| A-1290 | $S(=O)_2CF_3$ | H | H-156 |
| A-1291 | $S(=O)_2CF_3$ | H | H-157 |
| A-1292 | $S(=O)_2CF_3$ | H | H-158 |
| A-1293 | $S(=O)_2CF_3$ | H | H-159 |
| A-1294 | $S(=O)_2CF_3$ | H | H-160 |
| A-1295 | $S(=O)_2CF_3$ | H | H-161 |
| A-1296 | $S(=O)_2CF_3$ | H | H-162 |

Also preferred are the compounds of formula (I) corresponding to the compounds as disclosed in Table 1 to Table 90, wherein $R^w$ is $CH_3$ instead of $C_2H_5$.

Also preferred are the compounds of formula (I) corresponding to the compounds as disclosed in Table 1 to Table 90, wherein $R^w$ is $C_3H_7$ instead of $C_2H_5$.

In a preferred embodiment, the compound of formula (I) is a compound of formula (I.A) or (I.B), wherein the moiety of formula (H) is selected from H-1 to H-9, H-17 to H-25, H-33 to H-41, H-49 to H-57, H-66 to H-73, H-81 to H-89, H-97 to H-105, H-113 to H-121, and H-129 to H-137, and wherein $R^1$ is H, $C_1$-$C_6$-alkyl, $C_1$-$C_6$-alkoxy, $C_1$-$C_6$-sulfenyl, $C_1$-$C_6$-sulfinyl, or $C_1$-$C_6$-sulfonyl, which groups are unsubstituted or halogenated;

$R^2$ is H, or $C_1$-$C_3$-alkyl;

$R^3$ is $C_1$-$C_3$-alkyl, $C_2$-$C_3$-alkenyl, $C_2$-$C_3$-alkynyl, $C_1$-$C_3$-alkoxy-$C_1$-$C_3$-alkyl, $C_3$-$C_5$-cycloalkyl, phenyl, benzyl, $C_3$-$C_6$-cycloalkyl-$C_1$-$C_3$-alkyl, which groups are unsubstituted or halogenated;

$R^4$ is $C_1$-$C_3$-alkyl or H;

$R^5$ is $C_1$-$C_3$-alkyl;

$R^6$ is H, or $C_1$-$C_3$-alkyl;

X is O or S.

In a another preferred embodiment, the compound of formula (I) is a compound of formula (I.A) wherein the moiety of formula (H) is selected from H-1 to H-162, preferably H-33 to H-48, H-81 to H-96, H-160, H-151, H-152, H-161, and H-163, and wherein $R^1$ is $C_1$-$C_3$-alkyl, which groups are unsubstituted or halogenated, preferably $CF_3$, $R^2$ H, halogen; $C_1$-$C_3$-alkyl, $C_1$-$C_3$-alkoxy, $C_2$-$C_3$-alkenyl, $C_2$-$C_3$-alkynyl, which groups are unsubstituted or halogenated, preferably H, $R^3$ $C_1$-$C_3$-alkyl, cyclopropyl, cyclopropyl-$C_1$-$C_2$-alkyl, which groups are unsubstituted or halogenated, preferably unsubstituted;

$R^6$ is H, or $CH_3$, preferably H;

X is O.

The invention also relates to a mixture of at least one compound of formula (I) with at least one mixing partner. Preferred are binary mixtures of one compound of formula (I) as component I with one mixing partner herein as component II. Preferred weight ratios for such binary mixtures are from 5000:1 to 1:5000, preferably from 1000:1 to 1:1000, more preferably from 100:1 to 1:100, particularly from 10:1 to 1:10. In such binary mixtures, components I and II may be used in equal amounts, or an excess of component I, or an excess of component II may be used.

Mixing partners can be selected from pesticides, in particular insecticides, nematicides, and acaricides, fungicides, herbicides, plant growth regulators, fertilizers. Preferred mixing partners are insecticides, nematicides, and fungicides.

The invention also relates to agrochemical compositions comprising an auxiliary and at least one compound of formula (I). An agrochemical composition comprises a pesticidally effective amount of a compound of formula (I).

The compounds of formula (I) can be converted into customary types of agro-chemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials e.g. seeds (e.g. GF). These and further compositions types are defined in the "Catalogue of pesticide formulation types and international coding system", Technical Monograph No. 2, 6th Ed. May 2008, CropLife International. The compositions are prepared in a known manner, e.g. described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders. Suitable solvents and liquid carriers are water and organic solvents. Suitable solid carriers or fillers are mineral earths. Suitable surfactants are surface-active compounds, e.g. anionic, cationic, nonionic, and amphoteric surfactants, block polymers, polyelectrolytes. Such surfactants can be used as emulsifier, dispersant, solubilizer, wetter, penetration enhancer, protective colloid, or adjuvant. Surfactants are listed in Mccutcheon's, Vol. 1: Emulsifiers & Detergents, Mccutcheon's Directories, Glen Rock, USA, 2008 (International or North American Ed.). Suitable anionic surfactants are alkali, alkaline earth, or ammonium salts of sulfonates, sulfates, phosphates, carboxylates. Suitable nonionic surfactants are alkoxylates, N-substituted fatty acid amides, amine oxides, esters, sugar-based surfactants, polymeric surfactants. Suitable cationic surfactants are qua-ternary surfactants.

The agrochemical compositions generally comprise between 0.01 and 95%, preferably between 0.1 and 90%, and most preferably between 0.5 and 75%, by weight of active substance. The active substances are employed in a purity of from 90% to 100%, preferably from 95% to 100%. Various types of oils, wetters, adjuvants, or fertilizer may be added to the active substances or the compositions comprising them as premix or, if appropriate not until immediately prior to use (tank mix). These agents can be admixed with the compositions according to the invention in a weight ratio of 1:100 to 100:1. The user applies the composition according to the invention usually from a predosage device, a knapsack sprayer, a spray tank, a spray plane, or an irrigation system. Usually, the agro-chemical composition is made up with water, buffer, and/or further auxiliaries to the desired application concentration and the ready-to-use spray liquor or the agrochemical composition according to the invention is thus obtained. Usually, 20 to 2000 liters, of the ready-to-use spray liquor are applied per hectare of agricultural useful area.

The compounds of formula (I) are suitable for use in protecting crops, plants, plant propagation materials, e.g. seeds, or soil or water, in which the plants are growing, from attack or infestation by animal pests. Therefore, the invention also relates to a plant protection method, which comprises contacting crops, plants, plant propagation materials, e.g. seeds, or soil or water, in which the plants are growing, to be protected from attack or infestation by animal pests, with a pesticidally effective amount of a compound of formula (I).

The compounds of formula (I) are also suitable for use in combating or controlling animal pests. Therefore, the invention also relates to a method of combating or controlling animal pests, which comprises contacting the animal pests, their habitat, breeding ground, or food supply, or the crops, plants, plant propagation materials, e.g. seeds, or soil, or the area, material or environment in which the animal pests are growing or may grow, with a pesticidally effective amount of a compound of formula (I).

The compounds of formula (I) are effective through both contact and ingestion to any and all developmental stages, such as egg, larva, pupa, and adult. The compounds of formula (I) can be applied as such or in form of compositions comprising them.

The application can be carried out both before and after the infestation of the crops, plants, plant propagation materials by the pests. The term "contacting" includes both direct contact (applying the compounds/compositions directly on the animal pest or plant) and indirect contact (applying the compounds/compositions to the locus).

The term "animal pest" includes arthropods, gastropods, and nematodes. Preferred animal pests according to the invention are arthropods, preferably insects and arachnids, in particular insects.

The term "plant" includes cereals, e.g. durum and other wheat, rye, barley, triticale, oats, rice, or maize (fodder maize and sugar maize/sweet and field corn); beet, e.g. sugar beet, or fodder beet; fruits, e.g. pomes, stone fruits, or soft fruits, e.g. apples, pears, plums, peaches, nectarines, almonds, cherries, papayas, strawberries, raspberries, blackberries or gooseberries; leguminous plants, e.g. beans, lentils, peas, alfalfa, or soybeans; oil plants, e.g. rapeseed (oilseed rape), turnip rape, mustard, olives, sunflowers, coconut, cocoa beans, castor oil plants, oil palms, ground nuts, or soybeans; cucurbits, e.g. squashes, pumpkins, cucumber or melons; fiber plants, e.g. cotton, flax, hemp, or jute; citrus fruit, e.g. oranges, lemons, grape-fruits or mandarins; vegetables, e.g. eggplant, spinach, lettuce (e.g. iceberg lettuce), chicory, cabbage, asparagus, cabbages, carrots, onions, garlic, leeks, tomatoes, potatoes, cucurbits or sweet peppers; lauraceous plants, e.g. avocados, cinnamon, or camphor; energy and raw material plants, e.g. corn, soybean, rapeseed, sugar cane or oil palm; tobacco; nuts, e.g. walnuts; pistachios; coffee; tea; bananas; vines; hop; sweet leaf (*Stevia*); natural rubber plants or ornamental and forestry plants, shrubs, broad-leaved trees or evergreens, *eucalyptus*; turf; lawn; grass. Preferred plants include potatoes sugar beets, tobacco, wheat, rye, barley, oats, rice, corn, cotton, soybeans, rapeseed, legumes, sunflowers, coffee, or sugar cane; fruits; vines; ornamentals; or vegetables, e.g. cucumbers, tomatoes, beans or squashes.

The term "seed" embraces seeds and plant propagules including true seeds, seed pieces, suckers, corms, bulbs, fruit, tubers, grains, cuttings, cut shoots, and means preferably true seeds.

"Pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions e.g. desired pesticidal effect and duration, weather, target species, locus, mode of application.

For use in treating crop plants, e.g. by foliar application, the rate of application of the active ingredients of this invention may be in the range of 0.0001 g to 4000 g per hectare, e.g. from 1 g to 2 kg per hectare or from 1 g to 750 g per hectare, desirably from 1 g to 100 g per hectare.

The compounds of formula (I) are also suitable for use against non-crop insect pests. For use against said non-crop pests, compounds of formula (I) can be used as bait composition, gel, general insect spray, aero-sol, as ultra-low volume application and bed net (impregnated or surface applied).

The term "non-crop insect pest" refers to pests, which are particularly relevant for non-crop targets, e.g. ants, termites, wasps, flies, ticks, mosquitoes, bed bugs, crickets, or cockroaches, such as: *Aedes aegypti, Musca domestica*, Tribolium spp.; termites such as *Reticulitermes flavipes, Coptotermes formosanus*; roaches such as Blatella *germanica, Periplaneta Americana*; ants such as *Solenopsis invicta, Linepithema humile*, and *Camponotus pennsylvanicus*. The bait can be a liquid, a solid or a semisolid preparation (e.g. a gel). For use in bait compositions, the typical content of active ingredient is from 0.001 wt % to 15 wt %, desirably from 0.001 wt % to 5 wt % of active compound.

The compounds of formula (I) and its compositions can be used for protecting wooden materials such as trees, board fences, sleepers, frames, artistic artifacts, etc. and buildings, but also construction materials, furniture, leathers, fibers, vinyl articles, electric wires and cables etc. from ants, termites and/or wood or textile destroying beetles, and for controlling ants and termites from doing harm to crops or human beings (e.g. when the pests invade into houses and public facilities or nest in yards, orchards or parks).

Customary application rates in the protection of materials are, e.g., from 0.001 g to 2000 g or from 0.01 g to 1000 g of active compound per $m^2$ treated material, desirably from 0.1 g to 50 g per $m^2$.

Insecticidal compositions for use in the impregnation of materials typically contain from 0.001 to 95 wt %, preferably from 0.1 to 45 wt %, and more preferably from 1 to 25 wt % of at least one repellent and/or insecticide.

Pests

The compounds of the invention are especially suitable for efficiently combating animal pests e.g. arthropods, and nematodes including:

insects from the sub-order of Auchenorrhyncha, e.g. Amrasca biguttula, *Empoasca* spp., *Nephotettix virescens, Sogatella furcifera*, Mahanarva spp., *Laodelphax striatellus, Nilaparvata lugens, Diaphorina citri;*

Lepidoptera, e.g. *Helicoverpa* spp., *Heliothis virescens, Lobesia botrana, Ostrinia nubilalis, Plutella xylostella, Pseudoplusia includens, Scirpophaga incertulas, Spodoptera* spp., *Trichoplusia ni, Tuta absoluta, Cnaphalocrocis medialis, Cydia pomonella, Chilo suppressalis, Anticarsia gemmatalis, Agrotis ipsilon, Chrysodeixis includens;*

True bugs, e.g. *Lygus* spp., Stink bugs such as *Euschistus* spp., *Halyomorpha halys, Nezara viridula, Piezodorus guildinii, Dichelops furcatus;*

*Thrips*, e.g. *Frankliniella* spp., *Thrips* spp., *Dichromothrips corbettii;*

Aphids, e.g. *Acyrthosiphon pisum, Aphis* spp., *Myzus persicae, Rhopalosiphum* spp., *Schizaphis graminum, Megoura viciae;*

Whiteflies, e.g. *Trialeurodes vaporariorum, Bemisia* spp.;

Coleoptera, e.g. *Phyllotreta* spp., Melanotus spp., *Meligethes aeneus, Leptinotarsa decimlineata, Ceutorhynchus* spp., *Diabrotica* spp., *Anthonomus grandis, Atomaria linearia, Agriotes* spp., *Popilla* spp., *Epilachna* spp.;

Flies, e.g. *Delia* spp., *Ceratitis* capitate, Bactrocera spp., *Liriomyza* spp.;

Coccoidea, e.g. Aonidiella *aurantia*, Ferrisia virgate;

Anthropods of class Arachnida (Mites), e.g. Penthaleus major, *Tetranychus* spp.;

Nematodes, e.g. *Heterodera glycines, Meloidogyne* spp., *Pratylenchus* spp., *Caenorhabditis elegans.*

The compounds of formula (I) are also especially suitable for controlling pests from the family of Pentatomidae, such as *Acrosternum* spp., *Euschistus* spp., *Halyomorpha* spp., *Nezara* spp., *Megacopta* spp., and *Piezodorus* spp., in particular *Euschistus servus* (brown stink bug), *Euschistus heros* (Neotropical brown stink bug), *Halyomorpha halys* (brown marmorated stink bug), *Nezara viridula* (southern green stink bug), *Megacopta cribraria* (globular stink bug), and *Piezodorus guildini* and soil pests like *Popilla japonica.*

Animal Health

The compounds of formula (I) are suitable for use in treating or protecting animals against infestation or infection by parasites. Therefore, the invention also relates to the use of a compound of the invention for the manufacture of a medicament for the treatment or protection of animals against infestation or infection by parasites. Furthermore, the invention relates to a method of treating or protecting animals against infestation and infection by parasites, which comprises orally, topically or parenterally administering or applying to the animals a parasiticidally effective amount of a compound of formula (I).

The invention also relates to the non-therapeutic use of compounds of the invention for treating or protecting animals against infestation and infection by parasites. Moreover, the invention relates to a non-therapeutic method of treating or protecting animals against infestation and infection by parasites, which comprises applying to a locus a parasiticidally effective amount of a compound of formula (I).

The compounds of the invention are further suitable for use in combating or controlling parasites in and on animals. Furthermore, the invention relates to a method of combating or controlling parasites in and on animals, which comprises contacting the parasites with a parasitically effective amount of a compound of formula (I).

The invention also relates to the non-therapeutic use of compounds of formula (I) for controlling or combating parasites. Moreover, the invention relates to a non-therapeutic method of combating or controlling parasites, which comprises applying to a locus a parasiticidally effective amount of a compound of formula (I).

The compounds of formula (I) can be effective through both contact (via soil, glass, wall, bed net, carpet, blankets or animal parts) and ingestion (e.g. baits). Furthermore, the compounds of formula (I) can be applied to any and all developmental stages.

The compounds of formula (I) can be applied as such or in form of compositions comprising them.

The term "locus" means the habitat, food supply, breeding ground, area, material or environment in which a parasite is growing or may grow outside of the animal.

As used herein, the term "parasites" includes endo- and ectoparasites. In some embodiments of the invention, endoparasites can be preferred. In other embodiments, ectoparasites can be preferred. Infestations in warm-blooded animals and fish include lice, biting lice, ticks, nasal bots, keds, biting flies, muscoid flies, flies, myiasitic fly larvae, chiggers, gnats, mosquitoes and fleas.

The compounds of the invention are especially useful for combating the following parasites: *Cimex lectularius, Rhipicephalus sanguineus*, and *Ctenocephalides felis.*

As used herein, the term "animal" includes warm-blooded animals (including humans) and fish. Preferred are mammals, such as cattle, sheep, swine, camels, deer, horses, pigs, poultry, rabbits, goats, dogs and cats, water buffalo, donkeys, fallow deer and reindeer, and also in furbearing animals such as mink, chinchilla and raccoon, birds such as hens, geese, turkeys and ducks and fish such as fresh- and salt-water fish such as trout, carp and eels. Particularly preferred are domestic animals, such as dogs or cats.

The compounds of formula (I) may be applied in total amounts of 0.5 mg/kg to 100 mg/kg per day, preferably 1 mg/kg to 50 mg/kg per day.

For oral administration to warm-blooded animals, the compounds of formula (I) may be formulated as animal feeds, animal feed premixes, animal feed concentrates, pills, solutions, pastes, suspensions, drenches, gels, tablets, boluses and capsules. For oral administration, the dosage form chosen should provide the animal with 0.01 mg/kg to 100 mg/kg of animal body weight per day of the compounds of formula (I), preferably with 0.5 mg/kg to 100 mg/kg of animal body weight per day.

Alternatively, the compounds of formula (I) may be administered to animals parenterally, e.g., by intraruminal, intramuscular, intravenous or subcutaneous injection. The compounds of formula (I) may be dispersed or dissolved in a physiologically acceptable carrier for subcutaneous injection. Alternatively, the compounds of formula (I) may be formulated into an implant for subcutaneous administration. In addition the compounds of formula (I) may be transdermally administered to animals. For parenteral administration, the dosage form chosen should provide the animal with 0.01 mg/kg to 100 mg/kg of animal body weight per day of the compounds of formula (I).

The compounds of formula (I) may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the compounds of formula (I). In addition, the compounds of formula (I) may be formulated as ear tags for animals, particularly quadrupeds e.g. cattle and sheep.

Oral solutions are administered directly.

Solutions for use on the skin are trickled on, spread on, rubbed in, sprinkled on or sprayed on.

Gels are applied to or spread on the skin or introduced into body cavities.

Pour-on formulations are poured or sprayed onto limited areas of the skin, the active compound penetrating the skin and acting systemically. Pour-on formulations are prepared by dissolving, suspending or emulsifying the active compound of formula (I) n suitable skin-compatible solvents or solvent mixtures.

Emulsions can be administered orally, dermally or as injections.

Suspensions can be administered orally or topically/dermally.

Semi-solid preparations can be administered orally or topically/dermally.

For the production of solid preparations, the active compound of formula (I) s mixed with suitable excipients, if appropriate with addition of auxiliaries, and brought into the desired form.

The compositions which can be used in the invention can comprise generally from about 0.001 to 95% of the compound of formula (I).

Ready-to-use preparations contain the compounds acting against parasites, preferably ectoparasites, in concentrations of 10 ppm to 80% by weight, preferably from 0.1 to 65% by weight, more preferably from 1 to 50% by weight, most preferably from 5 to 40% by weight.

Preparations which are diluted before use contain the compounds acting against ectoparasites in concentrations of 0.5 to 90% by weight, preferably of 1 to 50% by weight.

Furthermore, the preparations comprise the compounds of formula I against endoparasites in concentrations of 10 ppm to 2% by weight, preferably of 0.05 to 0.9% by weight, very particularly preferably of 0.005 to 0.25% by weight.

Solid formulations which release compounds of the invention may be applied in total amounts of 10 mg/kg to 300 mg/kg, preferably 20 mg/kg to 200 mg/kg, most preferably 25 mg/kg to 160 mg/kg body weight of the treated animal in the course of three weeks.

The following examples illustrate the invention.

A. Preparation of Compounds

Materials: Unless otherwise noted, reagents and solvents were purchased at highest commercial quality and used without further purification.

All reactions were monitored by thin-layer chromatography (TLC) using Merck silica gel 60 $F_254$ pre-coated plates (0.25 mm). Flash chromatography was carried out with Kanto Chemical silica gel (Kanto Chemical, silica gel 60N, spherical neutral, 0.040-0.050 mm, Cat.-No. 37563-84). $^1H$ NMR spectra were recorded on JEOL JNM-ECA-500 (500 MHz). Chemical shifts are expressed in ppm downfield from the internal solvent peaks for acetone-$d_6$ ($^1H$; δ=2.05 ppm) and $CD_3OD$ ($^1H$; δ=3.30 ppm), and J values are given in Hertz. The following abbreviations were used to explain the multiplicities: s=singlet, d=doublet, t=triplet, q=quartet, dd=double doublet, dt=double triplet, m=multiplet, br=broad. High-resolution mass spectra were measured on a JEOL JMS-T100LP.

Characterization: The compounds were characterized by coupled High Performance Liquid Chromatography with mass spectrometry (HPLC/MS).

UHPLC-MS on Shimadzu LCMS 2020 ESI. Analytical UHPLC column: C-18, 50 mm, 4.6 mm, 5 micron; mobile phase: 100 mM Ammonium Formate B: Acetonitrile Flow Rate: 1.2 mL/min, Injection Vol: 1 μL in 1.50 minutes; Gradient: 10% B to 100% B in 1.5 min, Hold 100% B for 1 min, 2.51 min 10% B Run time: 3 min at 400° C. MS-method: ESI positive; mass range (m/z) 100-800.

General abbreviations used: DMF is dimethylformamide; min is minutes; THF is tetrahydrofuran; DCM is dichlormethane; mL is milliliters Synthesis Example 1: Manufacture of 2-[5-ethylsulfonyl-6-[6-methyl-5-oxo-7-(trifluoromethyl)imidazo[1,2-c]pyrimidin-2-yl]-3-pyridyl]-2-methyl-propanenitrile (compound C-5)

Step 1) Preparation of 5-(1-cyano-1-methyl-ethyl)-3-ethylsulfanyl-N-methoxy-N-methyl-pyridine-2-carboxamide To a solution of 2.4 mmol 5-(1-cyano-1-methyl-ethyl)-3-ethylsulfanyl-pyridine-2-carboxylic acid (WO 2018/153778, p. 57) and 4.79 mmol N,O-dimethyl hydroxylamine in 15 ml DMF were added 1.6 ml diisopropylethylamine and 1.37 g HATU and the mixture was stirred for 12 hours at 20 to 25° C. The reaction was concentrated under reduced pressure to afford a crude residue. The crude residue was taken up in ethyl acetate and washed two times with $H_2O$. The combined organic layers were dried and concentrated under reduced pressure to afford a residue. The residue was purified by column chromatography under reversed phase conditions to afford 400 mg 5-(1-cyano-1-methyl-ethyl)-3-ethylsulfanyl-N-methoxy-N-methyl-pyridine-2-carboxamide.

LC-MS: mass found for $C_{14}H_{19}N_3O_2S$ $[M+H]^+$ 293.8; $t_R$=0.919 min (tR: retention time).

Step 2) Preparation of 2-(6-acetyl-5-ethylsulfanyl-3-pyridyl)-2-methyl-propanenitrile To a solution of 1.36 mmol 5-(1-cyano-1-methyl-ethyl)-3-ethylsulfanyl-N-methoxy-N-methyl-pyridine-2-carboxamide in 5 ml THF were added 0.91 ml of a 3 molar solution of $CH_3MgBr$ in diethyl ether at 0° C. under $N_2$-atmosphere. The resulting composition was warmed to 20 to 25° C. and stirred for additional 60 minutes. The composition was then diluted with ethyl acetate and a saturated aqueous solution of $NH_4Cl$. The aqueous layer was separated and extracted twice with ethyl acetate. The combined organic layers were dried and concentrated under reduced pressure to afford 318 mg 2-(6-acetyl-5-ethylsulfanyl-3-pyridyl)-2-methyl-propanenitrile. The crude product was used in the next step without further purification.

Step 3) Preparation of 2-[6-(2-bromoacetyl)-5-ethylsulfanyl-3-pyridyl]-2-methyl-propanenitrile A solution of 1.28 mmol 2-(6-acetyl-5-ethylsulfanyl-3-pyridyl)-2-methyl-propanenitrile was dissolved in 1.5 ml 25% HBr in $CH_3COOH$ acetic acid and a solution of 1.41 mmol $Br_2$ in 1.5 ml $CH_3COOH$ was added at 20 to 25° C. and stirred for 12 hours. The reaction was concentrated under reduced pressure to afford a crude residue. The crude residue was taken up in ethyl acetate and washed two times with $H_2O$. The combined organic layers were dried and concentrated under reduced pressure to afford the crude product. The crude product was used in the next step without further purification.

Step 4) Preparation of 2-[5-ethylsulfanyl-6-[6-methyl-5-oxo-7-(trifluoromethyl)imidazo[1,2-c]pyrimidin-2-yl]-3-pyridyl]-2-methyl-propanenitrile A solution of 1.28 mmol 2-[6-(2-bromoacetyl)-5-ethylsulfanyl-3-pyridyl]-2-methyl-propanenitrile and 1.07 mmol 4-amino-1-methyl-6-(trifluoromethyl)pyrimidin-2-one was dissolved in 8 ml $(CH_3)_3COH$ and heated to refluxation for 3 days. The reaction was then cooled to 20 to 25° C. and concentrated under reduced pressure to afford a crude residue. The crude residue was taken up in ethyl acetate and washed two times with $H_2O$. The organic layer was dried and concentrated under reduced pressure to afford a crude residue. The crude residue was purified by preparative HPLC to afford 46 mg of 2-[5-ethylsulfanyl-6-[6-methyl-5-oxo-7-(trifluoromethyl)-imidazo[1,2-c]pyrimidin-2-yl]-3-pyridyl]-2-methyl-propanenitrile.

LC-MS: mass found for $C_{19}H_{18}F_3N_5OS$ $[M+H]^+$ 421.8; $t_R$=1.101 min.

Step 5) Preparation of 2-[5-ethylsulfonyl-6-[6-methyl-5-oxo-7-(trifluoromethyl)imidazo[1,2-c]pyrimidin-2-yl]-3-pyridyl]-2-methyl-propanenitrile To a solution of 2-[5-ethylsulfanyl-6-[6-methyl-5-oxo-7-(trifluoromethyl)imidazo[1,2-c]pyrimidin-2-yl]-3-pyridyl]-2-methyl-propanenitrile (0.11 mmol) in $CH_3COOH$ (2 mL) was added sodium tungstate (0.003 mmol) and $H_2O_2$ (30% solution in $H_2O$, 0.22 mmol). The resulting reaction mixture was stirred at 20 to 25° C. for approximately 12 hours and then concentrated under reduced pressure to obtain a crude residue. The crude residue was taken up in ethyl acetate and washed two times with an aqueous saturated solution of $NaHCO_3$. The organic layer was dried and concentrated under reduced pressure to afford a residue. 2-[5-ethylsulfonyl-6-[6-methyl-5-oxo-7-(trifluoromethyl)imidazo[1,2-c]pyrimidin-2-yl]-3-pyridyl]-2-methyl-propanenitrile was obtained in sufficient purity (43 mg). mass found for $C_{19}H_{18}F_3N_5O_3S$ $[M+H]^+$ 454.0; $t_R$=1.063 min.

Synthesis Example 2: Preparation of 1-[6-[6-cyclopropyl-5-oxo-7-(trifluoromethyl)imidazo[1,2-c]pyrimidin-2-yl]-5-ethylsulfonyl-3-pyridyl]cyclopropanecarbonitrile (compound C-6)

Step 1): Manufacture of 5-bromo-3-ethylsulfanyl-pyridine-2-carbonitrile

A composition containing 5-bromo-3-nitro-pyridine-2-carbonitrile (0.087 mol) in DMF (200 mL) was prepared under stirring at −40° C., upon which sodium ethane thiolate was added (0.105 mol) portion wise over a period of 30 min under $N_2$-atmosphere at maintained temp between −40 to −50° C. The resulting reaction mixture was stirred at the same temperature for 10 minutes, then gradually allowed to reach 20 to 25° C. with continued stirring for 1 hour. After the completion of reaction, the reaction mixture was quenched and extracted with $CH_3COOCH_2CH_3$. The organic layers were washed, dried and concentrated under reduced pressure to get a crude residue. The crude residue was purified by column chromatography to afford 5-bromo-3-ethylsulfanyl-pyridine-2-carbonitrile as a yellow solid (17 g). $H^1$-NMR (500 MHz, $CDCl_3$): δ 8.52 (s, 1H), 7.85 (s, 1H), 3.07 (q, 2H, J=10 Hz), 1.43 (t, 3H, J=7.3 Hz). LC-MS: mass found for $C_8H_7BrN_2S$ $[M+H]^+$ found 244.

Step 2): Manufacture of 1-(5-bromo-3-ethylsulfanyl-2-pyridyl) ethanone

A composition containing 5-bromo-3-ethylsulfanyl-pyridine-2-carbonitrile (17 g) in THF (170 mL) was prepared under stirring at 0° C., upon which $CH_3MgBr$ (2 eq) was added dropwise over a period of 30 min at 0° C. to −5° C. under $N_2$-atmosphere. The resulting reaction mixture was stirred at 0° C. for 2 hours. After the completion of reaction, the reaction mixture was quenched and extracted. The organic layers were washed, dried and concentrated under reduced pressure to get crude residue. The crude residue was purified by crystallization. After treatment with $CH_3COOCH_2CH_3$ and heptane at −30° C., a precipitate was observed. The obtained solid was filtered and dried under reduced pressure to afford 1-(5-bromo-3-ethylsulfanyl-2-pyridyl) ethanone (14 g). $H^1$ NMR (500 MHz, DMSO): δ 8.57 (s, 1H), 8.05 (s, 1H), 3.01 (q, 2H, J=10 Hz), 2.59 (s, 3H), 1.26 (t, 3H, J=7.3 Hz). LC-MS: mass found for $C_9H_{10}BrNOS$ $[M+H]^+$ 261.

Step-3): Manufacture of 1-(5-bromo-3-ethylsulfonyl-2-pyridyl) ethanone

A composition containing 1-(5-bromo-3-ethylsulfanyl-2-pyridyl) ethanone (3.9 g) in $CH_2Cl_2$ (40 mL) was prepared under stirring at 0° C., upon which m-chloroperoxy benzoic acid was added (0.039 mol). The resulting reaction mixture was stirred at 20 to 25° C. for 3 to 4 hours. After the completion of reaction, the reaction mixture was quenched, and extracted with $CH_2Cl_2$. The combined organic layers were washed, dried and concentrated under reduced pressure to afford 1-(5-bromo-3-ethylsulfonyl-2-pyridyl) ethanone (3.2 g). $H^1$ NMR (500 MHz, $CDCl_3$): δ 9.12 (s, 1H), 8.55 (s, 1H), 3.55 (q, 2H J=12 Hz), 2.5 (s, 3H), 1.20 (t, 3H, J=7 Hz). LC-MS: mass found for $C_9H_{10}$ $BrNO_3$ S $[M+H]^+$ 292.

Step-4: Manufacture of 2-bromo-1-(5-bromo-3-ethylsulfonyl-2-pyridyl) ethanone

A composition containing 1-(5-bromo-3-ethylsulfonyl-2-pyridyl) ethanone (0.010 mol) in $CHCl_3$ (30 mL) was prepared under stirring at 0° C., upon which $CH_3COOH$ (30 mL) and HBr in $CH_3COOH$ (30 mL) were added and stirred for few minutes. Then, $Br_2$ (0.012 mol) in $CHCl_3$ was added. The resulting reaction mixture was heated to 60° C. for 1 hour. After the completion of reaction, the reaction mixture was quenched, and extracted with $CH_2Cl_2$. The combined organic layers were washed, dried, and concentrated under reduced pressure to afford a crude residue. The crude residue was purified by column chromatography to afford 2-bromo-1-(5-bromo-3-ethylsulfonyl-2-pyridyl) ethanone (2.2 g). $H^1$ NMR (500 MHz, $CDCl_3$): δ 9.17 (s, 1H), 8.63 (s, 1H), 4.92 (s, 2H), 3.59 (q, 2H J=12 Hz), 1.20 (t, 3H, J=7 Hz). LC-MS: mass found for $C_9H_9Br_2NO_3S$ $[M+H]^+$ 372.

Step 5): Manufacture of 2-(5-bromo-3-ethylsulfonyl-2-pyridyl)-6-cyclopropyl-7-(trifluoromethyl) imidazo[1,2-c]pyrimidin-5-one A composition containing 2-bromo-1-(5-bromo-3-ethylsulfonyl-2-pyridyl) ethanone (0.006 mol) in $(CH_3)_3COH$ (4 mL) was prepared under stirring, upon which 1-cyclopropyl-4-imino-6-(trifluoromethyl)pyrimidin-2-one (0.036 mol) was added. Molecular sieves were added to the above reaction mixture (2 g) and the resultant reaction mixture was heated to 120° C. for 24 hours. After the completion of reaction, the reaction mixture was filtered through celite bed, and the filtrate was collected and concentrated under reduced pressure to get a crude residue. The crude residue was purified by column chromatography to afford 2-(5-bromo-3-ethylsulfonyl-2-pyridyl)-6-cyclopropyl-7-(trifluoromethyl)imidazo[1,2-c]pyrimidin-5-one (1.5 g). $H^1$-NMR (500 MHz, DMSO): δ 9.10 (s, 1H), 8.53 (s, 1H), 8.28 (s, 1H), 7.52 (s, 1H), 4.06 (q, 2H, J=10 Hz), 3.17 (s, 1H), 1.23 (t, 3H, J=7 Hz), 1.09 (dd, 4H, J=4.5 Hz). LC-MS: mass found for $C_{17}H_{14}BrF_3N_4O_3S$ $[M+H]^+$ found 492.

Step 6): Manufacture of 2-[6-[6-cyclopropyl-5-oxo-7-(trifluoromethyl)imidazo[1,2-c]pyrimidin-2-yl]-5-ethylsulfonyl-3-pyridyl]acetonitrile A composition containing 2-(5-bromo-3-ethylsulfonyl-2-pyridyl)-6-cyclopropyl-7-(trifluoromethyl)imidazo[1,2-c] pyrimidin-5-one (2.0396 mmol) in DMF (5 mL) was prepared at 25° C., upon which 2-trimethylsilylacetonitrile (2.4475 mmol), tris(dibenzylideneacetone) dipalladium (0) (0.0510 mmol), and xantphos (0.1020 mmol) were added. The resulting reaction mixture was degassed for 15 minutes under $N_2$-atmosphere, followed by the addition of $ZnF_2$ (1.2238 mmol). The reaction mixture was then heated to 120° C. for 12 hours in a Radley's reactor. After the completion of the reaction, the reaction mixture was quenched with $H_2O$, and extracted with $CH_3COOCH_2CH_3$. The combined organic layers were washed, dried, and concentrated under reduced pressure to get a crude residue. The crude residue was purified by column chromatography to afford 2-[6-[6-cyclopropyl-5-oxo-7-(trifluoromethyl)imidazo[1,2-c]pyrimidin-2-yl]-5-ethylsulfonyl-3-pyridyl]acetonitrile (0.220 g). $H^1$-NMR (500 MHz, DMSO-d6): δ 9.10 (d, J=2.4 Hz, 1H), 8.45 (d, J=2.4 Hz, 1H), 8.28 (s, 1H), 7.51 (s, 1H), 4.07 (q, J=7.3 Hz, 2H), 3.86 (s, 2H), 3.17 (s, 1H), 1.25 (t, J=7.4 Hz, 3H), 1.19-1.00 (m, 4H). LC-MS: mass found for $C_{19}H_{18}F_3N_5O_3S$ $[M+H]^+$ 452.0.

Step 7): Manufacture of 1-[6-[6-cyclopropyl-5-oxo-7-(trifluoromethyl)imidazo[1,2-c]pyrimidin-2-yl]-5-ethylsulfonyl-3-pyridyl]cyclopropanecarbonitrile A composition comprising 2-[6-[6-cyclopropyl-5-oxo-7-(trifluoromethyl)imidazo[1,2-c]pyrimidin-2-yl]-5-ethylsulfonyl-3-pyridyl]acetonitrile (0.31 mmol) and $K_2CO_3$ (0.624 mmol) in $CH_3CN$ (2 mL) was prepared under stirring at 0° C., upon which 1-chloro-2-bromoethane (0.66 mmol) was added dropwise. The resulting reaction mixture was stirred at 20 to 25° C. for 1 to 2 hours. After the completion of the reaction, the reaction mixture was quenched with $H_2O$ and extracted with $CH_3COOCH_2CH_3$. The combined organic layers were dried and concentrated under reduced pressure to afford a crude residue. The crude residue was purified by column chromatography to afford 1-[6-[6-cyclopropyl-5-oxo-7-(trifluoromethyl)imidazo[1,2-c]pyrimidin-2-yl]-5-ethylsulfonyl-3-pyridyl]cyclopropanecarbonitrile (0.1 g). $H^1$-NMR (500 MHz, DMSO-d6): $^1H$ NMR (500 MHz, DMSO-$d_6$): δ 8.84 (d, J=2.4 Hz, 1H), 8.35 (d, J=2.4 Hz, 1H), 8.25 (s, 1H), 7.51 (s, 1H), 4.07 (q, J=7.3 Hz, 2H), 3.17 (s, 1H), 2.03-1.87 (m, 2H), 1.87-1.73 (m, 2H), 1.25 (t, J=7.4 Hz, 3H), 1.19-1.00 (m, 4H). LC-MS: mass found for $C_{21}H_{18}F_3N_5O_3S$ $[M+H]^+$ 478.0.

Synthesis Example 3:2-[3-ethylsulfonyl-5-[(E)-2,2,2-trifluoroethoxyiminomethyl]-2-pyridyl]-6-methyl-7-(trifluoromethyl)imidazo[1,2-c]pyrimidin-5-one (compound C-3)

Step 1): Preparation of 2-(5-bromo-3-ethylsulfonyl-2-pyridyl)-6-methyl-7-(trifluoromethyl)imidazo[1,2-c]pyrimidin-5-one A composition of 16 mmol of 2-bromo-1-(5-bromo-3-ethylsulfonyl-2-pyridyl) ethenone (WO2016/071214, p. 78) and 4-amino-1-methyl-6-(trifluoromethyl)pyrimidin-2-one (16 mmol) was in 10 ml $(CH_3)_3COH$ was prepared and heated to refluxation for 12 hours. The resulting reaction mixture was then cooled to 20 to 25° C. and the precipitate was collected by filtration to afford 2-(5-bromo-3-ethylsulfonyl-2-pyridyl)-6-methyl-7-(trifluoromethyl)imidazo-[1,2-c]pyrimidin-5-one (5 g).

LC-MS: mass found for $C_{15}H_{12}N_4O_3F_3SBr$ $[M+H]^+$ 466.9; $t_R$=1.122 min.

Step 2): Preparation of 2-(3-ethylsulfonyl-5-vinyl-2-pyridyl)-6-methyl-7-(trifluoromethyl)imidazo[1,2-c]pyrimidin-5-one A composition comprising 5 mmol of 2-(5-bromo-3-ethylsulfonyl-2-pyridyl)-6-methyl-7-(trifluoromethyl)imidazo-[1,2-c]pyrimidin-5-one, 7.7 mmol of tributyl(vinyl) tin and 0.42 g 1,1'-bis(diphenylphospino)ferrocene Pd(II) dichloride in 200 ml toluene was prepared and stirred at 100° C. for 36 hours. The composition was then cooled to 20 to 25° C. and washed with an aqueous saturated solution of KF. The combined organic layers were dried, and concentrated under reduced pressure to afford a crude residue. The crude residue was purified by column chromatography to afford 1.4 g of 2-(3-ethylsulfonyl-5-vinyl-2-pyridyl)-6-methyl-7-(trifluoromethyl)imidazo[1,2-c]pyrimidin-5-one. LC-MS: mass found for $C_{17}H_{15}N_4O_3F_3S$ $[M+H]^+$413.0; $t_R$=1.067 min.

Step 3): Preparation of 5-ethylsulfonyl-6-[6-methyl-5-oxo-7-(trifluoromethyl)imidazo[1,2-c]pyrimidin-2-yl]pyridine-3-carbaldehyde To a composition containing 3.4 mmol of 2-(3-ethylsulfonyl-5-vinyl-2-pyridyl)-6-methyl-7-(trifluoromethyl)imidazo[1,2-c]pyrimidin-5-one in 50 ml THF/water (1:1) was added a solution of $OsO_4$ in $(CH_3)_3COH$ (2,5%, 1 g) and 6.8 mmol $NalO_4$ at 0° C. The resulting reaction mixture was slowly warmed to 20 to 25° C. and stirred for approximately 12 hours. The reaction mixture was quenched with a saturated aqueous solution of sodium thiosulfate, and extracted with $CH_3COOHCH_2CH_3$. The combined organic layers were dried and concentrated under reduced pressure to afford a crude residue. The crude residue was purified by column chromatography under reversed phase conditions to afford 1 g of 5-ethylsulfonyl-6-[6-methyl-5-oxo-7-(trifluoromethyl)imidazo[1,2-c]pyrimidin-2-yl]pyridine-3-carbaldehyde. LC-MS: mass found for $C_{16}H_{13}N_4O_4F_3S$ $[M+H]^+$ 432.9.0 (hydrate); $t_R$=0.976 min.

Step 4): Preparation of 2-[3-ethylsulfonyl-5-[(E)-2,2,2-trifluoroethoxyiminomethyl]-2-pyridyl]-6-methyl-7-(trifluoromethyl)imidazo[1,2-c]pyrimidin-5-one A composition comprising 0.14 mmol of 5-ethylsulfonyl-6-[6-methyl-5-oxo-7-(trifluoromethyl)-imidazo[1,2-c]pyrimidin-2-yl]pyridine-3-carbaldehyde and 2 ml $CH_3CH_2OH$ was added 0.16 mmol 2,2,2-trifluoroethoxyammonium chloride and 15 mg $(CH_3CH_2)_3N$. The resulting reaction mixture was stirred at 60° C. for 4 hours and then concentrated under reduced pressure to obtain a crude residue. The residue was taken up in $H_2O$ and extracted with $CH_2Cl_2$. The combined organic layers were dried and concentrated under reduced pressure to afford a crude residue. The crude residue was purified by column chromatography under reversed phase conditions to afford 18 mg of 2-[3-ethylsulfonyl-5-[(E)-2,2,2-trifluoroethoxyiminomethyl]-2-pyridyl]-6-methyl-7-(trifluoromethyl)imidazo[1,2-c]pyrimidin-5-one. LC-MS: mass found for $C_{18}H_{15}N_5O_4F_6S$ $[M+H]^+$ 511.8; $t_R$=1.192 min.

Synthesis Example 4: Manufacture of (2Z)-2-[6-[6-cyclopropyl-5-oxo-7-(trifluoromethyl)imidazo[1,2-c]pyrimidin-2-yl]-5-ethylsulfonyl-3-pyridyl]-2-hydroxyimino-acetonitrile (compound C-8)

To a stirred composition of 2-[6-[6-cyclopropyl-5-oxo-7-(trifluoromethyl)imidazo[1,2-c]pyrimidin-2-yl]-5-ethylsulfonyl-3-pyridyl]acetonitrile (1.77 mmol) and sodium methoxide (5.3 mmol) in $CH_3CH_2OH$ (8 mL) at 0° C. was added isopentyl-nitrite (3.5 mmol) dropwise. The resulting reaction mixture was stirred at 20 to 25° C. for 16 hours. After the completion of the reaction, the reaction mixture was quenched with $H_2O$ and extracted with $CH_3COOCH_2CH_3$. The combined organic layers were separated, dried and concentrated to afford a crude residue. The crude residue was purified by column chromatography to afford (2Z)-2-[6-[6-cyclopropyl-5-oxo-7-(trifluoromethyl)imidazo[1,2-c]pyrimidin-2-yl]-5-ethylsulfonyl-3-pyridyl]-2-hydroxyimino-acetonitrile as a pale yellow solid (0.7 g, 81% yield). 1H-NMR (500 MHz, DMSO-d6): δ 9.22 (s, 1H), 8.48 (s, 1H), 8.20 (d, J=3.1 Hz, 1H), 7.49 (s, 1H), 5.76 (s, 2H), 3.17 (s, 1H), 1.22 (dt, J=10.8, 7.4 Hz, 3H), 1.18-0.94 (m, 4H). LC-MS: mass found for $C_{19}H_{15}F_3N_6O_4S$ $[M+H]^+$ 481.0.

Synthesis Example 5: Manufacture of 6-cyclopropyl-2-[3-ethylsulfonyl-5-(1-oxa-2-azaspiro[4.4]non-2-en-3-yl)-2-pyridyl]-7-(trifluoromethyl)imidazo[1,2-c]pyrimidin-5-one (compound C-13)

Step 1): Synthesis of 6-cyclopropyl-2-[3-(ethanesulfonyl)-5-ethenylpyridin-2-yl]-7-(trifluoromethyl)imidazo[1,2-c]pyrimidin-5-one A composition comprising 2-[5-bromo-3-(ethane sulfonyl)pyridin-2-yl]-6-cyclopropyl-7-(trifluoromethyl)imidazo[1,2-c]pyrimidin-5-one (2.036 mmol) in dry 1,4 dioxane (20 ml) was added tributyl(vinyl) tin (2.504 mmol) and the resulting reaction mixture was purged with a nitrogen balloon for 5 minutes. Then, 1,1'-Bis(diphenylphosphino)ferrocene]dichloropalladium (II) (0.3054 mmol) was added and the reaction mixture was heated for 18 hours to 100° C. The reaction mixture was poured in $H_2O$ (30 ml) and $CH_3COOCH_2CH_3$ (60 ml) was added. The resulting mixture was filtered through a celite bed; the filtrate was collected and extracted. The combined organic extracts were dried and concentrated under reduced pressure to afford a crude product. The crude product was purified by column chromatography to afford 6-cyclopropyl-2-[3-(ethanesulfonyl)-5-ethenylpyridin-2-yl]-7-(trifluoromethyl)imidazo[1,2-c]pyrimidin-5-one as a beige solid (0.75 g). $H^1$-NMR (500 MHz, DMSO-d6): δ 9.07 (d, J=2.1 Hz, 1H), 8.44 (d, J=2.1 Hz, 1H), 8.26 (s, 1H), 7.51 (s, 1H), 6.97 (dd, J=17.8, 11.1 Hz, 1H), 6.20 (d, J=17.8 Hz, 1H), 5.60 (d, J=11.1 Hz, 1H), 4.05 (q, J=7.4 Hz, 2H), 3.18 (d, J=4.5 Hz, 1H), 1.24 (t, 3H), 1.15 (m, 2H), 1.11 (m, 2H). LC-MS: mass found for $C_{19}H_{17}F_3N_4O_3S$ $[M+H]^+$ 439.0.

Step 2): Synthesis of 6-[6-cyclopropyl-5-oxo-7-(trifluoromethyl)imidazo[1,2-c]pyrimidin-2-yl]-5-(ethanesulfonyl)pyridine-3-carbaldehyde To a composition of 6-cyclopropyl-2-[3-(ethanesulfonyl)-5-ethenylpyridin-2-yl]-7-(trifluoromethyl)imidazo[1,2-c]pyrimidin-5-one (4.675 mmol) in dry 1,4 dioxane (30 ml) was added $OsO_4$ (1.660 mmol) at 0° C. and the resulting reaction mixture was stirred for 5 min upon which $NaIO_4$ was added (23.401 mmol). The reaction mixture was then stirred for 18 hours at 25° C. Subsequently, the reaction mixture was poured into $H_2O$ water (60 ml) and extracted. The combined organic layers were dried and concentrated under reduced pressure to afford the crude product. The crude product was purified by column chromatography to afford 6-[6-cyclopropyl-5-oxo-7-(trifluoromethyl)imidazo[1,2-c]pyrimidin-2-yl]-5-(ethanesulfonyl)pyridine-3-carbaldehyde (1.5 g). $H^1$ NMR (500 MHz, DMSO-d6): δ 9.11 (d, J=2.1 Hz, 1H), 8.55 (d, J=2.1 Hz, 1H), 8.31 (s, 1H), 7.43 (s, 1H), 3.83 (d, J=7.4 Hz, 2H), 3.10 (d, J=4.4 Hz, 1H), 1.17 (t, J=7.4 Hz, 3H), 1.14-1.02 (m, 5H). LC-MS: mass found for $C_{18}H_{15}F_3N_4O_4S$ $[M+H]^+$ 441.0.

Step 3): Synthesis (3E)-6-[6-cyclopropyl-5-oxo-7-(trifluoromethyl)imidazo[1,2-c]pyrimidin-2-yl]-5-ethylsulfonyl-pyridine-3-carbaldehyde oxime (compound I.x)

To a composition comprising 6-[6-cyclopropyl-5-oxo-7-(trifluoromethyl)imidazo[1,2-c]pyrimidin-2-yl]-5-ethylsulfonyl-pyridine-3-carbaldehyde (0.15 g, 0.340 mmol) in dry $CH_3OH$ (5 ml) was added $[NH_3OH]Cl$ (0.3747 mmol) at 25° C. and the resulting reaction mixture was stirred for 18 hours at 25° C. After the completion the reaction, the reaction mixture was concentrated under reduced pressure to afford the crude product. The crude product was washed with ($CH_3COOCH_2CH_3$: n-pentane in a ratio of 1:4), filtered and dried to afford (3E)-6-[6-cyclopropyl-5-oxo-7-(trifluoromethyl)imidazo[1,2-c]pyrimidin-2-yl]-5-ethylsulfonyl-pyridine-3-carbaldehyde oxime (0.122 g). $H^1$ NMR (500 MHz, DMSO-d6): 12.06 (s, 1H), 9.01 (d, J=2.3 Hz, 1H), 8.59 (d, J=2.1 Hz, 1H), 8.34 (s, 1H), 8.27 (s, 1H), 7.44 (s, 1H), 3.98 (d, J=7.4 Hz, 2H), 3.27-3.09 (m, 1H), 1.19 (t, J=7.5 Hz, 3H), 1.14 (m, J=6.8 Hz, 2H), 1.05 (m, 2H). LC-MS: mass found for $C_{18}H_{16}F_3N_5O_4S$ $[M+H]^+$ 456.

Step 4): Manufacture of 6-cyclopropyl-2-[3-ethylsulfonyl-5-(1-oxa-2-azaspiro[4.4]non-2-en-3-yl)-2-pyridyl]-7-(trifluoromethyl)imidazo[1,2-c]pyrimidin-5-one To a stirred composition comprising (3E)-6-[6-cyclopropyl-5-oxo-7-(trifluoromethyl)imidazo[1,2-c]pyrimidin-2-yl]-5-ethylsulfonyl-pyridine-3-carbaldehyde oxime (0.21 mmol) in NaClO (10-15 wt % aqueous solution, 5 mL) and THF (5 V, 2 mL) at 0° C., was added methylene cyclopentane (0.018 mg, 0.21 mmol) dropwise. The resultant reaction mixture was stirred at 20 to 25° C. for 3 hours. After the completion of the reaction, the reaction mixture was quenched and extracted. The combined organic layers were, dried and concentrated under reduced pressure to afford a crude product. The crude product was purified by column chromatography to afford 6-cyclopropyl-2-[3-ethylsulfonyl-5-(1-oxa-2-azaspiro[4.4]non-2-en-3-yl)-2-pyridyl]-7-(trifluoromethyl)imidazo-[1,2-c]pyrimidin-5-one as an off white solid (0.55 g 45.84% yield). $H^1$ NMR (500 MHz, DMSO-d6): δ 9.10 (s, 1H), 8.59 (s, 1H), 8.32 (s, 1H), 7.53 (s, 1H), 4.11 (d, J=7.4 Hz, 2H), 3.52 (s, 2H), 3.17 (s, 1H), 1.97 (s, 3H), 1.86-1.60 (m, 8H), 1.34-1.18 (m, 2H), 1.10 (s, 2H). LC-MS: mass found for $C_{24}H_{24}F_3N_5O_4S$ $[M+H]^+$ 536.0.

Synthesis Example 6: Manufacture of 6-cyclopropyl-2-[2-ethylsulfonyl-4-[(E)-N-hydroxy-C-methyl-carbonimidoyl]phenyl]-7-(trifluoromethyl)imidazo[1,2-c]pyrimidin-5-one (compound C-21)

Step 1): Manufacture of 2-(4-acetyl-2-ethylsulfonyl-phenyl)-6-cyclopropyl-7-(trifluoromethyl)imidazo[1,2-c]pyrimidin-5-one A stirred composition of 2-(4-bromo-2-ethylsulfonyl-phenyl)-6-cyclopropyl-7-(trifluoromethyl)-imidazo[1,2-c]pyrimidin-5-one (2.03 mmol) and tributyl(1-ethoxyvinyl) tin (2.03 mmol) in toluene (10 mL) was degassed under $N_2$-atmosphere for ten minutes, followed by addition of tetrakis-triphenylphosphin-palladium (1.04 mmol). The resultant reaction mixture was heated to 120° C. for 6 hours. After the completion of the reaction, the reaction mixture was quenched and extracted. The combined organic layer were dried and concentrated under reduced pressure to afford a crude product. The crude product was purified by column chromatography to afford 2-(4-acetyl-2-ethylsulfonyl-phenyl)-6-cyclopropyl-7-(trifluoromethyl)imidazo[1,2-c]pyrimidin-5-one (0.88 g). $H^1$ NMR (500 MHz, DMSO-d6): δ 8.43-8.32 (m, 1H), 7.99 (d, J=8.0 Hz, 1H), 7.96 (dd, J=8.0, 1.8 Hz, 1H), 7.78 (d, J=8.0 Hz, 1H), 7.59 (s, 1H), 4.33 (t, J=7.4 Hz, 2H), 3.41 (d, J=17.5 Hz, 3H), 3.17 (s, 1H), 2.70 (s, 3H), 1.20-1.07 (m, 4H). LC-MS: mass found for $C_{20}H_{18}F_3N_2O_4S$ $[M+H]^+$ 454.0.

Step 2): Manufacture of 6-cyclopropyl-2-[2-ethylsulfonyl-4-[(E)-N-hydroxy-C-methyl-carbonimidoyl]phenyl]-7-(trifluoromethyl)imidazo[1,2-c]pyrimidin-5-one To a stirred composition of 2-(4-acetyl-2-ethylsulfonyl-phenyl)-6-cyclopropyl-7-(trifluoromethyl)-imidazo[1,2-c]pyrimidin-5-one (0.79 mmol) in $CH_3CH_2OH$ (5 mL) at 0° C., was added $[NH_3OH]Cl$ (0.95 mmol). The resultant reaction mixture was heated to 90° C. for 4 hours. After completion of the reaction, the reaction mixture was quenched and extracted. The combined organic layers were dried and concentrated under reduced pressure to afford a crude product. The crude product was purified by column chromatography to afford 6-cyclopropyl-2-[2-ethylsulfonyl-4-[(E)-N-hydroxy-C-methyl-carbonimidoyl]phenyl]-7-(trifluoromethyl)imidazo[1,2-c]pyrimidin-5-one (0.23 g). $H^1$-NMR (500 MHz, DMSO-d6): δ 8.43-8.32 (m, 1H), 7.99 (d, J=8.0 Hz, 1H), 7.96 (dd, J=8.0, 1.8 Hz, 1H), 7.78 (d, J=8.0 Hz, 1H), 7.59 (s, 1H), 4.33 (t, J=7.4 Hz, 2H), 3.41 (d, J=17.5 Hz, 3H), 3.17 (s, 1H), 2.70 (s, 3H), 1.20-1.07 (m, 4H). LC-MS: mass found for $C_{20}H_{19}F_3N_4O_4S$ $[M+H]^+$ 469.0.

Synthesis Example 7: Manufacture of 6-cyclopropyl-2-[4-[(E)-N-(dimethylamino)-C-methyl-carbonimidoyl]-2-ethylsulfonyl-phenyl]-7-(trifluoromethyl) imidazo[1,2-c]pyrimidin-5-one (compound C-24)

To a stirred solution of 2-(4-acetyl-2-ethylsulfonyl-phenyl)-6-cyclopropyl-7-(trifluoromethyl)imidazo[1,2-c]pyrimidin-5-one (0.44 mmol) in $CH_3CH_2OH$ (2 mL) and $CH_3COOH$ (0.05 mL) at 0° C., was added N, N-dimethylhydrazine (0.88 mmol). The resulting reaction mixture was heated to 80° C. for 1 hour. After the completion of the reaction, the reaction was quenched and the reaction mixture was extracted. Organic layer was separated, dried and concentrated to get a crude residue. The crude residue was purified by column chromatography to afford 6-cyclopropyl-2-[4-[(E)-N-(dimethylamino)-C-methyl-carbonimidoyl]-2-ethylsulfonyl-phenyl]-7-(trifluoromethyl)imidazo[1,2-c]pyrimidin-5-one as a pale yellow solid (0.05 g). 1H-NMR (500 MHz, DMSO-d6): δ 8.47 (s, 1H), 8.29 (s, 1H), 8.11 (dd, J=8.0, 1.8 Hz, 1H), 7.83 (d, J=8.0 Hz, 1H), 7.49 (s, 1H), 3.61 (q, J=7.3 Hz, 2H), 3.17 (s, 1H), 2.60 (s, 6H), 2.37 (s, 3H), 1.24 (s, 3H), 1.20-1.07 (m, 4H). LC-MS: mass found for $C_{22}H_{24}F_3N_5O_3S$ $[M+H]^+$ 496.0.

With appropriate modification of the starting materials or intermediates thereof, the procedures as described in the preparation examples above were used to obtain further compounds as defined in Table B below.

TABLE B synthesized compounds of formula (I) and physical characterization data; n.m. means not measured

| Compound | Structure | Mass $[M + H]^+$ in g/mol measured by HPLC-MS (retention time [min]) | Chemical shift (δ) $^1$H-NMR (in DMSO-d6 at 500 MHz or as provided below) |
|---|---|---|---|
| C-1 | 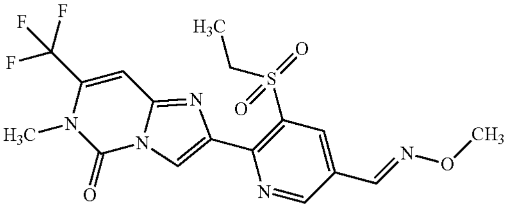 [SMILES: CCS(=O)(=O)c1cc(/C=N/OC)cnc1-c1cn2c(=O)n(C)c(C(F)(F)F)cc2n1] | 443.8 (1.093) | n.m. |
| C-2 | 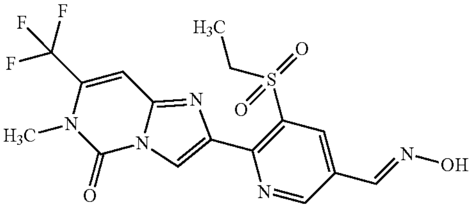 [SMILES: CCS(=O)(=O)c1cc(/C=N/O)cnc1-c1cn2c(=O)n(C)c(C(F)(F)F)cc2n1] | 430 (0.968) | n.m. |
| C-3 | 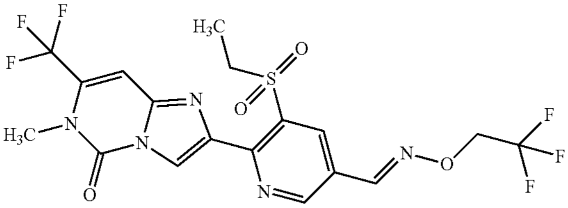 [SMILES: CCS(=O)(=O)c1cc(/C=N/OCC(F)(F)F)cnc1-c1cn2c(=O)n(C)c(C(F)(F)F)cc2n1] | 511.9 (1.207) | n.m. |
| C-4 | 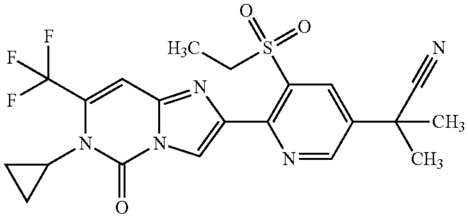 [SMILES: CCS(=O)(=O)c1cc(C(C)(C)C#N)cnc1-c1cn2c(=O)n(C3CC3)c(C(F)(F)F)cc2n1] | 480 (1.845) | δ 9.04 (s, 1H), 8.5 (s, 1H), 8.3 (s, 1H), 7.2 (s, 1H), 3.97 (q, 2H, J = 10 Hz), 3.2 (s, 1H), 1.85 (s, 6H), 1.30 ( dd, 4H, J = 4.5 Hz), 1.26 (t, 3H, J = 7 Hz) |

TABLE B-continued synthesized compounds of formula (I) and physical characterization data; n.m. means not measured

| Compound | Structure | Mass $[M + H]^+$ in g/mol measured by HPLC-MS (retention time [min]) | Chemical shift (δ) $^1$H-NMR (in DMSO-d6 at 500 MHz or as provided below) |
|---|---|---|---|
| C-5 | 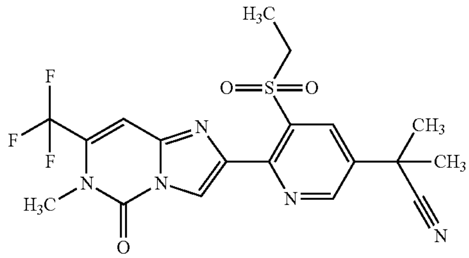 [SMILES: CCS(=O)(=O)c1cc(C(C)(C)C#N)cnc1-c1cn2c(=O)n(C)c(C(F)(F)F)cc2n1] | 454 (1.063) | n.m. |
| C-6 | 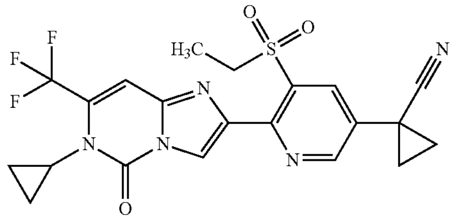 [SMILES: CCS(=O)(=O)c1cc(C2(C#N)CC2)cnc1-c1cn2c(=O)n(C3CC3)c(C(F)(F)F)cc2n1] | 478 (1.786) | 8.84 (d, J = 2.4 Hz, 1H), 8.35 (d, J = 2.4 Hz, 1H), 8.25 (s, 1H), 7.51 (s, 1H), 4.07 (q, J = 7.3 Hz, 2H), 3.17 (s, 1H), 2.03-1.87 (m, 2H), 1.87-1.73 (m, 2H), 1.25 (t, J = 7.4 Hz, 3H), 1.19-1.00 (m, 4H). |
| C-7 | 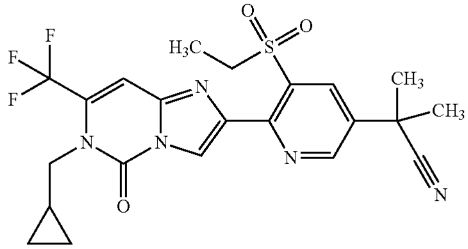 [SMILES: CCS(=O)(=O)c1cc(C(C)(C)C#N)cnc1-c1cn2c(=O)n(CC3CC3)c(C(F)(F)F)cc2n1] | 494.0 (1.984) | 9.16 (d, J = 2.3 Hz, 1H), 8.48 (d, J = 2.4 Hz, 1H), 8.36 (s, 1H), 7.61 (s, 1H), 4.06 (q, J = 7.4 Hz, 2H), 4.00 (d, J = 6.8 Hz, 2H), 1.87-1.80 (s, 6H), 1.7(m, 1H), 1.29-1.21 (t, 3H), 0.85 (m, J = 6.6 Hz, 2H), 0.57-0.50 (m, 2H) |
| C-8 | 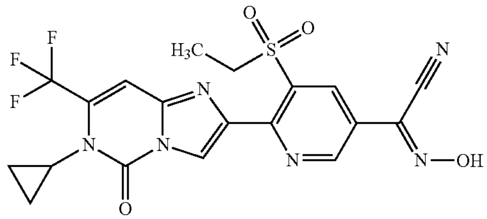 [SMILES: CCS(=O)(=O)c1cc(/C(C#N)=N/O)cnc1-c1cn2c(=O)n(C3CC3)c(C(F)(F)F)cc2n1] | 481.0 (1.711) | 9.22 (s, 1H), 8.48 (s, 1H), 8.20 (d, J = 3.1 Hz, 1H), 7.49 (s, 1H), 5.76 (s, 2H), 3.17 (s, 1H), 1.22 (dt, J = 10.8, 7.4 Hz, 3H), 1.18-0.94 (m, 4H) |
| C-9 | 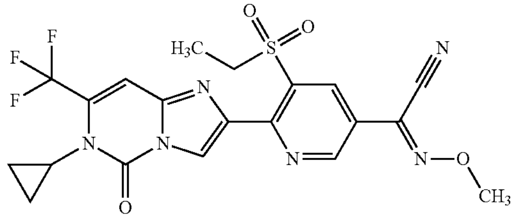 [SMILES: CCS(=O)(=O)c1cc(/C(C#N)=N/OC)cnc1-c1cn2c(=O)n(C3CC3)c(C(F)(F)F)cc2n1] | 495.0 (1.973) | 9.16 (s, 1H), 8.62 (s, 1H), 8.30 (s, 1H), 7.54 (s, 1H), 4.29 (t, J = 20.6 Hz, 3H), 4.16 (q, J = 7.0 Hz, 2H), 3.17 (s, 1H), 1.25 (q, J = 7.8 Hz, 4H), 1.12 (t, J = 7.1 Hz, 3H) |

TABLE B-continued synthesized compounds of formula (I) and physical characterization data; n.m. means not measured

| Comp-ound | Structure | Mass $[M + H]^+$ in g/mol measured by HPLC-MS (retention time [min]) | Chemical shift (δ) $^1$H-NMR (in DMSO-d6 at 500 MHz or as provided below) |
|---|---|---|---|
| C-10 | 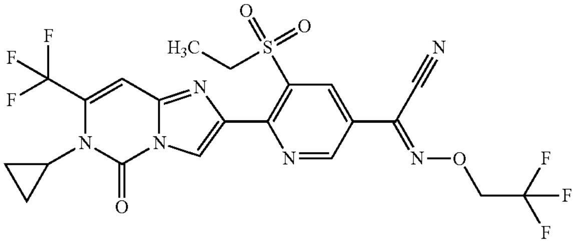 [SMILES: CCS(=O)(=O)c1cc(/C(C#N)=N/OCC(F)(F)F)cnc1-c1cn2c(=O)n(C3CC3)c(C(F)(F)F)cc2n1] | 563.0 (2.056) | 9.34 (s, 1H), 8.65 (s, 1H), 8.41 (s, 1H), 7.55 (s, 1H), 5.27 (dt, J = 23.2, 8.8 Hz, 2H), 4.16 (qd, J = 7.4, 1.9 Hz, 2H), 3.17 (s, 1H), 1.26 (q, J = 7.4 Hz, 3H), 1.20-1.02 (m, 4H). |
| C-11 | 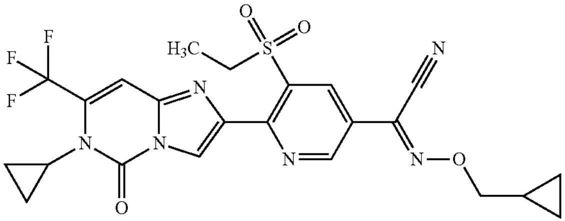 [SMILES: CCS(=O)(=O)c1cc(/C(C#N)=N/OCC2CC2)cnc1-c1cn2c(=O)n(C3CC3)c(C(F)(F)F)cc2n1] | 535.0 (2.061) | ($CDCl_3$): 9.17 (s, 1H), 8.61 (s, 1H), 8.37 (s, 1H), 7.54 (s, 1H), 4.34 (dd, J = 14.1, 7.4 Hz, 2H), 4.15 (q, J = 7.4 Hz, 2H), 3.18 (s, 2H), 1.26 (t, J = 7.4 Hz, 3H), 1.21-1.02 (m, 4H), 0.63 (dt, J = 7.9, 3.1 Hz, 2H), 0.51-0.35 (m, 2H). |
| C-12 | 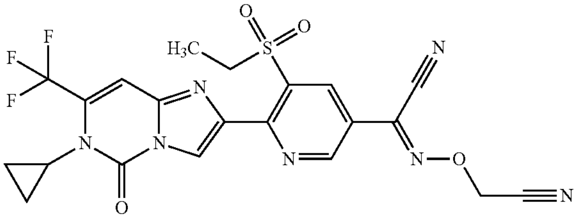 [SMILES: CCS(=O)(=O)c1cc(/C(C#N)=N/OCC#N)cnc1-c1cn2c(=O)n(C3CC3)c(C(F)(F)F)cc2n1] | 520.0 (1.816) | 9.17 (s, 1H), 8.66 (s, 1H), 8.41 (s, 1H), 7.55 (s, 1H), 5.56 (s, 2H), 4.18 (q, J = 7.4 Hz, 2H), 3.18 (s, 1H), 1.27 (t, J = 7.4 Hz, 3H), 1.12 (dt, J = 25.1, 7.0 Hz, 4H). |
| C-13 | 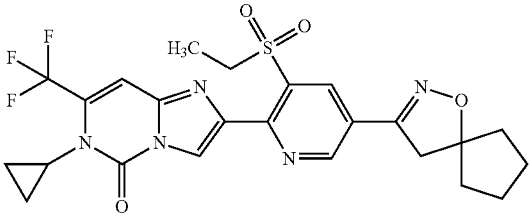 [SMILES: CCS(=O)(=O)c1cc(C2=NOC3(CCCC3)C2)cnc1-c1cn2c(=O)n(C3CC3)c(C(F)(F)F)cc2n1] | 536.0 (1.985) | 9.10 (s, 1H), 8.59 (s,1H), 8.32 (s, 1H), 7.53 (s, 1H), 4.11 (d, J = 7.4 Hz, 2H), 3.52 (s, 2H), 3.17 (s, 1H), 1.97 (s, 3H), 1.86-1.60 (m, 8H), 1.34-1.18 (m, 2H), 1.10 (s, 2H) |
| C-14 | 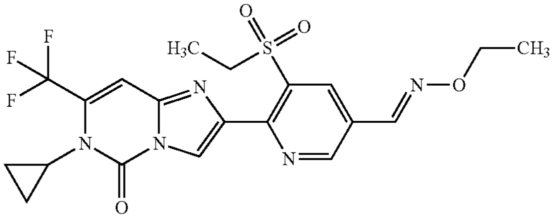 [SMILES: CCO/N=C/c1cnc(-c2cn3c(=O)n(C4CC4)c(C(F)(F)F)cc3n2)c(S(=O)(=O)CC)c1] | 484.0 (1.99) | 9.09 (s, 1H), 8.63 (d, J = 2.0 Hz, 1H), 8.49 (d, J = 1.9 Hz, 1H), 8.31 (s, 1H), 7.52 (s, 1H), 4.26 (q, J = 7.0 Hz, 2H), 4.09 (q, J = 7.4 Hz, 2H), 3.20-3.14 (m, 1H), 1.30 (t, J = 7.1 Hz, 6H), 1.24 (m, J = 7.4 Hz, 2H), 1.19 (m,7.0 Hz, 2H) |
| C-15 | 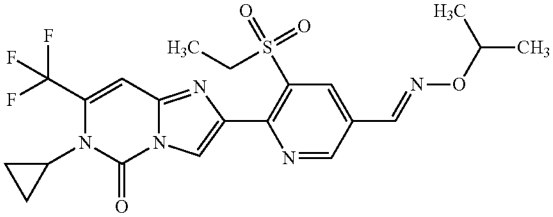 [SMILES: CCS(=O)(=O)c1cc(/C=N/OC(C)C)cnc1-c1cn2c(=O)n(C3CC3)c(C(F)(F)F)cc2n1] | 498.0 (2.05) | 9.09 (s, 1H), 8.63 (d, J = 2.0 Hz, 1H), 8.46 (d, J = 1.9 Hz, 1H), 8.30 (s, 1H), 7.52 (s, 1H), 4.58-4.41 (m, 1H), 4.09 (q, J = 7.4 Hz, 2H), 3.23-3.12 (m, 1H), 1.33 (d, J = 6.2 Hz, 6H), 1.29 (m, J = 6.2 Hz, 3H), 1.24 (dd, J = 10.6, 6.8 Hz, 2H), 1.19-1.04 (m, 2H) |

TABLE B-continued synthesized compounds of formula (I) and physical characterization data; n.m. means not measured

| Compound | Structure | Mass $[M + H]^+$ in g/mol measured by HPLC-MS (retention time [min]) | Chemical shift (δ) $^1$H-NMR (in DMSO-d6 at 500 MHz or as provided below) |
|---|---|---|---|
| C-16 | 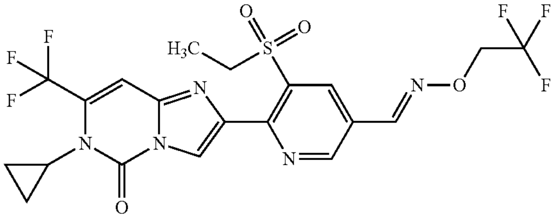 [SMILES: CCS(=O)(=O)c1cc(/C=N/OCC(F)(F)F)cnc1-c1cn2c(=O)n(C3CC3)c(C(F)(F)F)cc2n1] | 538.0 (1.89) | 9.10 (d, J = 1.9 Hz, 1H), 8.72 (s, 1H), 8.67 (d, J = 2.0 Hz, 1H), 8.33 (s, 1H), 7.53 (s, 1H), 4.92 (q, J = 9.1 Hz, 2H), 4.11 (q, J = 7.4 Hz, 2H), 3.17 (s, 1H), 1.24 (t, J = 7.4 Hz, 3H), 1.15 (d, J = 7.0 Hz, 2H), 1.10 (s, 2H) |
| C-17 | 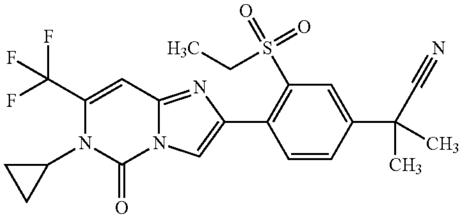 [SMILES: CCS(=O)(=O)c1cc(C(C)(C)C#N)ccc1-c1cn2c(=O)n(C3CC3)c(C(F)(F)F)cc2n1] | 479.0 (1.94) | (300 MHz): 8.28 (s, 1H), 8.19 (d, J = 2.1 Hz, 1H), 7.99 (dd, J = 8.1, 2.2 Hz, 1H), 7.86 (d, J = 8.1 Hz, 1H), 7.50 (s, 1H), 3.66 (q, J = 7.3 Hz, 2H), 3.17 (s, 1H), 1.78 (s, 6H), 1.12 (m, 7H) |
| C-18 | 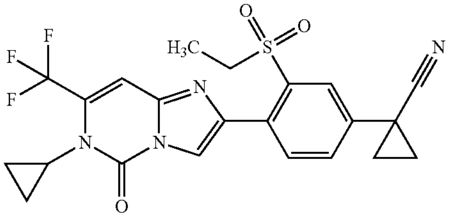 [SMILES: CCS(=O)(=O)c1cc(C2(C#N)CC2)ccc1-c1cn2c(=O)n(C3CC3)c(C(F)(F)F)cc2n1] | 477.0 (1.85) | (300 MHz): 8.27 (s, 1H), 8.06 (d, J = 2.1 Hz, 1H), 7.81 (d, J = 8.1 Hz, 1H), 7.68 (dd, J = 8.1, 2.1 Hz, 1H), 7.49 (s, 1H), 3.65 (q, J = 7.3 Hz, 2H), 3.16 (s, 1H), 1.91 (t, J = 3.9 Hz, 2H), 1.75-1.61 (m, 2H), 1.12 (m, 7H) |
| C-19 | 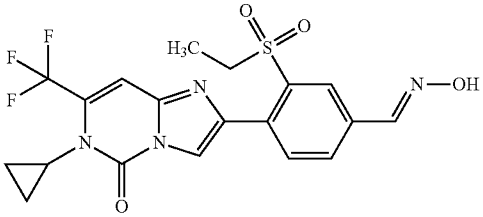 [SMILES: CCS(=O)(=O)c1cc(/C=N/O)ccc1-c1cn2c(=O)n(C3CC3)c(C(F)(F)F)cc2n1] | 455.0 (1.717) | 8.53 (d, J = 2.0 Hz, 1H), 8.08 (d, J = 2.0 Hz, 1H), 7.96 (s, 1H), 7.43 (d, J = 0.8 Hz, 2H), 6.48 (s, 1H), 4.34 (s, 2H), 3.17 (s, 1H), 3.01 (q, J = 7.3 Hz, 3H), 1.20 (t, J = 7.3 Hz, 4H) |
| C-20 | 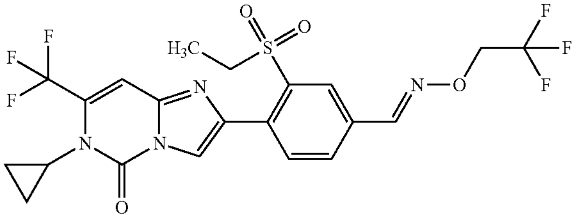 [SMILES: CCS(=O)(=O)c1cc(/C=N/OCC(F)(F)F)ccc1-c1cn2c(=O)n(C3CC3)c(C(F)(F)F)cc2n1] | 536.0 (2.048) | 8.68 (s, 1H), 8.44-8.26 (m, 2H), 8.04 (dd, J = 8.1, 1.8 Hz, 1H), 7.90 (s, 1H), 7.50 (s, 1H), 4.88 (q, J = 9.1 Hz, 2H), 3.66 (q, J = 7.4 Hz, 2H), 3.17 (s, 1H), 1.12 (m, 7H) |
| C-21 | 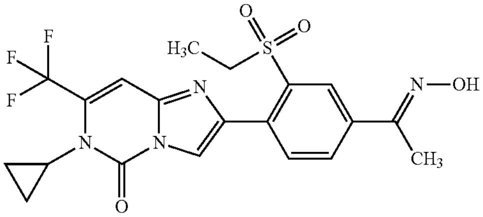 [SMILES: CCS(=O)(=O)c1cc(/C(C)=N/O)ccc1-c1cn2c(=O)n(C3CC3)c(C(F)(F)F)cc2n1] | 469.0 (1.762) | 8.43-8.32 (m, 1H), 7.99 (d, J = 8.0 Hz, 1H), 7.96 (dd, J = 8.0, 1.8 Hz, 1H), 7.78 (d, J = 8.0 Hz, 1H), 7.59 (s, 1H), 4.33 (t, J = 7.4 Hz, 2H), 3.41 (d, J = 17.5 Hz, 3H), 3.17 (s, 1H), 2.70 (s, 3H), 1.20-1.07 (m, 4H) |

TABLE B-continued synthesized compounds of formula (I) and physical characterization data; n.m. means not measured

| Compound | Structure | Mass $[M + H]^+$ in g/mol measured by HPLC-MS (retention time [min]) | Chemical shift (δ) $^1$H-NMR (in DMSO-d6 at 500 MHz or as provided below) |
|---|---|---|---|
| C-22 | 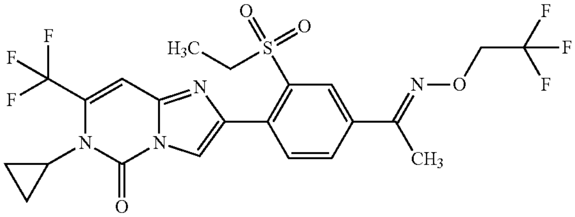 [SMILES: CCS(=O)(=O)c1cc(/C(C)=N/OCC(F)(F)F)ccc1-c1cn2c(=O)n(C3CC3)c(C(F)(F)F)cc2n1] | 551.0 (2.101) | 8.37 (d, J = 1.9 Hz, 2H), 8.32 (s, 1H), 8.09 (s, 1H), 7.50 (s, 1H), 4.89 (q, J = 9.1 Hz, 2H), 3.65 (q, J = 7.3 Hz, 2H), 3.17 (s, 1H), 2.35 (s, 3H), 1.24 (t, J = 7.3 Hz, 3H), 1.02 (m, 4H) |
| C-23 | 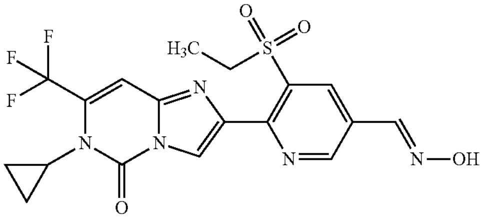 [SMILES: CCS(=O)(=O)c1cc(/C=N/O)cnc1-c1cn2c(=O)n(C3CC3)c(C(F)(F)F)cc2n1] | 456.0 (1.671) | 12.06 (s, 1H), 9.01 (d, J = 2.3 Hz, 1H), 8.59 (d, J = 2.1 Hz, 1H), 8.34 (s, 1H), 8.27 (s, 1H), 7.44 (s, 1H), 3.98 (d, J = 7.4 Hz, 2H), 3.27-3.09 (m, 1H), 1.19 (t, J = 7.5 Hz, 3H), 1.14 (m, J = 6.8 Hz, 2H), 1.05 (m, 2H) |
| C-24 | 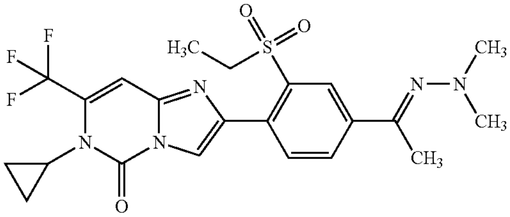 [SMILES: CCS(=O)(=O)c1cc(/C(C)=N/N(C)C)ccc1-c1cn2c(=O)n(C3CC3)c(C(F)(F)F)cc2n1] | 496.0 (1.98) | 8.47 (s, 1H), 8.29 (s, 1H), 8.11 (dd, J = 8.0, 1.8 Hz, 1H), 7.83 (d, J = 8.0 Hz, 1H), 7.49 (s, 1H), 3.61 (q, J = 7.3 Hz, 2H), 3.17 (s, 1H), 2.60 (s, 6H), 2.37 (s, 3H), 1.24 (s, 3H), 1.20-1.07 (m, 4H) |
| C-25 | 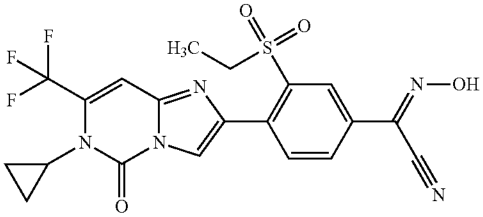 [SMILES: CCS(=O)(=O)c1cc(/C(C#N)=N/O)ccc1-c1cn2c(=O)n(C3CC3)c(C(F)(F)F)cc2n1] | 480.0 (1.79) | 8.51-8.22 (m, 2H), 8.11 (dd, J = 8.1, 2.0 Hz, 1H), 8.00 (dd, J = 11.0, 8.2 Hz, 1H), 7.51 (s, 1H), 3.70 (q, J =7.2 Hz, 2H), 3.17 (s, 1H), 1.15 (dt, J = 18.7, 7.2 Hz, 7H) |
| C-26 | 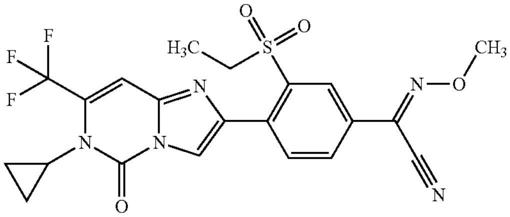 [SMILES: CCS(=O)(=O)c1cc(/C(C#N)=N/OC)ccc1-c1cn2c(=O)n(C3CC3)c(C(F)(F)F)cc2n1] | 494.0 (1.96) | 8.42-8.39 (m, 1H), 8.38 (s, 1H), 8.12 (dd, J = 8.1, 2.0 Hz, 1H), 8.01 (d, J = 8.1 Hz, 1H), 7.51 (s, 1H), 4.27 (s, 3H), 3.69 (q, J = 7.3 Hz, 2H), 3.17 (s, 1H), 1.13 (m, 7H) |
| C-27 | 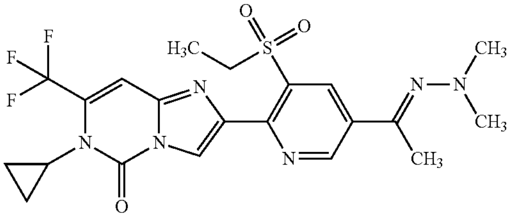 [SMILES: CCS(=O)(=O)c1cc(/C(C)=N/N(C)C)cnc1-c1cn2c(=O)n(C3CC3)c(C(F)(F)F)cc2n1] | 497.0 (1.89) | 9.18 (d, J = 2.0 Hz, 1H), 8.70 (d, J = 2.1 Hz, 1H), 8.28 (s, 1H), 7.52 (s, 1H), 4.06 (t, J = 7.3 Hz, 2H), 3.17 (s, 1H), 2.64 (s, 6H), 2.40 (s, 3H), 1.25 (q, J = 7.4, 6.2 Hz, 3H), 1.20-0.99 (m, 4H) |

B. Biological Examples

The activity of the compounds of formula (I) of the present invention could be demonstrated and evaluated in biological tests described in the following. If not otherwise specified, the test solutions are prepared as follows: The active compound is dissolved at the desired concentration in a mixture of 1:1 (vol: vol) distilled water:acetone. The test solution is prepared at the day of use. Test solutions are prepared in general at concentrations of 2500 ppm, 1415 ppm and 800 ppm (wt/vol).

Boll Weevil (*Anthonomus grandis*)

For evaluating control of boll weevil (*Anthonomus grandis*) the test unit consisted of 96-well-microtiter plates containing an insect diet and 5-10 *A. grandis* eggs. The compounds were formulated using a solution containing 75% v/v water and 25% v/v DMSO. Different concentrations of formulated compounds were sprayed onto the insect diet at 5 μl, using a custom built micro atomizer, at two replications. After application, microtiter plates were incubated at about 25±1° C. and about 75±5% relative humidity for 5 days. Egg and larval mortality was then visually assessed. In this test, compounds C-1, C-2, C-3, C-4, C-5 at 2500 ppm showed over 75% mortality in comparison with untreated controls. Compounds C-6, C-7, C-9, C-10, C-11, C-12, C-13, C-14, C-15, and C-16 at 800 ppm showed over 75% mortality in comparison with untreated controls.

Tobacco Budworm (*Heliothis virescens*)

For evaluating control of tobacco budworm (*Heliothis virescens*) the test unit consisted of 96-well-microtiter plates containing an insect diet and 15-25 *H. virescens* eggs. The compounds were formulated using a solution containing 75% v/v water and 25% v/v DMSO. Different concentrations of formulated compounds were sprayed onto the insect diet at 10 μl, using a custom built micro atomizer, at two replications. After application, microtiter plates were incubated at about 28±1° C. and about 80±5% relative humidity for 5 days. Egg and larval mortality was then visually assessed. In this test, compound C-1, C-2, C-3, C-4, C-5 at 2500 ppm showed over 75% mortality in comparison with untreated controls. Compounds C-6, C-7, C-9, C-10, C-11, C-13, C-14, C-15, and C-16 at 800 ppm showed over 75% mortality in comparison with untreated controls.

Green Peach Aphid (*Myzus persicae*)

For evaluating control of green peach aphid (*Myzus persicae*) through systemic means the test unit consisted of 96-well-microtiter plates containing liquid artificial diet under an artificial membrane. The compounds were formulated using a solution containing 75% v/v water and 25% v/v DMSO. Different concentrations of formulated compounds were pipetted into the aphid diet, using a custom built pipetter, at two replications. After application, 5-8 adult aphids were placed on the artificial membrane inside the microtiter plate wells. The aphids were then allowed to suck on the treated aphid diet and incubated at about 23±1° C. and about 50±5% relative humidity for 3 days. Aphid mortality and fecundity was then visually assessed. In this test, compound C-1, C-2, C-3, C-4, C-5 at 2500 ppm showed over 75% mortality in comparison with untreated controls. Compounds C-4, C-7, C-8, C-9, C-10, C-11, C-12, C-13, C-14, C-15, C-16, and C-23 at 800 ppm showed over 75% mortality in comparison with untreated controls.

Vetch Aphid (*Megoura viciae*)

For evaluating control of vetch aphid (*Megoura viciae*) through contact or systemic means the test unit consisted of 24-well-microtiter plates containing broad bean leaf disks. The compounds were formulated using a solution containing 75% v/v water and 25% v/v DMSO. Different concentrations of formulated compounds were sprayed onto the leaf disks at 2.5 μl, using a custom built micro atomizer, at two replications. After application, the leaf disks were air-dried and 5-8 adult aphids placed on the leaf disks inside the microtiter plate wells. The aphids were then allowed to suck on the treated leaf disks and incubated at about 23±1° C. and about 50±5% relative humidity for 5 days. Aphid mortality and fecundity was then visually assessed. In this test, compound C-1, C-3, C-4 at 2500 ppm showed over 75% mortality in comparison with untreated controls.

Greenhouse Whitefly (*Trialeurodes vaporarirorum*)

For evaluating control of Greenhouse Whitefly (*Trialeurodes vaporariorum*) the test unit consisted of 96-well-microtiter plates containing a leaf disk of egg plant leaf disk with white fly eggs. The compounds or mixtures were formulated using a solution containing 75% water and 25% DMSO. Different concentrations of formulated were sprayed onto the insect diet at 2.5 μl, using a custom built micro atomizer, at two replications. After application, microtiter plates were incubated at 23±1° C., 65±5% RH for 6 days. Mortality of hatched crawlers was then visually assessed. In this test, compound C-4, C-5 at 2500 ppm showed over 75% mortality in comparison with untreated controls. Compounds C-4, C-6, C-11, C-13, C-15, and C-16 at 800 ppm showed over 75% mortality in comparison with untreated controls.

Yellow Fever Mosquito (*Aedes aegypti*)

For evaluating control of yellow fever mosquito (*Aedes aegypti*) the test unit consisted of 96-well-microtiter plates containing 200 μl of tap water per well and 5-15 freshly hatched *A. aegypti* larvae. The active compounds were formulated using a solution containing 75% (v/v) water and 25% (v/v) DMSO. Different concentrations of formulated compounds or mixtures were sprayed onto the insect diet at 2.5 μl, using a custom built micro atomizer, at two replications. After application, microtiter plates were incubated at 28±1° C., 80±5% RH for 2 days. Larval mortality was then visually assessed. In this test, compounds C-1, C-3, C-4, C-6, C-7, C-9, C-10, C-11, C-12, C-13, and C-14 at 800 ppm showed over 75% mortality in comparison with untreated controls.

Green Soldier Stink Bug (*Nezara viridula*)

The active compound is dissolved at the desired concentration in a mixture of 1:1 (vol: vol) distilled water:aceteone. Surfactant (Kinetic) is added at a rate of 0.01% (vol/vol). The test solution is prepared at the day of use. Soybean pods are placed in 90×50 mm glass Petri dishes lined with moistened filter paper and inoculated with ten late 3rd instar *N. viridula*. Using a hand atomizer, an approximately 2 ml solution is sprayed into each Petri dish. Treated set-up is kept at about 25-26° C. and relative humidity of about 65-70%. Percent mortality is recorded after 5 days. In this test, compounds C-1, C-3, C-4, C-5, C-6, C-7, C-9, C-10, C-11, C-14, C-15, and C-23 at 800 ppm showed over 75% mortality in comparison with untreated controls.

The invention claimed is:

1. A compound of formula (I)

(I)

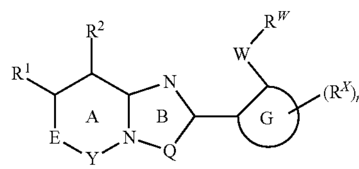

wherein the rings A and B are fully unsaturated;

Y is C═X, wherein X is O or S;

E is $N(R^3)$ or $C(R^4)$;

Q is N, $N(R^5)$ or $C(R^6)$;

$R^1$ is H, halogen, $C_1$-$C_6$-alkyl, $C_2$-$C_6$-alkenyl, $C_2$-$C_6$-alkynyl, $C_1$-$C_6$-alkoxy, $C_1$-$C_6$-alkoxy-$C_1$-$C_6$-alkyl, $C_3$-$C_6$-cycloalkyl, $C_3$-$C_6$-cycloalkoxy, $C_1$-$C_6$-sulfenyl, $C_1$-$C_6$-sulfinyl, or $C_1$-$C_6$-sulfonyl, which groups are unsubstituted or halogenated;

$R^3$, $R^5$ are independently $C_1$-$C_6$-alkyl, $C_1$-$C_6$-alkoxy, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which are unsubstituted or halogenated;

C(═O)$OR^A$, $NR^BR^C$, $C_1$-$C_6$-alkylen-$NR^BR^C$, O—$C_1$-$C_6$-alkylen-$NR^BR^C$, $C_1$-$C_6$-alkylen-CN, NH—$C_1$-$C_6$-alkylen-$NR^BR^C$, C(═O)$NR^BR^C$, C(═O)$R^D$, C(═S)$R^D$, $SO_2NR^BR^C$, $S(═O)_mR^E$;

phenyl or benzyl, wherein the phenyl ring is unsubstituted or substituted with one or more, same or different substituents $R^F$;

$R^2$, $R^4$, $R^6$ are independently H, halogen, $N_3$, CN, $NO_2$, SCN, $SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxyx-$C_1$-$C_4$-alkyl, which groups are unsubstituted or substituted with halogen, C(═O)$OR^A$, $NR^BR^C$, $NOR^A$, $ONR^BR^C$, $C_1$-$C_6$-alkylen-$NR^BR^C$, O—$C_1$-$C_6$-alkylen-$NR^BR^C$, $C_1$-$C_6$-alkylen-CN, NH—$C_1$-$C_6$-alkylen-$NR^BR^C$, C(═O)$NR^BR^C$, C(═O)$R^D$, C(═S)$R^D$, $SO_2NR^BR^C$, $S(═O)_mR^E$;

phenyl or benzyl, wherein the phenyl ring is unsubstituted or substituted with one or more, same or different substituents $R^F$;

G is phenyl, or a 5- or 6-membered hetaryl;

W is S, S(O), or $S(O)_2$;

$R^X$ is —C(CN)$R^7R^8$, —C($R^O$)═N—N($R^MR^N$), —C($R^O$)═N—O($R^L$); $C_3$-$C_6$-cycloalkyl, which is substituted with CN and which either does not have any further substituents, or which is further substituted with one or more, same or different substituents $R^9$; or a group of formula (I.1)

(I.1)

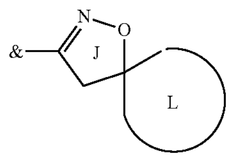

wherein the ring L is a 5- or 6-membered saturated, partially or fully unsaturated carbo- or heterocycle;

wherein the ring L is a saturated, partially or fully saturated carbo- or heterocycle, which carobo- or heterocycle is unsubstituted or substituted with one or more, same or different substituents $R^{10}$, and wherein said heterocyclic ring contains one or more, same or different and wherein said heteroatoms O and N are oxidized or non-oxidized;

wherein ring J is partially or fully unsaturated and unsubstituted or substituted with one or more, same or different substituents $R^{11}$; and wherein "&" means the connection to the remainder of the molecule at the position of $R^X$ in formula (I);

$R^7$, $R^8$ are independently H, halogen, CN, $C_1$-$C_6$-alkyl, $C_1$-$C_6$-haloalkyl, $C_3$-$C_6$-cycloalkyl, $C_1$-$C_4$-alkoxy, $C_1$-$C_4$-alkoxy-$C_1$-$C_4$-alkyl, $C_1$-$C_4$-alkylsulfanyl, $C_1$-$C_4$-alkylsulfanyl-$C_1$-$C_4$-alkyl, $C_1$-$C_4$-alkylsulfinyl-$C_1$-$C_4$-alkyl, $C_1$-$C_4$-alkylsulfonyl-$C_1$-$C_4$-alkyl or $C_1$-$C_4$-alkoxycarbonyl;

$R^9$ halogen, CN, $NH_2$, C(═O)H, OH, $C_3$-$C_6$-cycloalkyl, C(═O)OH, C(═O)$NH_2$, $C_1$-$C_4$-haloalkoxy, $C_1$-$C_4$-alkoxy, $C_1$-$C_4$-haloalkylsulfanyl, $C_1$-$C_4$-haloalkylsulfinyl, $C_1$-$C_4$-haloalkylsulfonyl, $C_1$-$C_4$-alkoxycarbonyl, $C_1$-$C_4$-haloalkoxycarbonyl, $C_1$-$C_4$-alkylcarbonyl, $C_1$-$C_4$-haloalkylcarbonyl, di-($C_1$-$C_4$)alkylaminocarbonyl, $C_1$-$C_4$-alkylaminocarbonyl, $C_1$-$C_4$-alkylcarbonylamino, di-($C_1$-$C_4$)alkylcarbonylamino, $C_1$-$C_4$-alkoxycarbonylamino, or a group —C($R^{91}$)═$NOR^{92}$;

phenyl, which is unsubstituted or substituted with one or more, same or different substituents selected from halogen, CN, $C_1$-$C_4$-alkyl, $C_1$-$C_4$-haloalkyl, $C_1$-$C_4$-haloalkoxy, $C_1$-$C_4$-alkoxy, $C_1$-$C_4$-haloalkylsulfanyl, $C_1$-$C_4$-haloalkylsulfinyl, $C_1$-$C_4$haloalkylsulfonyl and C(═O) $C_1$-$C_4$-haloalkyl;

$C_1$-$C_4$-alkyl which is unsubstituted or substituted with one or more, same or different substituents $R^{93}$;

$R^{91}$ and $R^{92}$ are independently H, $C_1$-$C_4$-alkyl, or $C_1$-$C_4$-haloalkyl;

$R^{93}$ is halogen, CN, $NH_2$, C(═O)H, OH, $C_3$-$C_6$-cycloalkyl, hydroxycarbonyl, aminocarbonyl, $C_1$-$C_4$-haloalkoxy, $C_1$-$C_4$-alkoxy, $C_1$-$C_4$-haloalkylsulfanyl, $C_1$-$C_4$-haloalkylsulfinyl, $C_1$-$C_4$-haloalkylsulfonyl, $C_1$-$C_4$-alkoxycarbonyl, $C_1$-$C_4$-haloalkoxycarbonyl, $C_1$-$C_4$-alkylcarbonyl, $C_1$-$C_4$-haloalkylcarbonyl, di-($C_1$-$C_4$) alkylaminocarbonyl, $C_1$-$C_4$alkylaminocarbonyl, $C_1$-$C_4$-alkylcarbonylamino, di-($C_1$-$C_4$)alkylcarbonylamino, $C_1$-$C_4$-alkoxycarbonylamino, a group —C($R^{91}$)═$NOR^{92}$;

each $R^{10}$, $R^{11}$ are independently H, halogen, CN, OH; $C_1$-$C_6$-alkyl, $C_3$-$C_6$-cycloalkyl, $C_1$-$C_4$-alkoxy, or $C_1$-$C_4$-alkoxy-$C_1$-$C_4$-alkyl, which groups are unsubstituted or halogenated;

each $R^A$ is independently H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are unsubstituted or substituted with halogen;

phenyl or benzyl, wherein the phenyl ring is unsubstituted or substituted with one or more, same or different substitutents $R^F$;

each $R^B$ is independently H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, $C_1$-$C_6$-alkyl-carbonyl, $C_1$-$C_6$-alkoxy-carbonyl, which groups are unsubstituted or substituted with halogen;

phenyl or benzyl, which groups are unsubstituted or substituted with one or more, same or different substituents $R^F$;

each $R^C$ is independently H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, $C_1$-$C_6$-alkyl-carbonyl, or $C_1$-$C_6$-alkoxy-carbonyl, which groups are unsubstituted or substituted with halogen;

phenyl or benzyl, wherein the phenyl ring is unsubstituted or substituted with one or more, same or different substituents $R^F$;

each moiety $NR^BR^C$ may also form an N-bound, saturated 5- to 8-membered heterocycle, which in addition to the nitrogen atom may have 1 or 2 further heteroatoms or heteroatom moieties selected from O, $S(=O)_m$ and N—R', wherein R' is H or $C_1$-$C_6$-alkyl and wherein the N-bound heterocycle is unsubstituted or substituted with one or more, same or different substituents selected from halogen, $C_1$-$C_4$-alkyl, $C_1$-$C_4$-haloalkyl, $C_1$-$C_4$-alkoxy and $C_1$-$C_4$-haloalkoxy;

each $R^D$ is independently H, CN, OH, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are unsubstituted or substituted with halogen;

phenyl or benzyl, wherein the phenyl ring is unsubstituted or substituted with one or more, same or different substituents $R^F$;

each $R^E$ is independently $C_1$-$C_6$-alkyl, $C_3$-$C_6$-cycloalkyl, $C_3$-$C_6$-cycloalkyl-$C_1$-$C_4$-alkyl, which are unsubstituted or substituted with halogen; or phenyl or benzyl, wherein the phenyl ring is unsubstituted or substituted with one or more, same or different substituents $R^F$;

each $R^L$ is independently H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are unsubstituted or substituted with one or more, same or different substituents selected from halogen and CN;

phenyl or benzyl, wherein the phenyl ring is unsubstituted or substituted with one or more, same or different substituents $R^F$;

each $R^M$ is independently H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, $C_1$-$C_6$-alkyl-carbonyl, $C_1$-$C_6$-alkoxy-carbonyl, which groups are unsubstituted or substituted with halogen;

phenyl or benzyl, which groups are unsubstituted or substituted with one or more, same or different substituents $R^F$;

each $R^N$ is independently H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, $C_1$-$C_6$-alkyl-carbonyl, $C_1$-$C_6$-alkoxy-carbonyl, which groups are unsubstituted or substituted with halogen;

phenyl or benzyl, wherein the phenyl ring is unsubstituted or substituted with one or more, same or different substituents $R^F$;

each moiety $NR^MR^N$ may also form an N-bound, saturated 5- to 8-membered heterocycle, which in addition to the nitrogen atom may have 1 or 2 further heteroatoms or heteroatom moieties selected from O, $S(=O)_m$ and N—R', wherein R' is H or $C_1$-$C_6$-alkyl and wherein the N-bound heterocycle is unsubstituted or substituted with one or more, same or different substituents selected from halogen, $C_1$-$C_4$-alkyl, $C_1$-$C_4$-haloalkyl, $C_1$-$C_4$-alkoxy and $C_1$-$C_4$-haloalkoxy;

each $R^O$ is independently H, CN, OH, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which groups are unsubstituted or substituted with halogen;

phenyl or benzyl, wherein the phenyl ring is unsubstituted or substituted with one or more, same or different substituents $R^F$;

each $R^F$ is independently halogen, $N_3$, OH, CN, $NO_2$, SCN, $SF_5$, $C_1$-$C_6$ alkyl, $C_1$-$C_6$-alkoxy, $C_2$-$C_6$-alkenyl, $C_2$-$C_6$-alkynyl, $C_1$-$C_6$-alkoxy-$C_1$-$C_4$ alkyl, $C_1$-$C_6$-alkoxy-$C_1$-$C_4$-alkoxy, $C_3$-$C_6$-cycloalkyl, $C_3$-$C_6$ cycloalkoxy, $C_3$-$C_6$-cycloalkyl-$C_1$-$C_4$ alkyl, $C_3$-$C_6$-cycloalkoxy-$C_1$-$C_4$ alkyl, which groups are unsubstituted or substituted with halogen;

$R^W$ is $C_1$-$C_6$-alkyl, $C_3$-$C_6$-cycloalkyl, $C_3$-$C_6$-cycloalkyl-$C_1$-$C_4$-alkyl, which groups are halogenated or non-halogenated;

benzyl, or phenyl, which is unsubstituted or substituted with $R^F$;

the index n is 1, if G is phenyl or a 6-membered hetaryl; or 1, if G is a 5-membered hetaryl; and the index m is 0, 1, or 2;

and the N-oxides, stereoisomers, tautomers, and agriculturally or veterinarily acceptable salts thereof.

2. The compound of formula (I) according to claim 1, wherein $R^1$ is H, $C_1$-$C_3$-alkyl, or $C_1$-$C_3$-alkoxy, which groups are unsubstituted or halogenated;

$R^2$ is H, halogen, $C_1$-$C_3$-alkyl, $C_1$-$C_3$-alkoxy, $C_2$-$C_3$-alkenyl, or $C_2$-$C_3$-alkynyl, which groups are unsubstituted or halogenated.

3. The compound of formula (I) according to claim 1, wherein the compound of formula (I) is a compound of formula (I.A), (I.B), or (I.C);

(I.A)

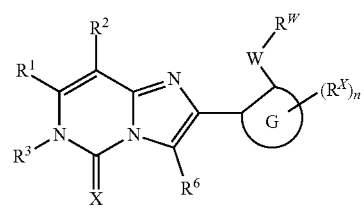

(I.B)

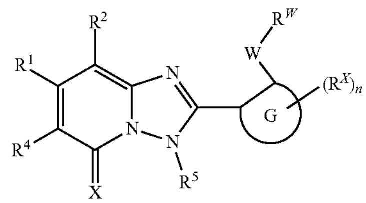

(I.C)

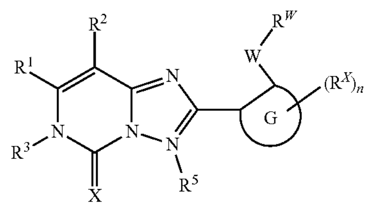

wherein all variables have a meaning as defined for formula (I).

4. The compound of formula (I.A) according to claim 3, wherein $R^3$ $C_1$-$C_3$-alkyl, $C_3$-$C_6$-cycloalkyl, $C_3$-$C_6$-cycloalkyl-$C_1$-$C_2$-alkyl, which groups are unsubstituted or halogenated;

$R^6$ is H, or $C_1$-$C_3$-alkyl or $C_1$-$C_3$-haloalkyl.

5. The compound of formula (I.B) according to claim 3, wherein $R^4$ is H, or $C_1$-$C_3$ alkyl, or $C_1$-$C_3$-haloalkyl;

$R^5$ is $C_1$-$C_3$-alkyl, or $C_1$-$C_3$-haloalkyl.

6. The compound of formula (I) according to claim 1, wherein G is phenyl or pyridyl.

7. The compound of formula (I) according to claim 1, wherein $R^W$ is $C_1$-$C_3$-alkyl or $C_1$-$C_3$-haloalkyl.

8. The compound of formula (I) according to claim 1, wherein $R^X$ is —C(CN)$R^7R^8$ or $C_3$-$C_6$-cycloalkyl, which is substituted with CN and which either does not have any further substituents, or which is further substituted with one or more, same or different substituents $R^9$;

$R^7$, $R^8$ are independently $C_1$-$C_3$-alkyl or $C_1$-$C_3$-haloalkyl;

$R^9$ is halogen, $C_1$-$C_3$-alkyl, or $C_1$-$C_3$-haloalkyl.

9. The compound of formula (I) according to claim 1, wherein $R^X$ is —C($R^O$)═N—O($R^L$) or —C($R^O$)═N—N($R^MR^N$); wherein each $R^O$ is independently H, CN, $C_1$-$C_3$-alkyl, or $C_1$-$C_3$-haloalkyl;

each $R^L$ is independently H; or $C_1$-$C_3$-alkyl, $C_3$-$C_5$-cycloalkyl, $C_3$-$C_5$-cycloalkyl-$C_1$-$C_3$-alkyl, which groups are unsubstituted or substituted with halogen or CN;

each $R^M$, $R^N$ is independently H, $C_1$-$C_3$-alkyl, or $C_1$-$C_3$-haloalkyl;

or a group of formula (I.1), wherein the ring J is a 5-membered heterocycle; wherein the ring L is 5- or 6-membered saturated carbocycle, which is unsubstituted or substituted with one or more, same or different substituents selected from halogen, $C_1$-$C_3$-alkyl, and $C_1$-$C_3$-haloalkyl; and wherein ring J is unsubstituted or substituted with one or more, same or different substituents selected from halogen, $C_1$-$C_3$-alkyl, and $C_1$-$C_3$-haloalkyl.

10. A pesticidal mixture comprising the compound of formula (I), as defined in claim 1, and a further pesticidal ingredient.

11. A method for combating or controlling invertebrate pests, comprising contacting said pest or its food supply, habitat or breeding grounds with a pesticidally effective amount of at least one compound of the formula (I) according to claim 1.

12. A method for protecting growing plants from attack or infestation by invertebrate pests, comprising contacting a plant, or soil or water in which the plant is growing, with a pesticidally effective amount of at least one compound of the formula (I), according to claim 1.

13. A seed comprising a compound of the formula (I), as defined in claim 1, in an amount of from 0.1 g to 10 kg per 100 kg of seed.

* * * * *